US011898145B2

(12) United States Patent
Funder et al.

(10) Patent No.: US 11,898,145 B2
(45) **Date of Patent: *Feb. 13, 2024**

(54) ENHANCED OLIGONUCLEOTIDES FOR INHIBITING RTEL1 EXPRESSION

(71) Applicant: HOFFMANN-LA ROCHE INC., Little Falls, NJ (US)

(72) Inventors: Erik Funder, Hørsholm (DK); Natascha Hruschka, Basel (CH); Susanne Kammler, Hørsholm (DK); Erich Koller, Basel (CH); Brian Leonard, Basel (CH); Souphalone Luangsay, Basel (CH); Susanne Mohr, Basel (CH); Tobias Nilsson, Basel (CH); Søren Ottosen, Hørsholm (DK); Lykke Pedersen, Hørsholm (DK); Søren V. Rasmussen, Hørsholm (DK); Steffen Schmidt, Hørsholm (DK); Sabine Sewing, Basel (CH); Daniel Turley, Basel (CH); Johanna Marie Walther, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,754

(22) Filed: Feb. 1, 2022

(65) Prior Publication Data

US 2022/0251556 A1 Aug. 11, 2022

(30) Foreign Application Priority Data

Feb. 2, 2021 (EP) .................................... 21154701
Nov. 8, 2021 (EP) .................................... 21207002

(51) Int. Cl.
*C12N 15/113* (2010.01)
*A61P 31/20* (2006.01)
*A61K 31/7088* (2006.01)

(52) U.S. Cl.
CPC ........ *C12N 15/113* (2013.01); *A61K 31/7088* (2013.01); *A61P 31/20* (2018.01);
(Continued)

(58) Field of Classification Search
CPC .............. C12N 15/113; C12N 2310/11; C12N 2310/315; C12N 2310/3231;
(Continued)

(56) References Cited

U.S. PATENT DOCUMENTS

2021/0147850 A1* 5/2021 Berrera .................. A61P 31/20

FOREIGN PATENT DOCUMENTS

EP 2 742 135 6/2014
WO 98/39352 A1 9/1998
(Continued)

OTHER PUBLICATIONS

CDC. Pinkbook | Hepatitis B. Epidemiology of Vaccine Preventable Diseases. PDF snapshot from Jan. 17, 2021. (Year: 2021).*
(Continued)

*Primary Examiner* — Ram R Shukla
*Assistant Examiner* — Ruth Sophia Arieti
(74) *Attorney, Agent, or Firm* — McDonnell Boehnen Hulbert & Berghoff LLP

(57) ABSTRACT

The present disclosure provides antisense oligonucleotides targeting Regulator of telomere elongation helicase 1 (RTEL1). The disclosure also provides, enhanced antisense oligonucleotides targeting RTEL1 for use in treating and/or
(Continued)

preventing a hepatitis B virus (HBV) infection. Also disclosed are pharmaceutical compositions and their use.

17 Claims, 32 Drawing Sheets

Specification includes a Sequence Listing.

(52) U.S. Cl.
CPC .... *C12N 2310/11* (2013.01); *C12N 2310/315* (2013.01); *C12N 2310/3231* (2013.01); *C12N 2310/341* (2013.01); *C12N 2310/351* (2013.01)

(58) Field of Classification Search
CPC ........ C12N 2310/341; C12N 2310/351; C12N 2310/3341; C12N 2310/344; C12N 15/1137; A61K 31/7088; A61P 31/20; C12Y 306/01
See application file for complete search history.

(56) References Cited

FOREIGN PATENT DOCUMENTS

| | | | | |
|---|---|---|---|---|
| WO | WO 98/039352 | | 9/1998 | |
| WO | 99/14226 | A2 | 3/1999 | |
| WO | WO 99/014226 | | 3/1999 | |
| WO | 00/47599 | A1 | 8/2000 | |
| WO | WO 00/047599 | | 8/2000 | |
| WO | 2000/066604 | A2 | 11/2000 | |
| WO | WO 00/066604 | | 11/2000 | |
| WO | 2001/023613 | A1 | 4/2001 | |
| WO | WO 01/23613 | | 4/2001 | |
| WO | 2004/046160 | A2 | 6/2004 | |
| WO | WO 2004/046160 | | 6/2004 | |
| WO | 2005/014806 | A2 | 2/2005 | |
| WO | WO 2005/014806 | | 2/2005 | |
| WO | 2007/031091 | A2 | 3/2007 | |
| WO | WO 2007/031091 | | 3/2007 | |
| WO | 2007/094818 | A2 | 8/2007 | |
| WO | WO 2007/090071 | | 8/2007 | |
| WO | WO 2007/094818 | | 8/2007 | |
| WO | 2007/134181 | A2 | 11/2007 | |
| WO | WO 2007/134181 | | 11/2007 | |
| WO | 2008/150729 | A2 | 12/2008 | |
| WO | WO 2008/150729 | | 12/2008 | |
| WO | WO 2008/154401 | | 12/2008 | |
| WO | WO 2009/006478 | | 1/2009 | |
| WO | 2009/067647 | A1 | 5/2009 | |
| WO | WO 2009/067647 | | 5/2009 | |
| WO | WO 2010/036698 | | 4/2010 | |
| WO | 2010/077578 | A1 | 7/2010 | |
| WO | WO 2010/077578 | | 7/2010 | |
| WO | 2011/017521 | A2 | 2/2011 | |
| WO | WO 2011/017521 | | 2/2011 | |
| WO | WO 2011/156202 | | 12/2011 | |
| WO | 2012/024170 | A2 | 2/2012 | |
| WO | WO 2012/024170 | | 2/2012 | |
| WO | 2012/055362 | A1 | 5/2012 | |
| WO | 2012/143379 | A1 | 10/2012 | |
| WO | 2012/145697 | A1 | 10/2012 | |
| WO | WO 2012/143379 | | 10/2012 | |
| WO | WO 2012/145697 | | 10/2012 | |
| WO | 2013/003520 | A1 | 1/2013 | |
| WO | WO 2013/003520 | | 1/2013 | |
| WO | 2013/154798 | A1 | 10/2013 | |
| WO | 2013/159109 | A1 | 10/2013 | |
| WO | WO 2013/154798 | | 10/2013 | |
| WO | WO 2013/159109 | | 10/2013 | |
| WO | 2014/076195 | A1 | 5/2014 | |
| WO | 2014/076196 | A1 | 5/2014 | |
| WO | WO 2014/076195 | | 5/2014 | |
| WO | WO 2014/076196 | | 5/2014 | |
| WO | 2014/179620 | A1 | 11/2014 | |
| WO | 2014/179629 | A2 | 11/2014 | |
| WO | WO 2014/179620 | | 11/2014 | |
| WO | WO 2014/179629 | | 11/2014 | |
| WO | 2014/207232 | A1 | 12/2014 | |
| WO | WO 2014/207232 | | 12/2014 | |
| WO | 2015/113922 | A1 | 8/2015 | |
| WO | WO 2015/113922 | | 8/2015 | |
| WO | 2015/173208 | A2 | 11/2015 | |
| WO | WO 2015/173208 | | 11/2015 | |
| WO | 2016/055601 | A1 | 4/2016 | |
| WO | WO 2016/055601 | | 4/2016 | |
| WO | 2016/127000 | A1 | 8/2016 | |
| WO | WO 2016/127002 | | 8/2016 | |
| WO | 2017/015175 | A1 | 1/2017 | |
| WO | WO 2017/015175 | | 1/2017 | |
| WO | 2017/027350 | A2 | 2/2017 | |
| WO | WO 2017/027350 | | 2/2017 | |
| WO | 2017/178656 | A1 | 10/2017 | |
| WO | WO 2017/178656 | | 10/2017 | |
| WO | 2017/216390 | A1 | 12/2017 | |
| WO | WO 2017/216390 | | 12/2017 | |
| WO | 2020/011902 | A1 | 1/2020 | |
| WO | WO 2020/011902 | | 1/2020 | |
| WO | WO-2020011902 | A1 * | 1/2020 | ............. A61P 31/20 |

OTHER PUBLICATIONS

International Search Report and Written Opinion of the International Searching Authority, issued in connection with Int'l Appl. No. PCT/EP2022/052417, dated May 6, 2022, 16 pages.
Javanbakht et al., "Liver-Targeted Anti-HBV Single-Stranded Oligonucleotides with Locked Nucleic Acid Potently Reduce HBV Gene Expression In Vivo", Molecular Therapy-Nucleic Acids, vol. 11, Jun. 1, 2018, pp. 441-454.
Ansel et al., "Pharmaceutical Dosage Forms and Drug Delivery Systems," Williams & Wilkins, 6th Edition. pp. 105-116, 194-200; 1456-1457 (1995) (41 pages).
Bastin, R.J. et al., Salt Selection and Optimisation Procedures for Pharmaceutical New Chemical Entities, Organic Process Research & Development, (2000), vol. 4, pp. 427-435.
Bergstrom DE, "Unnatural nucleosides with unusual base pairing properties", Current Protocols in Nucleic Acid Chemistry, 2009, Suppl. 37 1.4.1, 32 pgs.
Biessen, E.A.L. et al., "Receptor-Dependent Cell Specific Delivery of Antisense Oligonucleotides," Developments in Cardiovascular Medicine, 1999, 24, pp. 285-299, 15 pages.
Caruthers et al., "Chemical Synthesis of Deoxyoligonucleotides by the Phosphoramidite Method," Methods Enzymol. 154: 287-313 (1987) (27 pages).
Deleavy, et al., Designing Chemically Modified Oligonucleotides for Targeted Gene Silencing, Chemistry & Biology Review, Cell Press, Aug. 24, 2012, 18 pgs.
Duff, et al., "Intrabody tissue-specific delivery of antisense conjugates in animals: ligand-linker-antisense oligomer conjugates," Methods Enzvmol, Dec. 31, 2000, 313:297-321.
Edwards et al., "DNA damage repair genes controlling human papillomavirus (HPV) episome levels under conditions of stability and extreme instability", 2013 PLoS One vol. 8, e75406.
Freier, et al., The ups and downs of nucleic acid duplex stability: structure-stability studies on chemically-modified DNA:RNA duplexes, Nucleic Acids Research, 1997, vol. 25, No. 22, 15 pgs.
Gennaro et al., "Remington's Pharmaceutical Sciences," Mack Publishing Company. 17th ed., (1985) (9 pages).
Hirao et al., "Natural versus Artificial Creation of Base Pairs in DNA: Origin of Nucleobases from the Perspectives of Unnatural Base Pair Studies," Ace Chem Res. 45(12): 2055-2065 (2012) (11 pages).
Holdgate et al., "Measurements of Binding Thermodynamics in Drug Discovery," Drug Discov Today. 10(22):1543-1550 (2005) (8 pages).
Iobst et al., "Selective Sugar Binding to the Carbohydrate Recognition Domains of the Rat Hepatic and Macrophage Asialoglycoprotein Receptors," The Journal of Biological Chemistry, vol. 271, Issue 12, 1996, pp. 6686-6693.

(56) References Cited

OTHER PUBLICATIONS

McTigue et al., "Sequence-Dependent Thermodynamic Parameters for Locked Nucleic Acid (LNA)-DNA Duplex Formation," Biochemistry. 43(18):5388-5405 (2004) (18 pages).

Mergny, JL et al., "Analysis of Thermal Melting Curves," Oligonucleotides, 2003, vol. 13(6), pp. 515-537, 23 pages.

Mitsouka: A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition, Nucleic Acids Research, 2009, vol. 37, No. 4, 14 pgs.

Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).

Nassal, M., "HBV cccDNA: viral persistence reservoir and key obstacle for a cure of chronic hepatitis B", Gut. Dec. 2015, 64(12), 1972-84.

Santalucia J Jr., "A Unified View of Polymer, Dumbbell, and Oligonucleotide DNA Nearest-neighbor Thermodynamics," Proc Natl Acad Sci US A. 95(4):1460-1465 (1998) (6 pages).

Schertzer et al., "Human regulator of telomere elongation helicase 1 (RTEL1) is required for the nuclear and cytoplasmic trafficking of pre-U2 RNA", 2015, Nucleic Acid Res, vol. 43(3), p. 1834.

Seth et al., "Synthesis and Biophysical Evaluation of 2',4'-Constrained 2'O-Methoxyethyl and 2',4'-Constrained 2'O-Ethyl Nucleic Acid Analo !! lles," J. Org. Chem., 2010, 75:1569-1581.

Stephen Locarnini, et al., "Molecular genetics of HBV infection", Review Antivir Ther., vol. 15 Suppl 3, 2010, pp. 3-14. doi: 10.3851/IMP1619.

Sugimoto et al., "Thermodynamic Parameters to Predict Stability of RNA/DNA Hybrid Duplexes," Biochemistry. 34(35): 11211-11216 (1995) (6 pages).

Uhlmann, Recent advances in the medicinal chemistry of antisense oligonucleotides, Current Opinion in Drug Discovery & Development 2000, 12 pgs.

Vannier et al., "RTEL1: functions of a disease-associated helicase", 2014 Trends Cell Biol. vol 24 p. 416.

Wan et al., "The Medicinal Chemistry of Therapeutic Oligonucleotides," J Med Chem. 59(21):9645-9667 (2016) (23 pages).

* cited by examiner

Fig. 5A1 (GalNAc Residues)
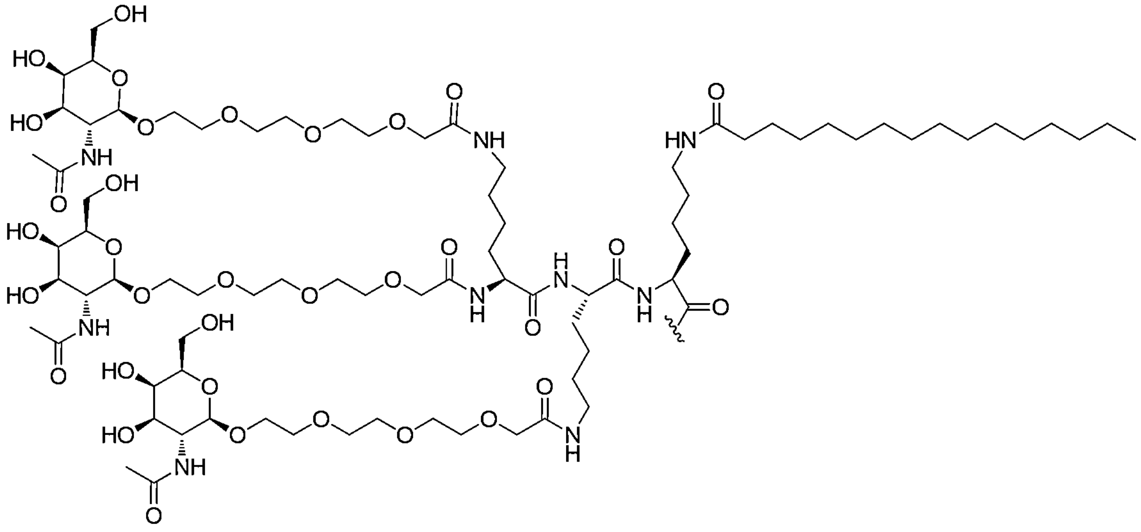
Fig. 5A2
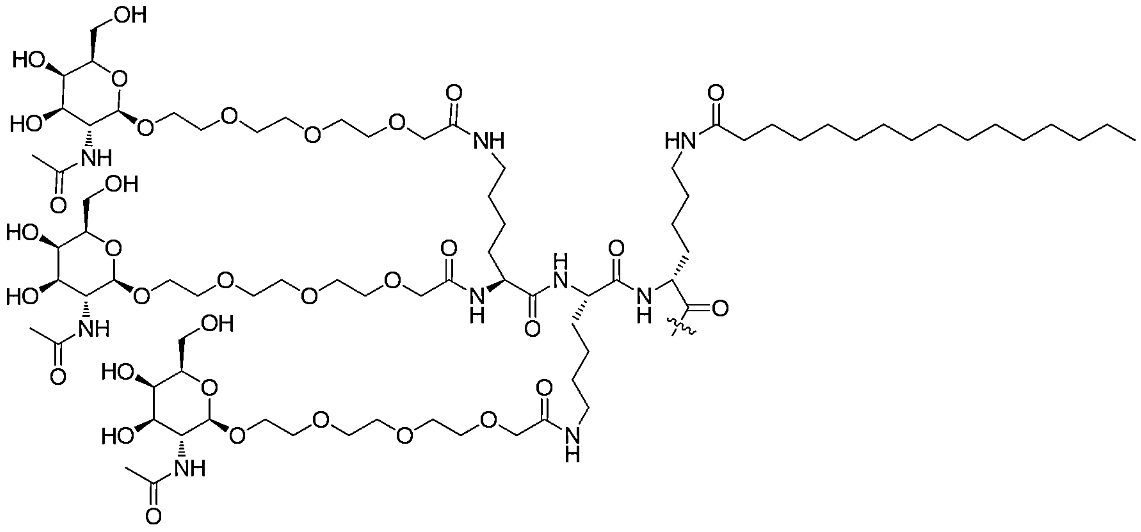

Fig. 5B1
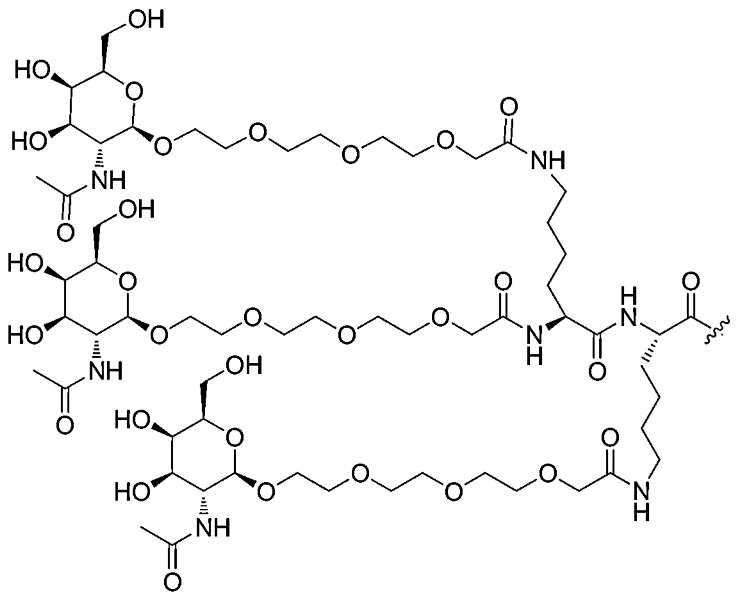
Fig. 5B2
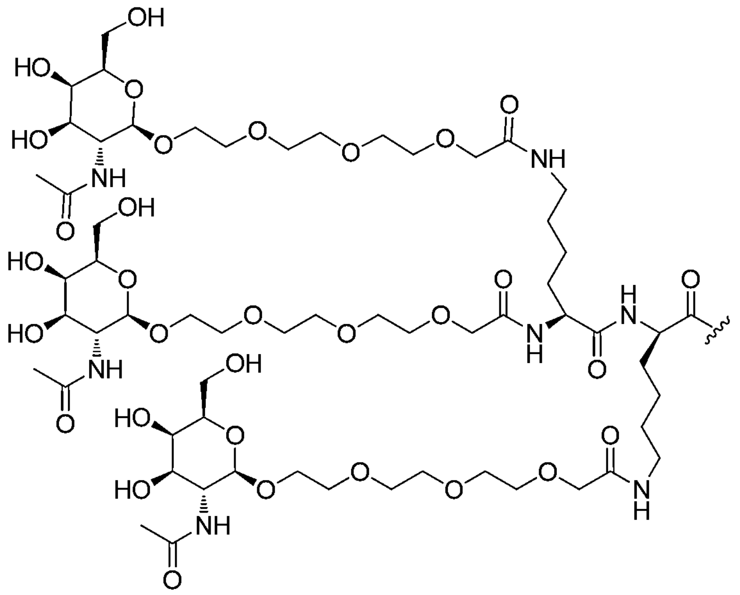

Fig. 5C1
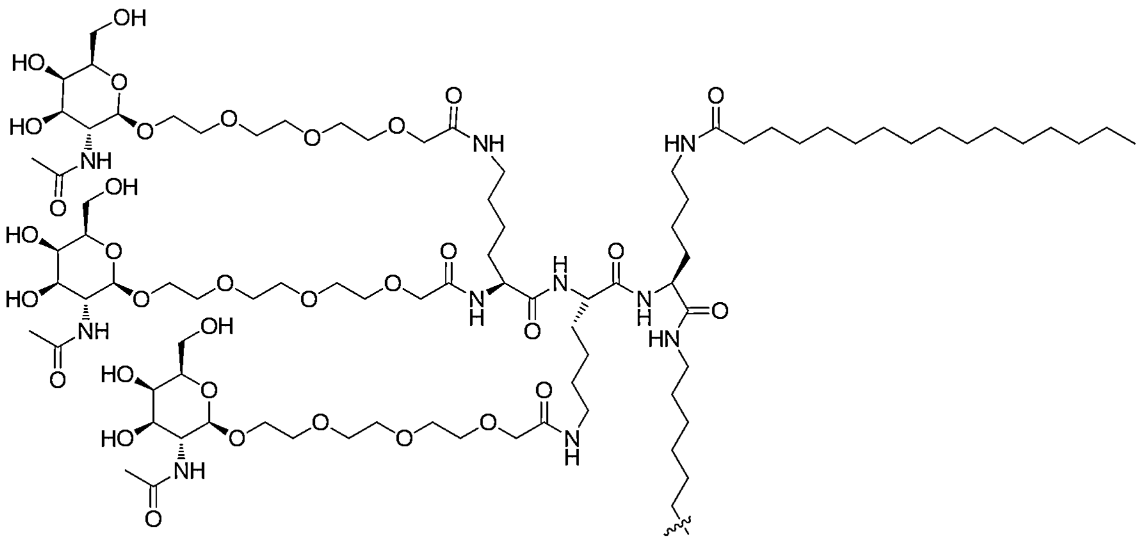
Fig. 5C2
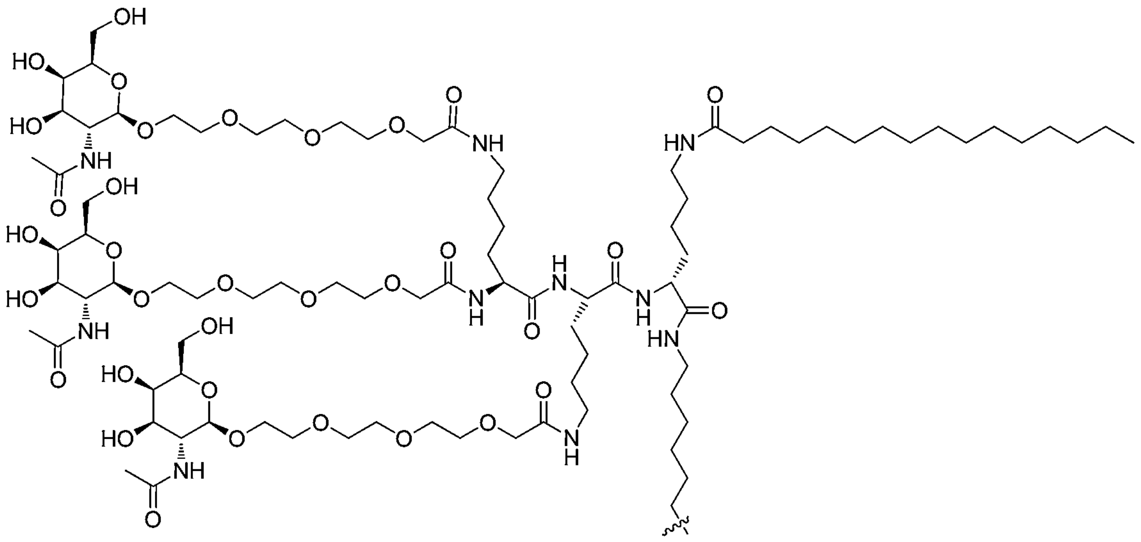

Fig. 5D1
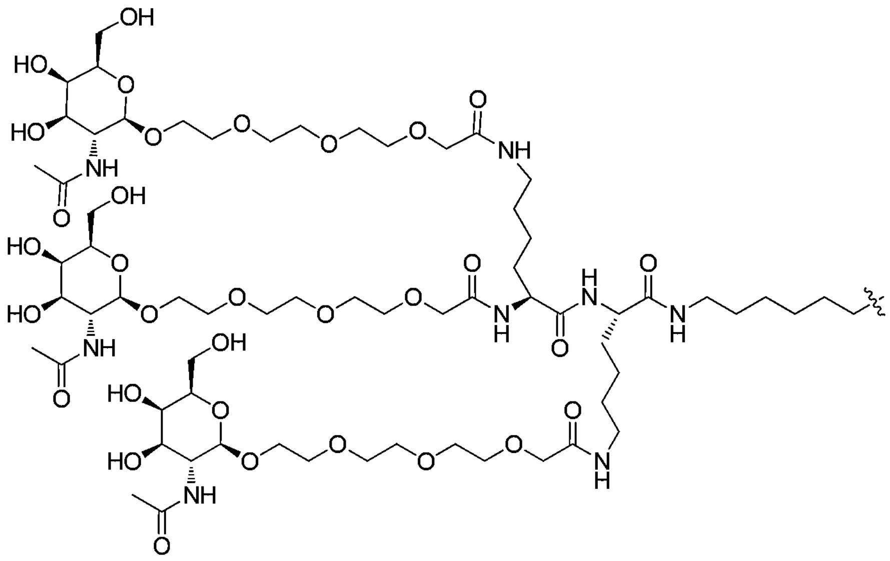
Fig. 5D2
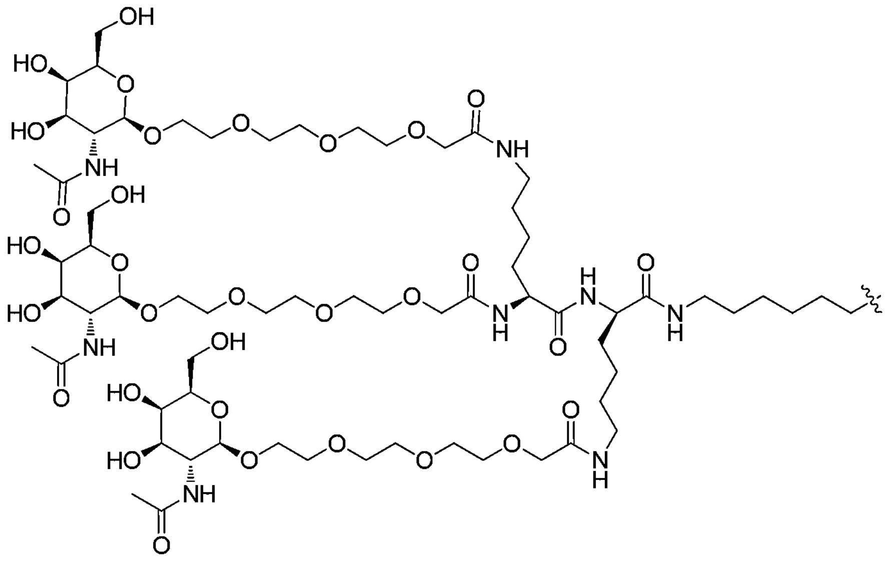

Fig. 5E1
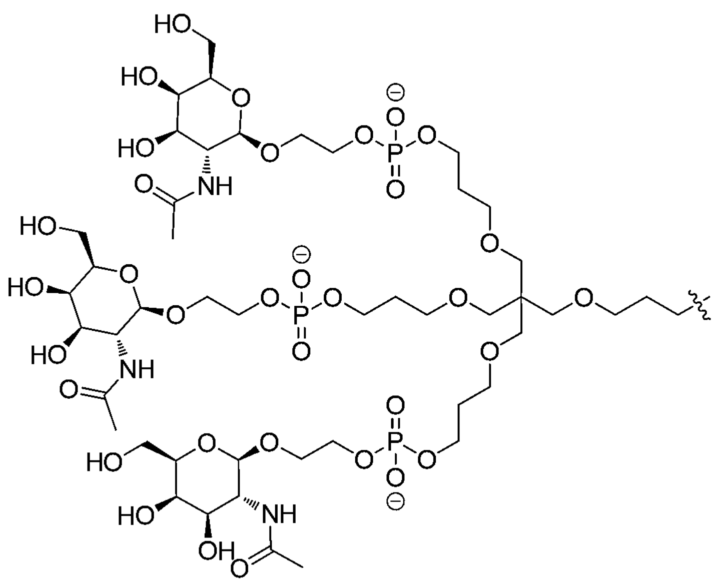
Fig. 5F1
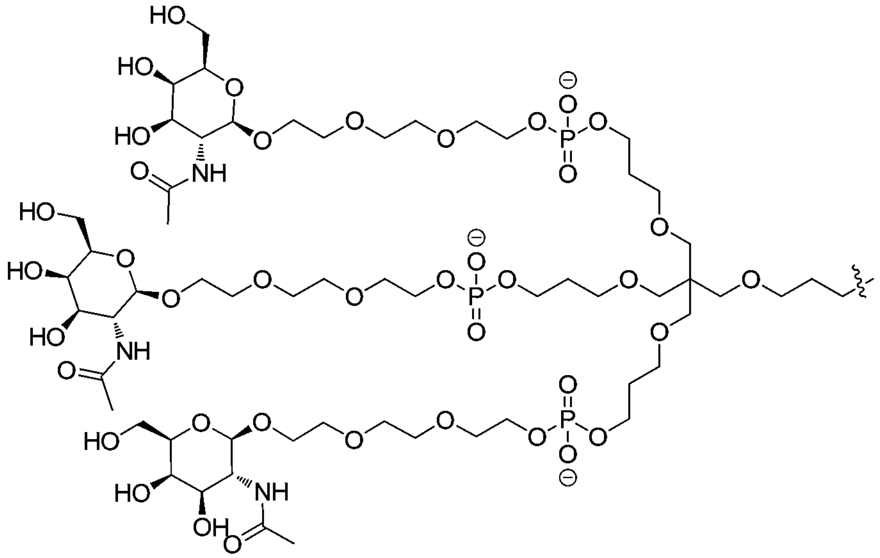

Fig. 5G1
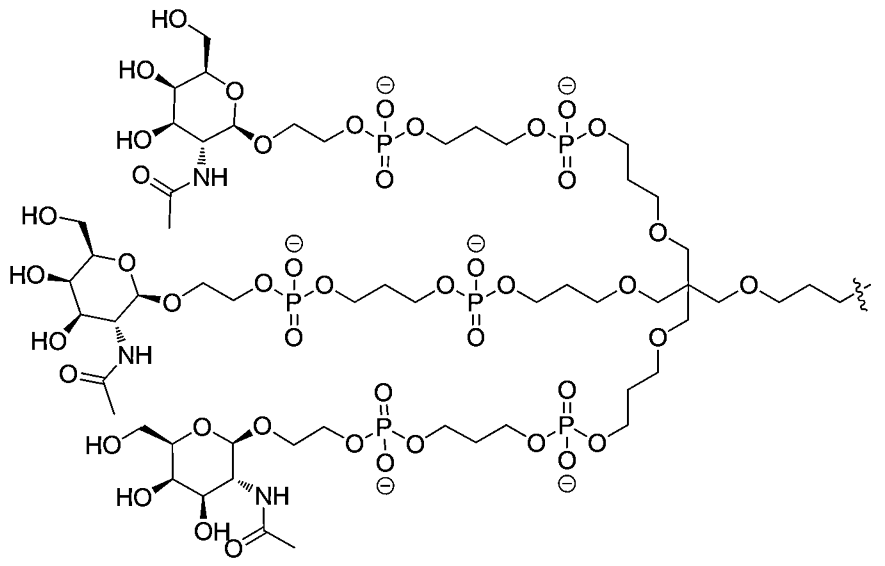
Fig. 5H1
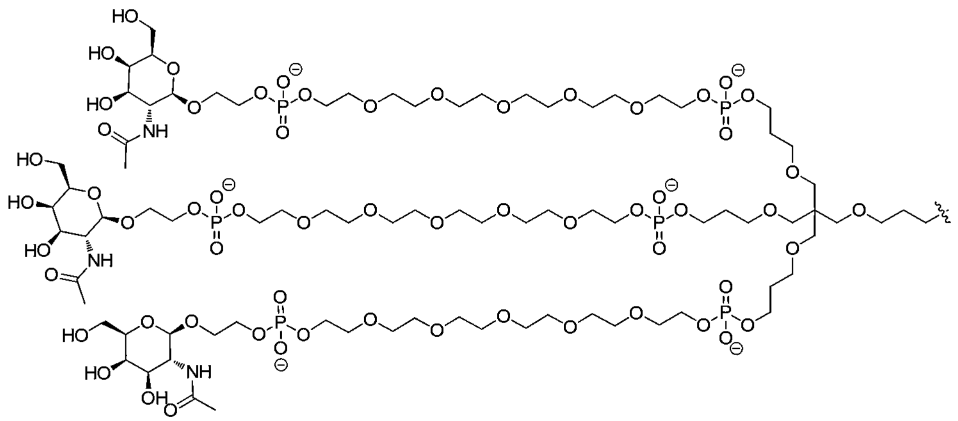

Fig 5I1
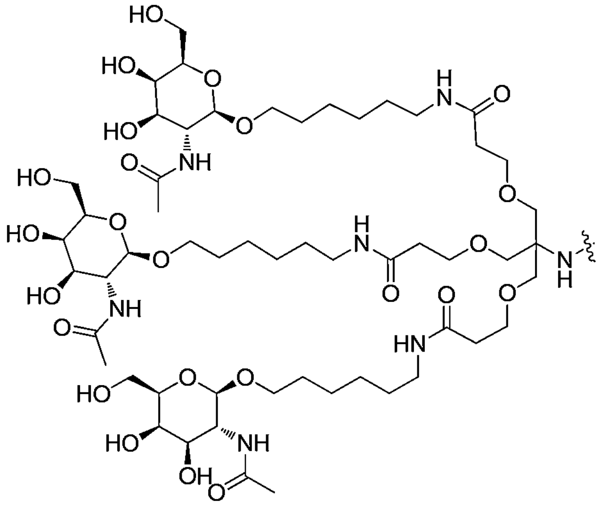
Fig. 5J1
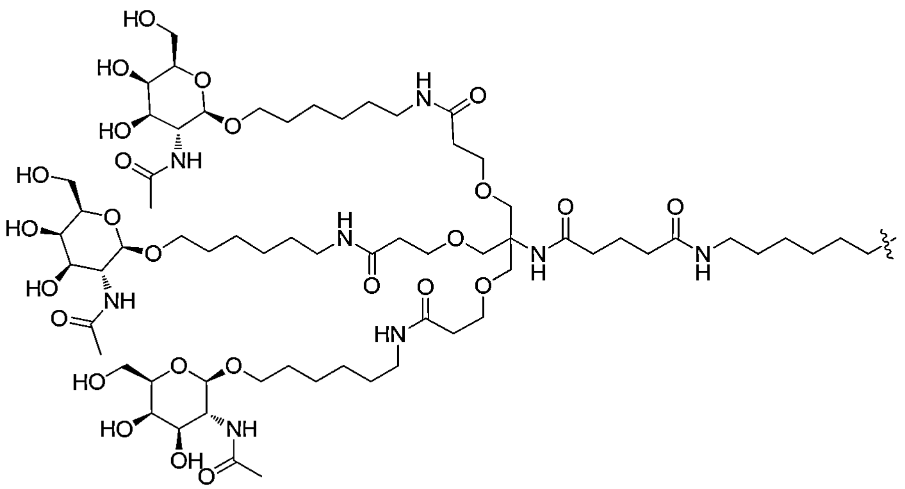

Fig. 5L1
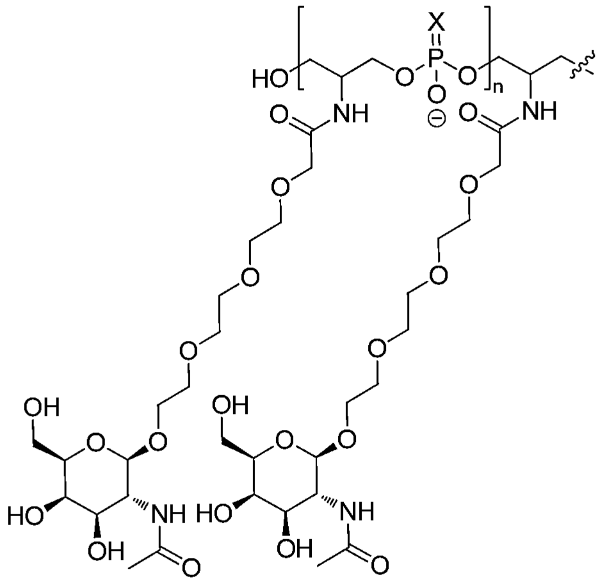

Fig. 5L2
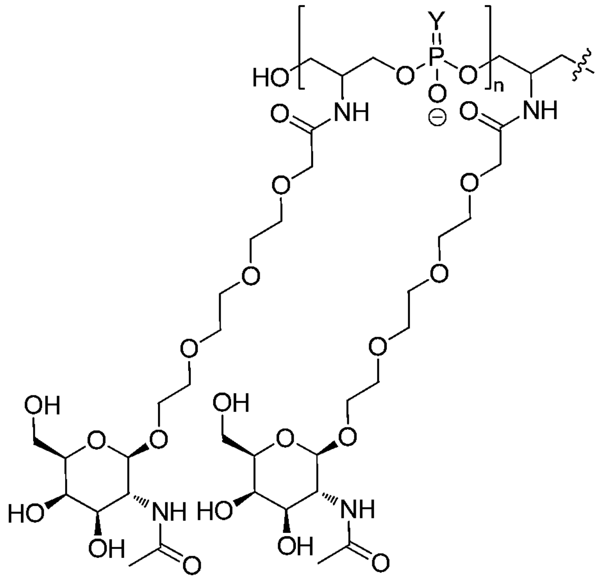

Fig. 6A1 (Compounds)
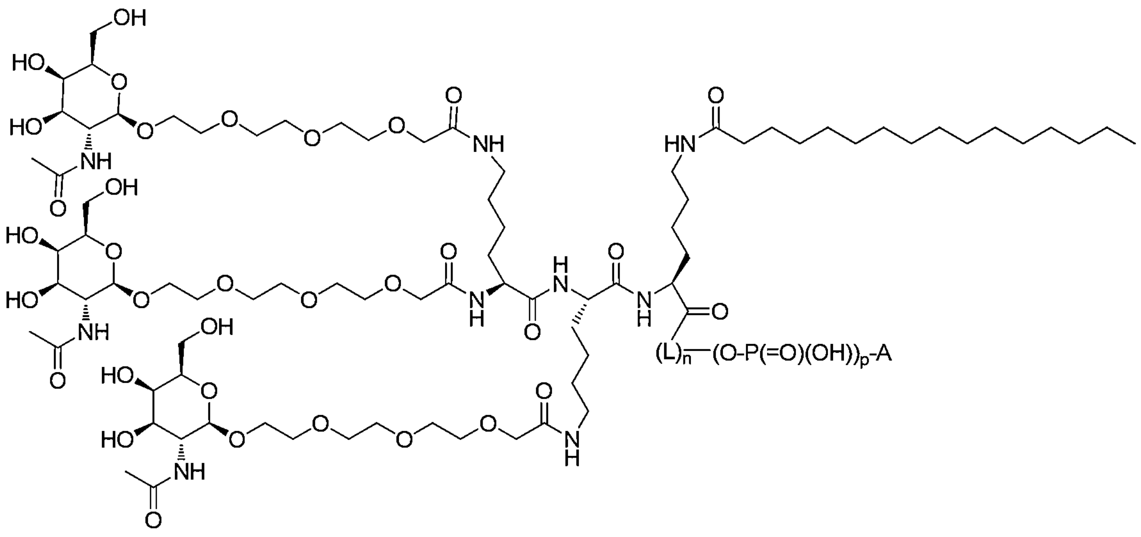
Fig. 6A2
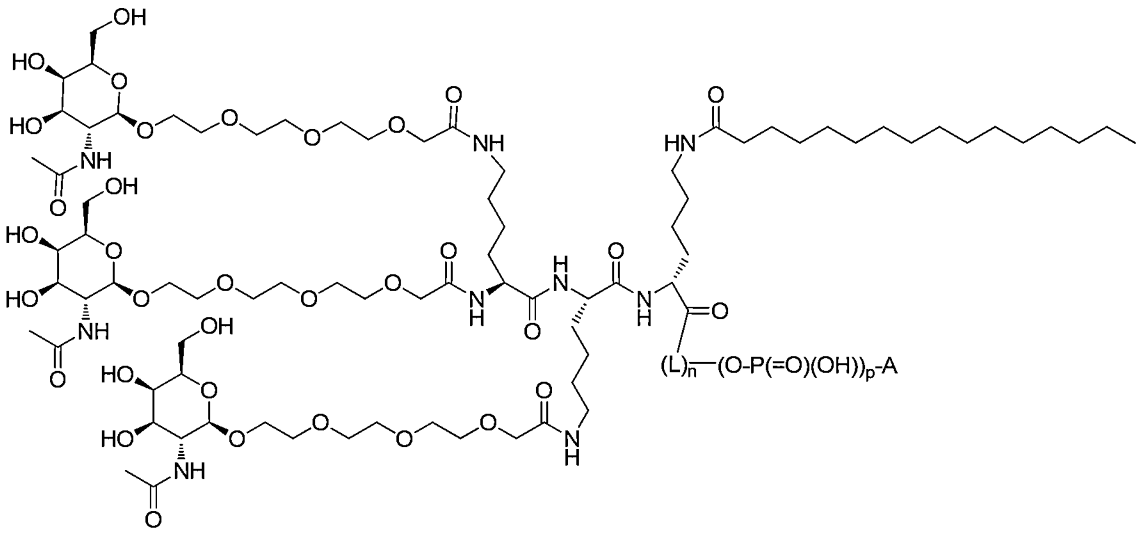

Fig. 6B1
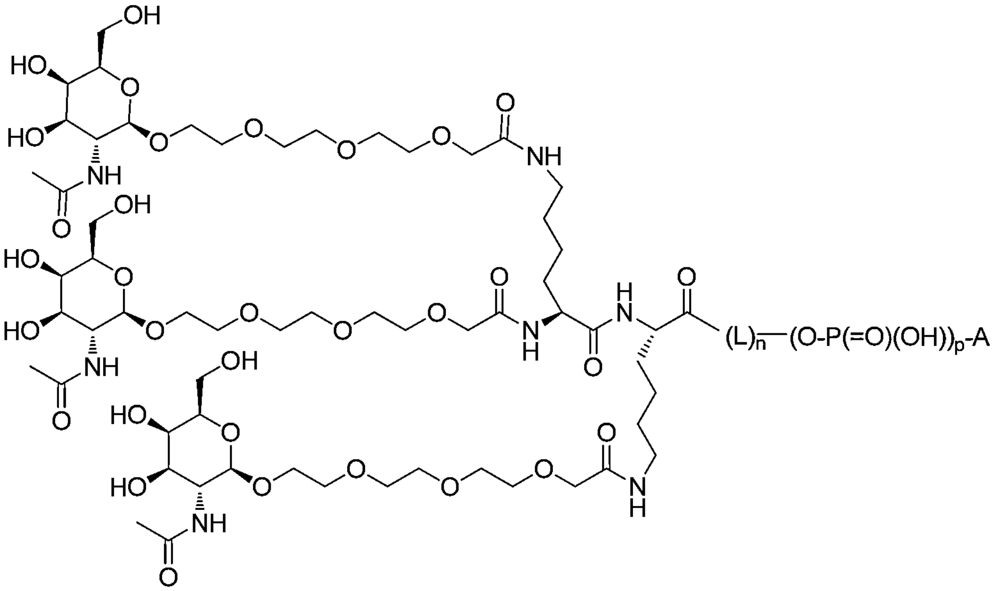
Fig. 6B2
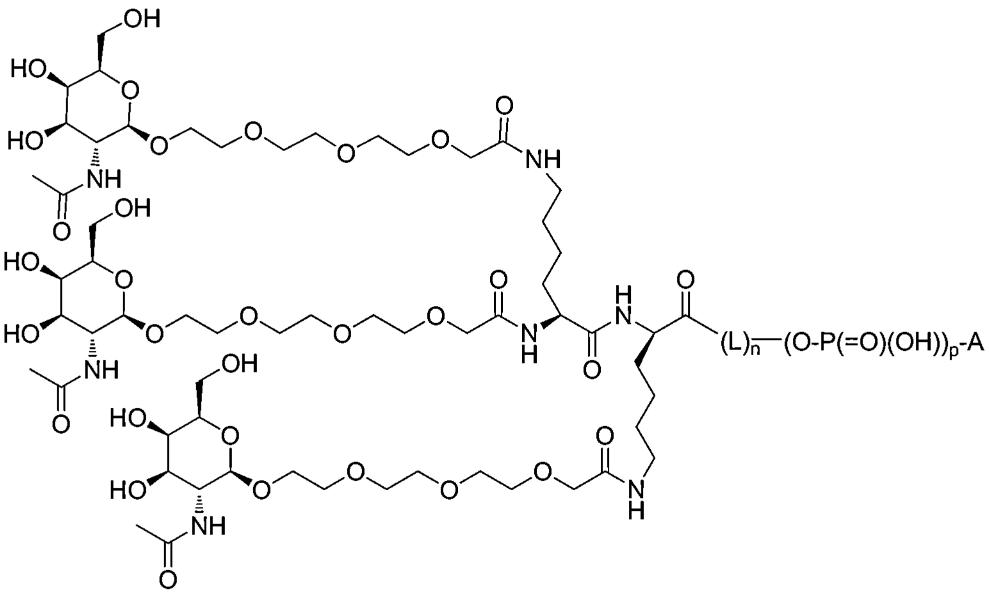

Fig. 6C1
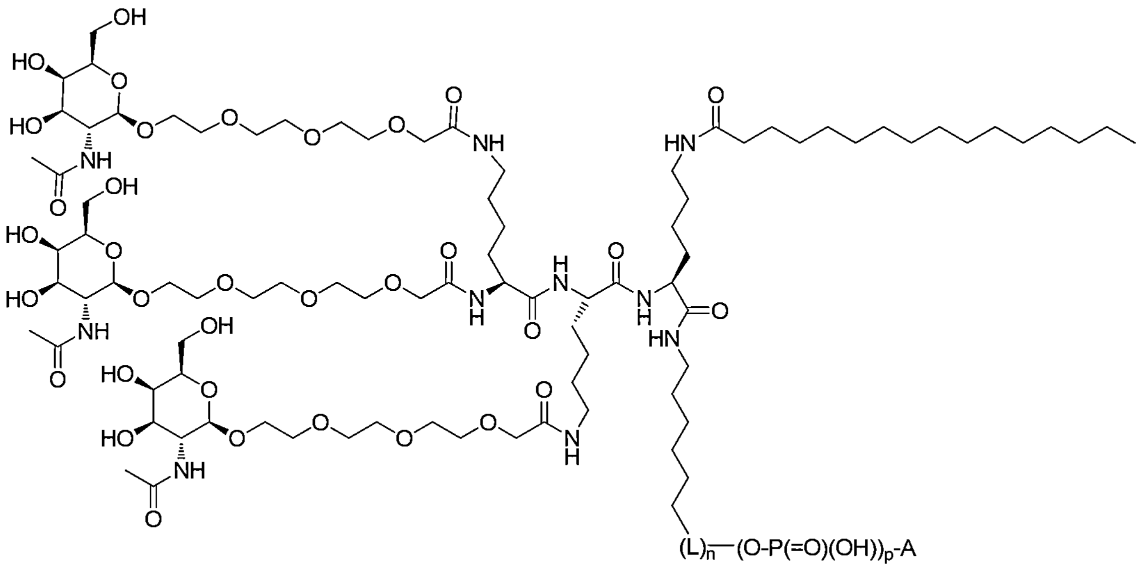
Fig. 6C2
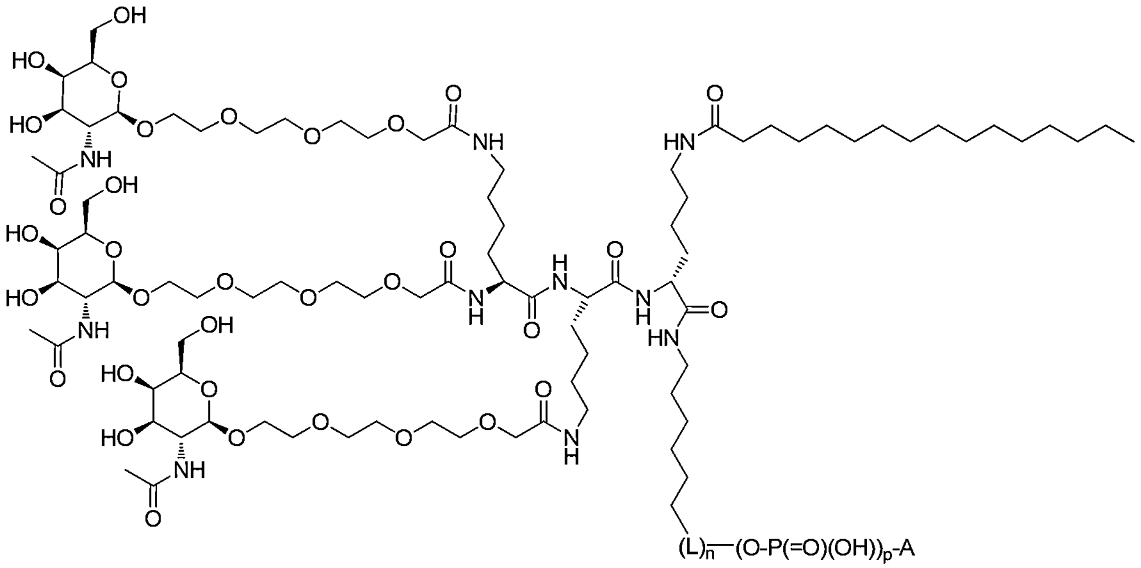

Fig. 6D1
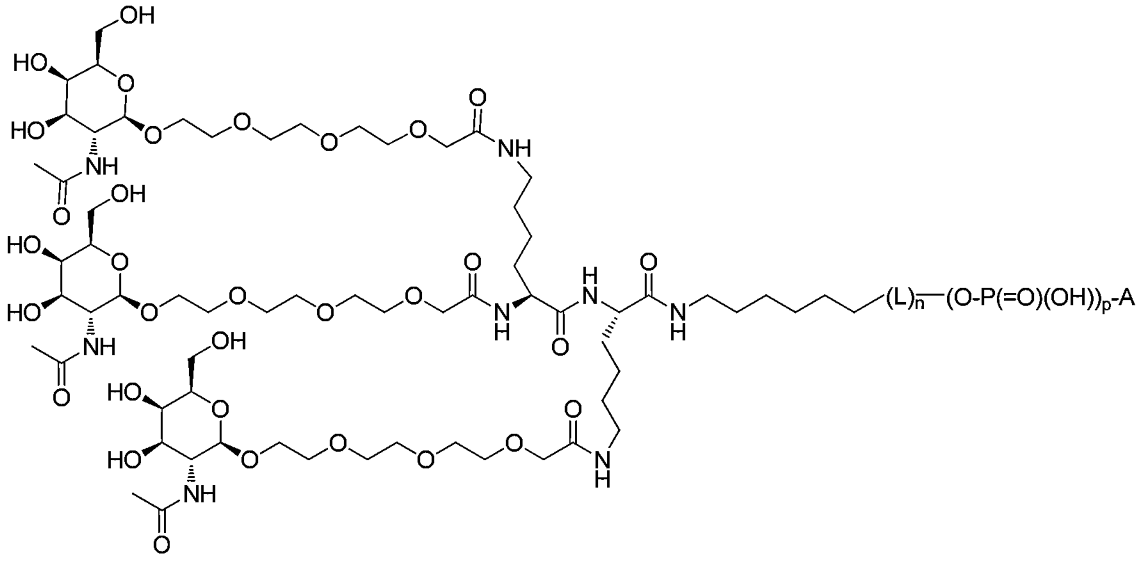
Fig. 6D2
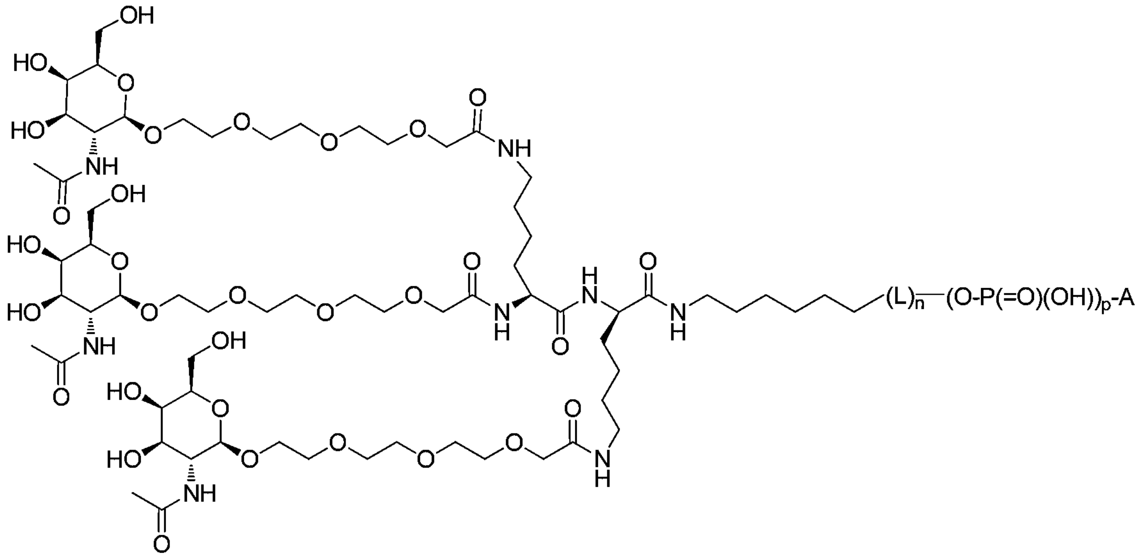

Fig. 6E1
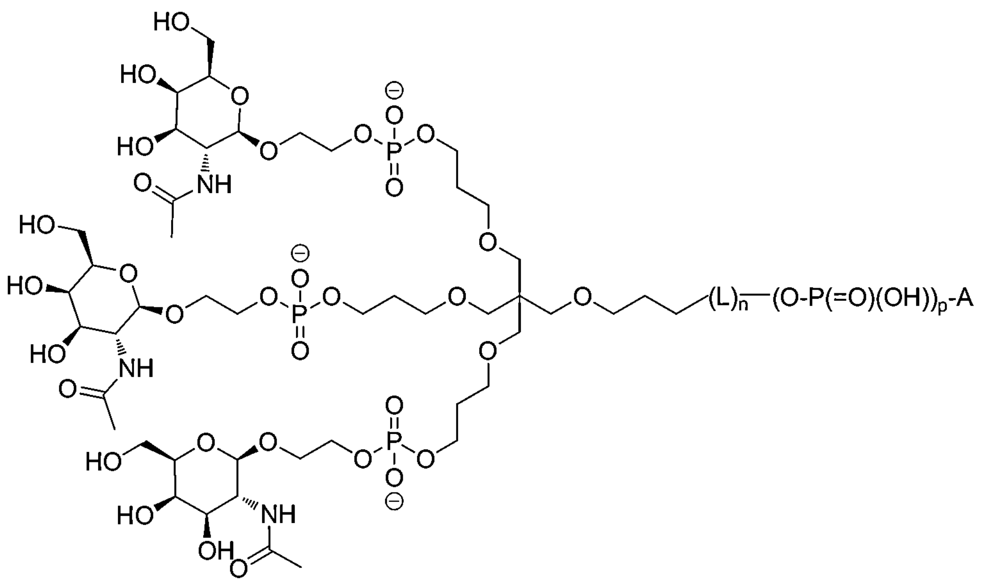
Fig. 6F1
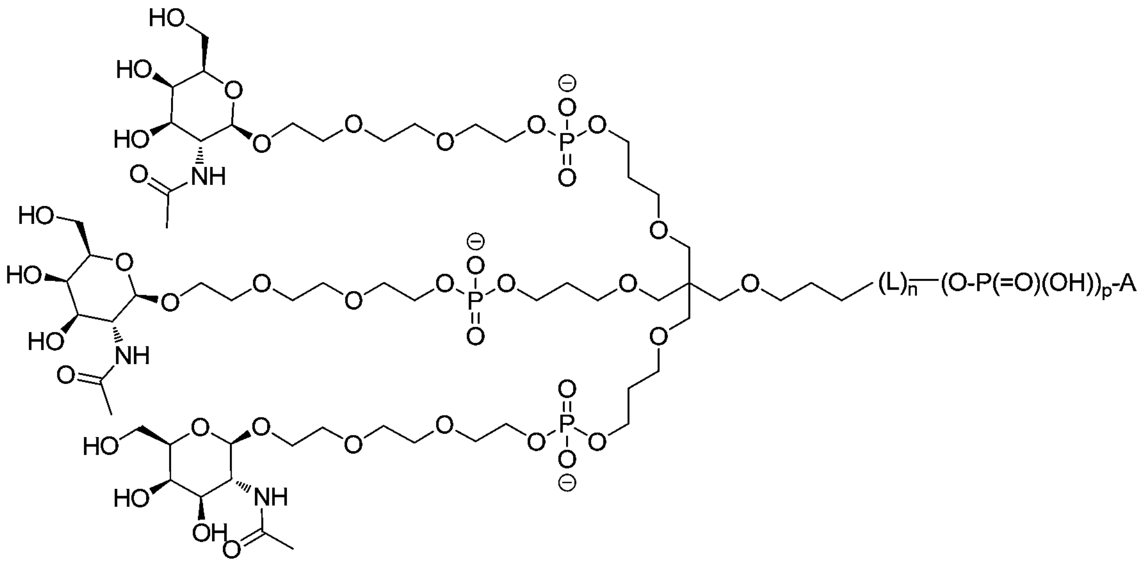

Fig. 6G1
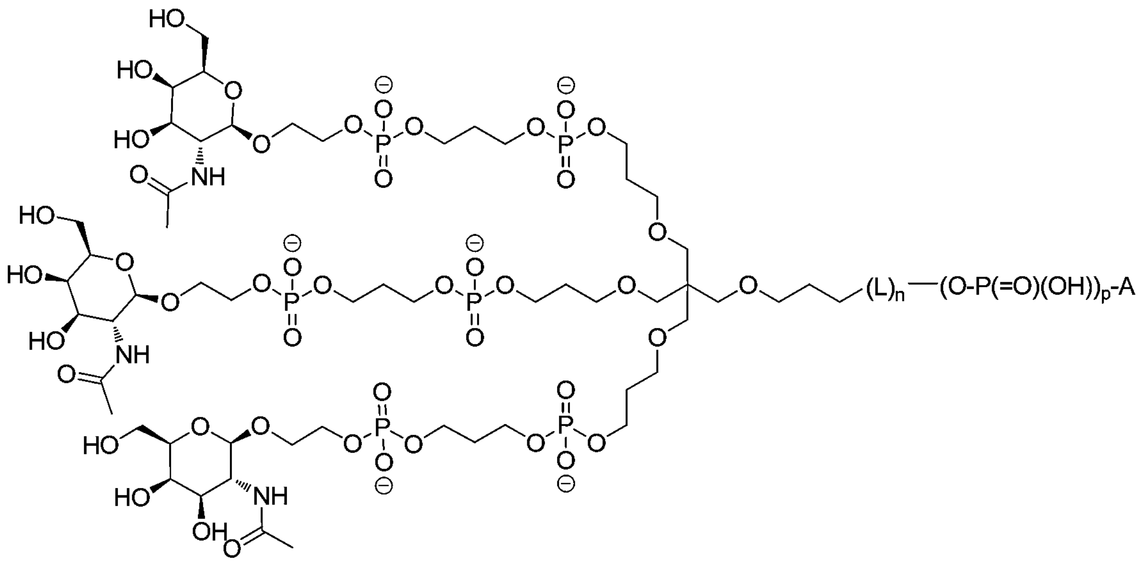
Fig. 6H1
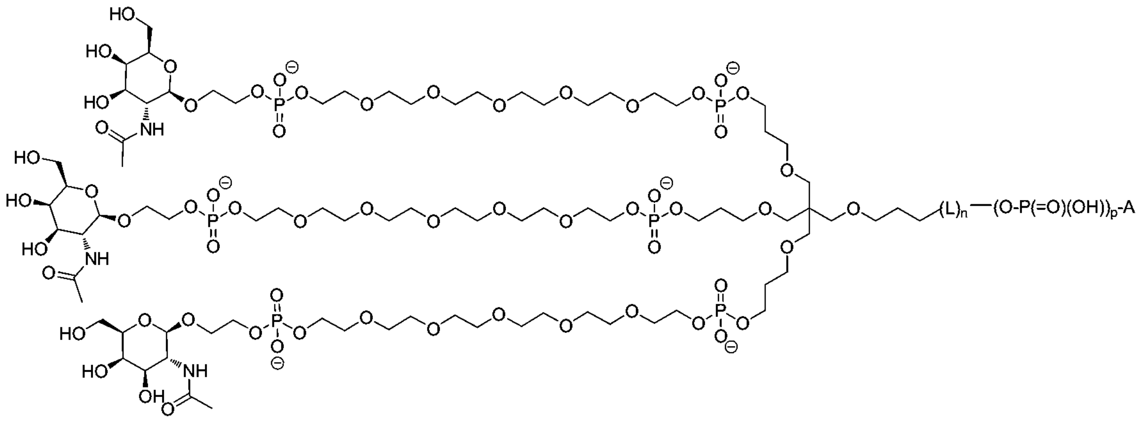

Fig. 6I1
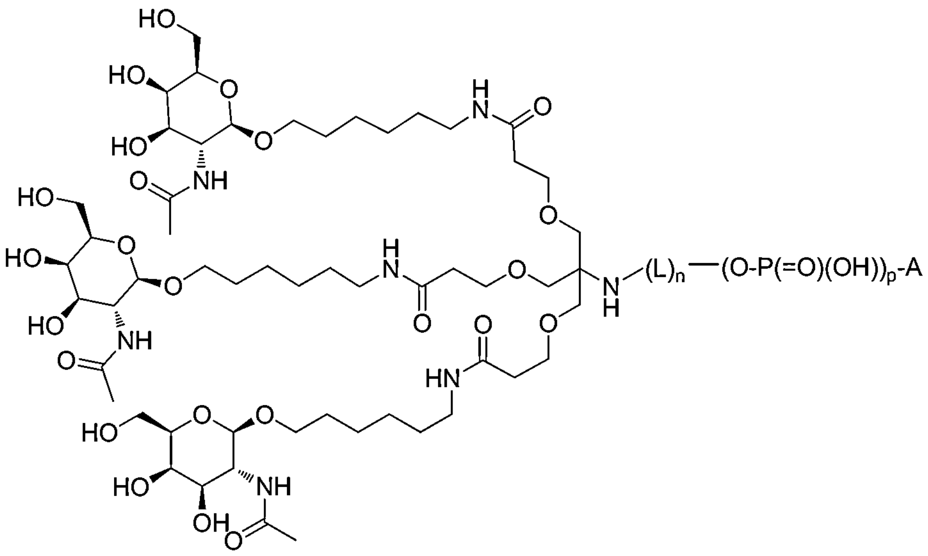
Fig. 6J1
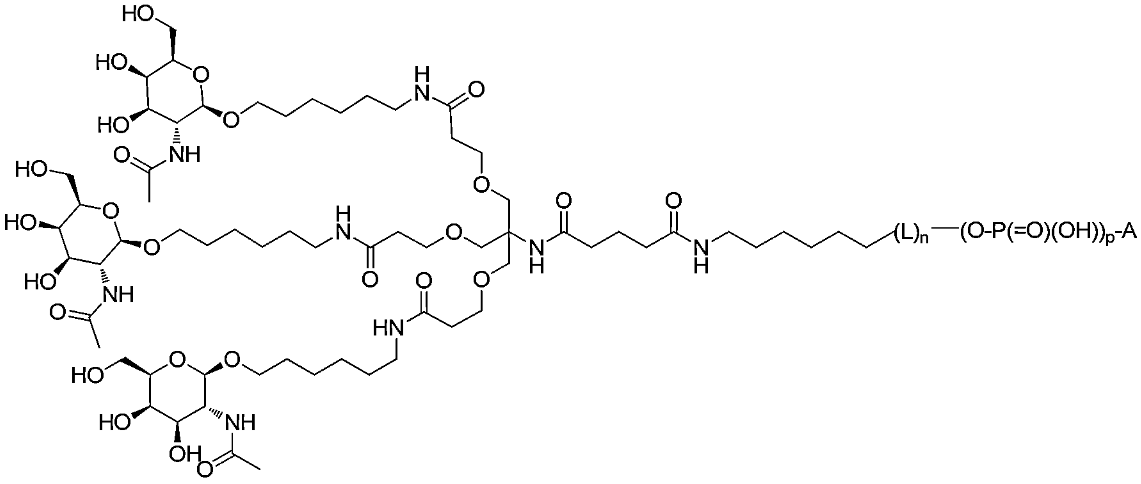

Fig. 6L1
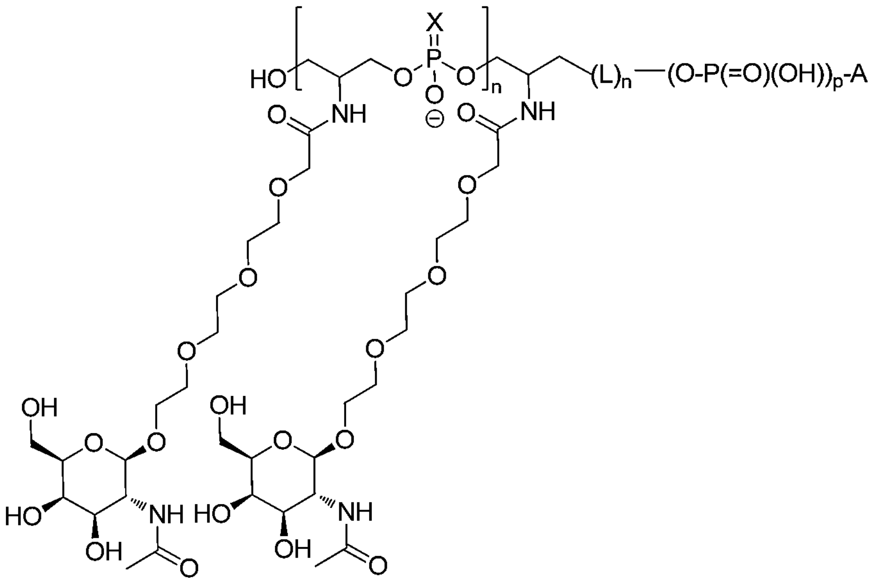
Fig. 6L2
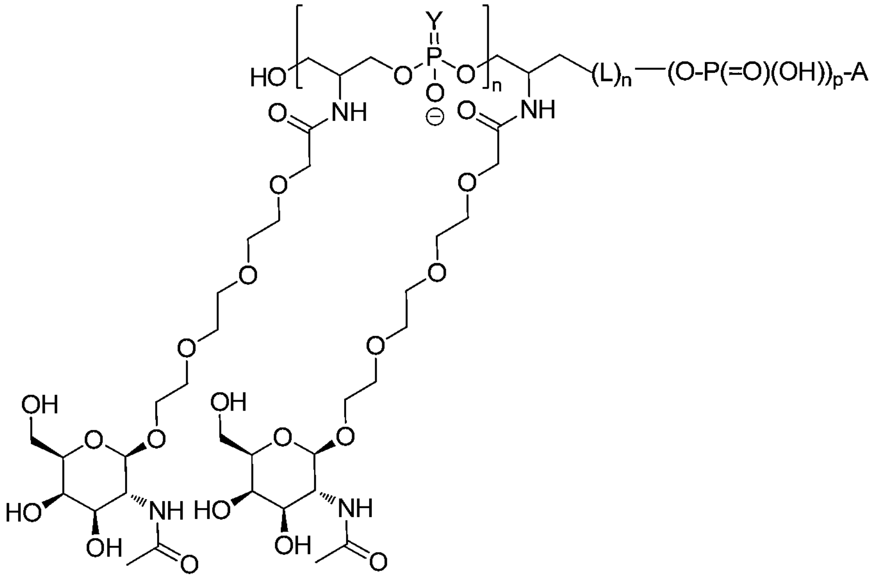

ENHANCED OLIGONUCLEOTIDES FOR INHIBITING RTEL1 EXPRESSION

CROSS-REFERENCE TO RELATED APPLICATIONS

This application claims priority to European Application No. 21154701.3 filed 2 Feb. 2021 and European Application No. 21207002.3 filed 8 Nov. 2021, the disclosures of which are incorporated herein, in their entireties, by this reference.

REFERENCE TO A SEQUENCE LISTING SUBMITTED VIA EFS-WEB

The content of the ASCII text file of the sequence listing named "RD35909US_SEQ_LISTING.TXT" which was created on Feb. 1, 2022, and is 112,314 bytes in size, submitted electronically via EFS-Web in this U.S. non-provisional patent application is incorporated by reference in its entirety.

FIELD OF INVENTION

The present invention relates to enhanced antisense oligonucleotides targeting RTEL1 (Regulator of telomere elongation helicase 1), leading to modulation of the expression of RTEL1 or modulation of RTEL1 activity. The invention, in particular, relates to the use of enhanced antisense oligonucleotides targeting RTEL1 for use in treating and/or preventing a hepatitis B virus (HBV) infection, in particular a chronic HBV infection. The invention, in particular, relates to the use of the enhanced antisense oligonucleotides targeting RTEL1 for destabilizing cccDNA, such as HBV cccDNA. Also comprised in the present invention is a pharmaceutical composition and its use in the treatment and/or prevention of an HBV infection.

BACKGROUND

Hepatitis B is an infectious disease caused by the hepatitis B virus (HBV), a small hepatotropic virus that replicates through reverse transcription. Chronic HBV infection is a key factor for severe liver diseases such as liver cirrhosis and hepatocellular carcinoma. Current treatments for chronic HBV infection are based on administration of pegylated type 1 interferons or nucleos(t)ide analogues, such as lamivudine, adefovir, entecavir, tenofovir disoproxil, and tenofovir alafenamide, which target the viral polymerase, a multifunctional reverse transcriptase. Treatment success is usually measured as loss of hepatitis B surface antigen (HBsAg). However, a complete HBsAg clearance is rarely achieved since Hepatitis B virus DNA persists in the body after infection. HBV persistence is mediated by an episomal form of the HBV genome which is stably maintained in the nucleus. This episomal form is called "covalently closed circular DNA" (cccDNA). The cccDNA serves as a template for all HBV transcripts, including pregenomic RNA (pgRNA), a viral replicative intermediate. The presence of a few copies of cccDNA might be sufficient to reinitiate a HBV infection. Current treatments for HBV do not target cccDNA. A cure of chronic HBV infection, however, would require the elimination of cccDNA (reviewed by Nassal, Gut. 2015 December; 64(12): 1972-84.

Regulator of telomere elongation helicase 1 (RTEL1) encodes a DNA helicase which functions in the stability, protection and elongation of telomeres and interacts with proteins in the shelterin complex known to protect telomeres during DNA replication. Mutations in this gene have been associated with dyskeratosis congenita and Hoyerall-Hreidarsson syndrome (See for example review by Vannier et al., 2014 Trends Cell Biol. Vol 24 p. 416).

Located in the nucleus, RTEL1 functions as an ATP-dependent DNA helicase implicated in telomere-length regulation, DNA repair and the maintenance of genomic stability. RTEL1 acts as an anti-recombinase to counteract toxic recombination and limit crossover during meiosis and regulates meiotic recombination and crossover homeostasis by physically dissociating strand invasion events and thereby promotes non-crossover repair by meiotic synthesis dependent strand annealing (SDSA) as well as disassembly of D loop recombination intermediates. In addition, RTEL1 disassembles T-loops and prevents telomere fragility by counteracting telomeric G4-DNA structures, which together ensure the dynamics and stability of the telomere.

RTEL1 has been identified in a siRNA screen as a stabilizer of HPV episomes: (Edwards et al., 2013 PLoS One Vol 8, e75406). siRNA targeting RTEL1 has likewise been used to identify interactants with RTEL1 in Hoyeraal-Hreidarsson syndrome (Schertzer et al 2015 Nucleic Acid Res Vol 43 p. 1834). In addition, RTEL1 was identified as a HIV host dependency factor from a siRNA screen for essential host proteins to provide targets for inhibition HIV infection (WO 2007/094818).

In WO 2020/011902, it was shown that targeting RTEL1 with antisense oligonucleotides, resulted in reduction of RTEL1. Further, an effect on parameters of HBV infection, such as HBV cccDNA, pgRNA, HBsAg, and HBeAg, was observed.

There is a need for therapeutic agents, which can inhibit RTEL1 specifically. We have screened more than 1000 antisense oligonucleotides targeting human RTEL1 and identified sequences and compounds, which are particularly potent and effective to specifically target for human RTEL1. Specifically, four LNA gapmer oligonucleotides were identified which conferred a strong down-regulation of human RTEL1 in vitro. The identified LNA gapmer oligonucleotides target intronic regions of the human RTEL1 pre-mRNA.

OBJECTIVE OF THE INVENTION

The present invention provides antisense oligonucleotides and conjugates thereof which modulate RTEL1 ("Regulator of telomere elongation helicase 1") expression. We identified intronic target sequences present of the human RTEL1 pre-mRNA which may be targeted by antisense oligonucleotides, or conjugates thereof, to give effective RTEL1 inhibition. For example, targeting position 8681-8701 or 11753-11774 of SEQ ID NO: 1 is advantageous in terms of reducing RTEL1. Accordingly, an objective of the present invention is to provide enhanced antisense oligonucleotides targeting RTEL1, or conjugates thereof, wherein the antisense oligonucleotides are capable of inhibiting the expression of RTEL1 in vitro and in vivo, thereby reducing cccDNA in an HBV infected cell. The enhanced antisense oligonucleotides targeting RTEL1 or the conjugate thereof can be used in the treatment of HBV infection.

SUMMARY OF INVENTION

The present invention provides antisense oligonucleotides or conjugates thereof, which are complementary to, and are capable of inhibiting the expression of a RTEL1 nucleic acid, and for their use in medicine.

The invention provides for an antisense oligonucleotide which comprises a contiguous nucleotide sequence which is complementary to, such as fully complementary to a region of the human RTEL1 pre-mRNA (as illustrated in SEQ ID NO: 1), such as a region from nucleotides 8681-8701 or from nucleotides 11753-11774 of SEQ ID NO: 1.

In some embodiments, the antisense oligonucleotide or the contiguous nucleotide sequence is complementary to, such as fully complementary to a region from nucleotides 8681-8701 of SEQ ID NO: 1.

In some embodiments, the antisense oligonucleotide or the contiguous nucleotide sequence is complementary to, such as fully complementary to a region from nucleotides 11753-11774 of SEQ ID NO: 1, such as to a region from nucleotides 11757-11774, 11756-11774, or 11753-11770 of SEQ ID NO: 1.

The antisense oligonucleotide of the invention is typically 12-24 nucleotides in length, such as 12 to 22, such as 16 to 22 nucleotides in length, and comprises a contiguous nucleotide sequence of at least 12 nucleotides which is complementary to, such as fully complementary to a region of the human RTEL1 pre-mRNA (as illustrated in SEQ ID NO: 1), selected from nucleotides 8681-8701 and 11753-11774 of SEQ ID NO: 1.

The invention provides for an antisense oligonucleotide, 12-22 nucleotides in length, wherein said antisense oligonucleotide comprises a contiguous nucleotide sequence 12-22 nucleotides in length, wherein the contiguous nucleotide sequence is complementary, such as fully complementary, to SEQ ID NO 7, 8, 9 and/or 10.

The invention provides for an antisense oligonucleotide, 12-22 nucleotides in length (such as 15, 16, 17, 18, 19 or 20 nucleotides in length), wherein said antisense oligonucleotide comprises a contiguous nucleotide sequence 12-18 nucleotides in length (such as 15, 16, 17, or 18 nucleotides in length), wherein the contiguous nucleotide sequence is complementary, such as fully complementary, to SEQ ID NO 11.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 3, 4, 5 and 6; or at least 14 contiguous nucleotides thereof.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 3, 4, 5 and 6, or at least 15 contiguous nucleotides thereof.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 3, 4, 5 and 6, or at least 16 contiguous nucleotides thereof.

The invention provides for an antisense oligonucleotide, which comprises a contiguous nucleotide sequence, which is 100% identical to a sequence selected from the group consisting of SEQ ID NOs: 3, 4, 5 and 6, or at least 14 contiguous nucleotides thereof.

The invention provides for an antisense oligonucleotide, which comprises a contiguous nucleotide sequence selected from the group consisting of SEQ ID NOs: 3, 4, 5 and 6.

The invention provides for an antisense oligonucleotide, which comprises a contiguous nucleotide sequence, which is 100% identical to SEQ ID NO: 3 (AATTTTACATACTCTGGT), or at least 14, 15, 16 or 17 contiguous nucleotides thereof.

The invention provides for an antisense oligonucleotide, which comprises a contiguous nucleotide sequence, which is 100% identical to SEQ ID NO: 4 (AATTTTACATACTCTGGTC), or at least 14, 15, 16, 17 or 18 contiguous nucleotides thereof.

The invention provides for an antisense oligonucleotide, which comprises a contiguous nucleotide sequence, which is 100% identical to SEQ ID NO: 5 (TTACATACTCTGGTCAAA), or at least 14, 15, 16, or 17 contiguous nucleotides thereof.

The invention provides for an antisense oligonucleotide, which comprises a contiguous nucleotide sequence, which is 100% identical to SEQ ID NO: 6 (CTTTATTATAACTTGAATCTC), or at least 14, 15, 16, 17, 18, 19, 20 or 21 contiguous nucleotides thereof.

The invention provides for an antisense oligonucleotide, which comprises the contiguous nucleotide of a compound selected from the group consisting of compound ID Nos 3_1, 4_1, 5_1 and 6_1 (see e.g. Table 6 below).

In some embodiments, the antisense oligonucleotide is not an antisense oligonucleotide selected from the group consisting of compound ID Nos 36_1, 35_1. 33_1, 34_1 and 37_1 of WO 2020/011902 A1 (see e.g. Table 6 of WO 2020/011902 A1).

In some embodiments, the antisense oligonucleotide is not an antisense oligonucleotide compound ID Nos 23_1 of WO 2020/011902 A1 (see e.g. Table 6 of WO 2020/011902 A1).

The invention provides for an antisense oligonucleotide selected from the group listed in Table 1, or a pharmaceutically acceptable salt thereof.

The invention provides for an antisense oligonucleotide selected from the group consisting of AATTttacatactctgGT (SEQ ID NO: 3, Compound ID No 3_1), AAttttacatactctGGTC (SEQ ID NO: 4, Compound ID No 4_1), TTacatactctggtCAAA (SEQ ID NO: 5, Compound ID No 5_1), and CTttattataactTgaAtCTC (SEQ ID NO: 6, Compound ID No 6_1), wherein capital letters are beta-D-oxy LNA nucleosides, lowercase letters are DNA nucleosides, all LNA Cs are LNA 5-methyl cytosine, and all internucleoside linkages are phosphorothioate internucleoside linkages.

The present invention also provides for a pharmaceutically acceptable salt of the antisense oligonucleotide of the present invention.

The invention provides for an antisense oligonucleotide selected from the group listed in Table 1, or a pharmaceutically acceptable salt thereof.

TABLE 1

Compound Table (Exemplary antisense oligonucleotides of the present invention)—HELM Annotation Format

| SEQ ID Number | Compound ID Number # | HELM Annotation Written 5'-3' | Comprised by conjugate shown in FIG. |
|---|---|---|---|
| 3 | 3_1 | [LR](A)[sP].[LR](A)[sP].[LR](T)[sP].[LR](T)[sP].[dR](T)[sP].[dR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[dR](G)[sP].[LR](G)[sP].[LR](T) | 1 |
| 4 | 4_1 | [LR](A)[sP].[LR](A)[sP].[dR](T)[sP].[dR](T)[sP].[dR](T)[sP].[dR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[LR](G)[sP].[LR](G)[sP].[LR](T)[sP].[LR]([5meC]) | 2 |
| 5 | 5_1 | [LR](T)[sP].[LR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[dR](G)[sP].[dR](G)[sP].[dR](T)[sP].[LR]([5meC])[sP].[LR](A)[sP].[LR](A)[sP].[LR](A) | 4 |
| 6 | 6_1 | [LR]([5meC])[sP].[LR](T)[sP].[dR](T)[sP].[dR](T)[sP].[dR](A)[sP].[dR](T)[sP].[dR](T)[sP].[dR](A)[sP].[dR](T)[sP].[dR](A)[sP].[dR](A)[sP].[dR](C)[sP].[dR](T)[sP].[LR](T)[sP].[dR](G)[sP].[dR](A)[sP].[LR](A)[sP].[dR](T)[sP].[LR]([5meC])[sP].[LR](T)[sP].[LR]([5meC]) | 3 |

Helm Annotation Key:
[LR](G) is a beta-D-oxy-LNA guanine nucleoside,
[LR](T) is a beta-D-oxy-LNA thymine nucleoside,
[LR](A) is a beta-D-oxy-LNA adenine nucleoside,
[LR]([5meC]) is a beta-D-oxy-LNA 5-methyl cytosine nucleoside,
[dR](G) is a DNA guanine nucleoside,
[dR](T) is a DNA thymine nucleoside,
[dR](A) is a DNA adenine nucleoside,
[dR](C) is a DNA cytosine nucleoside,
[sP]is a phosphorothioate internucleoside linkage,
P is a phosphodiester internucleoside linkage.

The invention thus provides for an antisense oligonucleotide selected from the group consisting of compound ID Nos #3_1, 4_1, 5_1 and 6_1.

The present invention further provides a conjugate comprising the antisense oligonucleotide of the present invention and at least one conjugate moiety covalently attached to said antisense oligonucleotide.

In some embodiments, the conjugate moiety is capable of binding to the asialoglycoprotein receptor, such as the human asialoglycoprotein receptor. For example, the conjugate moiety may comprise at least one asialoglycoprotein receptor targeting moiety selected from the group consisting of galactose, galactosamine, N-formyl-galactosamine, N-acetylgalactosamine, N-propionyl-galactosamine, N-n-butanoyl-galactosamine and N-isobutanoylgalactosamine.

In some embodiments, the asialoglycoprotein receptor-targeting moiety is N-acetylgalactosamine (GalNAc). Thus, the antisense oligonucleotide of the present invention may be conjugated to at least one conjugate moiety comprising at least one N-Acetylgalactosamine (GalNAc) moiety, such as at least one conjugate moiety comprising at least one N-Acetylgalactosamine (GalNAc) moiety as described below. According to one aspect of the invention, the conjugate moiety is a GalNAc residue R as described hereinunder.

In some embodiments, the conjugate moiety is an at least trivalent, such as a divalent, trivalent or tetravalent GalNAc residue R. Preferably the conjugate moiety is a trivalent GalNAc residue R. The term "trivalent GalNAc residue" as used herein refers to a residue comprising three N-Acetylgalactosamine moieties, i.e. preferably three moieties of formula

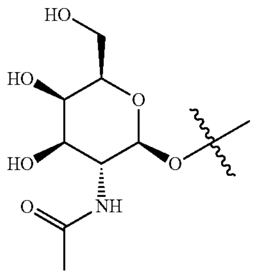 [SMILES: *O[C@@H]1O[C@H](CO)[C@H](O)[C@H](O)[C@H]1NC(C)=O]

The conjugate moiety or the GalNAc residue R, respectively, and the antisense oligonucleotide may be linked together via a linker L, such as a biocleavable linker L. Thus, the conjugate compound may comprise a linker L, which is positioned between the antisense oligonucleotide and the conjugate moiety or GalNAc residue R, respectively.

In one embodiment, the conjugate moiety is a tri-valent N-acetylgalactosamine (GalNAc), such as those shown in FIG. 5. In one embodiment, the conjugate moiety is the tri-valent N-acetylgalactosamine (GalNAc) of FIG. 5A-1 or FIG. 5A-2, or a mixture of both. In one embodiment, the conjugate moiety is the tri-valent N-acetylgalactosamine (GalNAc) of FIG. 5B-1 or FIG. 5B-2, or a mixture of both. In one embodiment, the conjugate moiety is the tri-valent N-acetylgalactosamine (GalNAc) of FIG. 5C-1 or FIG. 5C-2, or a mixture of both. In one embodiment, the conjugate moiety is the tri-valent N-acetylgalactosamine (GalNAc) of FIG. 5D-1 or FIG. 5D-2, or a mixture of both. The conjugate moiety and the antisense oligonucleotide may be linked together via a linker, such as a biocleavable linker. Thus, the conjugate compound may comprise a linker, which is positioned between the antisense oligonucleotide and the conjugate moiety.

In some embodiments, the linker comprises or consists of 1 to 10 linked nucleosides, such as 1, 2, 3, 4, 5, 6, 7, 8, 9 or 10 linked nucleosides, such as between 2 and 6 linked nucleosides, such as between 2 and 5 linked nucleosides, such as between 2 and 4 linked nucleosides. In some embodiments, the linker comprises two linked nucleotides. Thus, the nucleosides may be DNA nucleosides. Typically, the nucleosides are linked via phosphodiester internucleoside linkages. Moreover, the linker may be linked to the antisense compound via a phosphodiester internucleoside linkage.

Exemplary conjugates are provided in Table 2 (in HELM Annotation format). In addition to the compounds shown in Table 1, the compound comprise two nucleotides "ca" as cleavable linker at the 5' end. This is part of the HELM annotation of the sequence in table 2. The cleavable linker is cleaved off after successful GalNAc mediated delivery, leaving the compound as active drug.

The invention provides for a conjugate selected from the group of conjugates listed in Table 2, or a pharmaceutically acceptable salt thereof.

TABLE 2

Compound Table (Exemplary conjugates of the present invention)—HELM Annotation Format (for the annotation on the HELM annotation, see explanations for Table 1).

| SEQ ID Number | Oligo Compound ID Number # (acc. to Table 1 above) | HELM Annotation Written 5'-3'. | Exemplary compound—see FIG. |
|---|---|---|---|
| 3 | 3_1_GalNAc | {[5gn2c6]P.[dR](C)P.[dR](A)P.[LR](A)[sP].[LR](A)[sP].[LR](T)[sP].[LR](T)[sP].[dR](T)[sP].[dR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[dR](G)[sP].[LR](G)[sP].[LR](T) | 1 |
| 4 | 4_1_GalNAc | {[5gn2c6]P.[dR](C)P.[dR](A)P.[LR](A)[sP].[LR](A)[sP].[d R](T)[sP].[dR](T)[sP].[dR](T)[sP].[dR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[LR](G)[sP].[LR](G)[sP].[LR](T)[sP].[LR]([5meCD} | 2 |
| 5 | 5_1_GalNAc | [5gn2c6]P.[dR](C)P.[dR](A)P.[LR](T)[sP].[LR](T)[sP].[dR](A)[sP].[dR](C)[sP].[dR](A)[sP].[dR](T)[sP].[dR](A)[sP].[dR](C)[sP].[dR](T)[sP].[dR](C)[sP].[dR](T)[sP].[dR](G)[sP].[dR](G)[sP].[dR](T)[sP].[LR]([5meC])[sP].[LR](A)[sP].[LR](A)[sP].[LR](A) | 4 |
| 6 | 6_1_GalNAc | {[5gn2c6]P.[dR](C)P.[dR](A)P.[LR]([5meC])[sP].[LR](T)[sP].[dR](T)[sP].[dR](T)[sP].[dR](A)[sP].[dR](T)[sP].[dR](T)[sP].[dR](A)[sP].[dR](T)[sP].[dR](A)[sP].[dR](A)[sP].[dR](C)[sP].[dR](T)[sP].[LR](T)[sP].[dR](G)[sP].[dR](A)[sP].[LR](A)[sP].[dR](T)[sP].[LR]([5meC])[sP].[LR](T)[sP].[LR]([5meC]) | 3 |

In the above table, 5gn2c6 is a trivalent N-acetylgalactosamine (GalNAc) of FIG. 5D-1 or FIG. 5D-2, or a mixture of both. In some embodiments, 5gn2c6 is a GalNAc residue R having the formula:

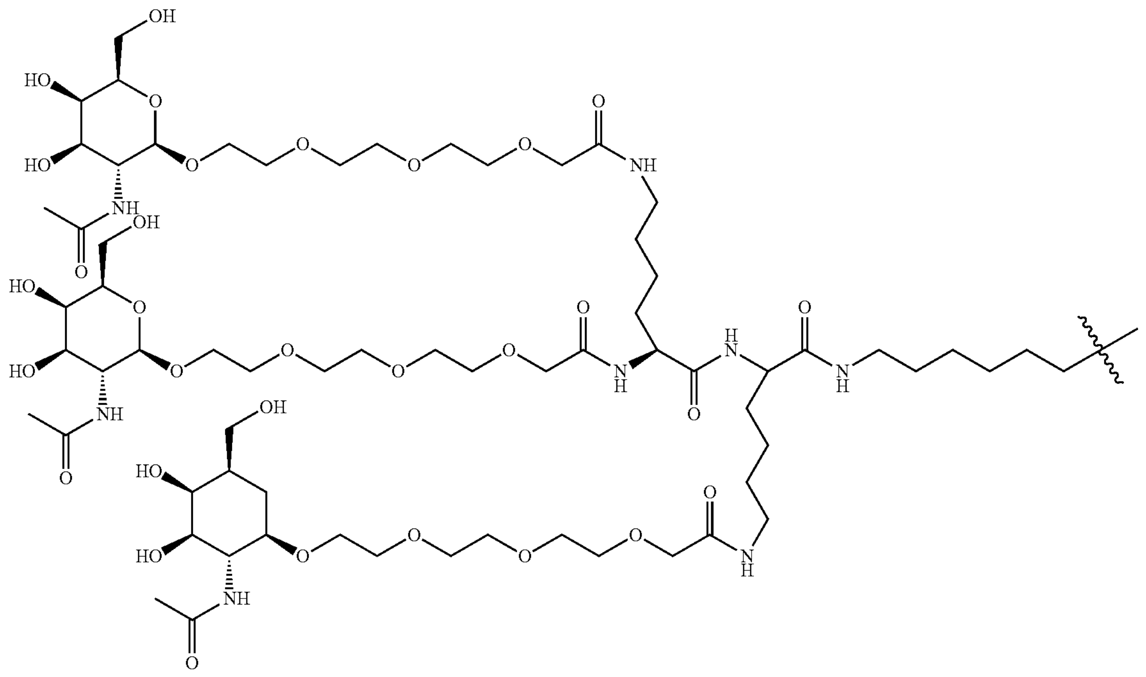 [SMILES: *CCCCCCNC(=O)C(CCCCNC(=O)COCCOCCOCCO[C@@H]1C[C@H](CO)[C@H](O)[C@H](O)[C@H]1NC(C)=O)NC(=O)[C@H](CCCCNC(=O)COCCOCCOCCO[C@@H]1O[C@H](CO)[C@H](O)[C@H](O)[C@H]1NC(C)=O)NC(=O)COCCOCCOCCO[C@@H]1O[C@H](CO)[C@H](O)[C@H](O)[C@H]1NC(C)=O]

It is to be understood that R as shown in the figure above is a mixture of the two stereoisomers shown in FIGS. 5D1 and 5D2.

According to a further aspect of the invention, R as shown in the figure above is the stereoisomer as shown in to FIG. 5D1.

According to a further aspect of the invention R as shown in the figure above is the stereoisomer as shown in FIG. 5D2.

The structures of the conjugates provided in Table 2 are shown in FIGS. 1 to 4.

The invention provides for the conjugate of FIG. 1, or a pharmaceutically acceptable salt thereof. The invention provides for the antisense oligonucleotide of Compound ID Number 3_1, or a pharmaceutically acceptable salt thereof.

The invention provides for the conjugate of FIG. 2, or a pharmaceutically acceptable salt thereof. The invention provides for the antisense oligonucleotide of Compound ID Number 4_1, or a pharmaceutically acceptable salt thereof.

The invention provides for the conjugate of FIG. 3, or a pharmaceutically acceptable salt thereof. The invention provides for the antisense oligonucleotide of Compound ID Number 6_1, or a pharmaceutically acceptable salt thereof.

The invention provides for the conjugate of FIG. 4, or a pharmaceutically acceptable salt thereof. The invention provides for the antisense oligonucleotide of Compound ID Number 5_1, or a pharmaceutically acceptable salt thereof.

The Compound of Formula (I)

The present invention also provides for compounds of the following formula (I)

(I)

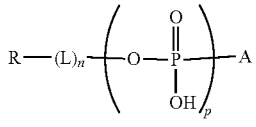

wherein n is 0 or 1 p is 0 or 1 with the proviso that in case n is 1, p is preferably 1, and with the proviso that in case n is 0 and p is 0, R is preferably H, L is a linker, preferably L is a linker comprising or consisting of 2-10 nucleosides, such as 2-5 nucleosides, R is a GalNAc residue, preferably a trivalent GalNAc residue, and A is an antisense oligonucleotide residue according to the present invention.

The term "antisense oligonucleotide residue" refers to an antisense oligonucleotide according to the present invention which is attached via its 5' end to residue R via $-(L)_n-(O-P(=O)(-OH)-)_p-$, such as an antisense oligonucleotide as shown in Table 6. Preferred antisense oligonucleotide residues are depicted in FIGS. 1A, 2A, 3A, 4A, 5A, 6A, 7A and 8A.

The GalNAc Residue R

R is a GalNAc residue, preferably a trivalent GalNAc residue. The term "GalNAc residue" as used herein refers to a residue comprising at least one N-Acetylgalactosamine (GalNAc) moiety, i.e. at least one moiety of formula

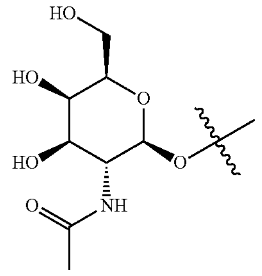 [SMILES: *O[C@@H]1O[C@H](CO)[C@H](O)[C@H](O)[C@H]1NC(C)=O]

The term “trivalent GalNAc residue” as used herein refers to a residue comprising three N-acetylgalactosamine (GalNAc) moieties, i.e. preferably three moieties of formula

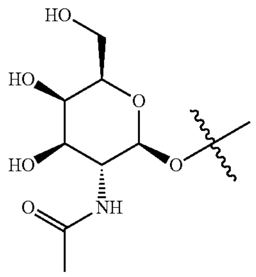 [SMILES: *O[C@@H]1O[C@H](CO)[C@H](O)[C@H](O)[C@H]1NC(C)=O]

Preferably, the GalNAc residue comprises at least one, preferably three GalNAc building blocks ($L^a$) having the following structure, ($L^a$)

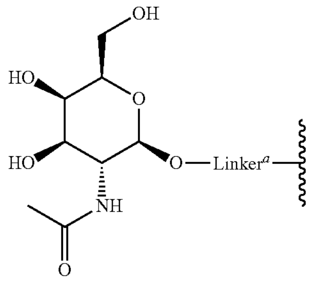

wherein $Linker^a$ is selected from alkyl groups, alkyl-oxy-alkyl groups, alkyl groups comprising at least one phosphodiester linkage, alkyl groups comprising at least one amide linkage, alkyl-oxy-alkyl groups comprising at least one phosphodiester linkage and alkyl-oxy-alkyl groups comprising at least one amide linkage.

The term “alkyl” refers to substituted or unsubstituted, linear or branched, alkyl groups, such as C1 to C20 alkyl groups, preferably, C2 to C8, such as C2, C3, C4, C5, C6, C7 or C8, alkyl groups. Preferably the alkyl groups are unsubstituted, more preferably linear and unsubstituted, alkyl groups.

The term “alkyl-oxy-alkyl” groups refers to at least two alkyl groups linked via an oxygen, preferably to ethyl-oxy-ethyl groups, such as $—(CH_2—O)_x—$ groups with integer x preferably being in the range of from 2 to 20, more preferably in the range of from 2 to 6, such as 2, 3, 4, 5 or 6, more preferably x is 3 or 5.

According to an aspect of the invention, the GalNAc building block ($L^a$) is selected from the group of the following structures ($L^a$).

If more than one residue ($L^a$) is present in a GalNAc residue, such as the three residues in the trivalent GalNAc residue, then all residues are preferably the same.

Most preferably, $L^a$ has the structure

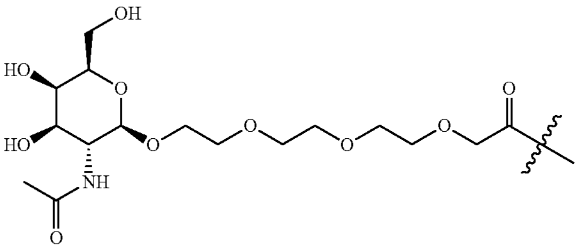 [SMILES: *C(=O)COCCOCCOCCO[C@@H]1O[C@H](CO)[C@H](O)[C@H](O)[C@H]1NC(C)=O]

In case, the conjugate moiety R comprises multiple, such as preferably three, GalNAc moieties, R comprises besides the GalNAc building blocks ($L^a$), a multivalent, preferably a tetravalent, building block ($L^b$), to which the building blocks ($L^a$) are preferably being attached, to the antisense oligonucleotide residue A via $-(L)_n-(O—P(=O)(—OH)—)_p—$.

$L^b$ is preferably selected from one of the following structures:

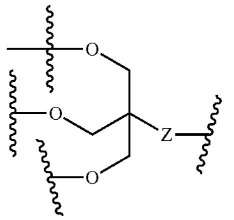

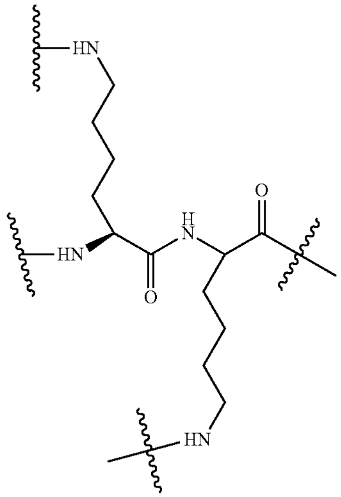

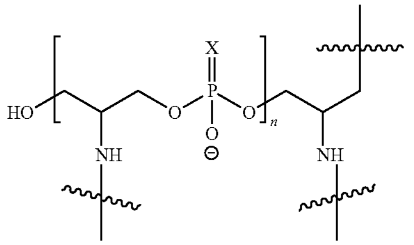

with X being O or S, and with Z being O or NH, and wherein n is of from 1 to 4, preferably 2 or 3, more preferably 2.

More preferably, $L^b$ has the structure

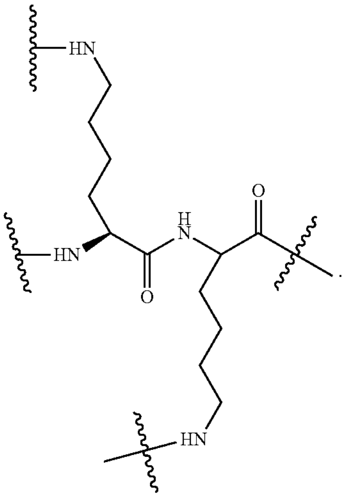 [SMILES: *NCCCCC(NC(=O)[C@H](CCCCN*)N*)C(*)=O]

It is to be understood that, $L^b$ has either the structure $L^{b*}$ or the structure $L^{b**}$ or is a mixture thereof.

According to a preferred aspect $L^b$ is a mixture of $L^{b*}$ and $L^{b**}$:

($L^{b*}$)

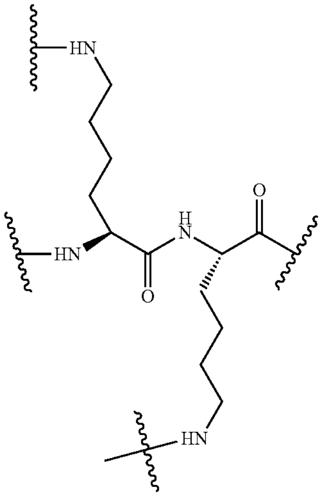

($L^{b**}$)

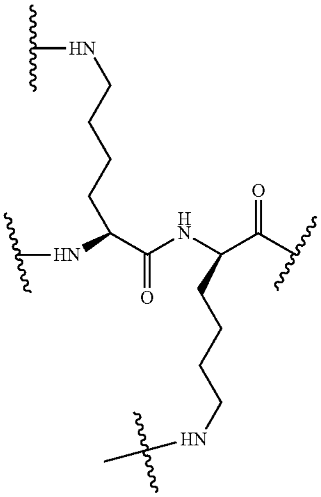

Thus, the conjugate moiety R preferably comprises a structure $(L_a)_3$-$L^b$-, more preferably R comprises one of the following structures

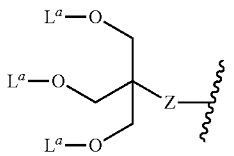

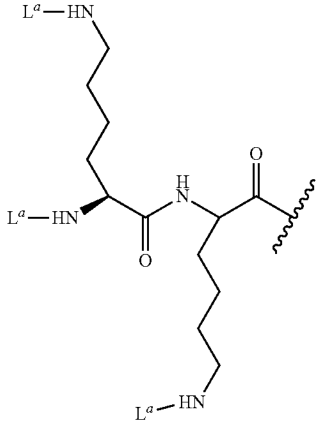

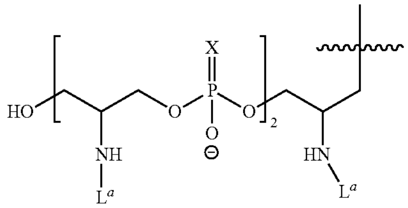

more preferably, the structure

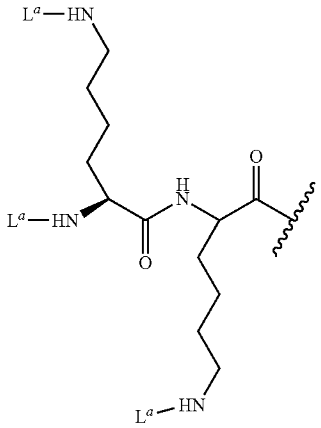

, wherein $L^b$ is preferably a mixture of $L^{b*}$ and $L^{b**}$, and wherein X is O or S, and with Z being O or NH, and wherein n is of from 1 to 3, preferably 2, and with $L^a$ being as described above, preferably with $L^a$ being selected from the group consisting of

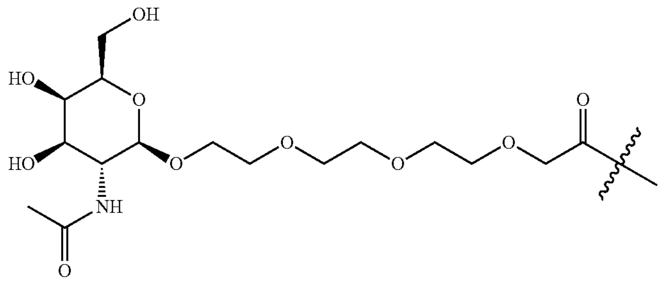
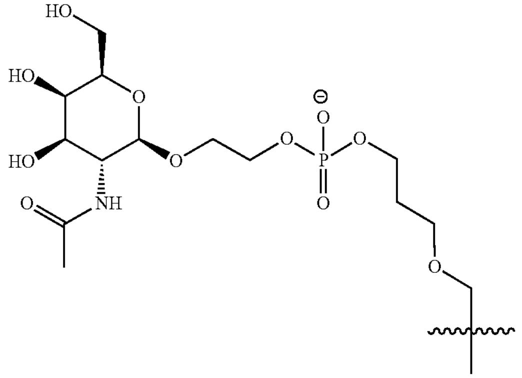
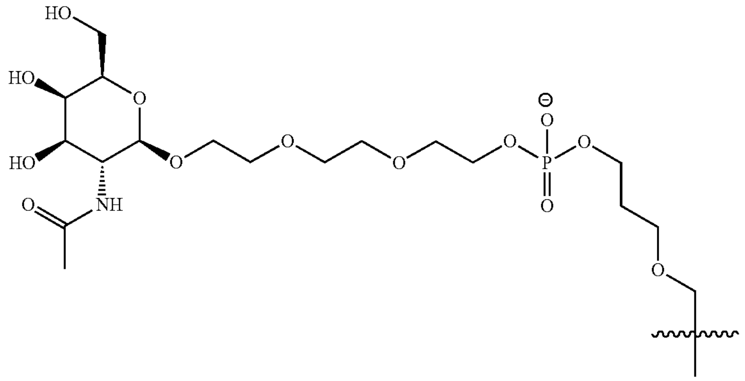
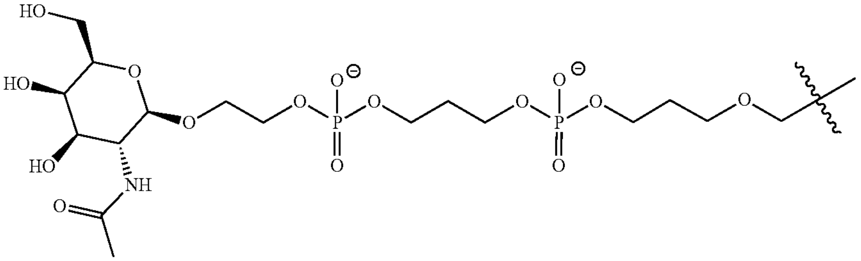
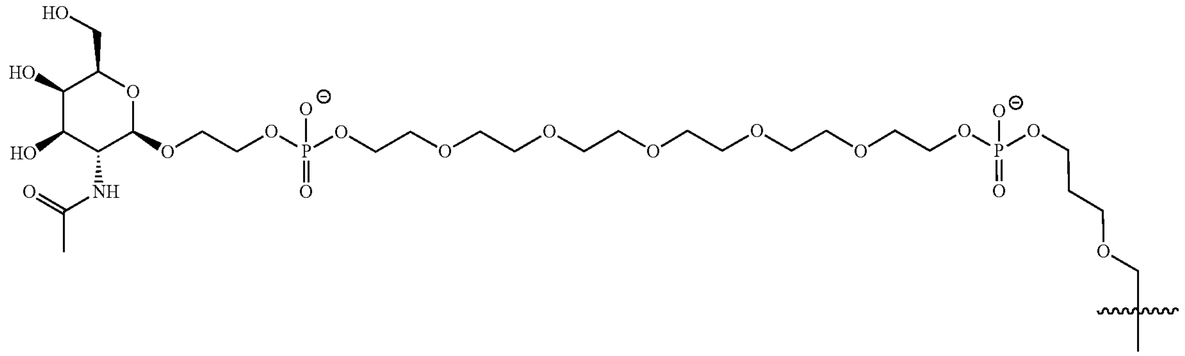

-continued
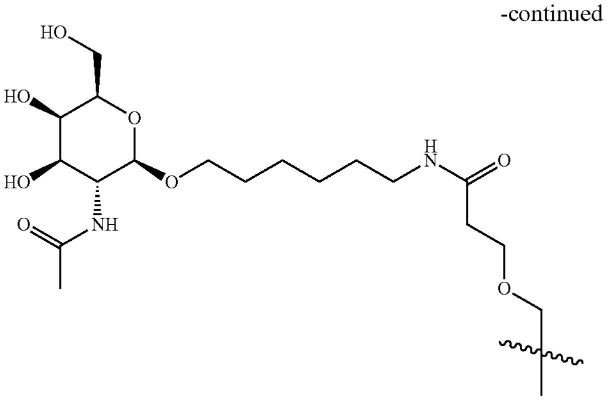
and mixtures thereof, wherein preferably all residues ($L^a$) within the GalNAc residue are the same.
In case $(L^a)_3$-$L^b$ is
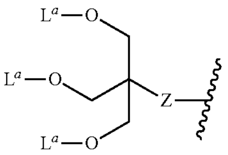
$L^a$ is more preferably selected from the group consisting of
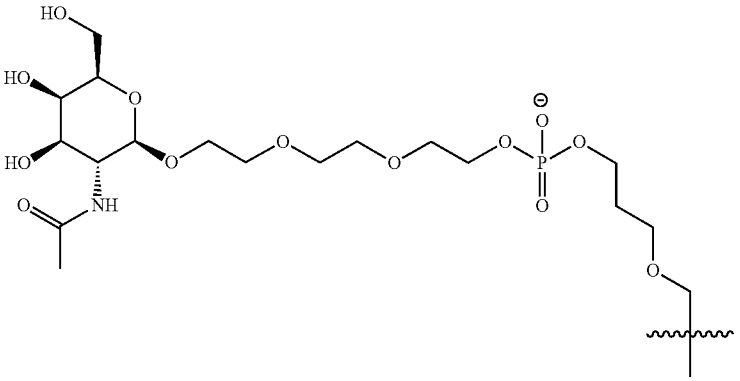
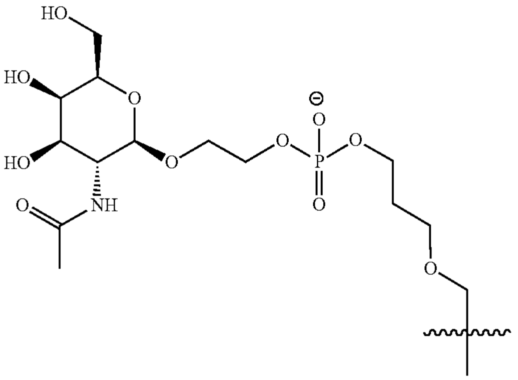

-continued
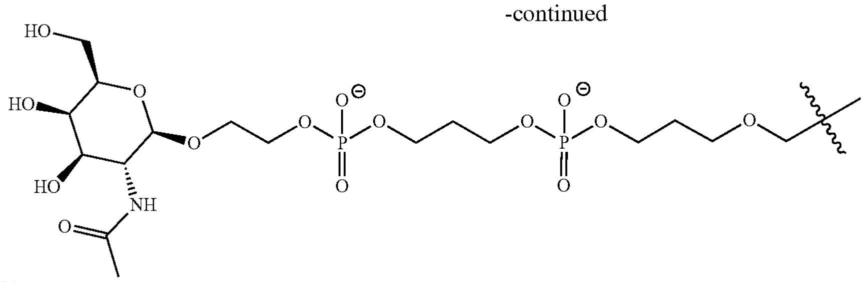
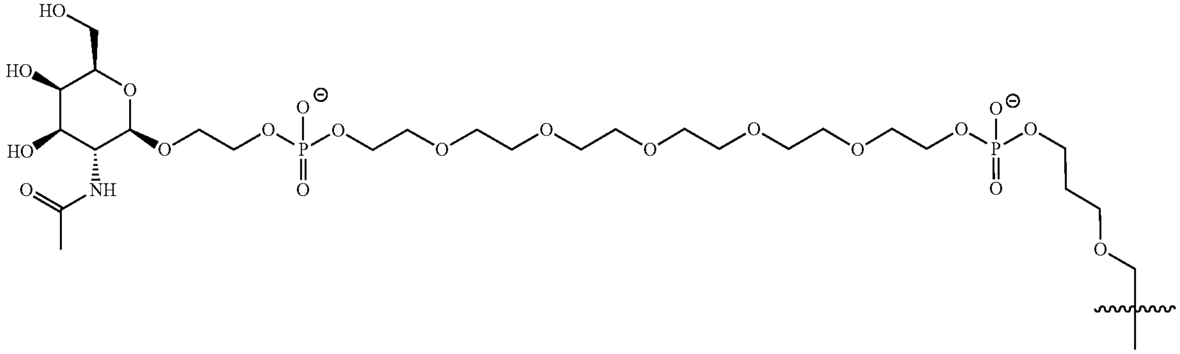
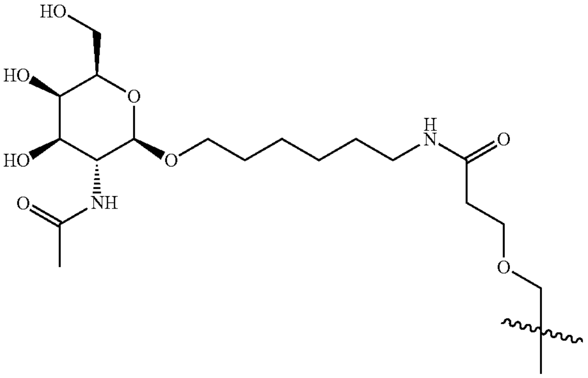 [SMILES: *COCCC(=O)NCCCCCCO[C@@H]1O[C@H](CO)[C@H](O)[C@H](O)[C@H]1NC(C)=O]
In case $(L^a)_3$-$L^b$ is
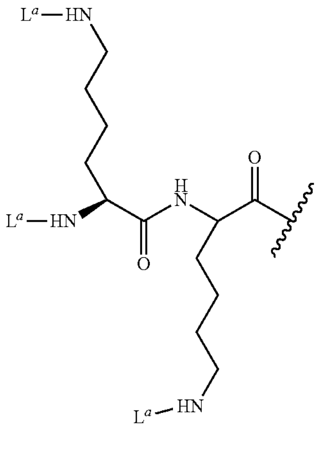
or
-continued
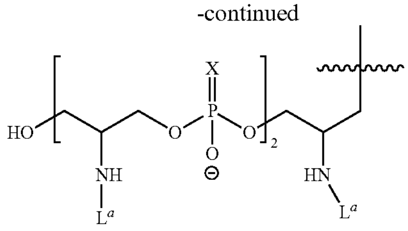
,
preferably
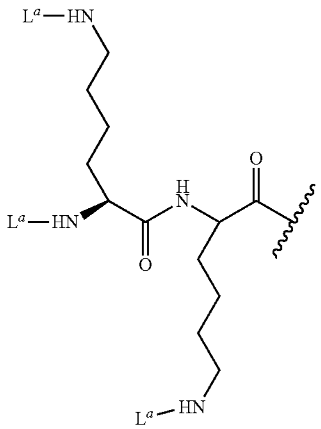
, $L^a$ is preferably

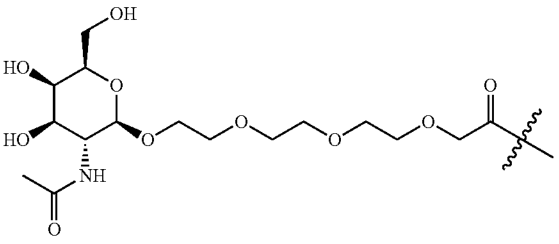 [SMILES: *C(=O)COCCOCCOCCO[C@@H]1O[C@H](CO)[C@H](O)[C@H](O)[C@H]1NC(C)=O]

Optionally, the conjugate moiety R additionally comprises a linker $L^c$. Thus, R preferably has the structure $(L^a)_3$-$L^b$-$(L^c)_c$- with integer c being 1 or 0.

Such linker compounds are known those skilled in the art and are suitably chosen to attach $(L^a)_3$-$L_b$ to the remaining part of the compound, i.e. to the antisense oligonucleotide residue via -$(L)_n$-(O—P(═O)(—OH)—$)_p$—.

Depending on the structure of $L^b$, $L^c$ is selected from the group consisting of alkyl, alkyl-oxy-alkyl, amino-alkyl (—NH-alkyl-), amino-alkyl-oxy-alkyl, unnatural amino acid residues, and natural amino acid residues. According to one aspect of the invention, $L^c$ is a substituted or unsubstituted lysine group.

According to one aspect of the invention, R is $(L^a)_3$-$L^b$-$(L^c)_c$ with c=1 and $(L^a)_3$-$L_b$ is

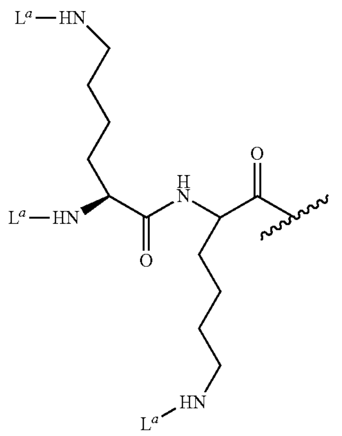

$L^c$ is preferably an amino-alkyl group or an amino acid, such as a substituted or unsubstituted lysine group, in particular $L^c$ is e.g. selected from the group consisting of

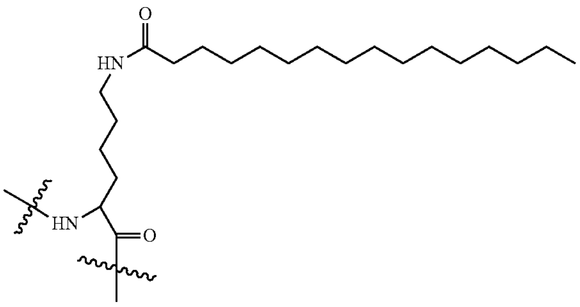

-continued

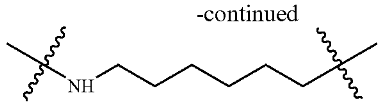

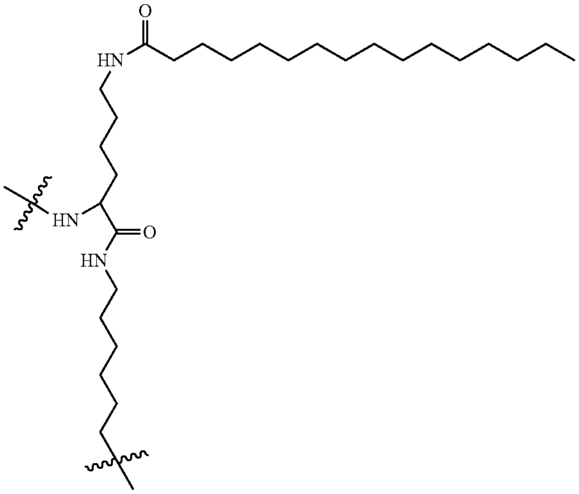

with the amino group being attached to the carbonyl group of $L^b$ thereby forming an amide bond. Preferred residues R according to this aspect are depicted in FIG. 5A1, 5A2; 5C1, 5C2, 5D1, 5D2. Thus, according to one aspect of the invention, R is selected from the group consisting of the residues depicted in FIGS. 5A1, 5A2; 5C1, 5C2, 5D1 and 5D2.

According to a further aspect of the invention, R has the structure $(L^a)_3$-$L^b$-$(L^c)_c$ with c being 0, and wherein $(L^a)_3$-$L_b$ is

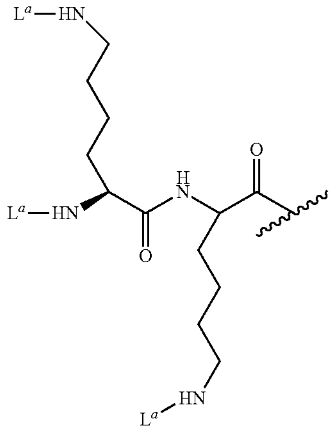

Preferred residues R according to this aspect of the invention are depicted in FIGS. 5B1 and 5B2.

According to a further aspect of the invention, R has the structure $(L^a)_3$-$L^b$-$(L^c)_c$ with $(L^a)_3$-$L_b$ being

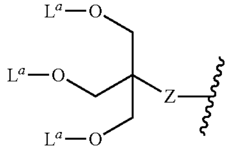

and with Z being O. In this case, c is preferably 1 and $L^c$ is preferably an alkyl group, more preferably a C3 to C6 alkyl group, more preferably a propyl group, most preferably a n-propyl group. Preferred residues R according to this aspect are depicted in FIGS. 5E1, 5F1, 5G1 and 5H1. Thus, according to one aspect of the invention, R is selected from the group consisting of the residues depicted in FIGS. 5E1, 5F1, 5G1 and 5H1

According to a further aspect of the invention, R has the structure $(L^a)_3$-$L^b$-$(L^c)_c$ with $(L^a)_3$-$L_b$ being

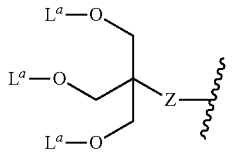

and with Z being NH. In this case c is preferably 1 and $L^c$ is preferably an alkyl group, an amino acid comprising group or a group having the following structure:

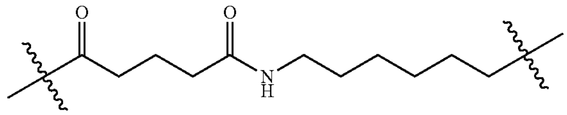 [SMILES: *CCCCCCNC(=O)CCCC(*)=O]

In particular, in this case $L^c$ is

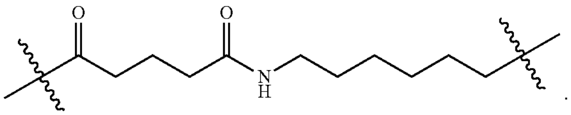 [SMILES: *CCCCCCNC(=O)CCCC(*)=O]

A preferred residue R according to this aspect of the invention is depicted in FIG. 5J1.

According to a further aspect of the invention, R has the structure $(L^a)_3$-$L^b$-$(L^c)_c$ with $(L^a)_3$-$L^b$ being

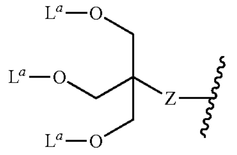

and with Z being NH and c being 0. A preferred residue R according to this aspect of the invention is depicted in FIG. 5I1.

According to one aspect of the invention, R is $(L^a)_3$-$L^b$-$(L^c)_c$ with c=0 and wherein $(L^a)_3$-$L_b$ is

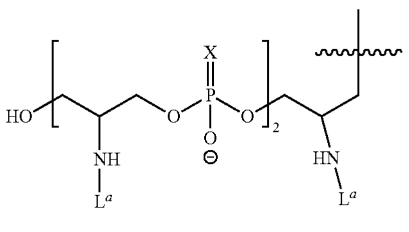

Preferred residues R according to this aspect of the invention are depicted in FIGS. 5L1 and 5L2.

Thus, R is preferably selected from the residues depicted in FIG. 5A1, 5A2; 5B1, 5B2, 5C1, 5C2, 5D1, 5D2, 5E1, 5F1, 5G1, 5H1, 5I1, 5J1, 5L1 5L2, and mixtures thereof, such as stereoisomeric mixtures of 5A1 and 5A2; of 5B1 and 5B2, of 5C1 and 5C2 or 5D1 and D2, more preferably R is selected from the residues depicted in 5D1, 5D2 and a mixture thereof, more preferably R is a mixture of the residues depicted in 5D1 and 5D2, such as a mixture having a molar ratio of 5D1 to 5D2 in the range of from 10:90 to 90:10, such as in the range of from 30:70 to 70:30, such as in the range of from 45:55 to 55:45.

Thus, compound (I) is preferably selected from the compounds depicted in FIGS. 6A1, 6A2; 6B1, 6B2, 6C1, 6C2, 6D1, 6D2, 6E1, 6F1, 6G1, 6H1, 611, 6J1, 6L1, 6L2 and mixtures thereof, such as stereoisomeric mixtures of 6A1 and 6A2; of 6B1 and 6B2, of 6C1 and 6C2 or of 6D1 and 6D2, more preferably compound (I) is selected from the group consisting of the compounds depicted in 6D1, 6D2, and mixtures thereof, more preferably compound (I) is a mixture of the compounds depicted in 6D1 and 6D2, such as a mixture having a molar ratio of 6D1 to 6D2 in the range of from 10:90 to 90:10, such as in the range of from 30:70 to 70:30, such as in the range of from 45:55 to 55:45.

The Linker L

In the above formula, L is a linker as defined herein, preferably L is a linker comprising or consisting of 2-10 nucleosides, such as 2-5 nucleosides, such as 2 nucleosides, wherein optionally the nucleosides are phosphodiester linked nucleosides.

As the linker L comprises between 1 and 10 linked nucleosides, such as 1, 2, 3, 4, 5, 6, 7, 8, 9 or 10 linked nucleosides, such as between 2 and 6 linked nucleosides, such as between 2 and 5 linked nucleosides, such as between 2 and 4 linked nucleosides. In some embodiments, the linker comprises two linked nucleotides. Thus, the nucleosides may be DNA nucleosides. Typically, the nucleosides are linked via phosphodiester internucleoside linkages. Moreover, the linker L may be linked to the antisense compound via a phosphodiester internucleoside linkage. Further, the linker L is linked to conjugate moiety R via a suitable function group, such as e.g., via an amide, an amine, an ether, an ester, a phosphodiester (—O—P(═O)(—OH)—O—) or thiophosphodiester (—O—P(═S)(—OH)—O—) linkage. It is to be understood that L may optionally additionally comprise alkyl groups or alkyl-oxy-alkyl groups between the nucleosides and the functional group linking L to R. In this case, the nucleosides are preferably linked via a phosphodiester bond to the alkyl groups or alkyl-oxy-alkyl group which in turn is linked to R via a suitable function group, such as e.g., via an amide, an amine, an ether, an ester, a phosphodiester (—O—P(═O)(—OH)—O—) or thiophosphodiester (—O—P(═S)(—OH)—O—) bond According to a preferred embodiment L is

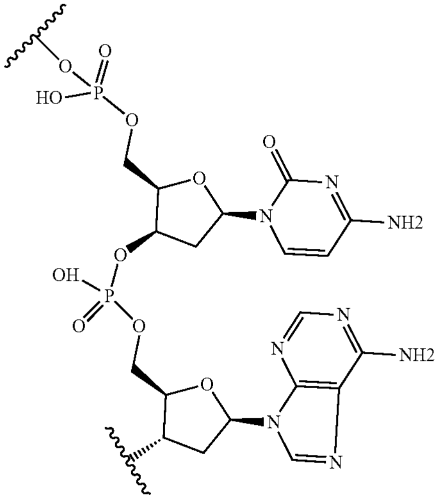 [SMILES: *OP(=O)(O)OC[C@H]1O[C@@H](n2ccc(N)nc2=O)C[C@H]1OP(=O)(O)OC[C@H]1O[C@@H](n2cnc3c(N)ncnc32)C[C@@H]1*]

The Antisense (A) Oligonucleotide Residue

A is an antisense oligonucleotide residue according to the present invention, such an antisense oligonucleotide shown in Table 6, being attached via its 5' prime end to R via $-(L)_n-(O—P(=O)(—OH)—)_p$. Preferably, A is an antisense oligonucleotide residue selected from the residues depicted in FIGS. 1A, 2A 3A and 4.

Thus, compound (I) is preferably selected from the compounds depicted in FIGS. 6A1, 6A2; 6B1, 6B2, 6C1, 6C2, 6D1, 6D2, 6E1, 6F1, 6G1, 6H1, 611, 6J1, 6L1 6L2, and mixtures thereof, such as stereoisomeric mixtures of 6A1 and 6A2; of 6B1 and 6B2, of 6C1 and 6C2 or of 6D1 and 6D2, more preferably compound (1) is selected from the compounds depicted in 6D1 and 6D2, and a mixture thereof, more preferably compound (1) is a mixture of compound 6D1 and 6D2, preferably with A being selected from the antisense oligonucleotide shown in Table 6, preferably with A being an antisense oligonucleotide residue selected from the residues depicted in FIGS. 1A, 2A 3A, 4A, 5A, 6A, 7A and 8A. and with L is a linker comprising or consisting of 2-10 nucleosides, such as 2-5 nucleosides, such as 2 nucleosides, wherein optionally the nucleosides are phosphodiester linked nucleosides, more preferably wherein L is

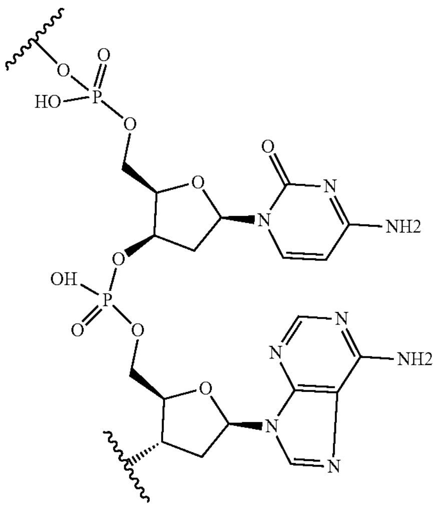 [SMILES: *OP(=O)(O)OC[C@H]1O[C@@H](n2ccc(N)nc2=O)C[C@H]1OP(=O)(O)OC[C@H]1O[C@@H](n2cnc3c(N)ncnc32)C[C@@H]1*]

In a further aspect, R is a residue having the structure (I)

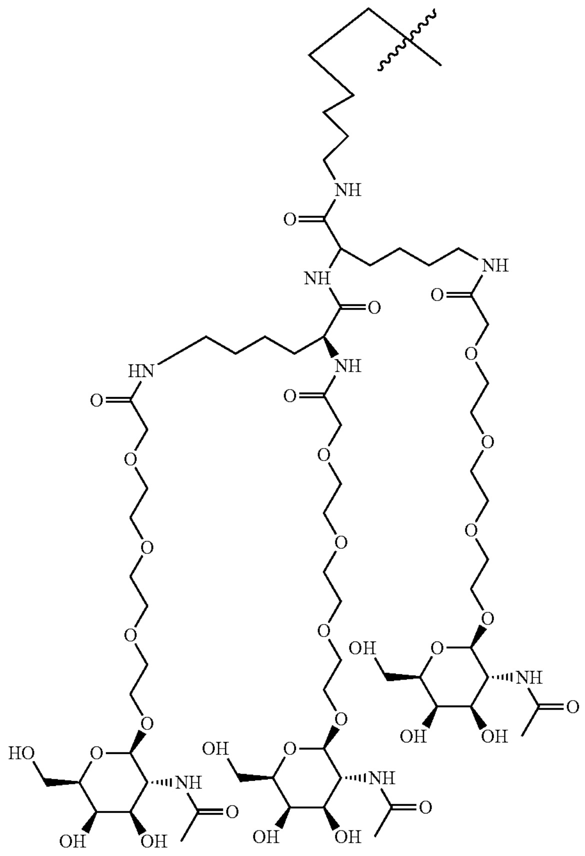 [SMILES: *CCCCCCNC(=O)C(CCCCNC(=O)COCCOCCOCCO[C@@H]1O[C@H](CO)[C@H](O)[C@H](O)[C@H]1NC(C)=O)NC(=O)[C@H](CCCCCNC(=O)COCCOCCOCCO[C@@H]1O[C@H](CO)[C@H](O)[C@H](O)[C@H]1NC(C)=O)NC(=O)COCCOCCOCCO[C@@H]1O[C@H](CO)[C@H](O)[C@H](O)[C@H]1NC(C)=O]

L is a linker as defined herein, preferably L is a linker comprising or consisting of 2-10 nucleosides, such as 2-5 nucleosides, such as 2 nucleosides, wherein optionally the nucleosides are phosphodiester linked nucleosides, more preferably L is

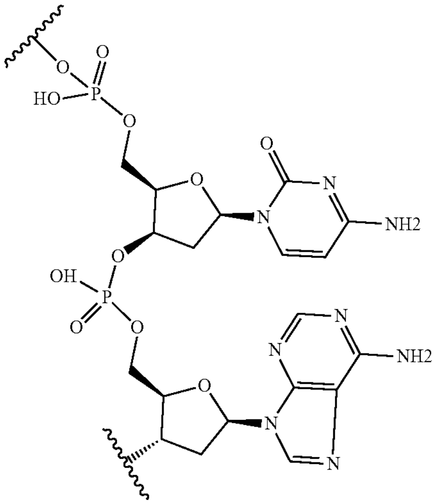 [SMILES: *OP(=O)(O)OC[C@H]1O[C@@H](n2ccc(N)nc2=O)C[C@H]1OP(=O)(O)OC[C@H]1O[C@@H](n2cnc3c(N)ncnc32)C[C@@H]1*]

and
A is an antisense oligonucleotide according to the present invention, such an as antisense oligonucleotide shown in Table 6.
According to one aspect of the invention, A is antisense oligonucleotide residue selected from the residues depicted in FIGS. 1A, 2A, 3A, and 4A,
for example A is an antisense oligonucleotide of the following formula:
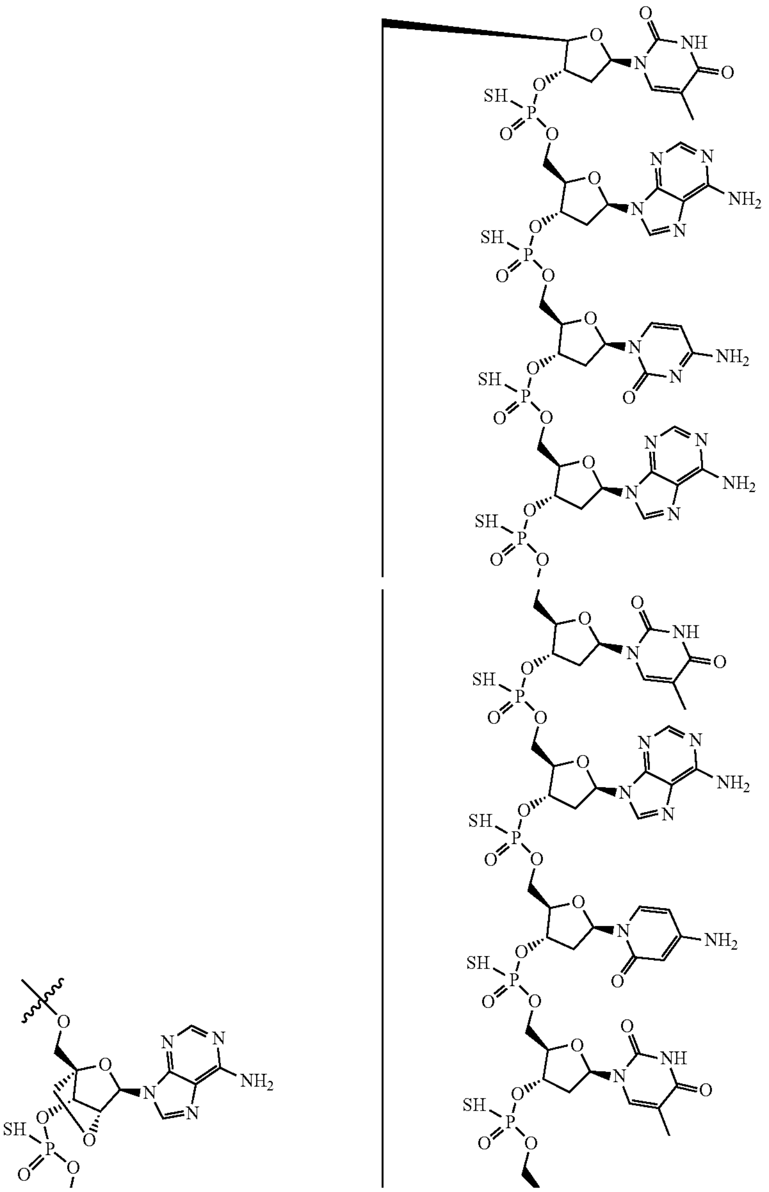

-continued

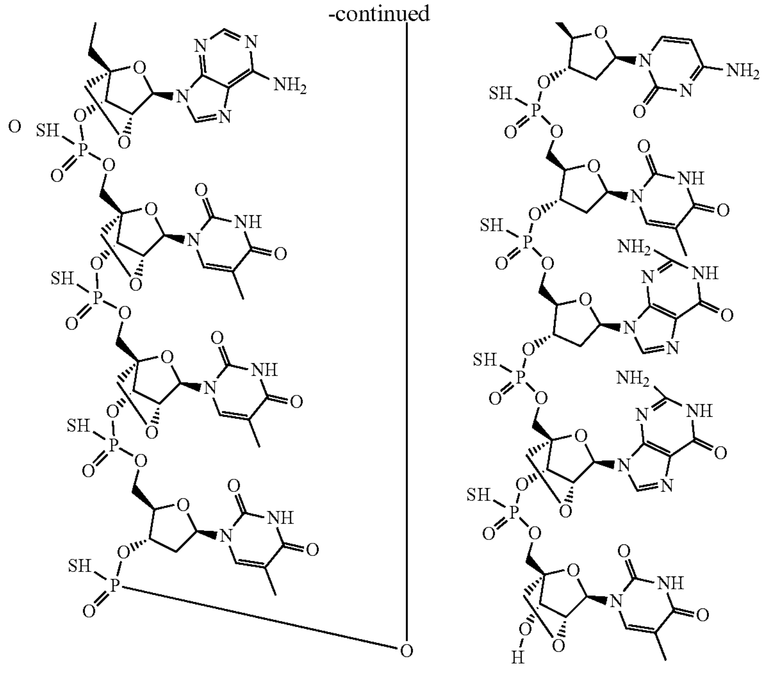

The invention provides pharmaceutical compositions comprising the antisense oligonucleotide of the invention or the conjugate thereof, and a pharmaceutically acceptable diluents, carriers, salts and/or adjuvants.

The invention provides for a pharmaceutically acceptable salt of the antisense oligonucleotide of the invention or the conjugate thereof. In some embodiments, the pharmaceutically acceptable salt is selected from the group consisting of a sodium salt, a potassium salt and an ammonium salt.

The invention provides for a pharmaceutical solution of the antisense oligonucleotide of the invention or the conjugate thereof, wherein the pharmaceutical solution comprises the antisense oligonucleotide of the invention or the conjugate thereof and a pharmaceutically acceptable solvent, such as saline.

The invention provides for the antisense oligonucleotide of the invention or the conjugate thereof in solid powdered form, such as in the form of a lyophilized powder.

The invention provides for a pharmaceutically acceptable salt of the antisense oligonucleotide of the invention or the conjugate thereof.

The invention provides for a pharmaceutically acceptable salt of the antisense oligonucleotide according to the invention, or the conjugate of the invention, wherein the pharmaceutically acceptable salt is a sodium or potassium salt.

The invention provides for a pharmaceutical composition comprising the antisense oligonucleotide of the invention, or the conjugate of the invention, or the salt of the invention and a pharmaceutically acceptable diluent, solvent, carrier, salt and/or adjuvant.

The invention provides for a method for inhibiting RTEL1 expression in a target cell, which is expressing RTEL1, said method comprising administering an antisense oligonucleotide of the invention, or the conjugate of the invention, or the salt of the invention, or the composition of the invention in an effective amount to said cell. The method may be an in vivo method or an in vitro method.

The invention provides for a method for treating and/or preventing an HBV infection in a subject such as a human, comprising administering a therapeutically or prophylactically effective amount of an antisense oligonucleotide of the invention, or the conjugate of the invention, or the salt of the invention, or the composition of the invention, such as to treat and/or prevent an HBV infection, such as a chronic HBV infection.

In some embodiments, the antisense oligonucleotide of the invention, or the conjugate of the invention, or the salt of the invention, or the pharmaceutical composition of the invention, is for the use in the treatment and/or prevention of an HBV infection, such as a chronic HBV infection.

The invention provides the antisense oligonucleotide of the invention, or the conjugate of the invention, or the pharmaceutical composition, or the salt of the invention for use in medicine.

In a further aspect, the invention provides methods for inhibition of RTEL1 expression in a target cell, which is expressing RTEL1, by administering an antisense oligonucleotide of the invention, or conjugate of the invention in an effective amount to said cell. In a further aspect, the invention provides methods for in vivo or in vitro method for inhibition of RTEL1 expression in a target cell, which is expressing RTEL1, by administering an antisense oligonucleotide, or the conjugate of the invention in an effective amount to said cell. The cell may for example be a human cell, such as a liver cell, such as a hepatocyte.

In a further aspect, the invention provides methods for reducing cccDNA in an HBV infected cell, by administering an antisense oligonucleotide of the invention, or conjugate of the invention in an effective amount to said cell. In a further aspect, the invention provides methods for in vivo or in vitro method for reducing cccDNA in an HBV infected cell, by administering an antisense oligonucleotide of the invention, or the conjugate of the invention in an effective amount to said cell.

In a further aspect, the invention provides methods for treating and/or preventing an HBV infection, such as a chronic HBV infection.

In a further aspect the antisense oligonucleotide of the invention, or the conjugate of the invention, or pharmaceutical composition of the invention is used in the treatment and/or prevention of viral liver infections such as HBV, HCV, HDV or a parasite infections such as malaria, toxoplasmosis, leishmaniasis and trypanosomiasis or liver cancer or metastases in the liver.

In a further aspect, the invention provides the antisense oligonucleotide, or the conjugate of the invention, or the pharmaceutical composition of the invention, for use in the manufacture of a medicament for the treatment and/or prevention of an HBV infection, such as a chronic HBV infection.

In a further aspect, the invention provides the antisense oligonucleotide, or the conjugate of the invention, or the pharmaceutical composition of the invention, for use in the manufacture of an antiviral drug.

The invention provides for the antisense oligonucleotide of the invention, or the conjugate of the invention, or the pharmaceutical composition of the invention, for use in the treatment of an HBV infection, such as a chronic HBV infection.

SEQUENCE LISTING

The sequence listing submitted with this application is hereby incorporated by reference. In the event of a discrepancy between the sequence listing and the specification or figures, the information disclosed in the specification (including the figures) shall be deemed to be correct.

BRIEF DESCRIPTION OF FIGURES

FIG. 5A1-FIG. 5L2: FIG. 5A1 through FIG. 5L2 illustrate exemplary GalNAc moieties. The compound in FIG. 5L is composed of monomeric GalNAc phosphoramidites added to the oligonucleotide while still on the solid support as part of the synthesis, X is S or O, Y is S or O, and n=1-3 (see WO 2017/178656). FIG. 5B and FIG. 5D are also termed GalNAc2 or GN2 herein, without and with C6 linker, respectively.

FIG. 6A1-FIG. 6L2: FIG. 6A1 through FIG. 6L2 illustrate exemplary antisense oligonucleotide conjugates, wherein the oligonucleotide is represented by the term "A" as described above. Compounds in FIG. 6A-D comprise a di-lysine brancher molecule, a PEG3 spacer and three terminal GalNAc carbohydrate moieties. In the compounds in FIG. 6A (FIG. 6A-1 and FIG. 6A-2 show two different diastereoisomers of the same compound) and FIG. 6B (FIG. 6B-1 and FIG. 6B-2 show two different diastereoisomers of the same compound) the oligonucleotide is attached directly to the asialoglycoprotein receptor targeting conjugate moiety without an alkyl linker. In the compounds in FIG. 6C (FIG. 6C-1 and FIG. 6C-2 show two different diastereoisomers of the same compound) and FIG. 6D (FIG. 6D-1 and FIG. 6D-2 show two different diastereoisomers of the same compound) the oligonucleotide is attached to the asialoglycoprotein receptor targeting conjugate moiety via a C6 linker. The compounds in FIG. 6E-K comprise a commercially available trebler brancher molecule and spacers of varying length and structure and three terminal GalNAc carbohydrate moieties. The compound in FIG. 6L is composed of monomeric GalNAc phosphoramidites added to the oligonucleotide while still on the solid support as part of the synthesis, wherein X=S or O, and independently Y=S or O, and n=1-3 (see WO 2017/178656).

FIG. 9A through FIG. 9E illustrate testing oligonucleotide antisense molecules and shorter metabolites thereof in vitro for concentration dependent potency and efficacy in human cell line MDA-MB-231. FIG. 9A) CMP ID 5_1, FIG. 9B) CMP ID 7_1, FIG. 9C) CMP ID 8_1, FIG. 9D) CMP ID 9_1, FIG. 9E) CMP ID 10_1.

FIG. 13A and FIG. 13B illustrate RTEL1 mRNA level and HBV cccDNA level in liver tissue from HBV-infected PXB-mice treated with GalNAc-conjugated CMP ID 5_1 and a control: FIG. 13A) Day 105, FIG. 13B) Day 56.

DEFINITIONS

HBV Infection

Figure 1:
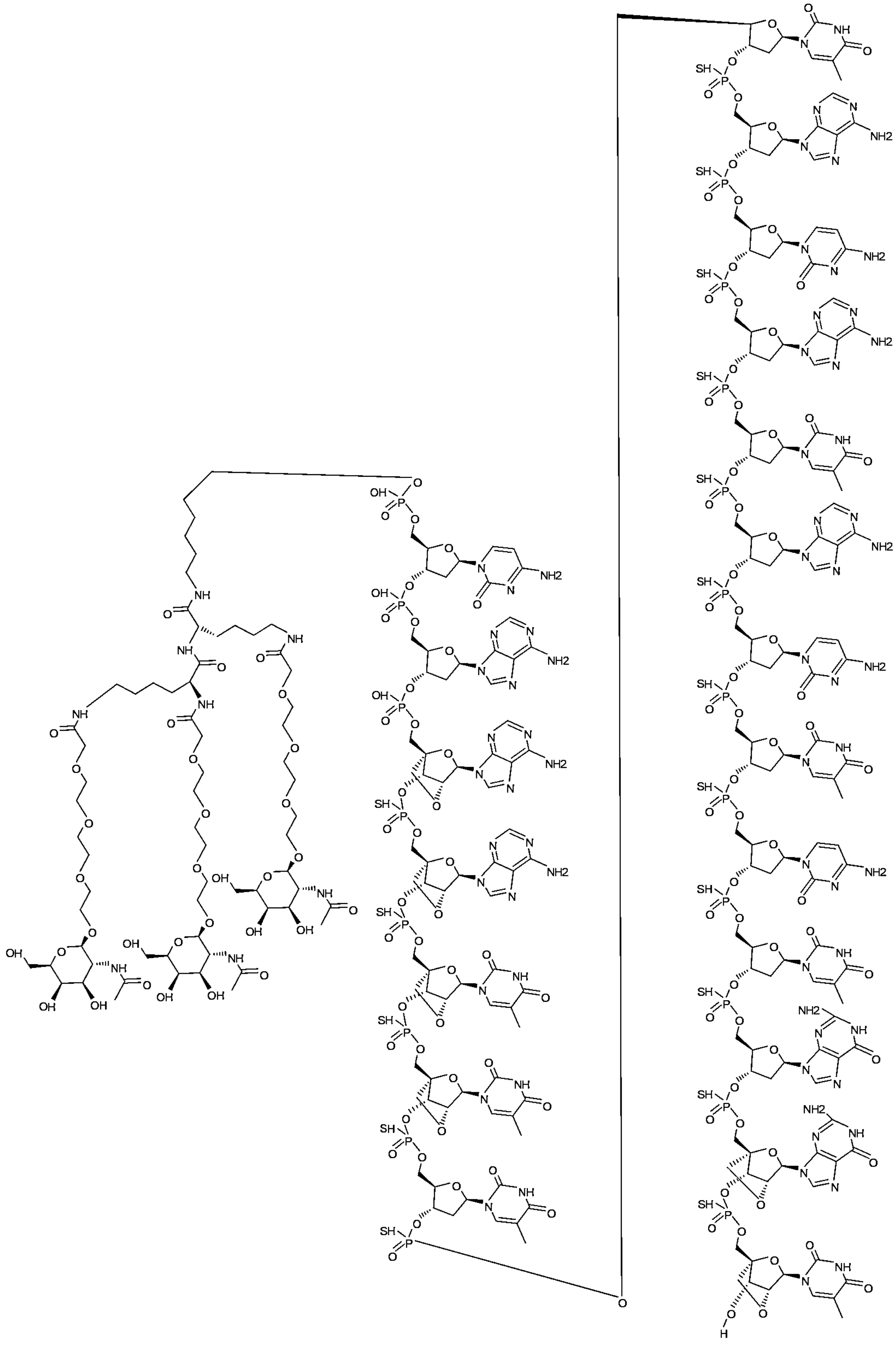
FIG. 1: Compound 3_1 (SEQ ID NO: 3) conjugated to a trivalent GalNAc moiety via a phosphodiester linked DNA dinucleotide
Figure 1A:
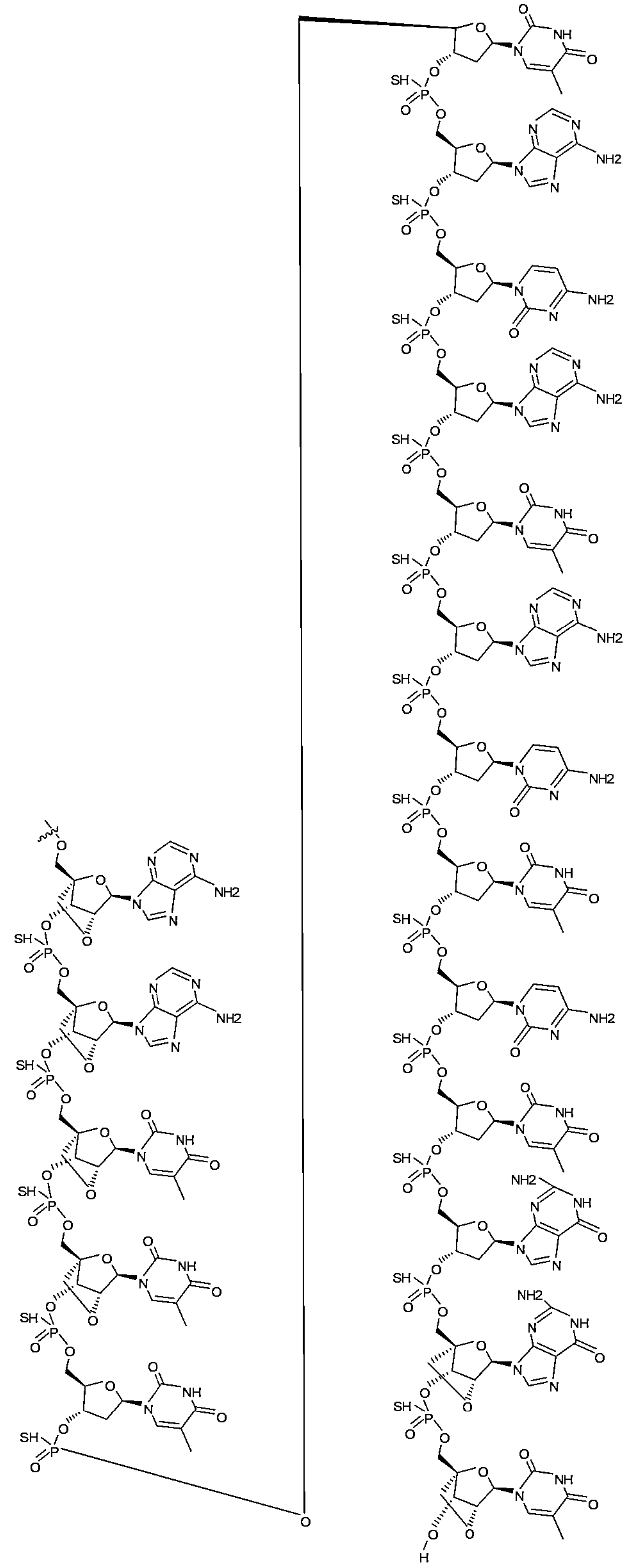
FIG. 1A: Residue A of Compound 3_1 (SEQ ID NO: 3)

The term "hepatitis B virus infection" or "HBV infection" is commonly known in the art and refers to an infectious disease that is caused by the hepatitis B virus (HBV) and affects the liver. A HBV infection can be an acute or a chronic infection. Chronic hepatitis B virus (CHB) infection is a global disease burden affecting 248 million individuals worldwide. Approximately 686,000 deaths annually are attributed to HBV-related end-stage liver diseases and hepatocellular carcinoma (HCC) (GBD 2013; Schweitzer et al., 2015). WHO projected that without expanded intervention, the number of people living with CHB infection will remain at the current high levels for the next 40-50 years, with a cumulative 20 million deaths occurring between 2015 and 2030 (WHO 2016). CHB infection is not a homogenous disease with singular clinical presentation. Infected individuals have progressed through several phases of CHB-associated liver disease in their life; these phases of disease are also the basis for treatment with standard of care (SOC). Current guidelines recommend treating only selected CHB-infected individuals based on three criteria—serum ALT level, HBV DNA level, and severity of liver disease (EASL, 2017). This recommendation was due to the fact that SOC i.e. nucleos(t)ide analogs (NAs) and pegylated interferon-alpha (PEG-IFN), are not curative and must be administered for long periods of time thereby increasing their safety risks. NAs effectively suppress HBV DNA replication; however, they have very limited/no effect on other viral markers. Two hallmarks of HBV infection, hepatitis B surface antigen (HBsAg) and covalently closed circular DNA (cccDNA) are the main targets of novel drugs aiming for HBV cure. In the plasma of CHB individuals, HBsAg subviral (empty) particles outnumber HBV virions by a factor of $10^3$ to $10^5$ (Ganem & Prince, 2014); its excess is believed to contribute to immunopathogenesis of the disease, including inability of individuals to develop neutralizing anti-HBs antibody, the serological marker observed following resolution of acute HBV infection.

cccDNA (Covalently Closed Circular DNA)

cccDNA is the viral genetic template that resides in the nucleus of infected hepatocytes, where it gives rise to all HBV RNA transcripts needed for productive infection and is responsible for viral persistence during natural course of chronic HBV infection (Locarnini & Zoulim, 2010 Antivir Ther. 15

Suppl 3:3-14). Actin as a viral reservoir, cccDNA is the source of viral rebound after cessation of treatment, necessitating long term, often, lifetime treatment. PEG-IFN can only be administered to a small subset of CHB due to its various side effects.

Consequently, novel therapies that can deliver a complete cure, defined by degradation or elimination of HBV cccDNA, to the majority of CHB patients are highly needed.

Compound

Herein, the term "compound" means any molecule capable of inhibition RTEL1 expression or activity. Particular compounds of the invention are antisense oligonucleotides according to the invention or any conjugate comprising such a nucleic acid molecule. For example, herein the compound may be a nucleic acid molecule targeting RTEL1, in particular an antisense oligonucleotide.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides such as 2' sugar modified nucleosides. The oligonucleotide of the invention may comprise one or more modified internucleoside linkages, such as one or more phosphorothioate internucleoside linkages.

Antisense Oligonucleotides

The term "antisense oligonucleotide" as used herein is defined as oligonucleotides capable of modulating expression of a target gene by hybridizing to a target nucleic acid, in particular, to a contiguous sequence on a target nucleic acid. Antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

In some embodiments, the single stranded antisense oligonucleotide of the invention may not contain RNA nucleosides.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.

Contiguous Nucleotide Sequence

The term "contiguous nucleotide sequence" refers to the region of the oligonucleotide, which is complementary to the target nucleic acid. The term is used interchangeably herein with the term "contiguous nucleobase sequence" and the term "oligonucleotide motif sequence". In some embodiments, all the nucleosides of the oligonucleotide constitute the contiguous nucleotide sequence. In some embodiments, the oligonucleotide comprises the contiguous nucleotide sequence, such as a F-G-F' gapmer region, and may optionally comprise further nucleotide(s), for example a nucleotide linker region which may be used to attach a functional group (e.g. a conjugate group) to the contiguous nucleotide sequence. The nucleotide linker region may or may not be complementary to the target nucleic acid. In some embodiments, the nucleobase sequence of the antisense oligonucleotide is the contiguous nucleotide sequence.

Nucleotides and Nucleosides

Nucleotides and nucleosides are the building blocks of oligonucleotides and polynucleotides, and for the purposes of the present invention include both naturally occurring and non-naturally occurring nucleotides and nucleosides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. Advantageously, one or more of the modified nucleosides of the antisense oligonucleotide of the invention comprise a modified sugar moiety. The term "modified nucleoside" may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. The oligonucleotides of the invention may therefore comprise one or more modified internucleoside linkages such as a one or more phosphorothioate internucleoside linkages, or one or more phosphorodithioate internucleoside linkages.

In some embodiments, at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments, all of the internucleoside linkages of the oligonucleotide, or contiguous nucleotide sequence thereof, are phosphorothioate.

In some advantageous embodiments, all the internucleoside linkages of the contiguous nucleotide sequence of the oligonucleotide are phosphorothioate, or all the internucleoside linkages of the oligonucleotide are phosphorothioate linkages.

It is recognized that, as disclosed in EP 2 742 135, antisense oligonucleotides may comprise other internucleoside linkages (other than phosphodiester, phosphorothioate and phosphorodithioate), for example alkyl phosphonate/methyl phosphonate internucleoside, which according to EP 2 742 135 may for example be tolerated in an otherwise DNA phosphorothioate the gap region.

Nucleobase

The term nucleobase includes the purine (e.g. adenine and guanine) and pyrimidine (e.g. uracil, thymine and cytosine) moiety present in nucleosides and nucleotides, which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments, the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides comprising sugar modified nucleosides and DNA nucleosides. The antisense oligonucleotide of the invention is advantageously a chimeric oligonucleotide.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

The term "fully complementary", refers to 100% complementarity.

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant ($K_d$) of the reaction by $\Delta G°=-RT\ln(K_d)$, where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for ΔG° measurements. ΔG° can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments, the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments, the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

The Target

The term "target" as used herein refers to the mammalian protein RTEL1 ("Regulator of telomere elongation helicase 1), alternatively known as "KIAA1088" or "C20ORF41" or "Regulator of telomere length" or "Telomere length regulator" or "Chromosome 20 open reading frame 41". The *Homo sapiens* RTEL1 gene is located at chromosome 20, 63,657,810 to 63,696,253, complement (*Homo sapiens* Updated Annotation, Release 109.20200228, GRCh38.p13). The RTEL1 protein is an ATP-dependent DNA helicase implicated in telomere-length regulation, DNA repair and the maintenance of genomic stability. The amino acid sequence of human RTEL1 is known in the art and can be assessed via UniProt, see UniProt entry Q9NZ71 for human RTEL1, hereby incorporated by reference.

Target Nucleic Acid

According to the present invention, the target nucleic acid is a nucleic acid, which encodes mammalian RTEL1 and may for example be a gene, a RNA, a mRNA, and pre-mRNA, a mature mRNA or a cDNA sequence. The target may therefore be referred to as an RTEL1 target nucleic acid.

The antisense oligonucleotide of the invention may for example target exon regions of a mammalian RTEL1, or may for example target intron region in the RTEL1 pre-mRNA. The human RTEL1 gene encodes 15 transcripts of these 7 are protein coding and therefore potential nucleic acid targets. Table 3 lists predicted exon and intron regions of the 7 transcripts, as positioned on the human RTEL1 pre-mRNA of SEQ ID NO: 1.

TABLE 3

Transcript-, exonic- and intronic regions in the human RTEL1 pre-mRNA (SEQ ID NO: 1) for the different protein coding RTEL1 mRNA transcripts

| | Transcript region | | Exonic regions | | | Intron regions | | |
|---|---|---|---|---|---|---|---|---|
| Transcript ID | start | end | Exon | start | end | intron | start | end |
| RTEL1-205 | 1 | 38444 | 1 | 1 | 657 | 1 | 657 | 1424 |
| ENST00000370018 | | | 2 | 1424 | 1695 | 2 | 1695 | 3489 |
| | | | 3 | 3489 | 3687 | 3 | 3687 | 4041 |
| | | | 4 | 4041 | 4134 | 4 | 4134 | 4737 |
| | | | 5 | 4737 | 4818 | 5 | 4818 | 5020 |
| | | | 6 | 5020 | 5080 | 6 | 5080 | 8195 |
| | | | 7 | 8195 | 8270 | 7 | 8270 | 9660 |
| | | | 8 | 9660 | 9744 | 8 | 9744 | 14747 |
| | | | 9 | 14747 | 14812 | 9 | 14812 | 16131 |
| | | | 10 | 16131 | 16284 | 10 | 16284 | 20336 |
| | | | 11 | 20336 | 20374 | 11 | 20374 | 20459 |
| | | | 12 | 20459 | 20537 | 12 | 20537 | 22040 |
| | | | 13 | 22040 | 22137 | 13 | 22137 | 22855 |
| | | | 14 | 22855 | 22910 | 14 | 22910 | 27714 |
| | | | 15 | 27714 | 27788 | 15 | 27788 | 27982 |
| | | | 16 | 27982 | 28063 | 16 | 28063 | 29829 |
| | | | 17 | 29829 | 29961 | 17 | 29961 | 30128 |
| | | | 18 | 30128 | 30241 | 18 | 30241 | 30330 |
| | | | 19 | 30330 | 30370 | 19 | 30370 | 30492 |
| | | | 20 | 30492 | 30577 | 20 | 30577 | 30719 |
| | | | 21 | 30719 | 30796 | 21 | 30796 | 31246 |
| | | | 22 | 31246 | 31323 | 22 | 31323 | 31693 |
| | | | 23 | 31693 | 31839 | 23 | 31839 | 31941 |
| | | | 24 | 31941 | 32056 | 24 | 32056 | 32278 |
| | | | 25 | 32278 | 32401 | 25 | 32401 | 32485 |
| | | | 26 | 32485 | 32632 | 26 | 32632 | 32996 |
| | | | 27 | 32996 | 33138 | 27 | 33138 | 33933 |
| | | | 28 | 33933 | 34028 | 28 | 34028 | 34996 |
| | | | 29 | 34996 | 35194 | 29 | 35194 | 35334 |
| | | | 30 | 35334 | 35474 | 30 | 35474 | 36563 |
| | | | 31 | 36563 | 36679 | 31 | 36679 | 36932 |

TABLE 3-continued

Transcript-, exonic- and intronic regions in the human RTEL1 pre-mRNA (SEQ ID NO: 1) for the different protein coding RTEL1 mRNA transcripts

| | Transcript region | | Exonic regions | | | Intron regions | | |
|---|---|---|---|---|---|---|---|---|
| Transcript ID | start | end | Exon | start | end | intron | start | end |
| | | | 32 | 36932 | 37165 | 32 | 37165 | 37257 |
| | | | 33 | 37257 | 37412 | 33 | 37412 | 37519 |
| | | | 34 | 37519 | 37671 | 34 | 37671 | 37969 |
| | | | 35 | 37969 | 38444 | | | |
| RTEL1-203 | 485 | 38433 | 1 | 485 | 657 | 1 | 657 | 1424 |
| ENST00000360203 | | | 2 | 1424 | 1695 | 2 | 1695 | 3489 |
| | | | 3 | 3489 | 3687 | 3 | 3687 | 4041 |
| | | | 4 | 4041 | 4134 | 4 | 4134 | 4737 |
| | | | 5 | 4737 | 4818 | 5 | 4818 | 5020 |
| | | | 6 | 5020 | 5080 | 6 | 5080 | 8195 |
| | | | 7 | 8195 | 8270 | 7 | 8270 | 9660 |
| | | | 8 | 9660 | 9744 | 8 | 9744 | 14747 |
| | | | 9 | 14747 | 14812 | 9 | 14812 | 16131 |
| | | | 10 | 16131 | 16284 | 10 | 16284 | 20336 |
| | | | 11 | 20336 | 20374 | 11 | 20374 | 20459 |
| | | | 12 | 20459 | 20537 | 12 | 20537 | 22040 |
| | | | 13 | 22040 | 22137 | 13 | 22137 | 22855 |
| | | | 14 | 22855 | 22910 | 14 | 22910 | 27714 |
| | | | 15 | 27714 | 27788 | 15 | 27788 | 27982 |
| | | | 16 | 27982 | 28063 | 16 | 28063 | 29829 |
| | | | 17 | 29829 | 29961 | 17 | 29961 | 30128 |
| | | | 18 | 30128 | 30241 | 18 | 30241 | 30330 |
| | | | 19 | 30330 | 30370 | 19 | 30370 | 30492 |
| | | | 20 | 30492 | 30577 | 20 | 30577 | 30719 |
| | | | 21 | 30719 | 30796 | 21 | 30796 | 31246 |
| | | | 22 | 31246 | 31323 | 22 | 31323 | 31693 |
| | | | 23 | 31693 | 31839 | 23 | 31839 | 31941 |
| | | | 24 | 31941 | 32056 | 24 | 32056 | 32278 |
| | | | 25 | 32278 | 32401 | 25 | 32401 | 32485 |
| | | | 26 | 32485 | 32632 | 26 | 32632 | 32996 |
| | | | 27 | 32996 | 33138 | 27 | 33138 | 33933 |
| | | | 28 | 33933 | 34028 | 28 | 34028 | 34996 |
| | | | 29 | 34996 | 35194 | 29 | 35194 | 35334 |
| | | | 30 | 35334 | 35474 | 30 | 35474 | 36563 |
| | | | 31 | 36563 | 36679 | 31 | 36679 | 36932 |
| | | | 32 | 36932 | 37165 | 32 | 37165 | 37257 |
| | | | 33 | 37257 | 37412 | 33 | 37412 | 37519 |
| | | | 34 | 37519 | 37841 | 34 | 37841 | 37969 |
| | | | 35 | 37969 | 38433 | | | |
| RTEL1-212 | 482 | 38171 | 1 | 482 | 657 | 1 | 657 | 1424 |
| ENST00000508582 | | | 2 | 1424 | 1695 | 2 | 1695 | 3489 |
| | | | 3 | 3489 | 3687 | 3 | 3687 | 4041 |
| | | | 4 | 4041 | 4134 | 4 | 4134 | 4665 |
| | | | 5 | 4665 | 4818 | 5 | 4818 | 5020 |
| | | | 6 | 5020 | 5080 | 6 | 5080 | 8195 |
| | | | 7 | 8195 | 8270 | 7 | 8270 | 9660 |
| | | | 8 | 9660 | 9744 | 8 | 9744 | 14747 |
| | | | 9 | 14747 | 14812 | 9 | 14812 | 16131 |
| | | | 10 | 16131 | 16284 | 10 | 16284 | 20336 |
| | | | 11 | 20336 | 20374 | 11 | 20374 | 20459 |
| | | | 12 | 20459 | 20537 | 12 | 20537 | 22040 |
| | | | 13 | 22040 | 22137 | 13 | 22137 | 22855 |
| | | | 14 | 22855 | 22910 | 14 | 22910 | 27714 |
| | | | 15 | 27714 | 27788 | 15 | 27788 | 27982 |
| | | | 16 | 27982 | 28063 | 16 | 28063 | 29829 |
| | | | 17 | 29829 | 29961 | 17 | 29961 | 30128 |
| | | | 18 | 30128 | 30241 | 18 | 30241 | 30330 |
| | | | 19 | 30330 | 30370 | 19 | 30370 | 30492 |
| | | | 20 | 30492 | 30577 | 20 | 30577 | 30719 |
| | | | 21 | 30719 | 30796 | 21 | 30796 | 31246 |
| | | | 22 | 31246 | 31323 | 22 | 31323 | 31693 |
| | | | 23 | 31693 | 31839 | 23 | 31839 | 31941 |
| | | | 24 | 31941 | 32056 | 24 | 32056 | 32278 |
| | | | 25 | 32278 | 32401 | 25 | 32401 | 32485 |
| | | | 26 | 32485 | 32632 | 26 | 32632 | 32996 |
| | | | 27 | 32996 | 33138 | 27 | 33138 | 33933 |
| | | | 28 | 33933 | 34028 | 28 | 34028 | 34996 |
| | | | 29 | 34996 | 35194 | 29 | 35194 | 35334 |
| | | | 30 | 35334 | 35474 | 30 | 35474 | 36563 |
| | | | 31 | 36563 | 36679 | 31 | 36679 | 36932 |
| | | | 32 | 36932 | 37165 | 32 | 37165 | 37257 |
| | | | 33 | 37257 | 37412 | 33 | 37412 | 37519 |
| | | | 34 | 37519 | 37671 | 34 | 37671 | 37969 |

TABLE 3-continued

Transcript-, exonic- and intronic regions in the human RTEL1 pre-mRNA (SEQ ID NO: 1) for the different protein coding RTEL1 mRNA transcripts

| | Transcript region | | Exonic regions | | | Intron regions | | |
|---|---|---|---|---|---|---|---|---|
| Transcript ID | start | end | Exon | start | end | intron | start | end |
| | | | 35 | 37969 | 38171 | | | |
| RTEL1-201 | 505 | 38434 | 1 | 505 | 650 | 1 | 650 | 3489 |
| ENST00000318100 | | | 2 | 3489 | 3687 | 2 | 3687 | 4041 |
| | | | 3 | 4041 | 4134 | 3 | 4134 | 4737 |
| | | | 4 | 4737 | 4818 | 4 | 4818 | 5020 |
| | | | 5 | 5020 | 5080 | 5 | 5080 | 8195 |
| | | | 6 | 8195 | 8270 | 6 | 8270 | 9660 |
| | | | 7 | 9660 | 9744 | 7 | 9744 | 14747 |
| | | | 8 | 14747 | 14812 | 8 | 14812 | 16131 |
| | | | 9 | 16131 | 16284 | 9 | 16284 | 20336 |
| | | | 10 | 20336 | 20374 | 10 | 20374 | 20459 |
| | | | 11 | 20459 | 20537 | 11 | 20537 | 22040 |
| | | | 12 | 22040 | 22137 | 12 | 22137 | 22855 |
| | | | 13 | 22855 | 22910 | 13 | 22910 | 27714 |
| | | | 14 | 27714 | 27788 | 14 | 27788 | 27982 |
| | | | 15 | 27982 | 28063 | 15 | 28063 | 29829 |
| | | | 16 | 29829 | 29961 | 16 | 29961 | 30128 |
| | | | 17 | 30128 | 30241 | 17 | 30241 | 30330 |
| | | | 18 | 30330 | 30370 | 18 | 30370 | 30492 |
| | | | 19 | 30492 | 30577 | 19 | 30577 | 30719 |
| | | | 20 | 30719 | 30796 | 20 | 30796 | 31246 |
| | | | 21 | 31246 | 31323 | 21 | 31323 | 31693 |
| | | | 22 | 31693 | 31839 | 22 | 31839 | 31941 |
| | | | 23 | 31941 | 32056 | 23 | 32056 | 32278 |
| | | | 24 | 32278 | 32401 | 24 | 32401 | 32485 |
| | | | 25 | 32485 | 32632 | 25 | 32632 | 32996 |
| | | | 26 | 32996 | 33138 | 26 | 33138 | 33933 |
| | | | 27 | 33933 | 34028 | 27 | 34028 | 34996 |
| | | | 28 | 34996 | 35194 | 28 | 35194 | 35334 |
| | | | 29 | 35334 | 35474 | 29 | 35474 | 36563 |
| | | | 30 | 36563 | 36679 | 30 | 36679 | 36932 |
| | | | 31 | 36932 | 37165 | 31 | 37165 | 37257 |
| | | | 32 | 37257 | 37412 | 32 | 37412 | 37519 |
| | | | 33 | 37519 | 37671 | 33 | 37671 | 37969 |
| | | | 34 | 37969 | 38434 | | | |
| RTEL1-202 | 551 | 16284 | 1 | 551 | 650 | 1 | 650 | 1424 |
| ENST00000356810 | | | 2 | 1424 | 1695 | 2 | 1695 | 3489 |
| | | | 3 | 3489 | 3687 | 3 | 3687 | 4041 |
| | | | 4 | 4041 | 4134 | 4 | 4134 | 4587 |
| | | | 5 | 4587 | 4818 | 5 | 4818 | 5020 |
| | | | 6 | 5020 | 5080 | 6 | 5080 | 8195 |
| | | | 7 | 8195 | 8270 | 7 | 8270 | 9660 |
| | | | 8 | 9660 | 9744 | 8 | 9744 | 14747 |
| | | | 9 | 14747 | 14812 | 9 | 14812 | 16131 |
| | | | 10 | 16131 | 16284 | | | |
| RTEL1-206 | 30530 | 33067 | 1 | 30530 | 30577 | 1 | 30577 | 30719 |
| ENST00000425905 | | | 2 | 30719 | 30796 | 2 | 30796 | 31246 |
| | | | 3 | 31246 | 31323 | 3 | 31323 | 31941 |
| | | | 4 | 31941 | 32056 | 4 | 32056 | 32278 |
| | | | 5 | 32278 | 32401 | 5 | 32401 | 32485 |
| | | | 6 | 32485 | 32632 | 6 | 32632 | 32996 |
| | | | 7 | 32996 | 33067 | | | |
| RTEL1-214 | 811 | 3653 | 1 | 811 | 943 | 1 | 943 | 1424 |
| ENST00000646389 | | | 2 | 1424 | 1695 | 2 | 1695 | 3489 |
| | | | 3 | 3489 | 3653 | | | |

Suitably, the target nucleic acid encodes an RTEL1 protein, in particular mammalian RTEL1, such as human RTEL1 (See for example tables 3 and 4) which provides the pre-mRNA sequences for human and monkey, RTEL1.

In some embodiments, the target nucleic acid is selected from SEQ ID NO: 1 and/or 2 or naturally occurring variants thereof (e.g. sequences encoding a mammalian RTEL1 protein).

If employing the antisense oligonucleotide of the invention, or the conjugate of the invention, in research or diagnostics the target nucleic acid may be a cDNA or a synthetic nucleic acid derived from DNA or RNA.

For in vivo or in vitro application, the antisense oligonucleotide of the invention is typically capable of inhibiting the expression of the RTEL1 target nucleic acid in a cell, which is expressing the RTEL1 target nucleic acid. The contiguous sequence of nucleobases of the antisense oligonucleotide of the invention is typically complementary to the RTEL1 target nucleic acid, as measured across the length of the antisense oligonucleotide, optionally with the exception of one or two mismatches, and optionally excluding nucleotide based linker regions which may link the antisense oligonucleotide to an optional functional group such as a conjugate, or other non-complementary terminal nucleotides (e.g. region D' or D"). The target nucleic acid may, in some embodiments, be a RNA or DNA, such as a messenger RNA, such as a pre-mRNA, such as human RTEL1, e.g. the human RTEL1 pre-mRNA sequence, such as that disclosed as SEQ ID NO: 1, or the cynomolgus monkey RTEL1 pre-mRNA sequence, such as that disclosed as SEQ ID NO: 2. SEQ ID NOs: 1 and 2 are DNA sequences—it will be understood that target RNA sequences have uracil (U) bases in place of the thymidine bases (T).

Further information on exemplary target nucleic acids is provided in Tables 4 and 5.

TABLE 4

Genome and assembly information for RTEL1 across species.

| Species | Chr. | Strand | Genomic coordinates Start | End | Assembly | ensembl gene_id |
|---|---|---|---|---|---|---|
| Human | 20 | fwd | 63657810 | 63696253 | GRCh38.p12 | ENSG00000258366 |
| Cynomolgus monkey | 10 | fwd | 95853726 | 95890939 | Macaca_fascicularis_5.0 | ENSMFAG00000043680 |

Fwd = forward strand.

The genome coordinates provide the pre-mRNA sequence (genomic sequence). The NCO reference provides the mRNA sequence (cDNA sequence).

TABLE 5

Sequence details for RTEL1 across species.

| Species | RNA type | Length (nt) | SEQ ID NO |
|---|---|---|---|
| Human | premRNA | 38444 | 1 |
| Monkey | premRNA | 37214 | 2 |

Note:
SEQ ID NO: 2 comprises regions of multiple NNNNs, where the sequencing has been unable to accurately refine the sequence, and a degenerate sequence is therefore included. For the avoidance of doubt the compounds of the invention are complementary to the actual target sequence and are not therefore degenerate compounds.

In some embodiments, the target nucleic acid is SEQ ID NO: 1.

In some embodiments, the target nucleic acid is SEQ ID NO: 2.

In some embodiments, the target nucleic acid is SEQ ID NO: 1 and 2.

Target Sequence

The term "target sequence" as used herein refers to a sequence of nucleotides present in the target nucleic acid, which comprises the nucleobase sequence, which is complementary to the oligonucleotide of the invention. In some embodiments, the target sequence consists of a region on the target nucleic acid with a nucleobase sequence that is complementary to the contiguous nucleotide sequence of the oligonucleotide of the invention. This region of the target nucleic acid may interchangeably be referred to as the target nucleotide sequence, target sequence or target region. In some embodiments, the target sequence is longer than the complementary sequence of a single oligonucleotide, and may, for example represent a preferred region of the target nucleic acid, which may be targeted by several oligonucleotides of the invention.

The oligonucleotide of the invention comprises a contiguous nucleotide sequence, which is complementary to and hybridizes to the target nucleic acid, such as a target sequence described herein.

The target sequence to which the oligonucleotide is complementary to generally comprises a contiguous nucleobases sequence of at least 10 nucleotides. The contiguous nucleotide sequence is between 10 to 30 nucleotides in length, such as 12 to 30, such as 14 to 20, such as 15 to 18 contiguous nucleotides in length, such as 15, 16, 17 contiguous nucleotides in length.

Target Sequence Regions

The inventors have identified particularly effective sequences of the RTEL1 target nucleic acid, which may be targeted by the oligonucleotide of the invention, or the conjugate thereof.

In some embodiments, the target sequence is SEQ ID NO 7.

In some embodiments, the target sequence is SEQ ID NO 8.

In some embodiments, the target sequence is SEQ ID NO 9.

In some embodiments, the target sequence is SEQ ID NO 10.

In some embodiments, the target sequence is SEQ ID NO 11.

```
SEQ ID NO 7:
TTTGACCAGAGTATGTAAAATT

SEQ ID NO 8:
ACCAGAGTATGTAAAATT

SEQ ID NO: 9:
GACCAGAGTATGTAAAATT

SEQ ID NO: 10:
TTTGACCAGAGTATGTAA

SEQ ID NO: 11:
GAGATTCAAGTTATAATAAAG
```

SEQ ID NOS: 7 to 11 are DNA sequences—it will be understood that target RNA sequences have uracil (U) bases in place of the thymidine bases (T).

The target sequences shown in SEQ ID NOs: 7 to 10 can be found in intron 8 of human RTEL1. The target sequence shown in SEQ ID No: 11 can be found in intron 7 of human RTEL1.

In some embodiments, the target sequence is the region from nucleotides 11753-11774 of SEQ ID NO: 1.

In some embodiments, the target sequence is the region from nucleotides 11757-11774 of SEQ ID NO: 1.

In some embodiments, the target sequence is the region from nucleotides 11756-11774 of SEQ ID NO: 1.

In some embodiments, the target sequence is the region from nucleotides 11753-11770 of SEQ ID NO: 1.

In some embodiments, the target sequence is the region from nucleotides 8681-8701 of SEQ ID NO: 1.

Target Cell

The term a "target cell" as used herein refers to a cell, which is expressing the target nucleic acid. In some embodiments, the target cell may be in vivo or in vitro. In some embodiments, the target cell is a mammalian cell such as a rodent cell, such as a mouse cell or a rat cell, or a primate cell such as a monkey cell or a human cell.

Typically, the target cell expresses the RTEL1 mRNA, such as the RTEL1 pre-mRNA or RTEL1 mature mRNA. For experimental evaluation a target cell may be used which expresses a nucleic acid which comprises a target sequence, such as the human RTEL1 pre-mRNA, e.g. SEQ ID NO: 1.

The poly A tail of RTEL1 mRNA is typically disregarded for antisense oligonucleotide targeting.

The antisense oligonucleotide of the invention is typically capable of inhibiting the expression of the RTEL1 target nucleic acid in a cell which is expressing the RTEL1 target nucleic acid (a target cell), for example either in vivo or in vitro.

Further, the target cell may be a hepatocyte. In one embodiment, the target cell is HBV infected primary human hepatocytes, either derived from HBV infected individuals or from a HBV infected mouse with a humanized liver (PhoenixBio, PXB-mouse).

In accordance with the present invention, the target cell may be infected with HBV. Further, the target cell may comprise HBV cccDNA. Thus, the target cell preferably comprises RTEL1 mRNA, such as the RTEL1 pre-mRNA or RTEL1 mature mRNA, and HBV cccDNA.

Naturally Occurring Variant

The term "naturally occurring variant" refers to variants of RTEL1 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian RTEL1 target nucleic acid, such as a target nucleic acid of SEQ ID NO: 1. In some embodiments, the naturally occurring variants have at least 99% homology to the human RTEL1 target nucleic acid of SEQ ID NO: 1.

Inhibition of Expression

The term "Inhibition of expression" as used herein is to be understood as an overall term for an oligonucleotide's ability to inhibit the amount or the activity of RTEL1 in a target cell. Inhibition of activity may be determined by measuring the level of RTEL1 pre-mRNA or RTEL1 mRNA, or by measuring the level of RTEL1 or RTEL1 activity in a cell. Inhibition of expression may therefore be determined in vitro or in vivo.

Typically, inhibition of expression is determined by comparing the inhibition of activity due to the administration of an effective amount of the antisense oligonucleotide to the target cell and comparing that level to a reference level obtained from a target cell without administration of the antisense oligonucleotide (control experiment), or a known reference level (e.g. the level of expression prior to administration of the effective amount of the antisense oligonucleotide, or a predetermine or otherwise known expression level).

For example a control experiment may be an animal or person, or a target cell treated with a saline composition or a reference oligonucleotide (often a scrambled control).

The term inhibition or inhibit may also be referred as down-regulate, reduce, suppress, lessen, lower, the expression of RTEL1, such as RTEL1 pre-mRNA.

The inhibition of expression may occur e.g. by degradation of pre-mRNA or mRNA (e.g. using RNase H recruiting oligonucleotides, such as gapmers).

High Affinity Modified Nucleosides

A high affinity modified nucleoside is a modified nucleotide which, when incorporated into the oligonucleotide enhances the affinity of the oligonucleotide for its complementary target, for example as measured by the melting temperature (Tm). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides, which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

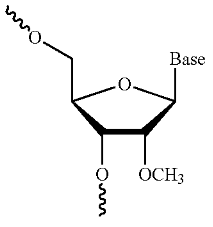
2'-O-Me

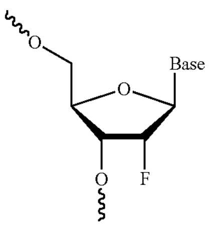
2'F-RNA

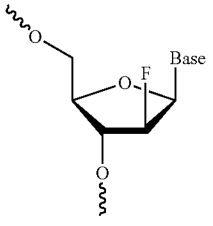
2'F-ANA

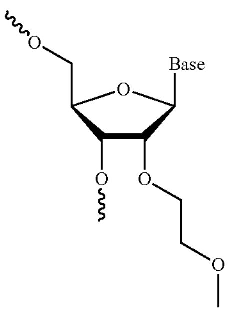
2'-O-MOE

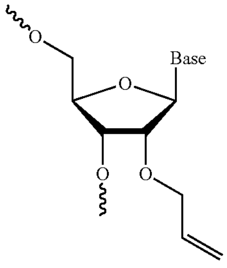
2'-O-Allyl

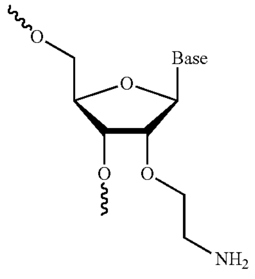
2'-O-Ethylamine

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1

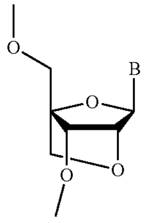
β-D-oxy LNA

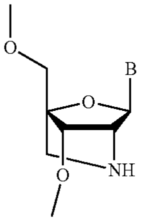
β-D-amino LNA

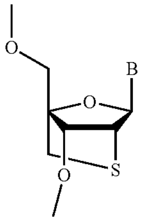
β-D-thio LNA

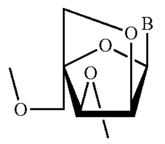
α-L-oxy LNA

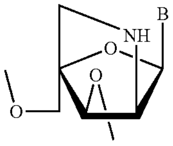
α-L-amino LNA

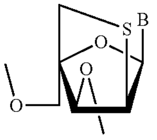
α-L-thio LNA

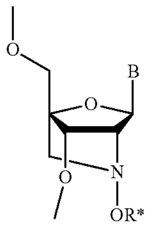
β-D-amino substituted LNA

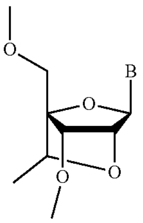
6'methylβ-D-oxy LNA

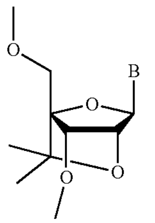
6'dimethylβ-D-oxy LNA

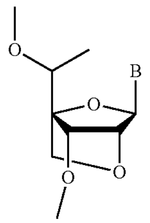
5'methylβ-D-oxy LNA

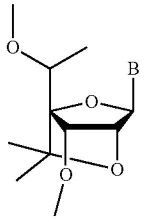
5'methyl, 6'dimethyl β-D-oxy LNA

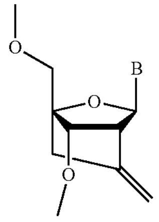
Carbocyclic(vinyl)β-D-LNA

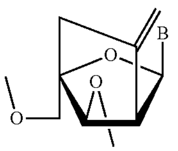
Carbocyclic(vinyl)α-L-LNA

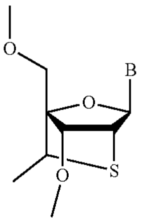
6'methyl thio β-D LNA

-continued

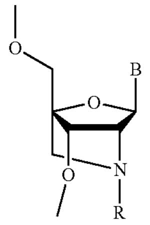

Substituted β-D amino LNA

Particular LNA nucleosides are beta-D-oxy-LNA, 6′-methyl-beta-D-oxy LNA such as (S)-6′-methyl-beta-D-oxy-LNA (ScET) and ENA. A particularly advantageous LNA is beta-D-oxy-LNA.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly an endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers.

RNase H Activity and Recruitment

The RNase H activity of an antisense oligonucleotide refers to its ability to recruit RNase H when in a duplex with a complementary RNA molecule. WO01/23613 provides in vitro methods for determining RNase H activity, which may be used to determine the ability to recruit RNase H. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RNase H activity, recombinant human RNase H1 is available from Creative Biomart® (Recombinant Human RNase H1 fused with His tag expressed in *E. coli*).

Gapmer

The antisense oligonucleotide of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5->3' orientation. The "gap" region (G) comprises a stretch of contiguous DNA nucleotides, which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank. In some embodiments, all internucleoside linkages between the nucleosides of the gapmer region of formula F-G-F' are phosphorothioate internucleoside linkages.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, such as from 15 to 20, such as 16 to 18 nucleosides.

By way of example, the gapmer oligonucleotide of the present invention can be represented by the following formulae:

$F_{1-8}$-$G_{5-16}$-$F'_{1-8}$, such as $F_{1-8}$-$G_{7-16}$-$F_{2-8}$, or $F_{1-8}$-$G_{11-16}$-$F'_{2-8}$, with the proviso that the overall length of the gapmer regions F-G-F' is at least 12, such as at least 14 nucleotides in length.

In an aspect of the invention the antisense oligonucleotide or contiguous nucleotide sequence thereof consists of or comprises a gapmer of formula 5'-F-G-F'-3', where region F and F' independently comprise or consist of 1-8 nucleosides, of which 1-4 are 2' sugar modified and defines the 5' and 3' end of the F and F' region, and G is a region between 6 and 16 nucleosides which are capable of recruiting RNase H.

Regions F, G and F' are further defined below and can be incorporated into the F-G-F' formula.

Gapmer—Region G

Region G (gap region) of the gapmer is a region of nucleosides which enables the oligonucleotide to recruit RNase H, such as human RNase H1, typically DNA nucleosides. RNase H is a cellular enzyme, which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments, consist of 6, 7, 8, 9, 10, 11, 12, 13, 14, 15 or 16 contiguous DNA nucleosides. Further, region G may have a length of 11 to 16 contiguous DNA nucleotides.

One or more cytosine (C) DNA in the gap region may in some instances be methylated (e.g. when a DNA c is followed by a DNA g), such residues are annotated as 5-methyl-cytosine $r^e$q. In some embodiments, the gap region G may consist of 6, 7, 8, 9, 10, 11, 12, 13, 14, 15 or 16 contiguous phosphorothioate linked DNA nucleosides.

In some embodiments, all internucleoside linkages in the gap are phosphorothioate linkages.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 2-4 contiguous nucleotides in length. In some embodiments, the length of region F is 2 contiguous nucleotides. In some embodiments, the length of region F is 3 contiguous nucleotides. In some embodiments, the length of region F is 4 contiguous nucleotides.

Advantageously the 5' most nucleoside of region F is a sugar modified nucleoside. In some embodiments, the two 5' most nucleosides of region F are sugar modified nucleosides. In some embodiments, the 5' most nucleoside of region F is an LNA nucleoside. In some embodiments, the two 5' most nucleosides of region F are LNA nucleosides.

Region F' is 1-8 contiguous nucleotides in length, such as 2-6 contiguous nucleotides in length. In some embodiments, the length of region F' is 2 contiguous nucleotides. In some embodiments, the length of region F' is 4 contiguous nucleotides. In some embodiments, the length of region F' is 5 contiguous nucleotides. In some embodiments, the length of region F' is 6 contiguous nucleotides. Advantageously, the 3' most nucleoside of region F' is a sugar modified nucleoside. In some embodiments, the two 3' most nucleosides of region F' are sugar modified nucleosides. In some embodiments, the two 3' most nucleosides of region F' are LNA nucleosides. In some embodiments, the 3' most nucleoside of region F' is an LNA nucleoside.

It should be noted that when the length of region F is one, it is advantageously an LNA nucleoside. Further, it is noted that when the length of region F and/or F' is two, both nucleosides of region F and/or F' are advantageously LNA nucleosides.

In some embodiments, the sugar modified nucleosides in region F and F' consist of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as beta-D-oxy LNA nucleosides. In an alternative embodiment, all the sugar modified nucleosides of region F and F' are LNA nucleosides, such as beta-D-oxy LNA nucleosides, wherein region F or F', or both regions F and F' may comprise DNA nucleosides (an alternating flank, see definition of these for more details).

In some embodiments, the 5' most and the 3' most nucleosides of region F and F' are LNA nucleosides, such as beta-D-oxy LNA nucleosides.

In some embodiments, the internucleoside linkage between region F and region G and/or the internucleoside linkage between region F' and region G is a phosphorothioate internucleoside linkage. In some embodiments, the internucleoside linkages between the nucleosides of region F or F', F and F' are phosphorothioate internucleoside linkages.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments, the LNA gapmer is of formula: $[LNA]_{1-5}$-[region G]-$[LNA]_{1-5}$, wherein region G is or comprises a region of contiguous DNA nucleosides which are capable of recruiting RNaseH.

MOE Gapmers

A MOE gapmers is a gapmer wherein regions F and F' consist of MOE nucleosides. In some embodiments, the MOE gapmer is of design $[MOE]_{1-8}$-$[Region\ G]_{5-16}$-$[MOE]_{1-8}$, such as $[MOE]_{2-7}$-$[Region\ G]_{6-14}$-$[MOE]_{2-7}$, such as $[MOE]_{3-6}$-$[Region\ G]_{8-12}$-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleoside. In some embodiments, wherein at least one of region F and F', or both region F and F' comprise at least one LNA nucleoside, the remaining nucleosides of region F and F' are independently selected from the group consisting of MOE and LNA. In some embodiments, wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Alternating Flank Gapmers

Flanking regions may comprise both LNA and DNA nucleoside and are referred to as "alternating flanks" as they comprise an alternating motif of LNA-DNA-LNA nucleosides. Gapmers comprising at least one alternating flank are referred to as "alternating flank gapmers". "Alternative flank gapmers" are thus LNA gapmer oligonucleotides where at least one of the flanks (F or F') comprises DNA in addition to the LNA nucleoside(s). In some embodiments, at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides. Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flak regions can be annotated as a series of integers, representing a number of LNA nucleosides (L) followed by a number of DNA nucleosides (D), for example [L]1-3-[D]1-3-[L]1-3 or [L]1-2-[D]1-2-[L]1-2-[D]1-2-[L]1-2 oligonucleotide designs these will often be represented as numbers such that 2-2-1 represents 5' [L]2-[D]2-[L] 3', and 1-1-1-1-1 represents 5' [L]-[D]-[L]-[D]-[L] 3'. The length of the flank (region F and F') in oligonucleotides with alternating flanks may be as described herein above for these regions, such as 4 to 8, such as 5 to 6 nucleosides, such as 4, 5, 6 or 7 modified nucleosides. It may be advantageous to have at least two LNA nucleosides at the 3' end of the 3' flank (F'), to confer additional exonuclease resistance.

Region D' or D" in an Oligonucleotide

The oligonucleotide of the invention may in some embodiments comprise or consist of the contiguous nucleotide sequence of the oligonucleotide, which is complementary to the target nucleic acid, such as a gapmer region F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively, it may be used to provide exonuclease protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments, the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

F-G-F'; in particular $F_{1-8}$-$G_{5-16}$-$F'_{2-8}$

D'-F-G-F', in particular $D'_{1-3}$-$F_{1-8}$-$G_{5-16}$-$F'_{2-8}$

F-G-F'-D", in particular $F_{1-8}$-$G_{5-16}$-$F'_{2-8}$-$D''_{1-3}$

D'-F-G-F'-D", in particular $D'_{1-3}$-$F_{1-8}$-$G_{5-16}$-$F'_{2-8}$-$D''_{1-3}$ In some embodiments, the internucleoside linkage positioned between region D' and region F is a phosphodiester linkage. In some embodiments, the internucleoside linkage positioned between region F' and region D" is a phosphodiester linkage.

Conjugate

The term conjugate as used herein refers to an oligonucleotide, which is covalently linked to a non-nucleotide moiety (conjugate moiety or region C or third region). The conjugate moiety may be covalently linked to the antisense oligonucleotide, optionally via a linker group, such as region D' or D"

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103.

In some embodiments, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

Exemplary conjugate moieties include those capable of binding to the asialoglycoprotein receptor (ASGPR). In particular, tri-valent N-acetylgalactosamine conjugate moieties are suitable for binding to the ASGPR, see for example WO 2014/076196, WO 2014/207232 and WO 2014/179620. Such conjugates serve to enhance uptake of the oligonucleotide to the liver.

In some embodiments, the conjugate is an antibody or an antibody fragment which has a specific affinity for a transferrin receptor, for example as disclosed in WO 2012/143379 herby incorporated by reference. In some embodiments, the non-nucleotide moiety is an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments, of the invention the conjugate or oligonucleotide conjugate of the invention may optionally, comprise a linker region (second region or region B and/or region Y), which is positioned between the oligonucleotide or contiguous nucleotide sequence complementary to the target nucleic acid (region A or first region) and the conjugate moiety (region C or third region).

Biocleavable linkers (Region B) comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment, the biocleavable linker is susceptible to S1 nuclease cleavage. In some embodiments, the physiologically labile linker (biocleavable) comprises between 1 and 10 linked nucleosides, such as 1, 2, 3, 4, 5, 6, 7, 8, 9 or 10 linked nucleosides, such as between 2 and 6 linked nucleosides, such as between 2 and 5 linked nucleosides, such as between 2 and 4 linked nucleosides, where at least two consecutive linkages are biocleavable, such as phosphodiester linkages, such as at least 3 or 4 or 5 consecutive phosphodiester linkages. Preferably the nucleosides are DNA or RNA.

In one embodiment, the linker between the oligonucleotide and the conjugate moiety is a physiologically labile linker composed of 2 to 5 consecutive phosphodiester linked nucleosides comprising at least two consecutive phosphodiester linkages at the 5' or 3' terminal of the contiguous nucleotide sequence of the antisense oligonucleotide.

In some embodiments, the physiologically labile linker comprises or consists of a DNA dinucleotide with a sequence selected from the group consisting of AA, AT, AC, AG, TA, TT, TC, TG, CA, CT, CC, CG, GA, GT, GC, or GG, where there is a phosphodiester linkage between the two DNA nucleosides and at least one further phosphodiester at the 5' or 3' end of the dinucleotide linking either the oligonucleotide of the nucleic acid molecule to the dinucleotide or the conjugate moiety to the dinucleotide. For example, the linker may by a CA dinucleotide. In some embodiments, the physiologically labile linker comprises or consists of a DNA trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG, where there are phosphodiester linkages between the DNA nucleosides and potentially a further phosphodiester at the 5' or 3' end of the trinucleotide. Phosphodiester containing biocleavable linkers are described in more detail in WO 2014/076195 (hereby incorporated by reference). In a conjugate compound with a biocleavable linker at least about 50% of the conjugate moiety is cleaved from the oligonucleotide, such as at least about 60% cleaved, such as at least about 70% cleaved, such as at least about 80% cleaved, such as at least about 85% cleaved, such as at least about 90% cleaved, such as at least about 95% of the conjugate moiety is cleaved from the oligonucleotide cleaved when compared against a standard.

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups. The oligonucleotide conjugates of the present invention can be constructed of the following regional elements A-C, A-B-C, A-B-Y-C, A-Y-B-C or A-Y-C. In some embodiments, the linker (region Y) is an amino alkyl, such as a C2-C36 amino alkyl group, including, for example C6 to C12 amino alkyl groups. In some embodiments, the linker (region Y) is a C6 amino alkyl group.

Preferably, the cleavable linker is cleaved after delivery of the conjugate of the present invention to its target cell. For example, the linker is cleaved off after GalNAc mediated delivery of the conjugate to the target cell (such as a liver cell), leaving the naked compound as active drug. For example, the conjugates tested in the Examples section contain a CA dinucleotide linker.

Pharmaceutically Acceptable Salts

The term "pharmaceutically acceptable salts" refers to those salts, which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition, these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compounds of the present invention can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic. Prophylactic can be understood as preventing an HBV infection from turning into a chronic HBV infection or the prevention of severe liver diseases such as liver cirrhosis and hepatocellular carcinoma caused by a chronic HBV infection.

Prevention

Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a HBV infection" includes preventing a HBV infection from occurring in a subject, and preventing the occurrence of symptoms of a HBV infection. In the present invention in particular the prevention of HBV infection in children from HBV infected mothers are contemplated. Also contemplated is the prevention of an acute HBV infection turning into a chronic HBV infection.

Patient

For the purposes of the present invention, the "subject" or "patient" may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably, the subject is human. In some embodiments, the patient is suffering from a disease as referred to herein, such as HBV infection. In some embodiments, the patient is susceptible to said disease.

DETAILED DESCRIPTION OF THE INVENTION

Hepatitis B virus (HBV) covalently closed circular DNA (cccDNA) in infected hepatocytes is responsible for persistent chronic infection and reactivation, being the template for all viral subgenomic transcripts and pre-genomic RNA (pgRNA) to ensure both newly synthesized viral progeny and cccDNA pool replenishment via intracellular nucleocapsid recycling. RTEL1 is associated with cccDNA stability. Inhibition of RTEL1 leads to destabilization of cccDNA in HBV infected subjects, which in turn opens the opportunity for a complete cure of chronically infected HBV patients.

One aspect of the present invention is an enhanced antisense oligonucleotide targeting RTEL1, or a conjugate thereof for use in the treatment and/or prevention of HBV infection, in particular a chronic HBV infection.

In one embodiment, the antisense oligonucleotide targeting RTEL1, or a conjugate thereof can for example reduce the expression of RTEL1 protein, the binding of RTEL1 protein to cccDNA and thereby reducing cccDNA and/or pgRNA in an infected cell, such as an HBV infected cell.

In one embodiment, the antisense oligonucleotide targeting RTEL1, or a conjugate thereof is capable of reducing HBsAg and/or HBeAg in vivo in an HBV infected individual.

In one embodiment, the antisense oligonucleotide targeting RTEL1, or a conjugate thereof is capable of reducing cccDNA in vivo in an HBV infected individual.

In one embodiment, the antisense oligonucleotide targeting RTEL1, or a conjugate thereof is capable of reducing pgRNA in vivo in an HBV infected individual.

The Antisense Oligonucleotide of the Invention

The enhanced antisense oligonucleotides of the invention or conjugates thereof are potentially excellent RTEL1 inhibitors since they can target the RTEL1 transcript and promote its degradation either via RNase H cleavage.

One aspect of the present invention is an enhanced antisense oligonucleotide or conjugates thereof for use in treatment and/or prevention of HBV infection.

The present section describes novel oligonucleotides suitable for use in treatment and/or prevention of HBV infection.

The antisense oligonucleotides of the present invention or conjugates thereof are capable of inhibiting expression of RTEL1 in vitro and in vivo. The inhibition is achieved by hybridizing an oligonucleotide to a target nucleic acid encoding RTEL1 or which is involved in the regulation of RTEL1. The target nucleic acid may be a mammalian RTEL1 sequence, such as the sequence of SEQ ID NO: 1 and/or 2.

In some embodiments, the antisense oligonucleotide of the invention or conjugates thereof capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments, the antisense oligonucleotide of the invention or conjugates thereof may be capable of inhibiting expression levels of RTEL1 mRNA by at least 60% or 70% in vitro using 10 μM in PXB-PHH cells. In some embodiments, the antisense oligonucleotide of the invention or conjugates thereof may be capable of inhibiting expression levels of RTEL1 protein by at least 50% in vitro using 10 μM in PXB-PHH cells, this range of target reduction is advantageous in terms of selecting antisense oligonucleotides with good correlation to the cccDNA reduction. Suitably, the examples provide assays, which may be used to measure RTEL1 RNA inhibition (e.g. Example 1). The target inhibition is triggered by the hybridization between a contiguous nucleotide sequence of the antisense oligonucleotide and the target nucleic acid. In some embodiments, the antisense oligonucleotide of the invention comprises mismatches between the antisense oligonucleotide and the target nucleic acid. Despite mismatches hybridization to the target nucleic acid may still be sufficient to show a desired inhibition of RTEL1 expression. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

An aspect of the present invention relates to an enhanced antisense oligonucleotide of 12 to 60 nucleotides in length, which comprises a contiguous nucleotide sequence of at least 10 nucleotides in length, such as at least 12 to 30 nucleotides in length, which is at least 95% complementary, such as fully complementary, to a mammalian RTEL1 target nucleic acid, in particular a human RTEL1 nucleic acid. The antisense oligonucleotide is capable of inhibiting the expression of RTEL1.

In some embodiments, the antisense oligonucleotide of the present invention comprises a contiguous nucleotide sequence of 12 to 22 nucleotides, such as of 15 to 20 nucleotides, with at least 90% complementarity, such as fully complementary, to the target nucleic acid of SEQ ID NO: 7.

In some embodiments, antisense oligonucleotide comprises a contiguous nucleotide sequence of 15 to 18 nucleotides, such as of 17 or 18 nucleotides, with at least 90% complementarity, such as fully complementary, to the target nucleic acid of SEQ ID NO: 8.

In some embodiments, antisense oligonucleotide comprises a contiguous nucleotide sequence of 15 to 19 nucleotides, such as of 18 or 19 nucleotides, with at least 90% complementarity, such as fully complementary, to the target nucleic acid of SEQ ID NO: 9.

In some embodiments, antisense oligonucleotide comprises a contiguous nucleotide sequence of 15 to 18 nucleotides, such as of 17 or 18 nucleotides, with at least 90% complementarity, such as fully complementary, to the target nucleic acid of SEQ ID NO: 10.

In some embodiments, the antisense oligonucleotide of the present invention comprises a contiguous nucleotide sequence of 12 to 22 nucleotides, such as of 17 to 22 nucleotides, with at least 90% complementarity, such as fully complementary, to the target nucleic acid of SEQ ID NO: 11.

In some embodiments, the antisense oligonucleotide comprises a contiguous nucleotide sequence of 15 to 22 nucleotides, such as of 15 to 18 nucleotides, such as of 17 or 18 nucleotides with at least 90% complementarity, such as fully complementary, to the target nucleic acid selected from the following regions of SEQ ID NO: 1: 8681-8701 of SEQ ID NO: 1, 11753-11774 of SEQ ID NO: 1, such as to a region from nucleotides 11757-11774, 11756-11774, or 11753-11770 of SEQ ID NO: 1.

An aspect of the invention relates to an antisense oligonucleotide, which is an antisense oligonucleotide of 12 to 30 nucleotides in length, comprising a contiguous nucleotide sequence of at least 10 nucleotides, such as 10 to 30 nucleotides in length, which is at least 90% complementary, such as fully complementary, to a mammalian RTEL1.

A further aspect of the present invention relates to an antisense oligonucleotide comprising a contiguous nucleotide sequence of 12 to 20, such as 15 to 22, nucleotides in length with at least 90% complementarity, such as fully complementary, to the target nucleic acid of SEQ ID NO: 1.

In some embodiments, the antisense oligonucleotide comprises a contiguous sequence of 10 to 30 nucleotides in length, which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

It is advantageous if the antisense oligonucleotide of the invention, or contiguous nucleotide sequence thereof is fully complementary (100% complementary) to a region of the target nucleic acid, or in some embodiments, may comprise one or two mismatches between the oligonucleotide and the target nucleic acid.

In some embodiments, the antisense oligonucleotide sequence is 100% complementary to a corresponding target nucleic acid of SEQ ID NO: 1.

In some embodiments, the antisense oligonucleotide or the contiguous nucleotide sequence of the invention is at least 95% complementarity, such as fully (or 100%) complementary, to the target nucleic acid of SEQ ID NO: 1 and SEQ ID NO: 2.

In some embodiments, the contiguous nucleotide sequence comprises a sequence of nucleobases selected from the group consisting of SEQ ID NO: 3, 4, 5 and 6, or at least 14 contiguous nucleotides thereof.

In some embodiments, the antisense oligonucleotide of the invention or contiguous nucleotide sequence thereof, comprises or consists of 10 to 30 nucleotides in length, such as from 12 to 25, such as 11 to 22, such as from 12 to 20, such as from 14 to 18 or 14 to 16 contiguous nucleotides in length.

In some embodiments, the antisense oligonucleotide or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 10, 11, 12, 13, 14, 15, 16, 17, 18, 19, 20, 21 or 22 contiguous nucleotides in length.

In some embodiments, the antisense oligonucleotide or contiguous nucleotide sequence thereof comprises or consists of a sequence selected from SEQ ID NO: 3, 4, 5 and 6.

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 7.

The invention provides antisense oligonucleotides, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 8.

The invention provides antisense oligonucleotides, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 9.

The invention provides antisense oligonucleotides, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 10.

The invention provides antisense oligonucleotides, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 11.

In advantageous embodiments, the antisense oligonucleotide comprises one or more sugar modified nucleosides, such as one or more 2' sugar modified nucleosides, such as one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In some embodiments, the contiguous nucleotide sequence comprises LNA nucleosides.

In some embodiments, of the oligonucleotide of the present invention, all LNA nucleosides are beta-D-oxy LNA nucleosides.

In some embodiments, the contiguous nucleotide sequence comprises LNA nucleosides and DNA nucleosides.

In some embodiments, the contiguous nucleotide sequence comprises 2'-O-methoxyethyl (2'MOE) nucleosides.

In some embodiments, the contiguous nucleotide sequence comprises 2'-O-methoxyethyl (2'MOE) nucleosides and DNA nucleosides.

Advantageously, the 3' most nucleoside of the antisense oligonucleotide, or contiguous nucleotide sequence thereof is a 2'sugar modified nucleoside.

Advantageously, the antisense oligonucleotide comprises at least one modified internucleoside linkage, such as phosphorothioate or phosphorodithioate.

In some embodiments, the at least one internucleoside linkage in the contiguous nucleotide sequence is a phosphorothioate internucleoside linkages.

In some embodiments, at least one internucleoside linkage in the contiguous nucleotide sequence is a phosphorodithioate internucleoside linkages.

In some embodiments, at least one internucleoside linkage in the contiguous nucleotide sequence is a phosphodiester internucleoside linkages.

In some embodiments, all the internucleoside linkages within the contiguous nucleotide sequence are phosphorothioate internucleoside linkages.

In some embodiments, at least 75% the internucleoside linkages within the antisense oligonucleotide, or contiguous nucleotide sequence thereof, are phosphorothioate internucleoside linkages.

In some embodiments, all the internucleoside linkages within the antisense oligonucleotide, or contiguous nucleotide sequence thereof, are phosphorothioate internucleoside linkages.

In an advantageous embodiment of the invention the antisense oligonucleotide of the invention is capable of recruiting RNase H, such as RNase H1. In some embodiments, the antisense oligonucleotide of the invention, or the contiguous nucleotide sequence thereof is a gapmer.

In some embodiments, the antisense oligonucleotide, or contiguous nucleotide sequence thereof, consists or comprises a gapmer of formula 5'-F-G-F'-3'.

In some embodiments, region G consists of 6-16 DNA nucleoside, such as 11 to 16 DNA nucleosides. In some embodiments, region F comprises 2 to 4 DNA nucleosides and/or region F' comprises DNA 2 to 6 nucleosides.

In some embodiments, region F and F' each comprise at least one LNA nucleoside.

In some embodiments, the oligonucleotide of the present invention is a LNA gapmer with uniform flanks. For example, the LNA gapmer with uniform flanks may have a design selected from the following designs: 4-12-2, 2-13-4 and 2-12-5. Table 6 lists preferred designs for each motif sequence.

In some embodiments, of the invention, the LNA gapmer is an alternating flank LNA gapmer. In some embodiments, the alternating flank LNA gapmer comprises at least one alternating flank (such as flank F'). In some embodiments, the alternating flank LNA gapmer comprises one alternating flank (such as flank F') and one uniform flank (such as flank F). For example, the LNA gapmer with one alternating F' flank may have the following design: 2-11-1-2-1-1-3.

The invention provides the following oligonucleotide compounds (Table 6):

TABLE 6 list of oligonucleotide motif sequences of the invention (indicated by SEQ ID NO), designs of these, as well as specific oligonucleotide compounds of the invention (indicated by CMP ID NO) designed based on the motif sequence.

| SEQ ID NO | Motif sequence | position on SEQ ID NO: 1 Start | end | Design | CMP ID NO | Oligo-nucleotide Compound |
|---|---|---|---|---|---|---|
| 3 | AATTTTACATACTCTGGT | 11757 | 11774 | 4-12-2 | 3_1 | AATTttacatactctgGT |
| 4 | AATTTTACATACTCTGGTC | 11756 | 11774 | 2-13-4 | 4_1 | AAttttacatactctGGTC |
| 5 | TTACATACTCTGGTCAAA | 11753 | 11770 | 2-12-5 | 5_1 | TTacatactctggtCAAA |
| 6 | CTTTATTATAACTTGAATCTC | 8681 | 8701 | 2-11-1-2-1-1-3 | 6_1 | CTttattataactTgaAtCTC |

The heading "Oligonucleotide compound" in the table represents specific designs of a motif sequence. Capital letters are beta-D-oxy LNA nucleosides, lowercase letters are DNA nucleosides, all LNA C are 5-methyl cytosine, all internucleoside linkages are phosphorothioate internucleoside linkages. The heading "Designs" refers to the gapmer design, F-G-F'. In classic gapmer design, i.e. gapmers with uniform flanks (e.g. 4-12-2), all the nucleotides in the flanks (F and F') are constituted of the same type of 2'-sugar modified nucleoside, e.g. LNA, cET, or MOE, and a stretch of DNA in the middle forming the gap (G). In gapmers with alternating flank designs, the flanks of oligonucleotide are annotated as a series of integers, representing a number of beta-D-oxy LNA nucleosides (L) followed by a number of DNA nucleosides (D). For example, a flank F' with a 1-2-1-1-3 motif represents LDDLDLLL(see CMP ID NO 6_1). Both flanks have a beta-D-oxy LNA nucleoside at the 5' and 3' terminal. The gap region (G), which is constituted of a number of DNA nucleosides is located between the flanks.

For some embodiments of the invention, the oligonucleotide is selected from the group of oligonucleotide compounds consisting of CMP-ID-NO: 3_1, 4_1, 5_1 and 6_1 (see Table 6).

In all instances, the F-G-F' design may further include region D' and/or D" as described in the "Definitions" section under "Region D' or D" in an oligonucleotide". In some embodiments, the oligonucleotide of the invention has 1, 2 or 3 phosphodiester linked nucleoside units, such as DNA units, at the 5' or 3' end, such as at the 5' end, of the gapmer region. In some embodiments, the oligonucleotide of the invention consists of two 5' phosphodiester linked DNA nucleosides followed by a F-G-F' gapmer region as defined above. Oligonucleotides that contain phosphodiester linked DNA units at the 5' or 3' end are suitable for conjugation and may further comprise a conjugate moiety as described herein. For delivery to the liver ASGPR targeting moieties are particular advantageous as conjugate moieties, see the Conjugate section for further details.

Conjugates

Since HBV infection primarily affects the hepatocytes in the liver it is advantageous to conjugate the enhanced antisense oligonucleotide of the invention to a conjugate moiety that will increase the delivery of the antisense oligonucleotide to the liver compared to the unconjugated antisense oligonucleotide. In one embodiment, liver targeting moieties are selected from moieties comprising cholesterol or other lipids or conjugate moieties capable of binding to the asialoglycoprotein receptor (ASGPR).

In some embodiments, the invention provides a conjugate comprising an antisense oligonucleotide of the invention covalently attached to a conjugate moiety.

The asialoglycoprotein receptor (ASGPR) conjugate moiety comprises one or more carbohydrate moieties capable of binding to the asialoglycoprotein receptor (ASPGR targeting moieties) with affinity equal to or greater than that of galactose. The affinities of numerous galactose derivatives for the asialoglycoprotein receptor have been studied (see for example: Jobst, S. T. and Drickamer, K. J B. C. 1996, 271, 6686) or are readily determined using methods typical in the art.

In one embodiment, the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine. Advantageously the asialoglycoprotein receptor targeting moiety is N-acetylgalactosamine (GalNAc).

To generate the ASGPR conjugate moiety the ASPGR targeting moieties (preferably GalNAc) can be attached to a conjugate scaffold. Generally, the ASPGR targeting moieties can be at the same end of the scaffold. In one embodiment, the conjugate moiety consists of two to four terminal GalNAc moieties linked to a spacer, which links each GalNAc moiety to a brancher molecule that can be conjugated to the antisense oligonucleotide.

In a further embodiment, the conjugate moiety is mono-valent, di-valent, tri-valent or tetra-valent with respect to asialoglycoprotein receptor targeting moieties. Advantageously the asialoglycoprotein receptor targeting moiety comprises N-acetylgalactosamine (GalNAc) moieties.

GalNAc conjugate moieties can include, for example, those described in WO 2014/179620 and WO 2016/055601 and PCT/EP2017/059080 (hereby incorporated by reference), as well as small peptides with GalNAc moieties attached such as Tyr-Glu-Glu-(aminohexyl GalNAc)3 (YEE (ahGalNAc)3; a glycotripeptide that binds to asialoglycoprotein receptor on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor).

The ASGPR conjugate moiety, in particular a trivalent GalNAc conjugate moiety, may be attached to the 3'- or 5'-end of the oligonucleotide using methods known in the art. In one embodiment, the ASGPR conjugate moiety is linked to the 5'-end of the oligonucleotide.

In one embodiment, the conjugate moiety is a tri-valent N-acetylgalactosamine (GalNAc), such as those shown in FIG. 5. In one embodiment, the conjugate moiety is the tri-valent N-acetylgalactosamine (GalNAc) of FIG. 5A-1 or FIG. 5A-2, or a mixture of both. In one embodiment, the conjugate moiety is the tri-valent N-acetylgalactosamine (GalNAc) of FIG. 5B-1 or FIG. 5B-2, or a mixture of both. In one embodiment, the conjugate moiety is the tri-valent N-acetylgalactosamine (GalNAc) of FIG. 5C-1 or FIG. 5C-2, or a mixture of both. In one embodiment, the conjugate moiety is the tri-valent N-acetylgalactosamine (GalNAc) of FIG. 5D-1 or FIG. 5D-2, or a mixture of both.

In some embodiments, the conjugate is selected from the group consisting of

Figure 2:
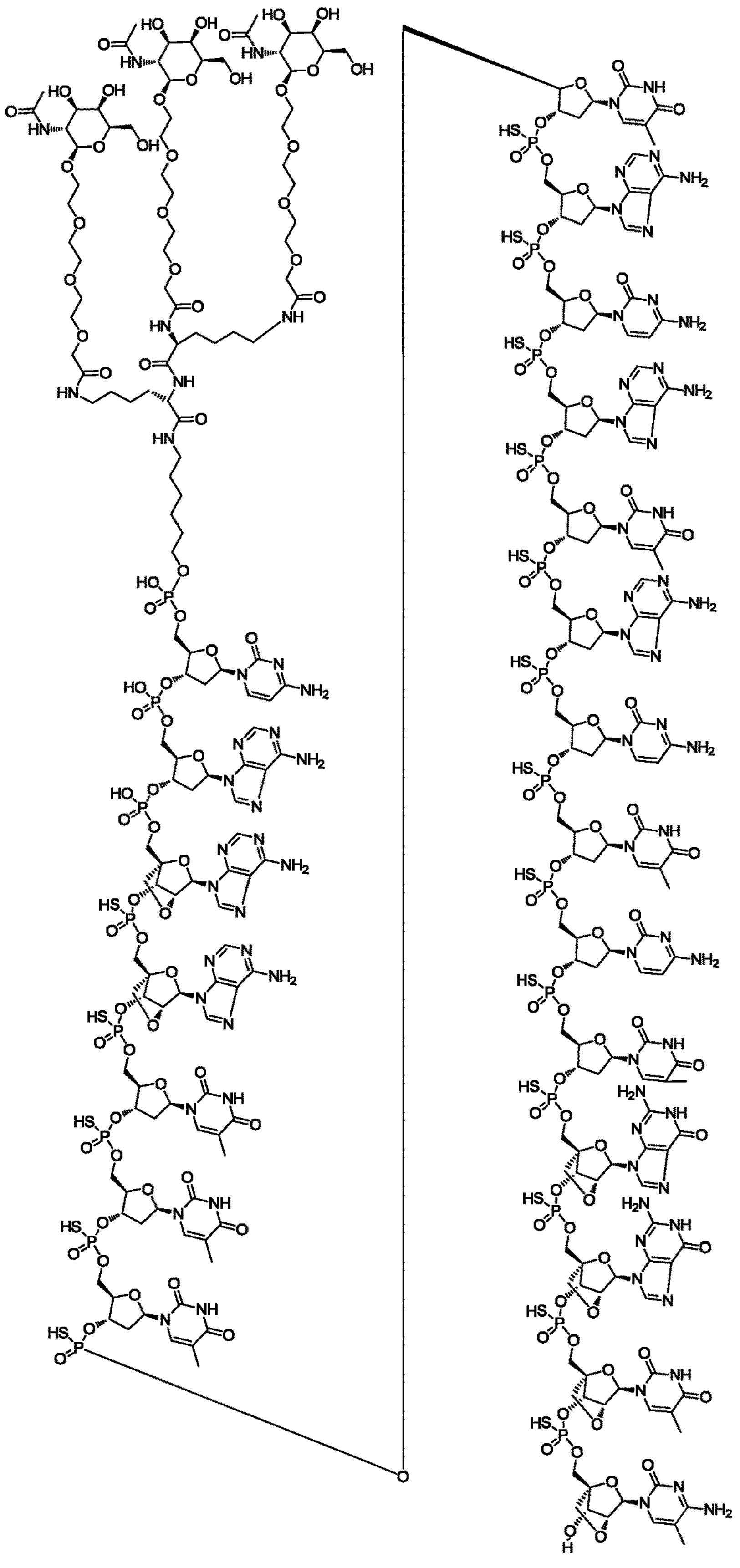
FIG. 2: Compound 4_1 (SEQ ID NO: 4) conjugated to a trivalent GalNAc moiety via a phosphodiester linked DNA dinucleotide
Figure 2A:
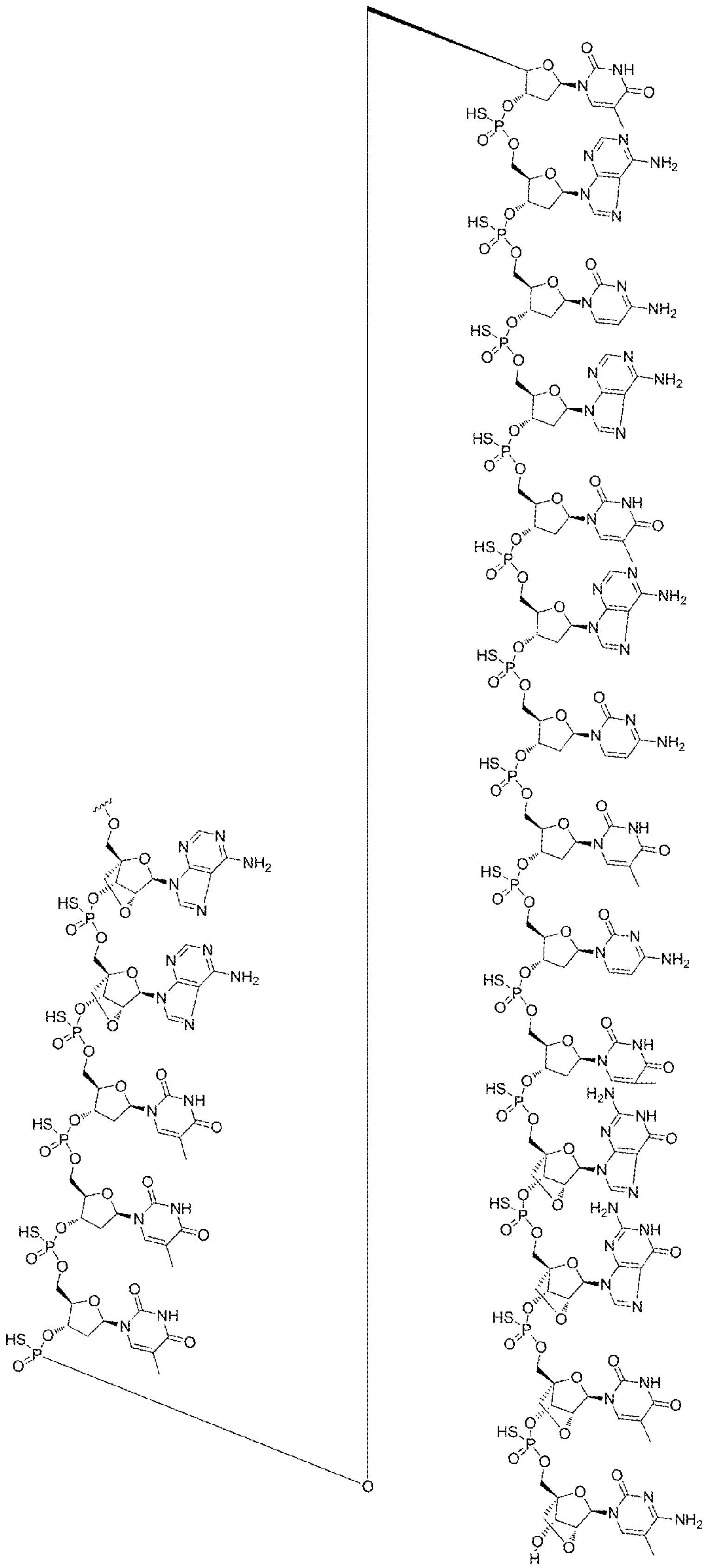
FIG. 2A: Residue A of Compound 4_1 (SEQ ID NO: 4)

5'-GN2-$C6_oC_oa_oA_sA_sT_sT_st_st_sa_s$ $C_sa_st_sa_sC_st_sC_st_sg_sG_sT_s$,

5'-GN2-$C6_oC_oa_oA_sA_st_st_st_st_sa_s$ $C_sa_st_sa_sc_st_sc_st_sG_sG_sT_s{}^mG_s$,

5'-GN2-$C6_oc_oa_o{}^mC_sT_st_st_sa_st_st_s$ $a_st_sa_sa_sC_st_sT_sg_sa_sA_st_s{}^mC_sT_s{}^mC_s$,
and -continued 5'-GN2-$C6_oc_oa_o$ $T_sT_sa_sc_sa_st_sa_s$ $c_st_sc_st_sg_sg_st_s{}^mC_sA_sA_sA_s$ wherein a capital letter represents a beta-D-oxy LNA nucleoside, a lower case letter represents a DNA nucleoside, wherein each LNA cytosine is 5-methyl cytosine, and wherein subscript s represents a phosphorothioate internucleoside linkage, and a subscript o represents a phosphodiester internucleoside linkage, and GN2-C6 is tri-valent N-acetylgalactosamine (GalNAc), such as those shown in FIG. 5, for example, such as the tri-valent N-acetylgalactosamine (GalNAc) of FIG. 5D-1 or FIG. 5D-2, or a mixture of both.

Chemical drawings representing some of the molecules are shown in FIGS. 1 to 4.

In some embodiments, the conjugate is the conjugate as shown in FIG. 1.

In some embodiments, the conjugate is the conjugate as shown in FIG. 2.

Figure 3:
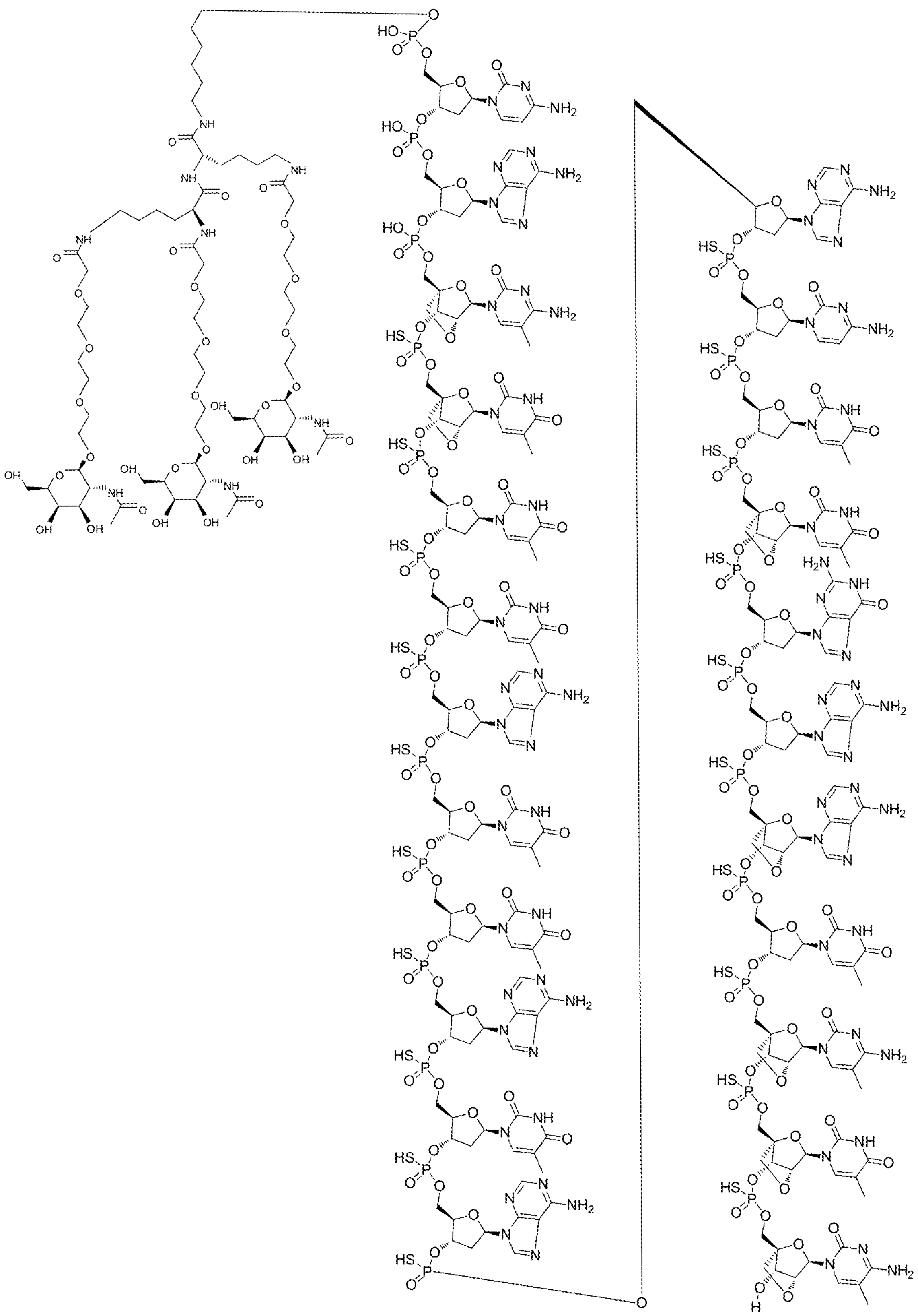
FIG. 3: Compound 6_1 (SEQ ID NO: 6) conjugated to a trivalent GalNAc moiety via a phosphodiester linked DNA dinucleotide
Figure 3A:
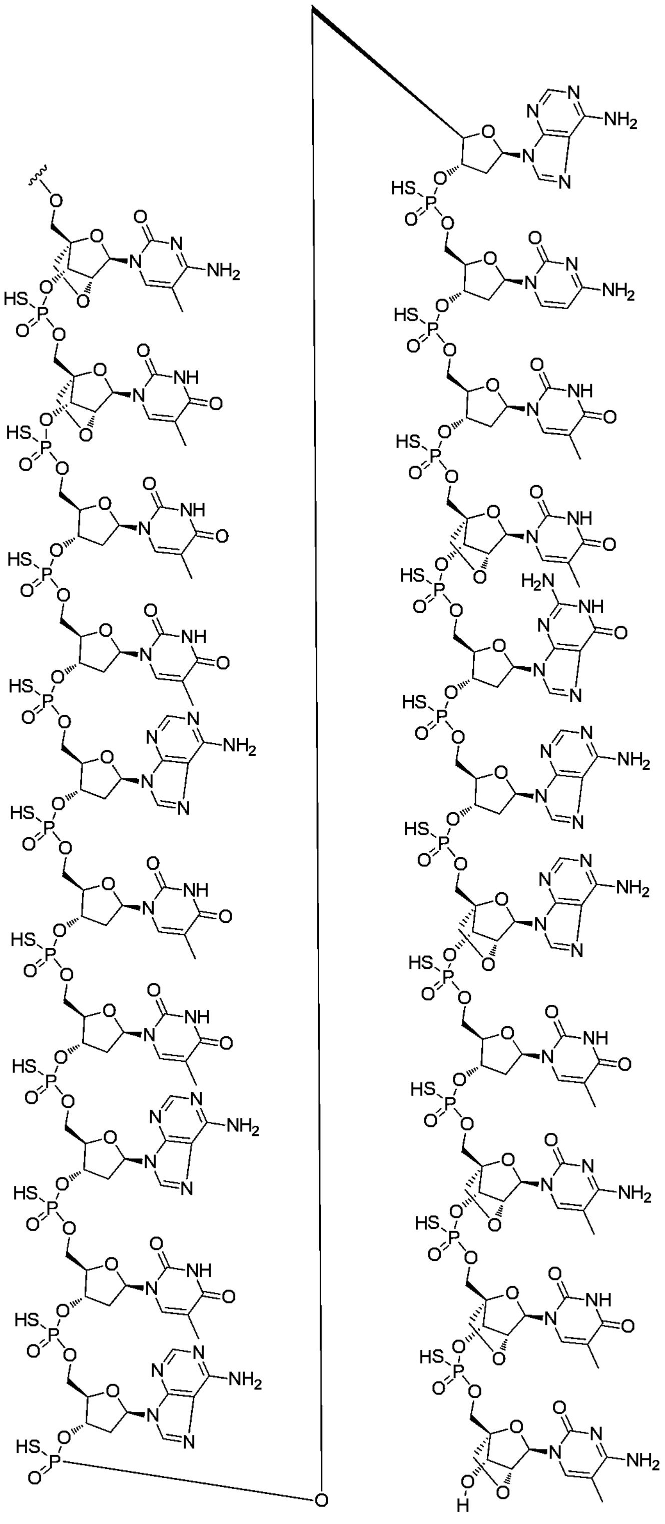
FIG. 3A: Residue A of Compound 6_1 (SEQ ID NO: 6)

In some embodiments, the conjugate is the conjugate as shown in FIG. 3.

Figure 4:
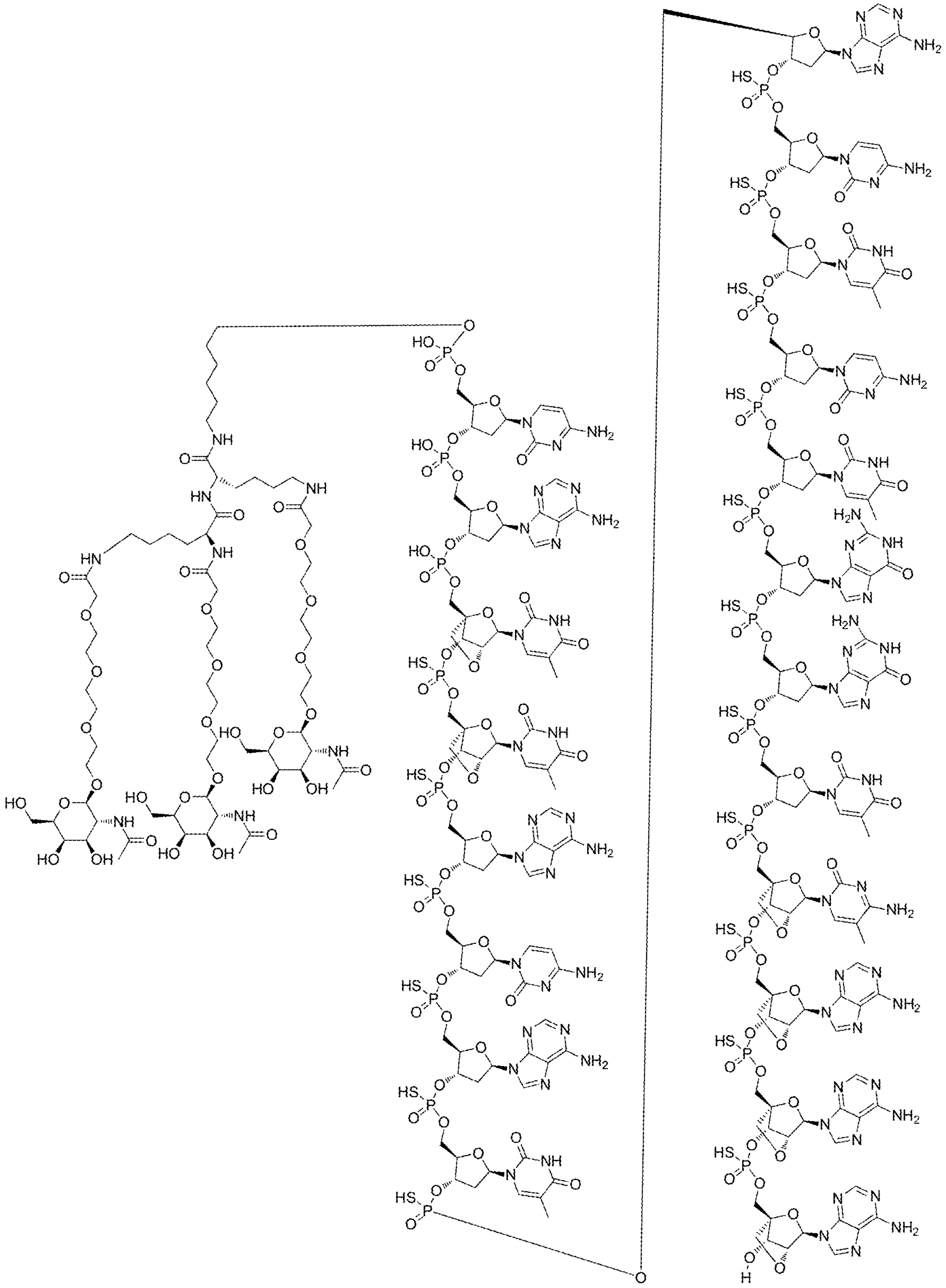
FIG. 4: Compound 5_1 (SEQ ID NO: 5) conjugated to a trivalent GalNAc moiety via a phosphodiester linked DNA dinucleotide
Figure 4A:
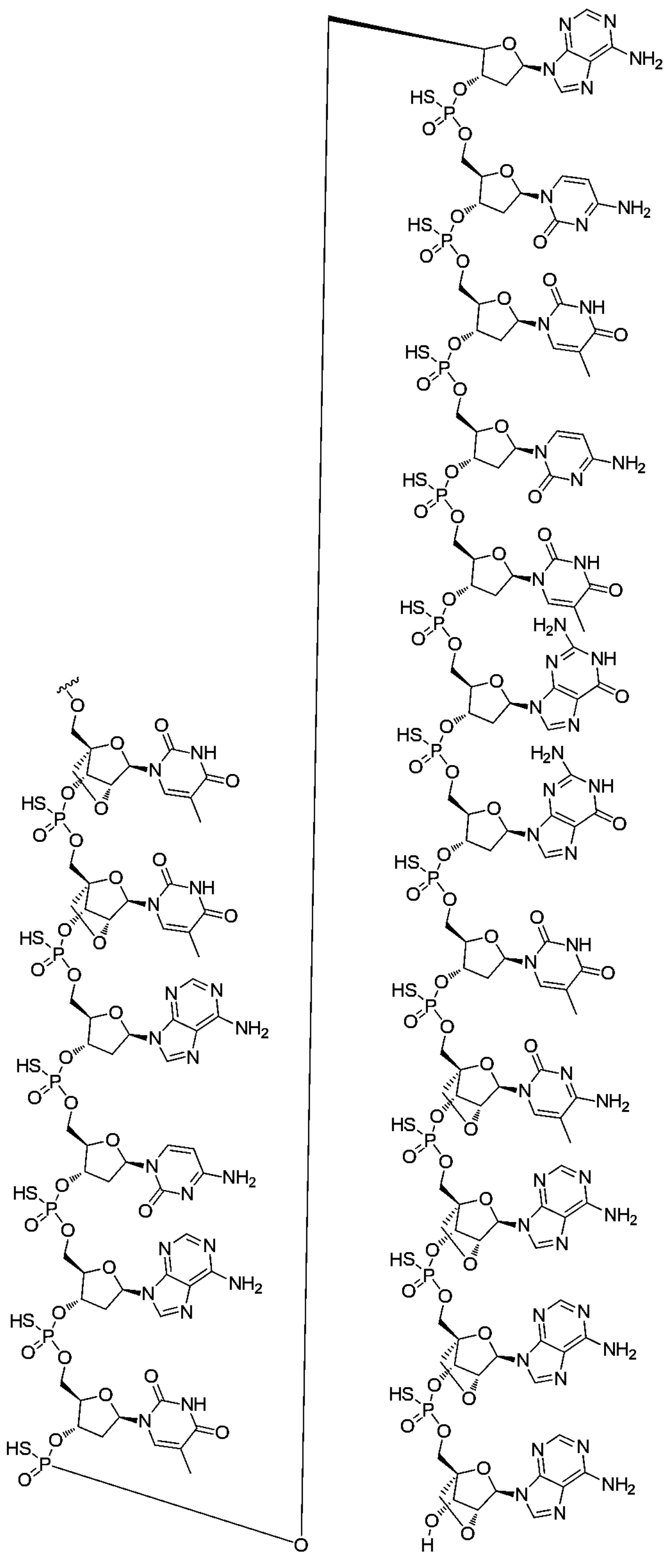
FIG. 4A: Residue A of Compound 5_1 (SEQ ID NO: 5)

In some embodiments, the conjugate is the conjugate as shown in FIG. 4.

The compounds illustrated in FIGS. 1-4 are shown in the protonated form—the S atom on the phosphorothioate linkage is protonated—it will be understood that the presence of the proton will depend on the acidity of the environment of the molecule, and the presence of an alternative cation (e.g. when the oligonucleotide is in salt form). Protonated phosphorothioates exist in tautomeric forms.

Pharmaceutically Acceptable Salts

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof, such as a pharmaceutically acceptable sodium salt, ammonium salt or potassium salt.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313).

In a further embodiment, the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments, the pharmaceutically acceptable diluent is sterile phosphate buffered saline. In some embodiments, the oligonucleotide is used in the pharmaceutically acceptable diluent at a concentration of 50-300 μM solution.

Suitable formulations for use in the present invention are found in Remington's Pharmaceutical Sciences, Mack Publishing Company, Philadelphia, Pa., 17th ed., 1985. Fora brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

In some embodiments, the antisense oligonucleotide of the invention or conjugate thereof, or pharmaceutically acceptable salt thereof is in a solid form, such as a powder, such as a lyophilized powder.

In some embodiments, the antisense oligonucleotide of the invention or conjugate thereof may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the antisense oligonucleotide of the invention or conjugate thereof is a prodrug. In particular, with respect to antisense oligonucleotide conjugates the conjugate moiety is cleaved off the oligonucleotide once the prodrug is delivered to the site of action, e.g. the target cell.

Applications

The enhanced antisense oligonucleotides of the invention thereof may be utilized as research reagents for, for example, diagnostics, therapeutics and prophylaxis.

In research, such antisense oligonucleotides may be used to specifically modulate the synthesis of RTEL1 protein in cells (e.g. in vitro cell cultures) and experimental animals thereby facilitating functional analysis of the target or an appraisal of its usefulness as a target for therapeutic intervention. Typically, the target modulation is achieved by degrading or inhibiting the mRNA producing the protein, thereby prevent protein formation or by degrading or inhibiting a modulator of the gene or mRNA producing the protein.

If employing the antisense oligonucleotides of the invention in research or diagnostics the target nucleic acid may be a cDNA or a synthetic nucleic acid derived from DNA or RNA.

Also encompassed by the present invention is an in vivo or in vitro method for modulating RTEL1 expression in a target cell, which is expressing RTEL1, said method comprising administering an antisense oligonucleotide, a conjugate thereof or pharmaceutical composition of the invention in an effective amount to said cell.

In some embodiments, the target cell, is a mammalian cell in particular a human cell. The target cell may be an in vitro cell culture or an in vivo cell forming part of a tissue in a mammal. In preferred embodiments, the target cell is present in in the liver. The target cell may be a hepatocyte.

One aspect of the present invention is related the antisense oligonucleotides, conjugate thereof or pharmaceutical compositions of the invention for use as a medicament.

In an aspect of the invention the antisense oligonucleotides, conjugate thereof or pharmaceutical composition of the invention is capable of reducing the cccDNA level in the infected cells and therefore inhibiting HBV infection. In particular, the antisense oligonucleotide or conjugate thereof is capable of affecting one or more of the following parameters i) reducing cccDNA and/or ii) reducing pgRNA and/or iii) reducing HBV DNA and/or iv) reducing HBV viral antigens in an infected cell.

For example, the antisense oligonucleotide or conjugate thereof that inhibits HBV infection may reduce i) the cccDNA levels in an infected cell by at least 40% such as 50%, 60%, 70%, 80%, or 90% reduction compared to controls; or ii) the level of pgRNA by at least 40% such as 50%, 60%, 70%, 80%, or 90% reduction compared to controls. The controls may be untreated cells or animals, or cells or animals treated with an appropriate control.

Inhibition of HBV infection may be measured in vitro using HBV infected primary human hepatocytes or in vivo using humanized hepatocytes PXB mouse model (available at PhoenixBio, see also Kakuni et al 2014 Int. J. Mol. Sci. 15:58-74). Inhibition of secretion of HBsAg and/or HBeAg may be measured by ELISA, e.g. by using the CLIA ELISA Kit (Autobio Diagnostic) according to the manufacturers' instructions. Reduction of intracellular cccDNA or HBV mRNA and pgRNA may be measured by qPCR, e.g. as described in the Materials and Methods section. Further methods for evaluating whether a test compound inhibits HBV infection are measuring secretion of HBV DNA by qPCR e.g. as described in WO 2015/173208 or using Northern Blot; in-situ hybridization, or immuno-fluorescence.

Due to the reduction of RTEL1 levels the antisense oligonucleotide, conjugate thereof or pharmaceutical compositions of the present invention can be used to inhibit development of or in the treatment of HBV infection. In particular, the destabilization and reduction of the cccDNA, the antisense oligonucleotide, conjugate thereof or pharmaceutical compositions of the present invention more efficiently inhibits development of or treats a chronic HBV infection as compared to a compound that only reduces secretion of HBsAg.

Accordingly, one aspect of the present invention is related to use of the antisense oligonucleotide, conjugate thereof or pharmaceutical compositions of the invention to reduce cccDNA and/or pgRNA in an HBV infected individual.

A further aspect of the invention relates to the use of the antisense oligonucleotide, conjugate thereof or pharmaceutical compositions of the invention to inhibit development of or treat a chronic HBV infection.

A further aspect of the invention relates to the use of the antisense oligonucleotide, conjugate thereof or pharmaceutical compositions of the invention to reduce the infectiousness of a HBV infected person. In a particular aspect of the invention, the antisense oligonucleotide, conjugate thereof or pharmaceutical compositions of the invention inhibits development of a chronic HBV infection.

The subject to be treated with the antisense oligonucleotide, conjugate thereof or pharmaceutical compositions of the invention (or which prophylactically receives antisense oligonucleotides, conjugates thereof or pharmaceutical compositions of the present invention) is preferably a human, more preferably a human patient who is HBsAg positive and/or HBeAg positive, even more preferably a human patient that is HBsAg positive and HBeAg positive.

Accordingly, the present invention relates to a method of treating a HBV infection, wherein the method comprises administering an effective amount of the antisense oligonucleotide, conjugate thereof or pharmaceutical compositions of the invention. The present invention further relates to a method of preventing liver cirrhosis and hepatocellular carcinoma caused by a chronic HBV infection.

The invention also provides for the use of an antisense oligonucleotide, conjugate thereof or a pharmaceutical composition of the invention for the manufacture of a medicament, in particular a medicament for use in the treatment of HBV infection or chronic HBV infection or reduction of the infectiousness of a HBV infected person. In preferred embodiments, the medicament is manufactured in a dosage form for subcutaneous administration.

The invention also provides for the use of an antisense oligonucleotide, conjugate thereof, the pharmaceutical composition of the invention for the manufacture of a medicament wherein the medicament is in a dosage form for intravenous administration.

The antisense oligonucleotide, conjugate thereof or the pharmaceutical composition of the invention may be used in a combination therapy. For example, antisense oligonucleotide, conjugate thereof or the pharmaceutical composition of the invention may be combined with other anti-HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO2012/145697, WO 2014/179629 and WO2017/216390), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

Combination Therapy

In some embodiments, the enhanced antisense oligonucleotide, conjugate thereof or the pharmaceutical composition of the invention is for use in a combination treatment with another therapeutic agent. The therapeutic agent can for example be the standard of care for the diseases or disorders described above.

By way of example, the antisense oligonucleotide, conjugate thereof or the pharmaceutical composition may be used in combination with other actives, such as oligonucleotide-based antivirals—such as sequence specific oligonucleotide-based antivirals—acting either through antisense (including other LNA oligomers), siRNAs (such as ARC520), aptamers, morpholinos or any other antiviral, nucleotide sequence-dependent mode of action.

By way of further example, the antisense oligonucleotide, conjugate thereof or the pharmaceutical composition may be used in combination with other actives, such as immune stimulatory antiviral compounds, such as interferon (e.g. pegylated interferon alpha), TLR7 agonists (e.g. GS-9620), or therapeutic vaccines.

By way of further example, the antisense oligonucleotide, conjugate thereof or the pharmaceutical composition may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (eg Myrcludex B).

In certain embodiments, the additional therapeutic agent may be an HBV agent, a Hepatitis C virus (HCV) agent, a chemotherapeutic agent, an antibiotic, an analgesic, a nonsteroidal anti-inflammatory (NSAID) agent, an antifungal agent, an antiparasitic agent, an anti-nausea agent, an antidiarrheal agent, or an immunosuppressant agent.

In particular, related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; pegasys; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Administration

The enhanced antisense oligonucleotides, conjugates thereof or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, or intra-muscular).

In a preferred embodiment, the antisense oligonucleotide, conjugates thereof or pharmaceutical compositions of the present invention are administered by a parenteral route including intravenous, intraarterial, subcutaneous, intraperitoneal or intramuscular administration. In one embodiment, the active antisense oligonucleotide or conjugate thereof is administered intravenously. In another embodiment, the active antisense oligonucleotide or conjugate thereof is administered subcutaneously.

In some embodiments, the antisense oligonucleotide, conjugate thereof or pharmaceutical composition of the invention is administered at a dose of 0.1-15 mg/kg, such as from 0.2-10 mg/kg, such as from 0.25-5 mg/kg. The administration can be once a week, every second week, every third week or even once a month.

The invention also provides for the use of the antisense oligonucleotide, or conjugate thereof of the invention as described for the manufacture of a medicament wherein the medicament is in a dosage form for subcutaneous administration.

Embodiments of the Invention

The following embodiments of the present invention may be used in combination with any other embodiments described herein. The definitions and explanations provided herein above, in particular in the sections "SUMMARY OF INVENTION", "DEFINITIONS" and DETAILED DESCRIPTION OF THE INVENTION" apply mutatis mutandis to the following.

1. An antisense oligonucleotide which comprises a contiguous nucleotide sequence with at least 90% complementarity, such as 100% complementarity to a RTEL1 nucleic acid, wherein the antisense oligonucleotide is capable of inhibiting the expression of RTEL1, such as human RTEL1, in a cell.
2. The antisense oligonucleotide of embodiment 1, wherein the contiguous nucleotide sequence is fully complementary to a region from nucleotides 11753-11774 of the human RTEL1 pre-mRNA as shown in in SEQ ID NO: 1, such as to a region from nucleotides 11757-11774, from nucleotides 11756-11774, or from nucleotides 11753-11770 of SEQ ID NO: 1.
3. The antisense oligonucleotide of embodiments 1 and 2, wherein the contiguous nucleotide sequence is fully complementary to SEQ ID NO: 7, 8, 9 and/or 10.
4. The antisense oligonucleotide of embodiment 1, wherein the contiguous nucleotide sequence is fully complementary to a region from nucleotides 8681-8701 of the human RTEL1 pre-mRNA as shown in in SEQ ID NO: 1.
5. The antisense oligonucleotide of embodiments 1 and 4, wherein the contiguous nucleotide sequence is fully complementary to SEQ ID NO: 11.
6. The antisense oligonucleotide of any one of embodiments 1 to 5, wherein the antisense oligonucleotide is 12-30 nucleotides in length, such as 12 to 22 nucleotides in length, such as 16 to 20 nucleotides in length.
7. The antisense oligonucleotide of any one of embodiments 1 to 6, wherein the contiguous nucleotide sequence is a contiguous sequence of at least 12 nucleotides, such as of 14, 15, 16, 17, 18, 19, or 20 nucleotides.
8. The antisense oligonucleotide of embodiment 7, wherein the contiguous nucleotide sequence is a contiguous sequence of 18 or 19 nucleotides.
9. The antisense oligonucleotide of any one of embodiments 1 to 8, wherein the contiguous nucleotide sequence is 100% identical to a sequence selected from the group consisting of SEQ ID NOs: 3, 4, 5 and 6, or at least 15 contiguous nucleotides thereof.
10. The antisense oligonucleotide of any one of embodiments 1 to 9, comprising one or more modified nucleosides in the contiguous nucleotide sequence.
11. The antisense oligonucleotide of embodiment 10, wherein the one or more modified nucleosides in the contiguous nucleotide sequence are 2' sugar modified nucleosides.
12. The antisense oligonucleotide of embodiment 11, wherein the one or more 2' sugar modified nucleosides are independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
13. The antisense oligonucleotide of any one of embodiments 10 to 12, wherein the one or more modified nucleosides are LNA nucleosides, such as oxy-LNA with the following 2'-4' bridge —O—$CH_2$—.
14. The antisense oligonucleotide of embodiment 13, wherein the one or more modified nucleosides are beta-D-oxy-LNA.
15. The antisense oligonucleotide of any one of embodiments 1 to 14, wherein at least one internucleoside linkage in the contiguous nucleotide sequence is a phosphorothioate internucleoside linkage.
16. The antisense oligonucleotide of any one of embodiments 1 to 15, wherein at least one internucleoside linkage in the contiguous nucleotide sequence is a phosphorodithioate internucleoside linkage.
17. The antisense oligonucleotide of any one of embodiments 1 to 16, wherein at least one internucleoside linkage in the contiguous nucleotide sequence is a phosphodiester internucleoside linkage.
18. The antisense oligonucleotide of embodiment 17, wherein all the internucleoside linkages within the contiguous nucleotide sequence are phosphorothioate internucleoside linkages.
19. The antisense oligonucleotide of any one of embodiments 1 to 18, wherein the antisense oligonucleotide is an antisense oligonucleotide which is capable of recruiting RNase H, such as RNase H1.
20. The antisense oligonucleotide of embodiment 19, wherein the antisense oligonucleotide, or contiguous nucleotide sequence thereof, consists of or comprises a gapmer of formula 5'-F-G-F'-3'.
21. The antisense oligonucleotide according to embodiment 20, wherein region G has a length of 6 to 16 DNA nucleosides, such as 11 to 16 DNA nucleosides.
22. The antisense oligonucleotide according to any one of embodiments 19 to 21, wherein region F and F' each comprise at least one LNA nucleoside, for example wherein region F and F' each comprise at least one LNA nucleoside.

23. The antisense oligonucleotide according to any one of embodiments 19 to 22, wherein region F has a length of 1 to 8 DNA nucleosides, such as of 2 to 4 DNA nucleosides.

24. The antisense oligonucleotide according to any one of embodiments 19 to 23, wherein region F' has a length of 1 to 8 DNA nucleosides, such as of 2 to 6 DNA nucleosides.

25. The antisense oligonucleotide according to any one of embodiments 19 to 24, wherein the antisense oligonucleotide, or contiguous nucleotide sequence thereof, consists of or comprises a gapmer of formula $F_{2-4}$-$G_{11-16}$-$F'_{2-6}$.

26. The antisense oligonucleotide according to any one of embodiments 19 to 25, wherein the gapmer comprises at least one alternating flank.

27. The antisense oligonucleotide according to any one of embodiments 19 to 25, wherein the gapmer comprises two uniform flanks.

28. The antisense oligonucleotide according to any one of embodiments 1 to 27, wherein the antisense oligonucleotide is selected from the group of antisense oligonucleotides consisting of

```
        (SEQ ID NO: 3, Compound ID No 3_1),
AATTttacatactctgGT

        (SEQ ID NO: 4, Compound ID No 4_1),
AAttttacatactctGGTC

        (SEQ ID NO: 5, Compound ID No 5_1),
TTacatactctggtCAAA
and

        (SEQ ID NO: 6, Compound ID No 6_1),
CTttattataactTgaAtCTC
```

wherein capital letters are beta-D-oxy LNA nucleosides, lowercase letters are DNA nucleosides, all LNA C are 5-methyl cytosine, all internucleoside linkages are phosphorothioate internucleoside linkages.

29. A conjugate comprising the antisense oligonucleotide according to any one of embodiments 1 to 28, and at least one conjugate moiety covalently attached to said antisense oligonucleotide.

30. The conjugate of embodiment 29, wherein the conjugate moiety comprises at least one asialoglycoprotein receptor targeting moiety selected from the group consisting of galactose, galactosamine, N-formyl-galactosamine, N-acetylgalactosamine, N-propionyl-galactosamine, N-n-butanoyl-galactosamine and N-isobutanoylgalactosamine.

31. The conjugate of embodiment 30, wherein the asialoglycoprotein receptor targeting moiety is N-acetylgalactosamine (GalNAc).

32. The compound of embodiment 30 or 31, wherein the conjugate moiety is mono-valent, di-valent, tri-valent or tetra-valent with respect to asialoglycoprotein receptor targeting moieties.

33. The compound of embodiment 32, wherein the conjugate moiety consists of two to four terminal GalNAc moieties and a spacer linking each GalNAc moiety to a brancher molecule that can be conjugated to the antisense compound.

34. The conjugate of embodiment 33, wherein the spacer is a PEG spacer.

35. The conjugate of any one of embodiments 30 to 34, wherein the conjugate moiety is a tri-valent N-acetylgalactosamine (GalNAc) moiety.

36. The compound of any one of embodiments 30 to 35, wherein the conjugate moiety is selected from one of the trivalent GalNAc moieties in FIG. 5.

37. The conjugate of embodiment 36, wherein the conjugate moiety is the trivalent GalNAc moiety in FIG. 5, such as the trivalent GalNAc moiety of FIG. 5D-1 or FIG. 5D-2, or a mixture of both.

38. The conjugate of any one of embodiments 29 to 37, comprising a linker, which is positioned between the antisense oligonucleotide and the conjugate moiety.

39. The conjugate of embodiment 38, wherein the physiologically labile linker comprises or consists of 2 to 5 consecutive phosphodiester linked nucleosides, such as 2 consecutive phosphodiester linked nucleosides.

40. The conjugate according to any one of embodiments 29 to 39, wherein the conjugate is selected from the group consisting of $$5'\text{-GN2-C6}_o c_o a_o A_s A_s T_s T_s t_s t_s a_s$$
$$c_s a_s t_s a_s c_s t_s c_s t_s g_s G_s T,$$

$$5'\text{-GN2-C6}_o c_o a_o A_s A_s t_s t_s t_s t_s a_s$$
$$c_s a_s t_s a_s c_s t_s c_s t_s G_s G_s T_s{}^m C,$$

$$5'\text{-GN2-C6}_o c_o a_o{}^m C_s T_s t_s t_s a_s t_s t_s$$
$$a_s t_s a_s a_s c_s t_s T_s g_s a_s A_s t_s{}^m C_s T_s{}^m C,$$
and $$5'\text{-GN2-C6}_o c_o a_o \ T_s T_s a_s c_s a_s t_s a_s$$
$$c_s t_s c_s t_s g_s g_s t_s{}^m C_s A_s A_s A$$

wherein a capital letter represents a beta-D-oxy LNA nucleoside, a lower case letter represents a DNA nucleoside, wherein each LNA cytosine is 5-methyl cytosine, and mc is 5-methyl cytosine DNA, and wherein subscript s represents a phosphorothioate internucleoside linkage, and a subscript o represents a phosphodiester internucleoside linkage, GN2-C6 is a residue of formula:

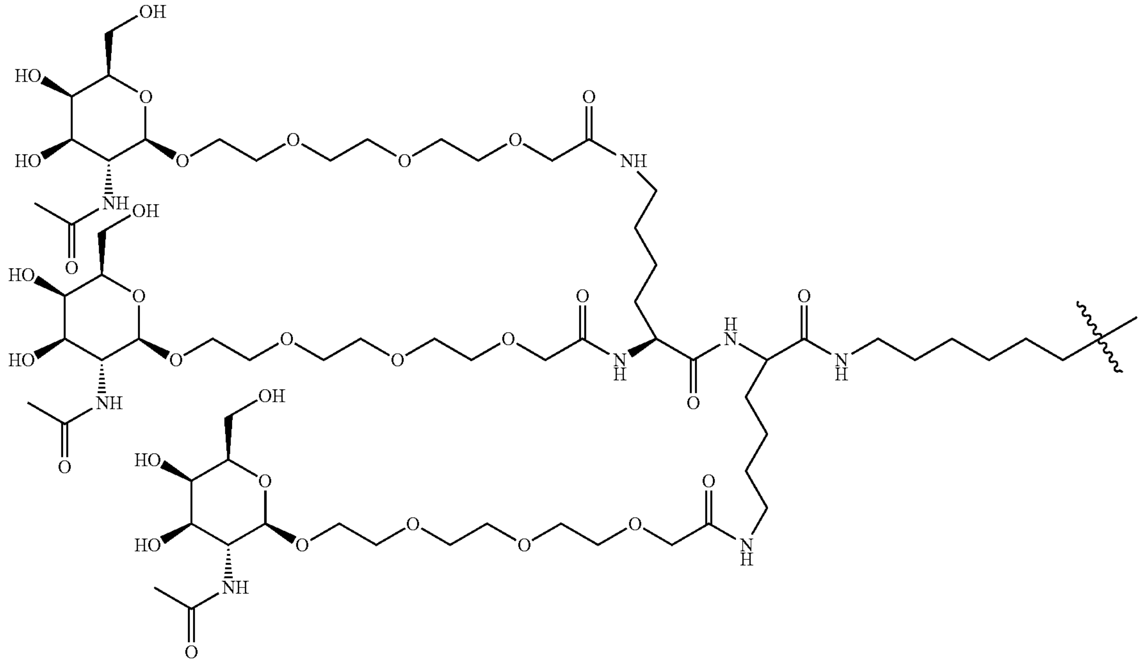 [SMILES: *CCCCCCNC(=O)C(CCCCNC(=O)COCCOCCOCCO[C@@H]1O[C@H](CO)[C@H](O)[C@H](O)[C@H]1NC(C)=O)NC(=O)[C@H](CCCCNC(=O)COCCOCCOCCO[C@@H]1O[C@H](CO)[C@H](O)[C@H](O)[C@H]1NC(C)=O)NC(=O)COCCOCCOCCO[C@@H]1O[C@H](CO)[C@H](O)[C@H](O)[C@H]1NC(C)=O]

wherein the residue GN2-C6 is attached via a phosphodiester linkage at the 5' end of the oligonucleotide, and/or wherein GN2-C6 is a tri-valent N-acetylgalactosamine (GalNAc) of FIG. 5D1 or FIG. 5D2, or a mixture of both, more preferably wherein GN2-C6 is a mixture of the tri-valent N-acetylgalactosamine (GalNAc) residues depicted in FIG. 5D1 or FIG. 5D2

41. A conjugate as shown in FIG. 1.
42. A conjugate as shown in FIG. 2.
43. A conjugate as shown in FIG. 3.
44. A conjugate as shown in FIG. 4.
45. A pharmaceutically acceptable salt of the oligonucleotide of any one of embodiments 1 to 28, or the conjugate according to any one of embodiments 29 to 44.
46. A pharmaceutical composition comprising the antisense oligonucleotide of any one of embodiments 1 to 28, the conjugate of any one of embodiments 29 to 44, or the pharmaceutically acceptable salt of embodiment 45, and a pharmaceutically acceptable diluent, solvent, carrier, salt and/or adjuvant.
47. An in vivo or in vitro method for modulating RTEL1 expression in a target cell which is expressing RTEL1, said method comprising administering the antisense oligonucleotide of any one of embodiments 1 to 28, the conjugate of any one of embodiments 29 to 44, the pharmaceutically acceptable salt of embodiment 45, or the pharmaceutical composition of embodiment 46 in an effective amount to said cell.
48. A method for treating or preventing a disease comprising administering a therapeutically or prophylactically effective amount of the antisense oligonucleotide of any one of embodiments 1 to 28, the conjugate of any one of embodiments 29 to 44, the pharmaceutically acceptable salt of embodiment 45, or the pharmaceutical composition of embodiment 46 to a subject suffering from or susceptible to the disease, wherein the disease is hepatitis B virus (HBV) infection, such as of chronic HBV infection.
49. The antisense oligonucleotide of any one of embodiments 1 to 28, the conjugate of any one of embodiments 29 to 44, the pharmaceutically acceptable salt of embodiment 45, or the pharmaceutical composition of embodiment 46 for use in medicine.
50. The antisense oligonucleotide of any one of embodiments 1 to 28, the conjugate of any one of embodiments 29 to 44, the pharmaceutically acceptable salt of embodiment 45, or the pharmaceutical composition of embodiment 46 for use in the treatment or prevention of hepatitis B virus (HBV) infection, such as of chronic HBV infection.
51. Use of the antisense oligonucleotide of any one of embodiments 1 to 28, the conjugate of any one of embodiments 29 to 44, the pharmaceutically acceptable salt of embodiment 45, or the pharmaceutical composition of embodiment 46, for the preparation of a medicament for treatment or prevention of hepatitis B virus (HBV) infection, such as of chronic HBV infection.

EXAMPLES

Materials and Methods

Oligonucleotide Synthesis

Oligonucleotide synthesis is generally known in the art. Below is a protocol, which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 μmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphodiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

The crude compounds are purified by preparative RP-HPLC on a Phenomenex Jupiter® C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations:

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography Primary Human Hepatocytes (PXB-PHH)

Fresh primary human hepatocytes (PXB-PHH) harvested from humanized mice (uPA/SCID mice)—herein called PHH—were obtained from PhoenixBio Co., Ltd (Japan) in 96-well format and cultured in modified hepatocyte clonal growth medium (dHCGM). dHCGM is a DMEM medium containing 100 U/ml Penicillin, 100 μg/ml Streptomycin, 20 mM Hepes, 44 mM $NaHCO_3$, 15 μg/ml L-proline, 0.25 μg/ml Insulin, 50 nM Dexamethazone, 5 ng/ml EGF, 0.1 mM Asc-2P, 2% DMSO and 10% FBS (Ishida et al., 2015).

Cells were cultured at 37° C., in a humidified atmosphere with 5% $CO_2$. Culture medium was replaced every 2 days until harvest, except over the weekend.

HBV Infection and Oligonucleotide Treatment

PHH were incubated with HBV (purified from chronic hepatitis B (CHB) individuals) at multiplicity of infection (MOI) of 40 together with 4% PEG for 24 hr. The virus inoculum was removed the following day and cells were washed 3 times with PBS before addition of fresh medium.

To allow for cccDNA establishment, compound treatment in PHH was started at day 3 post HBV infection. The cells were dosed in a 1:10 dilution step dose response manner starting at 10 μM. On Day 3, Day 5 and Day 7 post HBV infection, the cells were dosed with oligonucleotide compounds in a final volume of 100 μl/well of dHCGM Medium. 10 nM Entecavir (ETV) treatment was started at Day 5 post infection, ensuring real cccDNA measurement by qPCR, and medium including 10 nM ETV was changed every two days (except over the weekend) until cells were harvested at Day 16 post HBV infection. The experiments were performed in biological triplicates.

Real-Time PCR for Intracellular RTEL1 RNA

Total mRNA was extracted from the cells using a Qiagen BioRobot Universal System and the RNeasy 96 well Extraction Plates (RNeasy 96 BioRobot 8000 Kit (12)/Cat No. II D: 967152) according to the manufacturer's protocol. The mRNA expression levels were analyzed using Real-time PCR on the ABI QuantStudio™ 12 k Flex. Beta-actin (ACT B) was quantified by qPCR using TaqMan Fast Advanced Master Mix (Life Technologies, cat no. 4444558) in technical duplicates. qPCR for RTEL1 gene was performed with the Fast SYBR™ Green Master Mix (Life Technologies, Cat. No 4385612). Results were normalized over the human ACT B endogenous control. The mRNA expression was analyzed using the comparative cycle threshold 2-ΔΔCt method normalized to the reference gene ACT B and to non-treated cells. Primers used for ACTB RNA and RTEL1 RNA quantification are listed in Table 7:

TABLE 7

ACT B and RTEL1 RNA qPCR primers

| Parameter | Direction | Primer Sequence | Seq ID No |
|---|---|---|---|
| RTEL1 | Fwd | 5'- CCATCCTGGAC ATTGAGGACT-3' | 15 |
| | Rev | 5'- CAGGTTCCGGG ACAGGTAGTA-3' | 16 |

Housekeeping gene primers ACT B (VIC): Hs01060665_g1 (Thermo Fisher Scientific)

HBV cccDNA Quantification

DNA was extracted from HBV infected Primary Human Hepatocytes using an SDS Lysis Buffer (50 mM Tris pH8, 5 mM EDTA, 1% SDS). After lysing cells in 80 μl SDS lysis buffer, samples were frozen at −80° C. for minimum 2 hours. Samples were thawed at 37° C. and 1 μl of Proteinase K (cat no. AM25448 @ Ambion biosciences, 20 mg/mL Stock) was added to each well of the 96-well plate and samples were incubated at 56° C. for 30 minutes. After incubation, 3 volumes of ChIP DNA binding buffer from ZYMO Research Genomic DNA Clean & Concentrator kit (ZymoResearch, cat no. D4067) were added and DNA was purified following the manufacturer's protocol. DNA was eluted in 20 μl DNA Elution buffer and qPCR was performed using 2 μl DNA.

The cccDNA expression levels were quantified in technical duplicates using the comparative cycle threshold 2-ΔΔCt method. Quantitative real-time polymerase chain reaction measurements were performed on the QuantStudio 12K Flex PCR System (Applied Biosystems). Normalization was done to mitochondrial DNA (mitoDNA) and to non-treated cells as endogenous control using the Fast SYBR™ Green Master Mix (Life Technologies, Cat. No 4385612). Cycler settings were adjusted to incubation at 95° C. for 5 min, then 45 cycles of 95° C. for 1 sec and 60° C. for 35 sec. Primers used are listed Table 8 below (all probes in the chart are SYBR Green):

TABLE 8 cccDNA qPCR primers.

| Parameter | Direction | Primer Sequence | Seq ID No |
|---|---|---|---|
| cccDNA | Fwd | 5'-CGTCTGTGCCT TCTCATCTGC-3' | 17 |
| | Rev | 5'-GCACAGCTTGG AGGCTTGAA-3' | 18 |
| mitochondrial DNA | Fwd | 5'-CCGTCTGAACT ATCCTGCCC-3' | 19 |
| | Rev | 5'-GCCGTAGTCGG TGTACTCGT-3' | 20 |

Example 1: Effect of Antisense Oligonucleotides Targeting RTEL1 on RTEL1 RNA and on cccDNA in HBV Infected PHH Cells The effects of RTEL1 knock-down on RTEL1 RNA and on cccDNA were tested using the oligonucleotide compounds from Table 6. PHH were cultured as described in the Materials and Methods section. HBV infected PHH cells were treated with the compounds from Table 6 as described above. Following the 16 days-treatment, RTEL1 mRNA and cccDNA were measured by qPCR as described above. The results are shown in Table 9 as % of the average no drug control (NDC) samples (i.e. the lower the value the larger the inhibition/reduction).

TABLE 9

Effect on cccDNA following knockdown of RTEL1 with LNA ASO

| CMP ID NO | SEQ ID NO | Compound | cccDNA % of control (Mean) | cccDNA SD | RTEL1 % of control (Mean) | RTEL1 SD |
|---|---|---|---|---|---|---|
| 3_1 | 3 | AATTttaca tactctgGT | 28 | 13 | 19 | 3 |
| 4_1 | 4 | AAttttaca tactctGGT C | 3 | 1 | 24 | 2 |
| 5_1 | 5 | TTacatact ctggtCAAA | 21 | 6 | 35 | 11 |
| 6_1 | 6 | CTttattat aactTgaAt CTC | 39 | 5 | 21 | 8 |

For Compounds: Capital letters represent LNA nucleosides (beta-D-oxy LNA nucleosides were used), all LNA cytosines are 5-methyl cytosine, lower case letters represent DNA nucleosides. All internucleoside linkages are phosphorothioate internucleoside linkages.

Example 2: Testing In Vitro Efficacy of Antisense Oligonucleotides Targeting RTEL1 mRNA in Human MDA-MB-231 Cell Line at Different Concentrations for a Concentration Response Curve Human MDA-MB-231 cell lines were purchased from ATCC and maintained as recommended by the supplier in a humidified incubator at 37° C. with 5% $CO_2$. For assays, 3500 cells/well of were seeded in a 96 multi well plate in culture media. Cells were incubated for 24 hours before addition of oligonucleotides dissolved in PBS. Highest screening concentration of oligonucleotides: 50 µM and subsequent 1:1 dilutions in 8 steps. 3 days after addition of oligonucleotides, the cells were harvested. RNA was extracted using the PureLink™ Pro 96 RNA Purification kit (Thermo Fisher Scientific) according to the manufacturer's instructions and eluated in 50 µl water. The RNA was subsequently diluted 10 times with DNase/RNase free Water (Gibco) and heated to 90° C. for one minute.

For gene expressions analysis, One Step RT-qPCR was performed using gScript™ XLT One-Step RT-qPCR ToughMix®, Low ROX™ (Quantabio) in a duplex set up. The following TaqMan primer assays were used for qPCR: RTEL1_Hs00249668_ml [FAM-MGB] and endogenous control GUSB_Hs99999908_ml [VIC-MGB]. All primer sets were purchased from Thermo Fisher Scientific. 1050 determination was performed in GraphPad Prism7.04 from biological replicates n=2. The relative RTEL1 mRNA level at treatment with 50 µM oligonucleotide is shown in Table 10 as percent of control (PBS treated samples).

TABLE 10

$IC_{50}$ values and mRNA levels at Max $K_D$

| SEQ ID NO | Motif | CMP ID NO | Compound | $IC_{50}$ in MDA-MB-231 | SD | mRNA level at Max KD in MDA-MB-231 | SD |
|---|---|---|---|---|---|---|---|
| 3 | aattttaca tactctggt | 3_1 | AATTttaca tactctgGT | 0.6 | 0.1 | 38 | 1 |
| 4 | aattttaca tactctggt c | 4_1 | AAttttaca tactctGGT C | 0.3 | 0.1 | 14 | 1 |
| 5 | ttacatactc tggtcaaa | 5_1 | TTacatact ctggtCAAA | 0.9 | 0.3 | 9 | 4 |
| 6 | ctttattat aacttgaat ctc | 6_1 | CTttattat aactTgaAt CTC | 0.4 | 0.1 | 18 | 3 |

Figure 7:
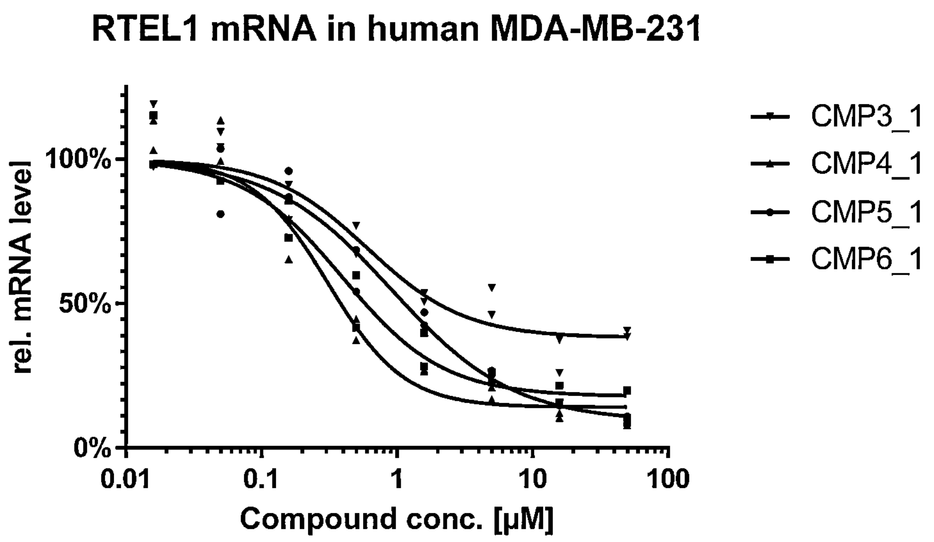
FIG. 7: Testing oligonucleotide CMP ID Nos 3_1, 4_1, 5_1 and 6_1 in vitro for concentration dependent potency and efficacy in human cell line MDA-MB-231.

The compounds show very good efficacy and potency towards knockdown of human RTEL1 mRNA as the concentration response curves in human cell line MDA-MB-231 display, provided in FIG. 7.

Example 3: Direct Comparison of In Vivo Efficacy of Compounds of the Present Invention and Prior Art Compounds In this experiment, the compounds of the present invention (CMP ID NOs: 3_1, 4_1, 5_1 and 6_1, see e.g. Table 6) were compared with compound disclosed in WO 2020/011902 A1. The tested prior art compounds are shown in Table 11 (CMP ID NOs: 7_1 to 23_1). Specifically, the effect on the RTEL1 mRNA level in human MDA-MB-231 cells was tested.

Human MDA-MB-231 cell line was purchased from ATCC and maintained as recommended by the supplier in a humidified incubator at 37° C. with 5% $CO_2$. For assays, 3500 cells/well of were seeded in a 96 multi well plate in culture media. Cells were incubated for 24 hours before addition of oligonucleotides dissolved in PBS. Highest screening concentration of oligonucleotides: 50 µM and subsequent 1:1 dilutions in 8 steps. 3 days after addition of oligonucleotides, the cells were harvested. RNA was extracted using the PureLink™ Pro 96 RNA Purification kit (Thermo Fisher Scientific) according to the manufacturer's instructions and eluated in 50 µl water. The RNA was subsequently diluted 10 times with DNase/RNase free Water (Gibco) and heated to 90° C. for one minute.

Figure 8:
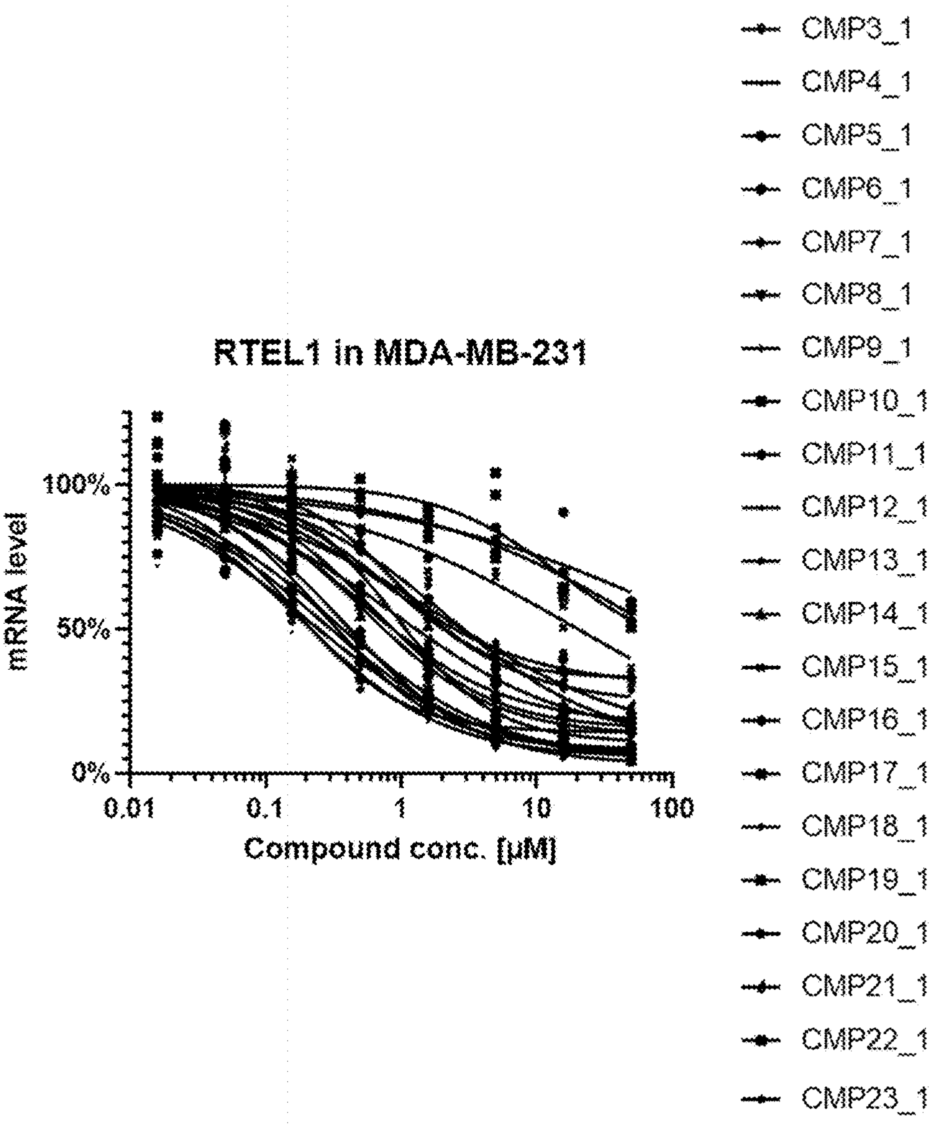
FIG. 8: Testing oligonucleotide CMP ID Nos 3_1, 4_1, 5_1 and 6_1 and prior art compounds (CMP ID Nos 7_1 to 23_1) in vitro for concentration dependent potency and efficacy in human cell line MDA-MB-231.

For gene expressions analysis, One Step RT-qPCR was performed using gScript™ XLT One-Step RT-qPCR Tough-Mix®, Low ROX™ (Quantabio) in a duplex set up. The following TaqMan primer assays were used for qPCR: RTEL1_Hs00249668_m1 [FAM-MGB] and endogenous control GUSB_Hs99999908_m1 [VIC-MGB]. All primer sets were purchased from Thermo Fisher Scientific. 1050 determination was performed in GraphPad Prism7.04 from biological replicates n=2. The relative RTEL1 mRNA level at treatment with 50 µM oligonucleotide is shown in Table 11 as percent of control (PBS treated samples). The results are also shown in FIG. 8.

TABLE 11

IC50 values and mRNA levels at Max KD

| CMP ID | SEQ ID NO | Compound | $IC_{50}$ In MDA-MB-231 | mRNA level at Max KD in MDA-MB-231 |
|---|---|---|---|---|
| 3_1 | 3 | AATTttacatactctgGT | 0.7 | 32 |
| 4_1 | 4 | AAttttacatactctGGTC | 0.2 | 6 |
| 5_1 | 5 | TTacatactctggtCAAA | 0.9 | 9 |
| 6_1 | 6 | CTttattataactTgaAtCTC | 0.2 | 7 |
| 7_1 | 21 | GAattttacatactctGGT | 0.6 | 15 |
| 8_1 | 22 | GAAttttacatactctgGTC | 0.3 | 8 |
| 9_1 | 23 | CAAaaaacagtaggTCC | 2.0 | 18 |
| 10_1 | 24 | Gagggaggtggag<sup>m</sup>cgTT | — | 55 |
| 11_1 | 25 | AGCTttattataacttgaAT | — | 55 |
| 12_1 | 26 | TTttacatactctggtCAAA | 0.8 | 17 |
| 13_1 | 27 | TTTtacatactctggTCA | 0.4 | 4 |
| 14_1 | 28 | GAgaattttacatactcTGG | 0.6 | 16 |
| 15_1 | 29 | GCatccaacaagtaattGT | — | 35 |
| 16_1 | 30 | GgtgggtggatgTTTC | 0.8 | 32 |
| 17_1 | 31 | GgtggtgtggagaAGC | — | 52 |
| 18_1 | 32 | GGCatccaacaagtaaTT | 2.1 | 22 |
| 19_1 | 33 | GGaataaaacagtaGGTC | 0.5 | 18 |
| 20_1 | 34 | GCcattttcactgtCAA | 0.3 | 7 |
| 21_1 | 35 | GTGcagaagtcagaacaAA | 0.9 | 26 |
| 22_1 | 36 | CAAAatgcccttacagtGA | 0.3 | 6 |
| 23_1 | 37 | GGAataaaacagtaGGT | 0.2 | 13 |

Example 4: Antisense Oligonucleotide Caspase Screen in HepG2 and 3T3 Cells for 24 Hours at 100 nM Concentration In this experiment, the toxicity of the compounds of the present invention (CMP ID NOs: 3_1, 4_1, 5_1 and 6_1, see e.g. Table 6) was assessed by a Caspase screen in HepG2 cells. The prior art compounds tested in Example 3 were included in this study. Further, shorter metabolites of the full-lengths CMP ID NOs: 3_1 and 5_1 were analysed (for more details, see Example 6).

HepG2 or 3T3 cells were cultivated at app. 70% confluence in MEM medium with GlutaMax™ (Gibco #41090; HepG2) or DMEM with Glutamax (Gibco #31966), completed with 5 mM HEPES (3T3), supplemented with 10% heat inactivated fetal calf serum. Cells were detached with 0.25% Trypsin-EDTA solution (Gibco #25200056) and seeded into black, clear 96-well plates (Corning #3904, NY, USA) at a density of $1 \times 10^4$ cells/well (HepG2) or $0.25 \times 10^4$ cells/well (3T3). 24h post-seeding cells were transiently transfected with Lipofectamine 2000 (Life Technologies #11668019) using 100 nM oligonucleotides dissolved in Opti-MEM (Gibco #31985). Caspase-3/7 activity was determined using the Caspase-Glo® 3/7 Assay (Promega Corporation, Madison WI, USA). Reconstituted Caspase-Glo® 3/7 reagent was added to the cells 24 hours post-transfection, incubated for 60 min, cell lysates were transferred into opaque 96-well plates (Corning #3600, NY, USA) before luminescence was determined on an Enspire multi-mode plate reader (Perkin Elmer) according to the manufacturer's instructions.

The results are shown in Table 12.

TABLE 12

Results of caspase scoring

| CMP-ID | SEQ ID NO | Compound | Caspase (% AW) in HepG2 | Caspase (% AW) in 3T3 |
|---|---|---|---|---|
| 3_1 | 3 | AATTttacatactctgGT | −4 | 20 |
| 3_1-1 | 38 | AATTttacatactctgG | −5 | 11 |
| 3_1-2 | 39 | AATTttacatactctg | −6 | 3 |
| 4_1 | 4 | AAttttacatactctGGTC | 32 | 23 |
| 5_1 | 5 | TTacatactctggtCAAA | 8 | 29 |
| 5_1-1 | 40 | TTacatactctggtCAA | 8 | 30 |
| 5_1-2 | 41 | TTacatactctggtCA | 0 | 13 |
| 6_1 | 6 | CTttattataactTgaAtCTC | 6 | 22 |
| 7_1 | 21 | GAattttacatactctGGT | 2 | 26 |
| 8_1 | 22 | GAAttttacatactctgGTC | 11 | 35 |
| 9_1 | 23 | CAAaaaacagtaggTCC | 2 | 26 |
| 10_1 | 24 | Gagggaggtggag<sup>m</sup>cgTT | 11 | −7 |
| 11_1 | 25 | AGCTttattataacttgaAT | 5 | 47 |
| 12_1 | 26 | TTttacatactctggtCAAA | 23 | 72 |
| 13_1 | 27 | TTTtacatactctggTCA | 33 | 47 |
| 14_1 | 28 | GAgaattttacatactcTGG | 13 | 44 |

TABLE 12-continued

| Results of caspase scoring | | | | |
|---|---|---|---|---|
| CMP-ID | SEQ ID NO | Compound | Caspase (% AW) in HepG2 | Caspase (% AW) in 3T3 |
| 15_1 | 29 | GCatccaacaagtaattGT | 53 | 102 |
| 16_1 | 30 | GgtgggtggatgTTTC | 114 | 12 |
| 17_1 | 31 | GgtggtgtggagaAGC | 110 | 80 |
| 18_1 | 32 | GGCatccaacaagtaaTT | 94 | 144 |
| 19_1 | 33 | GGaataaaacagtaGGTC | 44 | 73 |
| 20_1 | 34 | GCcattttcactgtCAA | 59 | 23 |
| 21_1 | 35 | GTGcagaagtcagaacaAA | 20 | 69 |
| 22_1 | 36 | CAAAatgcccttacagtGA | 143 | 44 |
| 23_1 | 37 | GGAataaaacagtaGGT | 70 | 51 |

Compounds with a value of more than 60% AW were considered as toxic (T). Compounds with a value of 40-60% AW were considered as medium toxic (MT). Compounds with a value of 20-40% AW were considered as mild toxic (M). Compounds with a value of less than 20% AW were considered as non-toxic (NT)

As it can be derived from Table 12, the compounds with CMP ID NO: 11_1 (MT), CMP ID NO: 12_1 (T), CMP ID NO: 13_1 (MT), CMP ID NO: 14_1 (MT), CMP ID NO: 15_1 (T), CMP ID NO: 16_1 (T), CMP ID NO: 17_1 (T), CMP ID NO: 18_1 (T), CMP ID NO: 19_1 (T), CMP ID NO: 20_1 (MT), CMP ID NO: 21_1, CMP ID NO: 22_1, and CMP ID NO: 23_1 showed medium tox (MT) or toxic (T) which deselects the compounds for further profiling.

Example 5: Testing In Vitro Efficacy of Full Length Antisense Oligonucleotides and Metabolites Thereof, Targeting RTEL1 mRNA in Human MDA-MB-231 Cell Line at Different Concentrations for a Concentration Response Curve It is known that antisense oligonucleotides are metabolized in the cell. In this experiment, full-length oligonucleotides and their metabolites from the 3' end (i.e. n−1, n−2, n−3, n−4, n−5, and n−6) are tested for their in vitro potency of reducing the RTEL1 mRNA target.

Human MDA-MB-231 cell line was purchased from ATCC and maintained as recommended by the supplier in a humidified incubator at 37° C. with 5% $CO_2$. For assays, 3500 cells/well of were seeded in a 96 multi well plate in culture media. Cells were incubated for 24 hours before addition of oligonucleotides dissolved in PBS. Highest screening concentration of oligonucleotides: 50 µM and subsequent dilutions in 8 steps. 3 days after addition of oligonucleotides, the cells were harvested. RNA was extracted using the PureLink™ Pro 96 RNA Purification kit (Thermo Fisher Scientific) according to the manufacturer's instructions and eluated in 50 µl water. The RNA was subsequently diluted 10 times with DNase/RNase free Water (Gibco) and heated to 90° C. for one minute.

For gene expressions analysis, One Step RT-qPCR was performed using gScript™ XLT One-Step RT-qPCR ToughMix®, Low ROX™ (Quantabio) in a duplex set up. The following TaqMan primer assays were used for qPCR: RTEL1_Hs01548056_m1 [FAM-MGB] and endogenous control GUSB_Hs99999908_m1 [VIC-MGB]. All primer sets were purchased from Thermo Fisher Scientific. The relative RTEL1 mRNA level is shown as percent of control (PBS treated samples) and $IC_{50}$ determined using GraphPad Prism7.04.

The results are shown in FIG. 9 and in Table 13

TABLE 13

| In vitro potency of full-length oligonucleotides and their metabolites | | | | |
|---|---|---|---|---|
| CMP-ID | SEQ ID NO | Compound | $IC_{50}$ in MDA-MB-231 [µM] | RTEL1 mRNA level (%) at 50 µM in MDA-MB-231 |
| 5_1 | 5 | **TTacatactctggtCAAA** | 0.6 | 2 |
| 5_1-1 | 40 | TTacatactctggtCAA | 0.4 | 3 |
| 5_1-2 | 41 | TTacatactctggtCA | 0.7 | 3 |
| 5_1-3 | 42 | TTacatactctggtC | 2.5 | 13 |
| 5_1-4 | 43 | TTacatactctggt | — | 33 |
| 5_1-5 | 44 | TTacatactctgg | — | 33 |
| 5 1-6 | 45 | TTacatactctg | — | 72 |
| 7_1 | 21 | GAattttacatactctGGT | 0.4 | 3 |
| 7_1-1 | 46 | GAattttacatactctGG | 1.0 | 11 |
| 7_1-2 | 47 | GAattttacatactcTG | — | 62 |
| 7_1-3 | 48 | GAattttacatactcT | — | 72 |
| 7_1-4 | 49 | GAattttacatactc | — | 72 |
| 7_1-5 | 50 | GAattttacatact | — | 79 |
| 7_1-6 | 51 | GAattttacatac | — | 84 |
| 8_1 | 22 | GAAttttacatactctgGTC | 0.1 | 3 |
| 8_1-1 | 52 | GAAttttacatactctgGT | 1.4 | 16 |
| 8_1-2 | 53 | GAAttttacatactctgG | 3.1 | 34 |
| 8_1-3 | 54 | GAAttttacatactctg | — | 68 |
| 8_1-4 | 55 | GAAttttacatactct | — | 67 |
| 8_1-5 | 56 | GAAttttacatactc | — | 68 |
| 8_1-6 | 57 | GAAttttacatact | | 77 |
| 9_1 | 23 | CAAaaaacagtaggTCC | 1.2 | 11 |
| 9_1-1 | 58 | CAAaaaacagtaggTC | — | 64 |
| 9_1-2 | 59 | CAAaaaacagtaggT | — | 73 |
| 9_1-3 | 60 | CAAaaaacagtagg | — | 68 |
| 9_1-4 | 61 | CAAaaaacagtag | — | 78 |
| 9_1-5 | 62 | CAAaaaacagta | — | 83 |
| 9_1-6 | 63 | CAAaaaacagt | — | 79 |
| 10_1 | 24 | Gagggaggtggag$^{m}$cgTT | — | 46 |

TABLE 13-continued

In vitro potency of full-length oligonucleotides and their metabolites

| CMP-ID | SEQ ID NO | Compound | $IC_{50}$ in MDA-MB-231 [μM] | RTEL1 mRNA level (%) at 50 μM in MDA-MB-231 |
|---|---|---|---|---|
| 10_1-1 | 64 | Gagggaggtggag$^m$cgT | — | 38 |
| 10_1-2 | 65 | Gagggaggtggag$^m$cg | — | 39 |
| 10_1-3 | 66 | Gagggaggtggag$^m$c | — | 34 |
| 10_1-4 | 67 | Gagggaggtggag | — | 47 |
| 10_1-5 | 68 | Gagggaggtgga | — | 51 |
| 10_1-6 | 69 | Gagggaggtgg | — | 54 |

Figure 9A:
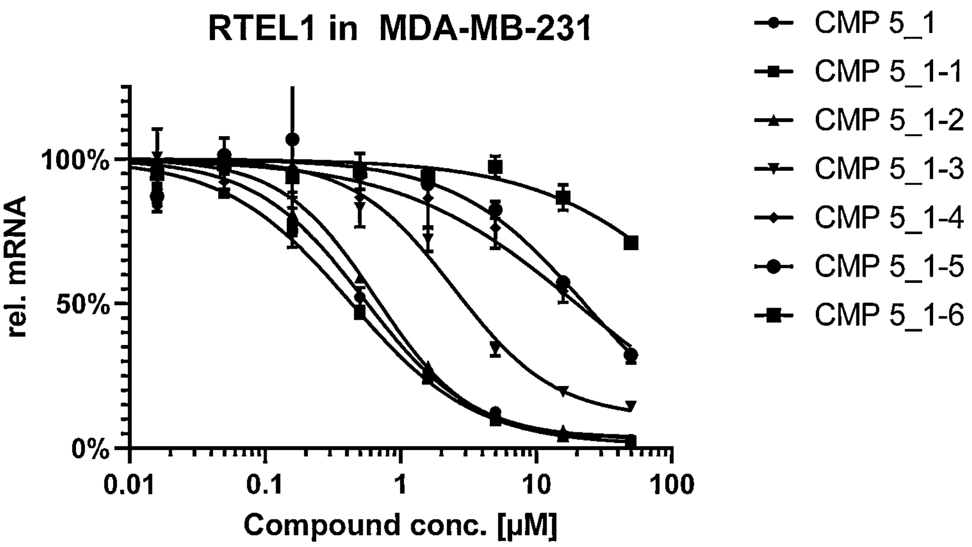
FIG. 9A-FIG. 9E.
Figure 9B:
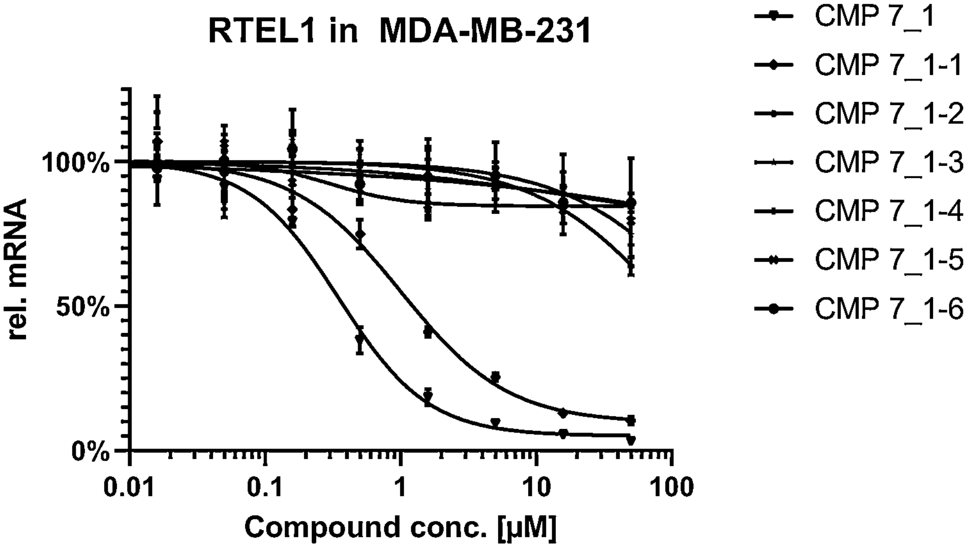
Figure 9C:
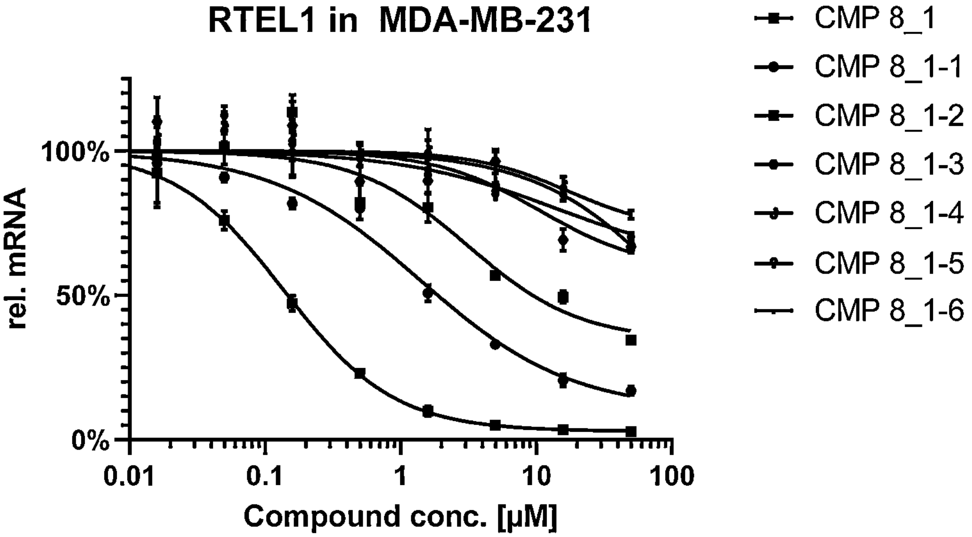
Figure 9D:
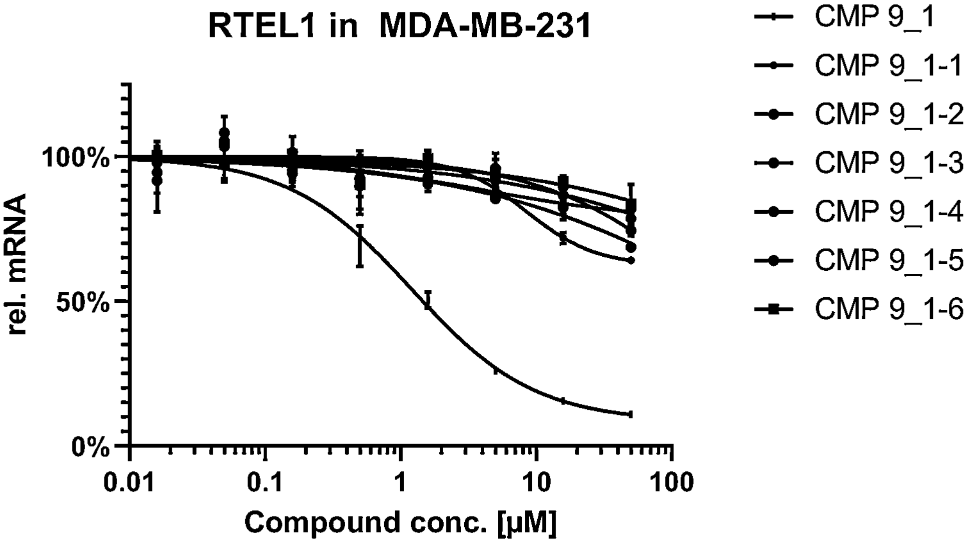
Figure 9E:
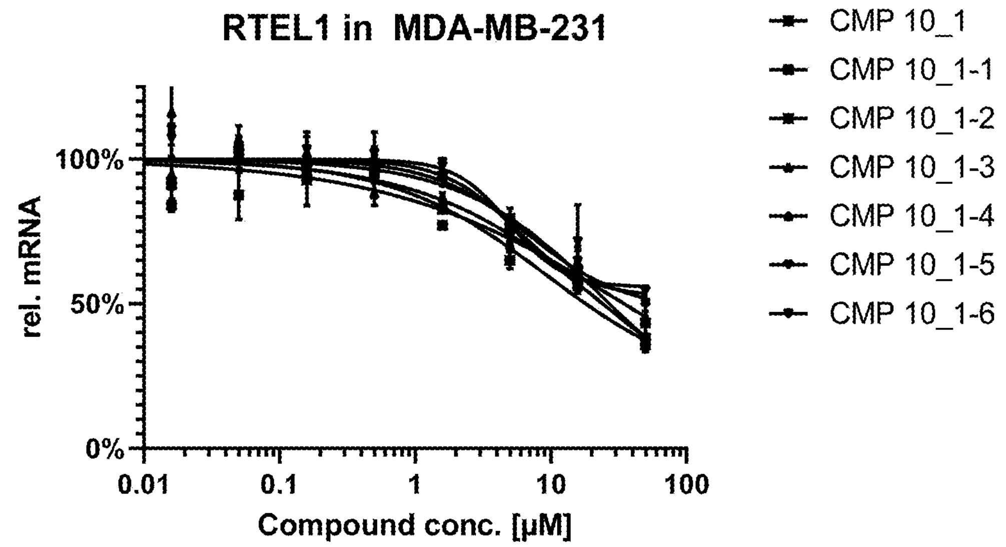

As can be derived from Table 13 and FIG. 9*a*, the full length oligonucleotide CMP 5_1 has an $IC_{50}$ of 0.6 μM. Advantageously, the first and second metabolite (CMP 5_1-1 and CMP 5_1-2) retains similar target knock down activity with an $IC_{50}$ of 0.4 μM and 0.7 μM respectively before further metabolites (n−3 to n−6) show reduction in maximum efficacy and potency. For all other compounds, already the n−1 and n−2 metabolites show significant loss of potency and/or maximum efficacy as compared to their respective full length sequence compound.

Example 6: In Vivo Study of CMP 5_1-GalNAc Antisense Oligonucleotide

Study Schedule

Figure 10:
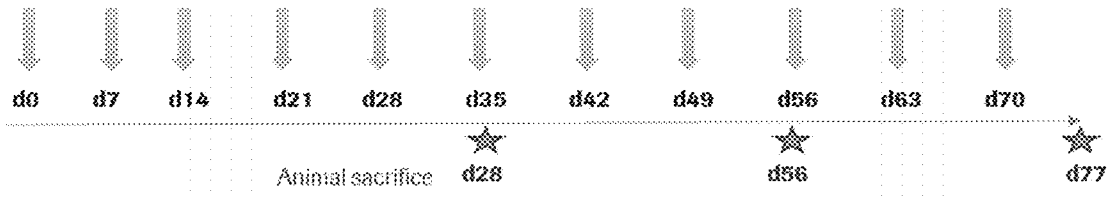
FIG. 10: Study protocol for in vivo analysis in mice treated with GalNAc-conjugated CMP ID 5_1

The study is run in HBV-infected PXB-Mice®, a chimeric mouse model with stable human hepatocyte engraftment (PhoenixBio) for a total of 77 days with 3 groups (vehicle, CMPD3_1_GalNAc, CMPD5_1_GalNAc) consisting of 20 animals each. Animals are dosed weekly using 10 mg/kg of compound or equivalent volume of vehicle. 5 animals of each group were sacrificed at day 28 and day 56, respectively. The remaining animals at day 77 after which the bioanalysis was performed on the livers of the animals. The study protocol is shown in FIG. 10.

Methods and Materials

GalNAc conjugates for CMP 3_1 and CMP 5_1 were generated by methods known in the art (see e.g. Javanbakh et al. Liver-Targeted Anti-HBV Single-Stranded Oligonucleotides with Locked Nucleic Acid Potently Reduce HBV Gene Expression In Vivo. Mol Ther Nucleic Acids. 2018 Jun. 1; 11:441-454. Epub 2018 Feb. 23. PMID: 29858079; PMCID: PMC5992345). The produced conjugates are shown in FIG. 1 and FIG. 4, respectively.

Animals and Handling

HBV genotype C-infected human liver-chimeric uPA/SCID mice (PXB mice; donor hepatocytes BD195 (Corning Incorporated)) were purchased from PhoenixBio Co, Ltd. Animal handling was done on site by PhoenixBio Co, Ltd. in Higashi-Hiroshima, Japan. Male mice aged at least 20 weeks at dosing start (day 0) with a weight of 18 g or more as determined on the day prior to dosing start (day −1) were selected for the study. Mice had been infected with HBV genotype C (Code No.: PBB004, Lot: 180118, PhoenixBio Co., Ltd.) at least 6 weeks prior to dosing start and showed serum HBV-DNA levels of >$1\times10^6$ copies/ml as determined by qPCR on day −7. Group randomization at study start was determined on day −1 based on the arithmetic mean values for body weight and geometric mean values for blood h-Alb concentration and serum HBV-DNA concentration.

All doses of 10 mg/kg were calculated based on the individual body weights of the mice which are taken prior to the administration on the days of dosing. All subject mice received an injection of the dose formulation into cervical subcutaneous tissue on the upper back on days 0, 7, 14, 28, 35, 42, 49, 56, 63, and 70 using disposable 1.0 mL syringes with permanently attached needles (Terumo Corporation).

On the respective sacrifice days, target animals were anesthetized with isoflurane anesthesia and sacrificed by cardiac puncture and exsanguination. Livers were extracted and the left lateral lobe divided into pieces of approximately 100 mg. Exact weight was recorded and liver samples were snap frozen in liquid nitrogen and stored at −80° C. until processed further.

Animals with signs of moribundity or weight loss of >20% of the initial body weight were sacrificed as required. All prematurely terminated/found dead animals as well as mice with thymoma/lymphoma on sacrifice were excluded from analysis.

Quantification of RTEL1 mRNA Expression

Liver tissue samples were kept frozen until lysed in MagNA Pure LC RNA Isolation Tissue Lysis Buffer (Product No. 03604721001, Roche) and RNA extraction continued using the MagNA Pure 96 Cellular RNA Large Volume Kit (Product No. 05467535001, Roche) on a MagNA Pure 96 Instrument (Roche) according to the user's manual and RNA concentration adjusted with water.

For gene expressions analysis, One Step RT-qPCR was performed using gScript™ XLT One-Step RT-qPCR ToughMix®, Low ROX™ (Quantabio). The following TaqMan primer assays were used for qPCR: Hs01548056_m1; Hs00249680_m1; Hs00249668_m1 and reference genes GAPDH_Hs99999905_m1; PGK1_Hs99999906_m1 and GUSB_Hs99999908_m1. All primer sets were purchased from Thermo Fisher Scientific. The relative mRNA expression levels are shown as percent relative to saline treated control group.

Figure 11:
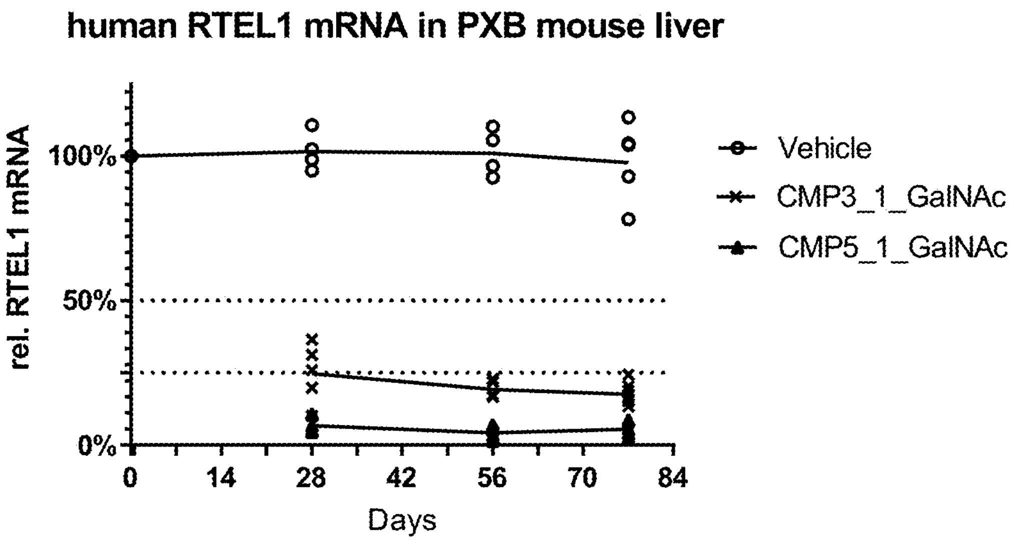
FIG. 11: Level of RTEL1 mRNA in liver tissue from PXB-mice treated with GalNAc-conjugated oligonucleotide antisense CMP ID Nos 3_1 and 5_1

The results are shown in FIG. 11. The analysis shows approximately 80% knockdown efficacy with CMP3_1_GalNAc at weekly dosing of 10 mg/kg and ca. 95% knockdown efficacy with CMP5_1_GalNAc at weekly dosing of 10 mg/kg.

Example 7: In Vitro Study in Primary Human Hepatocytes

Methods and Materials

Cell Culture

Primary human hepatocytes (PHH) isolated by the collagenase perfusion method from chimeric urokinase-type plasminogen activator/severe combined immunodeficiency (uPA/SCID) mice with humanized livers were obtained from PhoenixBio (Hiroshima, Japan). PHH were plated on type I collagen-coated 96-well plates at a concentration of $7\times10^4$ cells per well in modified hepatocyte clonal growth medium (dHCGM). dHCGM is a DMEM medium containing 100 U/ml Penicillin, 100 μg/ml Streptomycin, 20 mM Hepes, 44 mM $NaHCO_3$, 15 μg/ml L-proline, 0.25 μg/ml Insulin, 50 nM Dexamethazone, 5 ng/ml EGF, 0.1 mM Asc-2P, 2% DMSO and 10% FBS (Ishida et al., 2015). Cells were cultured at 37° C., in a humidified atmosphere with 5% $CO_2$. Culture medium was replaced every 2 days until harvest, except over the weekend.

HBV genotype C at multiplicity of infection (MOI) of 40 was then added to the cells in 96-well plates with a final concentration of 4% PEG 8000 (Sigma-Aldrich). Infected cells were incubated for 20 h at 37° C., and then washed two times with PBS to remove the HBV inoculum and refilled with complete media. At day 4 post-infection, cells were treated with different concentrations of LNA. Medium was changed with new LNA at day 6 and day 8 post-infection. Phosphate-buffered saline (PBS) was used as a "no drug" control (NDC). Supernatants and cells were harvested and used for HBV marker and target knockdown analysis on day 19 post-infection.

Cytotoxicity of the LNAs was assessed using Cell Counting Kit 8 (Sigma-Aldrich) according to the manufacturer's protocol and expressed as % cytotoxicity vs. NDC.

RNA Extraction and Real-Time Quantitative PCR

Intracellular mRNA was extracted from cells using a MagNA Pure 96 robot and the MagNA Pure 96 Cellular RNA Large Volume Kit (Roche) according to the manufacturer's protocol. Quantification of relative total HBV, RTEL1, pgRNA, and β-Glucuronidase (GusB) endogenous control mRNA was performed in technical duplicates using a QuantStudio 12K Flex (Life Technologies) using the TaqMan RNA-to-Ct 1-Step Kit (Applied Biosystems, #4392938). The mRNA expression was analyzed using the comparative cycle threshold 2-ΔΔCt method normalized to the reference gene GusB and to no drug control. TaqMan primers and assay IDs were as follows: RTEL1, Hs02568623_s1; Total HBV RNA Pa03453406_s1; HBV pgRNA AILJKX5. As reference gene GusB, Hs00939627_m1 was used. All primer & probe sets were obtained from ThermoFisher.

The results for 25 μM of antisense oligonucleotide are shown in Table 14 which, inter alia, includes information on cytotoxicity of the cell and RTEL1 mRNA knock down. CMP10_1 shows a high cellular cytotoxicity and poor efficacy in targeting RTEL1 mRNA. In addition, CMP9_1 shows the second poorest knock down of RTEL1 mRNA with 57% remaining RTEL1 mRNA.

TABLE 14

In vitro study in primary human hepatocytes (25 μM of antisense oligonucleotide)

| LNA @25 μM | % cytotoxicity | % RTEL1 mRNA vs. NDC | % pgRNA vs. NDC | % total HBV-RNA vs. NDC |
|---|---|---|---|---|
| 5_1 | 4 | 17 | 70 | 72 |
| 5_1_GalNAc | 5 | 15 | 57 | 46 |
| 7_1 | 1 | 24 | 83 | 76 |
| 8_1 | 3 | 13 | 74 | 81 |
| 9_1 | 2 | 57 | 103 | 94 |
| 10_1 | 30 | 101 | 61 | 53 |

The results for 5 μM of antisense oligonucleotide are shown in Table 15. CMP10_1 shows poor efficacy in targeting RTEL1 mRNA. In addition, CMP9_1 again shows the second poorest knock down of RTEL1 mRNA at 79% remaining RTEL1 mRNA.

TABLE 15

In vitro study in primary human hepatocytes (5 μM of antisense oligonucleotide)

| LNA@5 μM | % cytotoxicity | % RTEL1 mRNA vs. NDC | % pgRNA vs. NDC | % total HBV-RNA vs. NDC |
|---|---|---|---|---|
| 5_1 | 4 | 47 | 77 | 80 |
| 5_1_GalNAc | 2 | 29 | 62 | 72 |
| 7_1 | 0 | 40 | 84 | 92 |
| 8_1 | 1 | 28 | 78 | 101 |
| 9_1 | −1 | 79 | 146 | 130 |
| 10_1 | −4 | 106 | 175 | 116 |

Example 8: In Vivo Proof of Concept for CMP5_1-GalNAc

Study Schedule

Figure 12:
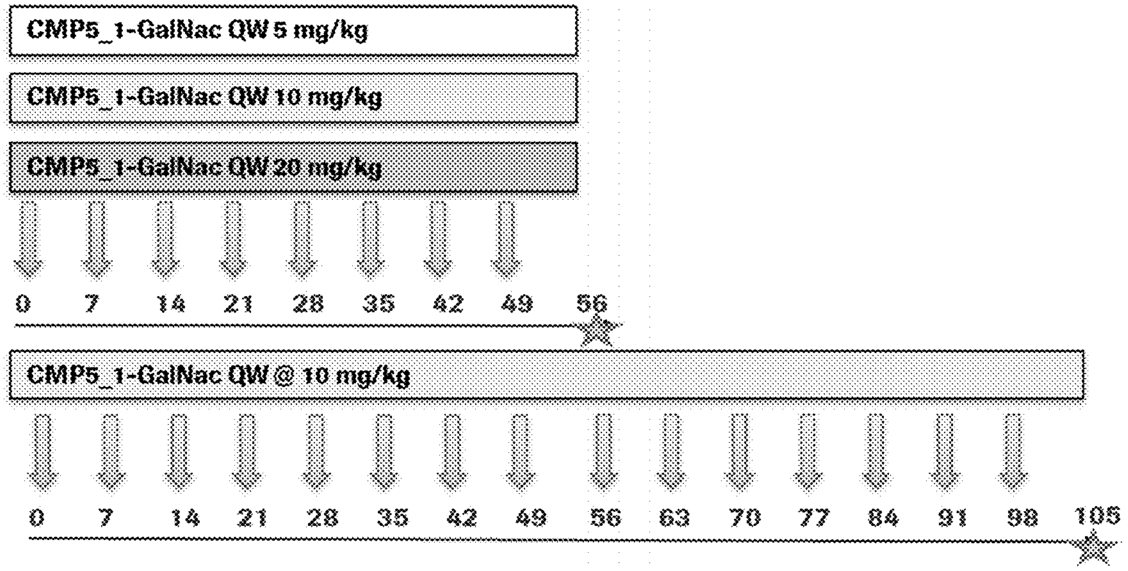
FIG. 12: Study protocol for in vivo analysis of HBV-infected PXB-mice treated with GalNAc-conjugated CMP ID 5_1.

The study is run in HBV-infected PXB-Mice®, a chimeric mouse model with stable human hepatocyte engraftment (PhoenixBio) with sacrifices at day 56 and day 105. CMP5_1-GalNac is evaluated after 8 weekly dosings of 5, 10, and 20 mg/kg (day 56, see FIG. 12). Additionally, CMP5_1-GalNac is also evaluated after 15 weekly dosings of 10 mg/kg (day 105). For each group, there was a separate vehicle control arm receiving the same volume of vehicle as the treated animals. All groups had a size of 6 mice at study start. The bioanalysis was performed on the livers of the animals.

Methods and Materials

Animals and Handling

HBV genotype C-infected human liver-chimeric uPA/SCID mice (PXB mice; donor hepatocytes BD195 (Corning Incorporated)) were purchased from PhoenixBio Co, Ltd. Animal handling was done by LSIM Safety Institute Corporation in Uto, Japan. Male mice aged at least 25 weeks at dosing start (day 0) with a weight of 18 g or more as determined on the day prior to dosing start (day −1) were selected for the study. Mice had been infected with HBV genotype C (Code No.: PBB004, Lot: 180118, PhoenixBio Co., Ltd.) at least 6 weeks prior to dosing start and showed serum HBV-DNA levels of >$1\times10^6$ copies/ml as determined by qPCR on day −7. Stratified randomization was performed at study start on day −1 based on body weight and blood h-Alb concentration as well as serum HBV-DNA concentration.

All doses were calculated based on the individual body weights of the mice which are taken prior to the administration on the days of dosing. All subject mice received an injection of the dose formulation or matched vehicle into cervical subcutaneous tissue on the upper back. Animal sacrificed on day 56 were injected on day 0, 7, 14, 21, 28, 35, 42, and 49 (see FIG. 12). The dose of 20 mg/kg/week was given in two consecutive injections of 10 mg/kg to avoid overloading the ASGPR in the chimeric livers. Thus, these mice were dosed on days 0, 1, 7, 8, 14, 15, 21, 22, 28, 29, 35, 36, 42, 43, 49, and 50. Animals sacrificed on day 105 had administration of 10 mg/kg on day 0, 7, 14, 21, 28, 35, 42, 49, 56, 63, 70, 77, 84, 91, and 98 (see FIG. 12) using disposable 1.0 mL syringes with permanently attached needles (Terumo Corporation).

On the respective sacrifice days, target animals were anesthetized with isoflurane anesthesia and sacrificed by cardiac puncture and exsanguination. Livers were extracted and the left lateral lobe divided into pieces of approximately 100 mg. Exact weight was recorded and liver samples were snap frozen in liquid nitrogen and stored at −80° C. until processed further.

Animals with signs of moribundity or weight loss of >20% of the initial body weight were sacrificed as required. All prematurely terminated/found dead animals as well as mice with thymoma/lymphoma on sacrifice were excluded from analysis.

cccDNA Determination by Southern Blot Analysis

Liver tissue was kept frozen until homogenization in DNA extraction buffer (50 mM Tris pH8, 5 mM EDTA, 150 mM NaCl, 1% SDS). The extract was first digested with RNase cocktail (ThermoFisher) for 30 min at ambient temperature followed by Proteinase K (ThermoFisher) for 2 h at 56° C. under light agitation. Debris was pelleted by centrifugation and DNA extracted from the supernatant by shaking three times with 1 volume UltraPure buffer-saturated phenol (ThermoFisher) followed by extraction with 1 volume of Phenol:Chloroform:Isoamyl Alcohol (25:24:1; ThermoFisher). DNA was then precipitated by adding 1 volume 100% ethanol and 60 mM (final) NaAc (SigmaAldrich) at −20° C. over night. DNA is then pelleted by centrifugation, the pellet washed with 70% ethanol and air-dried before resuspension in 10 mM Tris-HCl pH8 (ThermoFisher).

DNA content is quantified using NanoDrop (ThermoFisher) and concentration normalized to 1.5 μg/μl. 30 μg DNA are then subject to digestion with 70 U T5 Exonuclease (New England Biolabs) in 1× CutSmart buffer (New England Biolabs) for 2 h at 37° C. For each sample, equal volumes are mixed with Blue Juice loading buffer (ThermoFisher) and loaded onto a 0.95% agarose-TAE gel (SigmaAldrich). Between every (biological) group of samples, 1 lane loaded with DNA molecular weight marker VII (Roche) is added (same amount in each lane). After separation, the gel is transferred to fresh 0.2 M HCl (Acros Organics) for 10 minutes and then rinsed three times with water. Subsequently, the gel is placed in denaturing buffer (0.5 M NaOH, 1.5 M NaCl) for 30 min and rinsed once with water. Next, the gel is transferred to neutralizing buffer (0.5 M Tris pH7.5, 1.5 M NaCl) for 30 min. Finally, the gel is equilibrated with 20×SSC buffer (ThermoFisher) for 30 min. The DNA is then transferred to a Hybond-XL membrane (Cytiva) using a TurboBlotter kit (Cytiva) according to the manufacturer's instructions using 20×SSC buffer (ThermoFisher) for overnight transfer. After transfer, DNA is crosslinked to the membrane by irradiation with 1800 J UV radiation and the membrane dried.

For specific detection of HBV cccDNA, the DIG nucleic acid detection kit is used with DIG EasyHyb buffer and the DIG wash and blocking buffer set (all Roche) according to the manufacturer's instructions. The probe is generated by PCR using the DIG PCR probe kit (Roche) according to the manufacturer's instructions. A plasmid containing the HBV genotype C genome is used as template with the following primers: forward, GTTTTTCACCTCTGCCTAATCATC (SEQ ID NO: 70); reverse, GCAAAAAGTTGCATGGTGCTGGT (SEQ ID NO: 71).

Hybridization is performed with probe denatured at 100° C. for 5 min and then rapidly cooled to 4° C. at 37° C. overnight. Washes and detection are performed according to the manufacturer's instructions. Images are acquired using a FUSION FX system (Vilber) setting an appropriate exposure time to detect cccDNA in vehicle control samples. For analysis, the cccDNA band (2.1 kB size) is quantified using ImageStudio software (Licor). To account for uneven transfer, the 2.8 kB band of the DNA molecular weight marker VII is also quantified and cccDNA band intensities are normalized to the average intensity of the two bands framing the group. Individual values are then normalized to the average band intensity of the vehicle control group.

RTEL1 mRNA Analysis

Liver tissue samples were kept frozen until lysed in MagNA Pure LC RNA Isolation Tissue Lysis Buffer (Product No. 03604721001, Roche) and RNA extraction continued using the MagNA Pure 96 Cellular RNA Large Volume Kit (Product No. 05467535001, Roche) on a MagNA Pure 96 Instrument (Roche) according to the user's manual and RNA concentration adjusted with water.

For gene expressions analysis, One Step RT-qPCR was performed using gScript™ XLT One-Step RT-qPCR ToughMix®, Low ROX™ (Quantabio). The following TaqMan primer assays were used for qPCR: Hs01548056_m1; Hs00249680_m1; Hs00249668_m1 and referene genes GAPDH_Hs99999905_m1; PGK1_Hs99999906_m1 and GUSB_Hs99999908_m1. All primer sets were purchased from Thermo Fisher Scientific. The relative mRNA expression levels are shown as percent relative to saline treated control group.

Figure 13A:
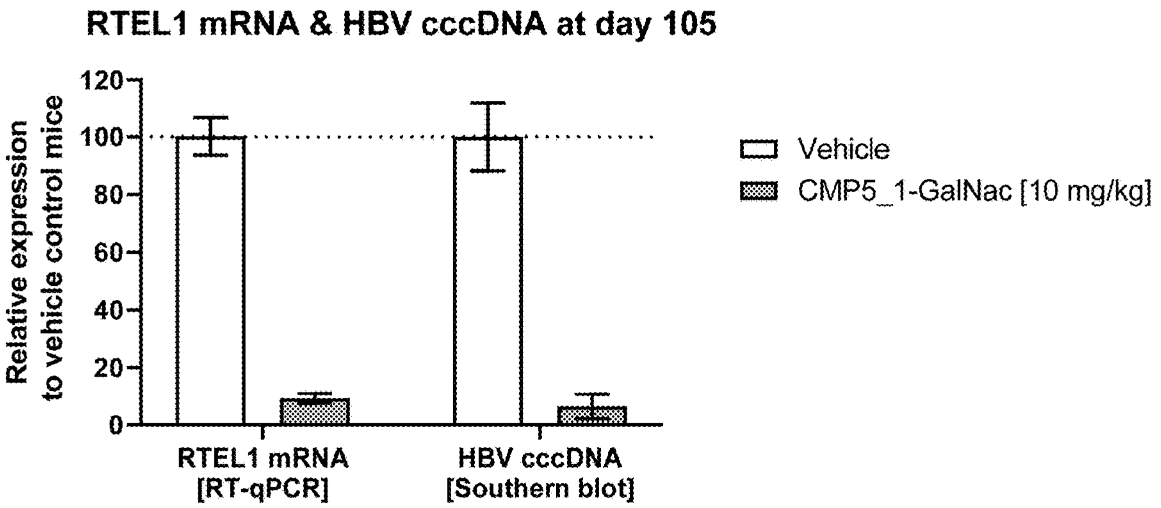
FIG. 13A-FIG. 13B.

FIG. 13A shows an example of weekly dosing of CMP5_1-GalNAc for 105 days gives reduction of RTEL1 mRNA to ~15% and cccDNA to ~20%

Figure 13B:
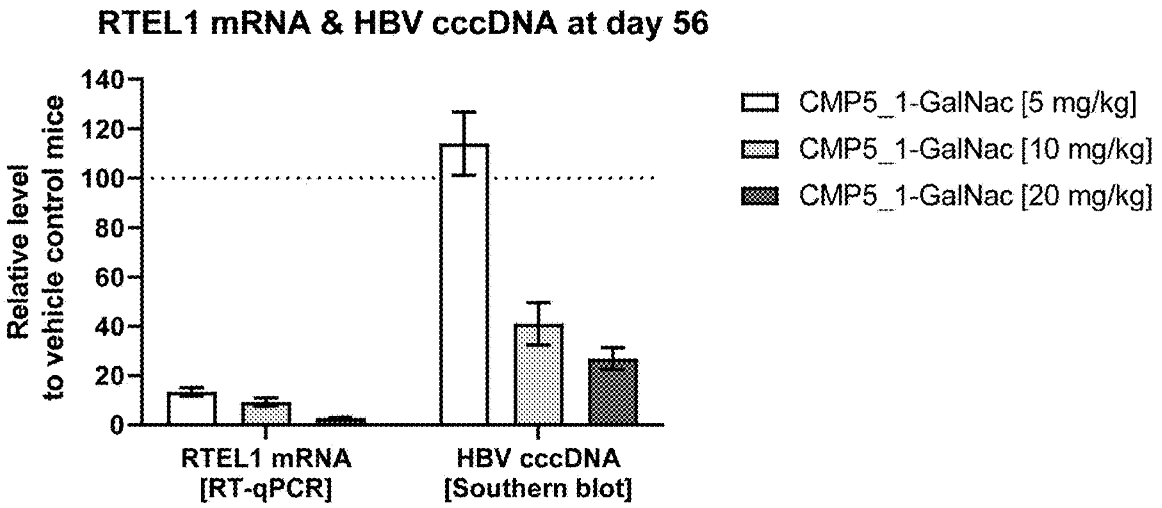

FIG. 13B shows knock-down of RTEL1 mRNA of 87%, 91%, and 97% after weekly dosing of 5, 10, and 20 mg/kg CMP5_1-GalNac, respectively, at day 56. cccDNA was reduced by 59% and 73% for 10 and 20 mg/kg CMP5_1-GalNac, respectively.

Conclusions:

It follows from the above Examples that CMP ID 5_1 displays a safe and efficacious compound for targeting the RTEL1 mRNA both in vivo and in vitro. We have here shown a favorable in vitro drug property profile of CMP ID_5_1 and we have showcased that the target of RTEL1 can be engaged very efficiently in vivo with the subsequent reduction of viral cccDNA. In addition, we have shown that by down regulating the RTEL1 mRNA a significant dose dependent effect on the viral cccDNA using hepatitis B infected humanized mouse models can be elicited. The compound 5_1 furthermore has a property of retaining activity after degradation from the 3' end. This means that the n−1 and n−2, from the 3' end, has a comparable in vitro potency as compared to the full length CMP ID_5_1. The n−3 degradation also still retains activity towards RTEL1 albeit with a lower in vitro potency. This profile gives the molecule a clear benefit as the metabolites of the parent molecule still elicit the wanted effect on RTEL1 mRNA.

The invention claimed is:

1. An antisense oligonucleotide consisting of CTttattataactTgaAtCTC (SEQ ID NO 6), wherein capital letters are beta-D-oxy LNA nucleosides, lowercase letters are DNA nucleosides, all LNA C are 5-methyl cytosine, and all internucleoside linkages are phosphorothioate internucleoside linkages.

2. The antisense oligonucleotide of claim 1, wherein at least one conjugate moiety is covalently attached to said antisense oligonucleotide.

3. The antisense oligonucleotide of claim 2, wherein the at least one conjugate moiety binds to the asialoglycoprotein receptor.

4. The antisense oligonucleotide of claim 2, wherein the conjugate moiety is:

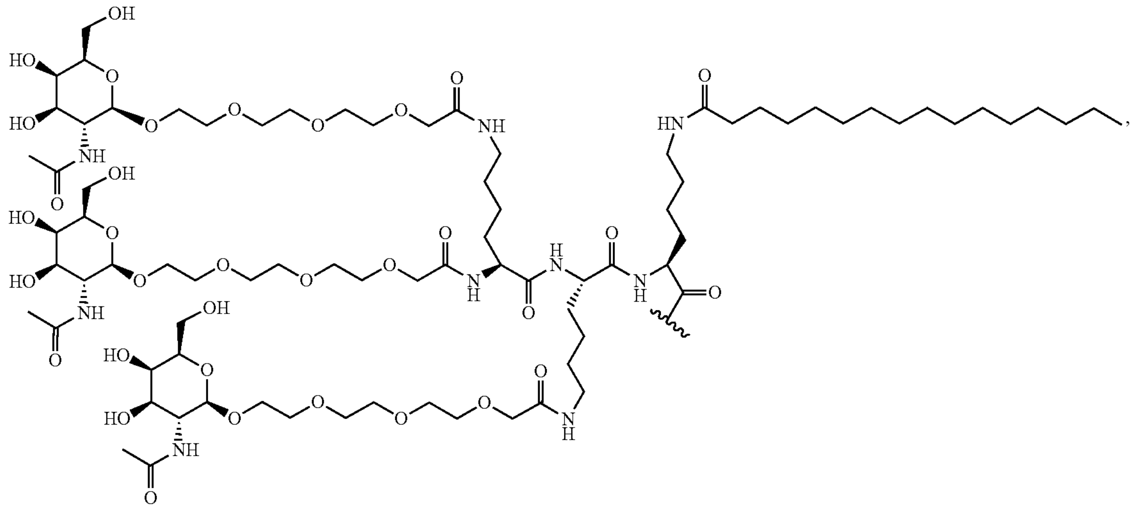

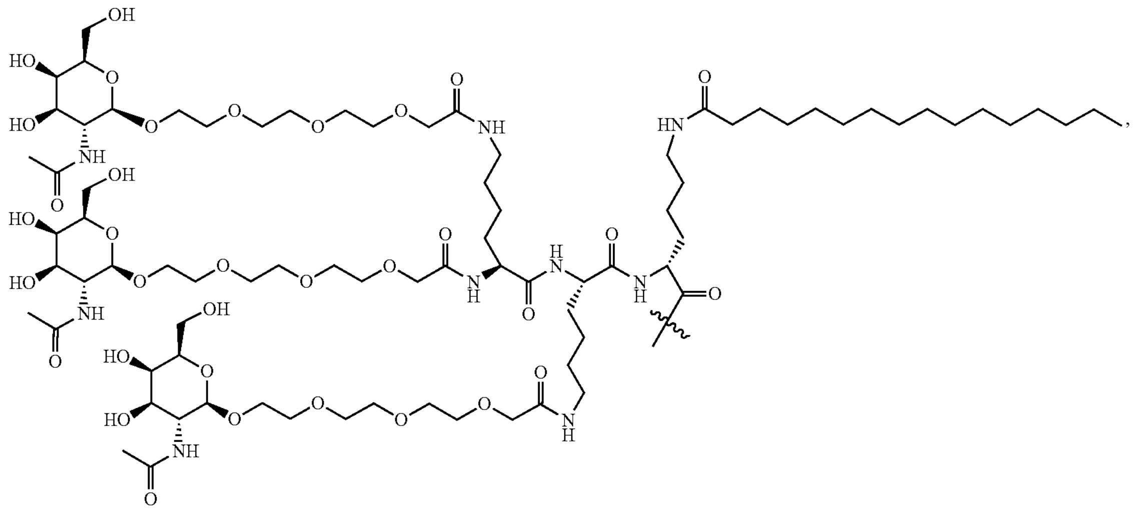

-continued
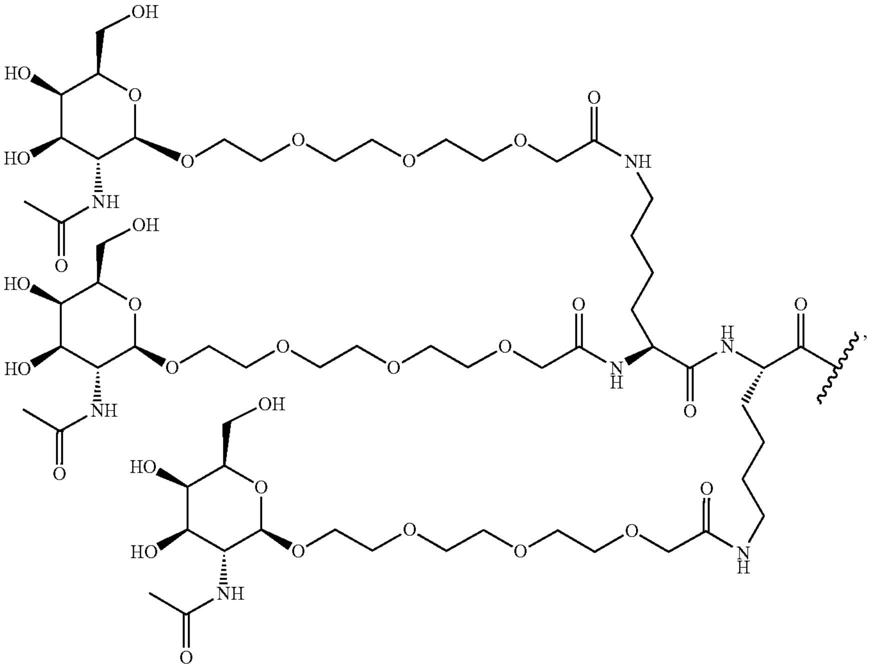
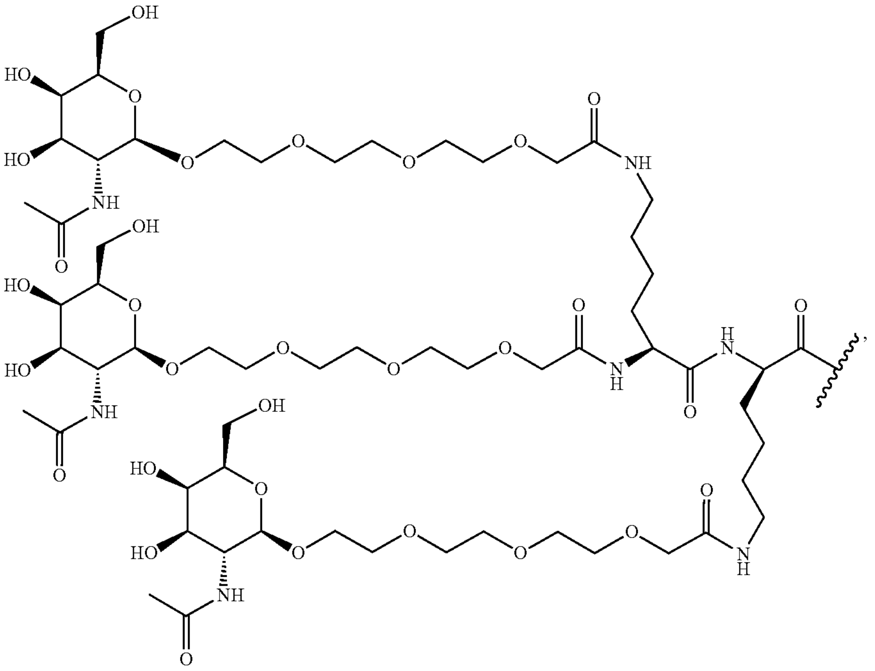

-continued
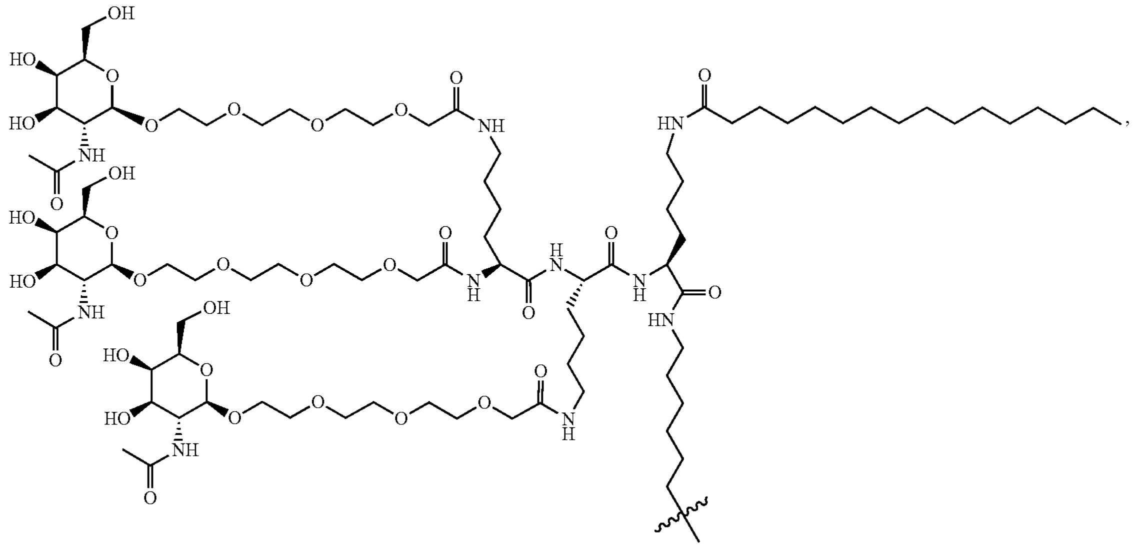
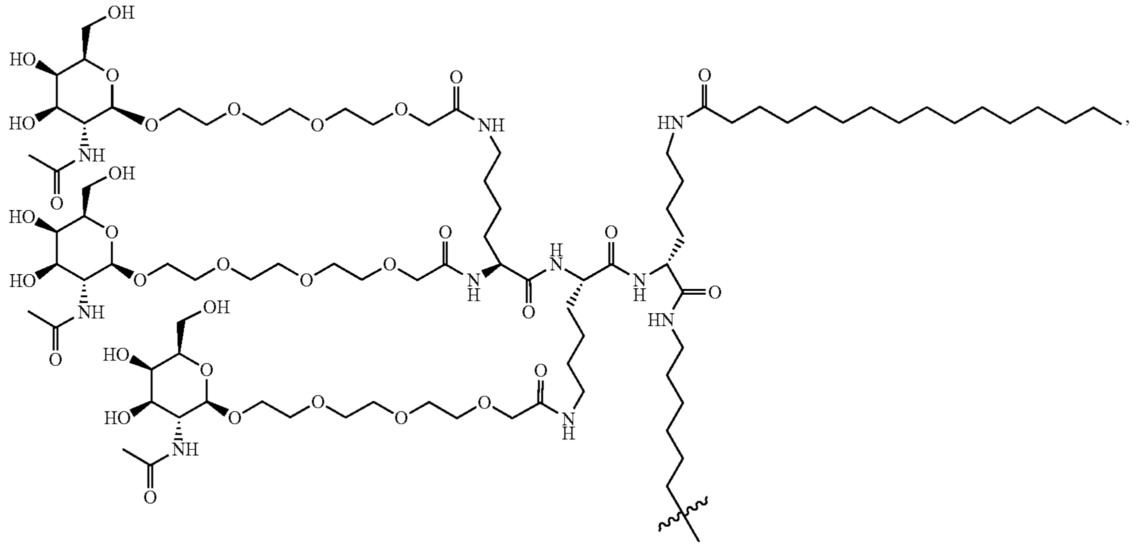

-continued
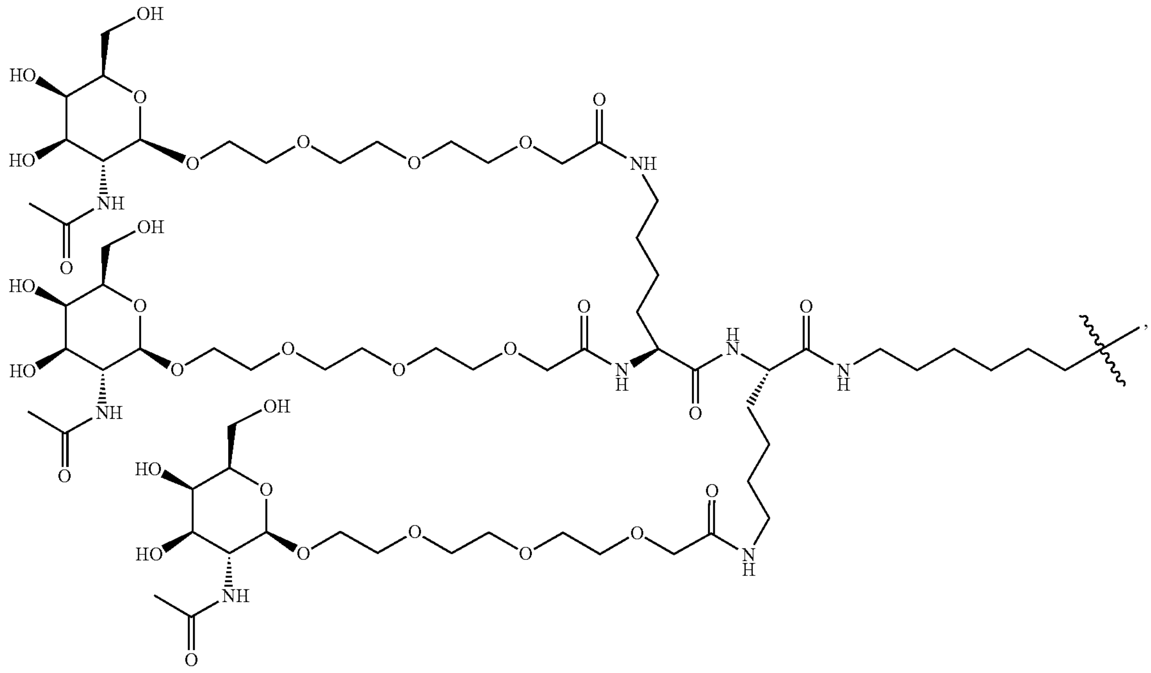
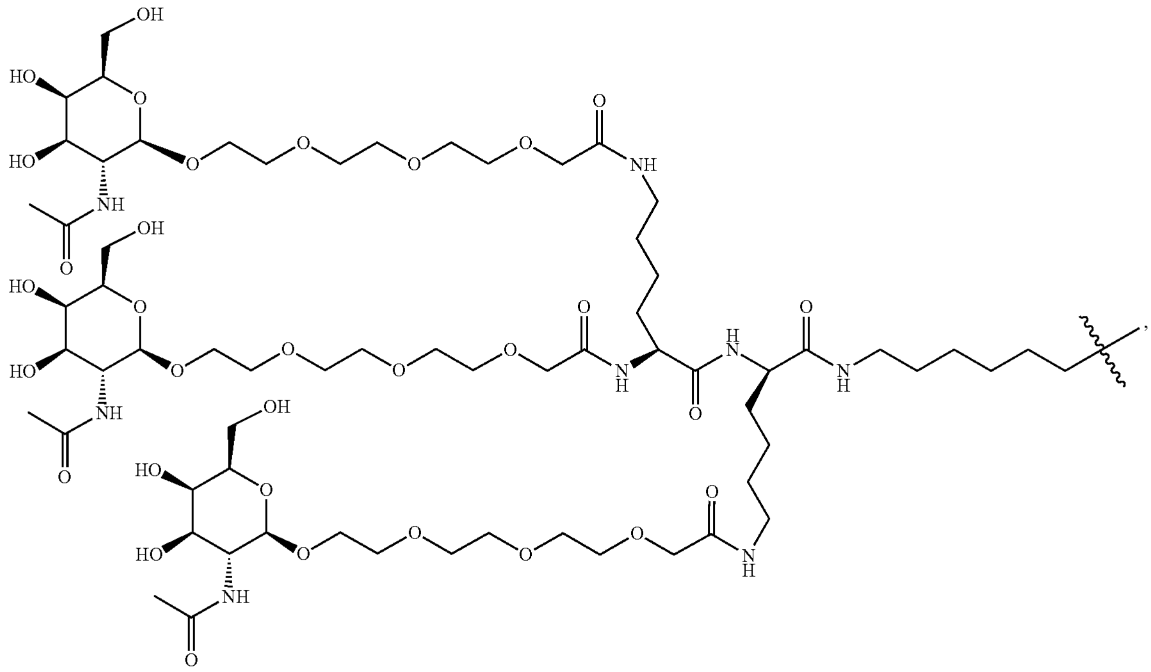

-continued
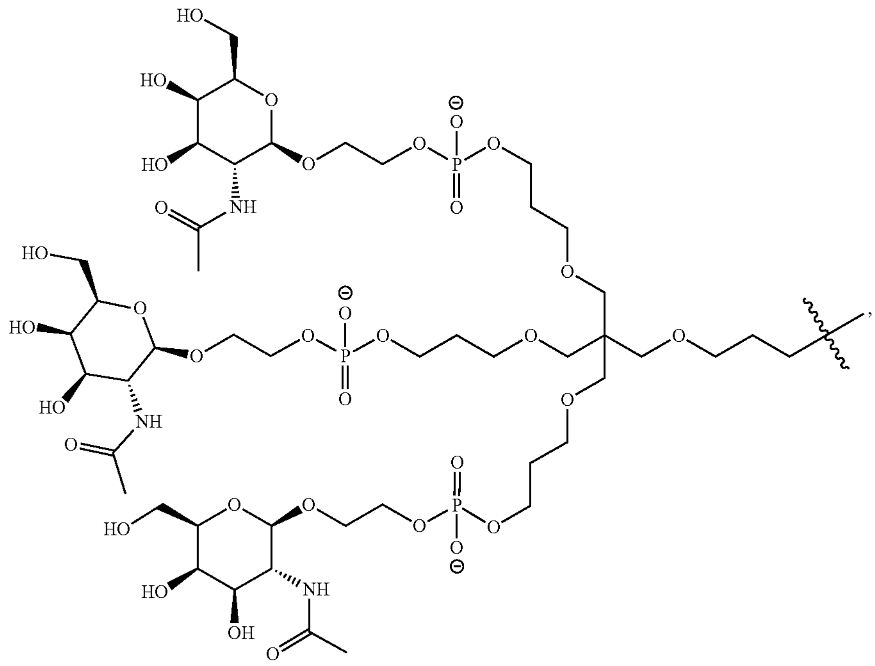
,
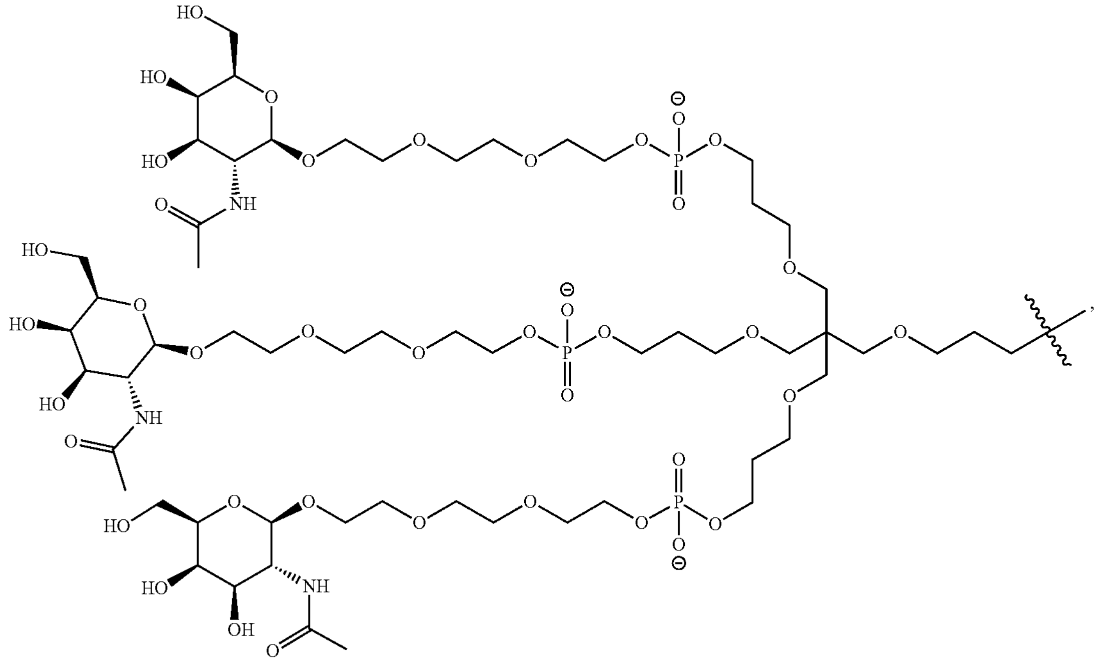
,

-continued
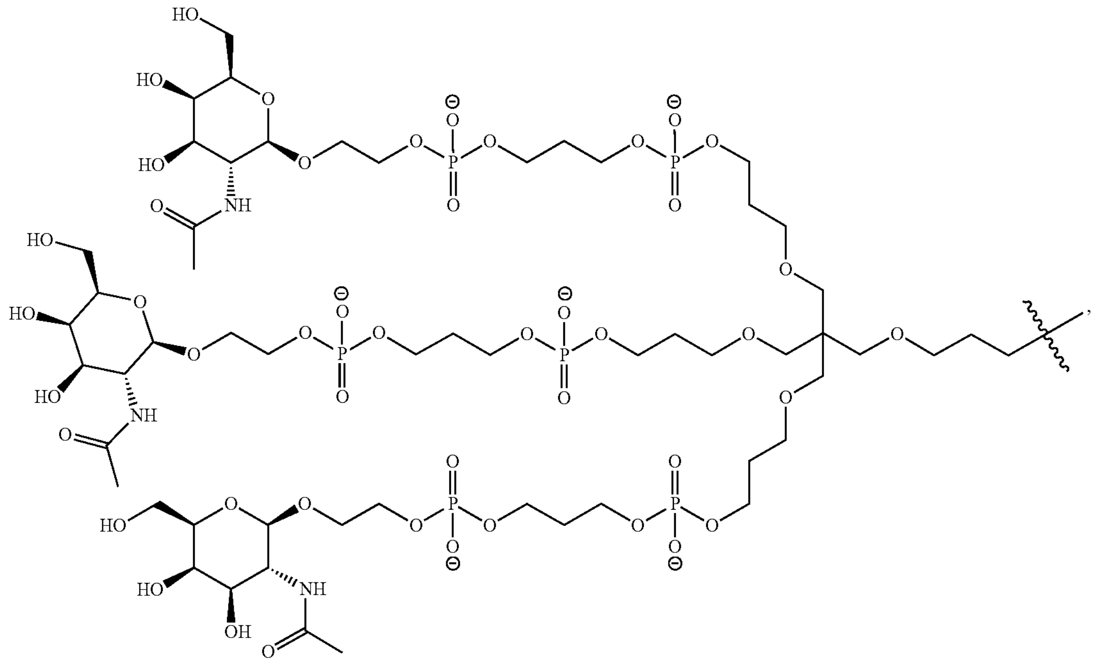
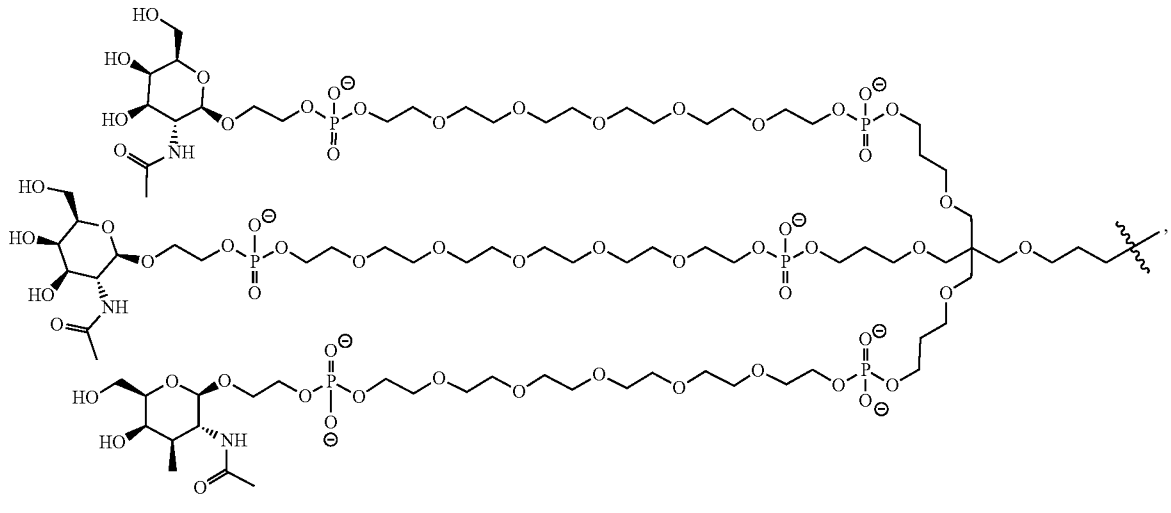

-continued
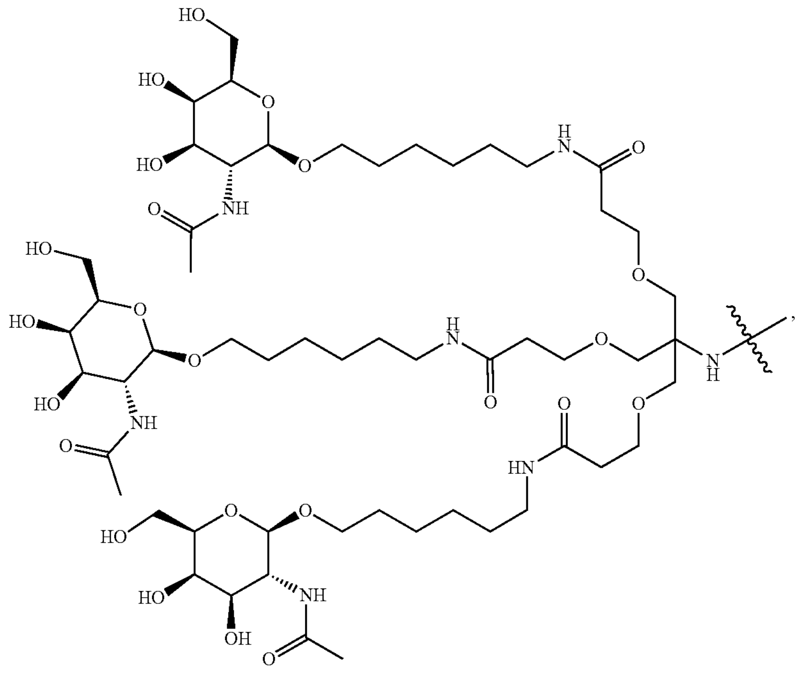
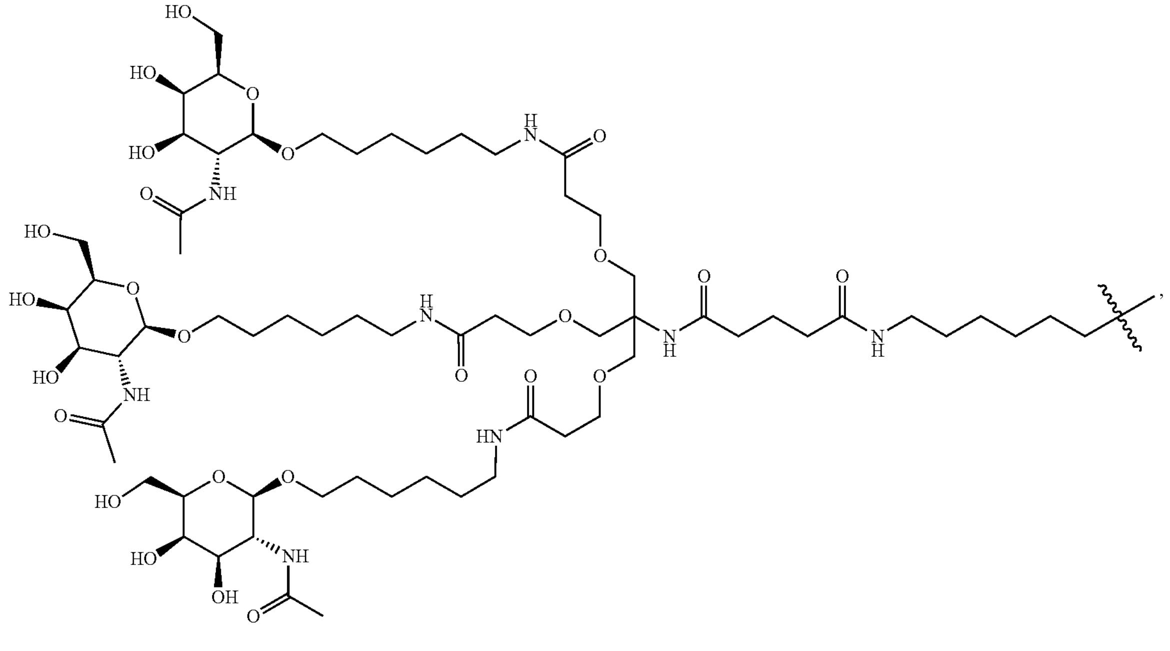

-continued
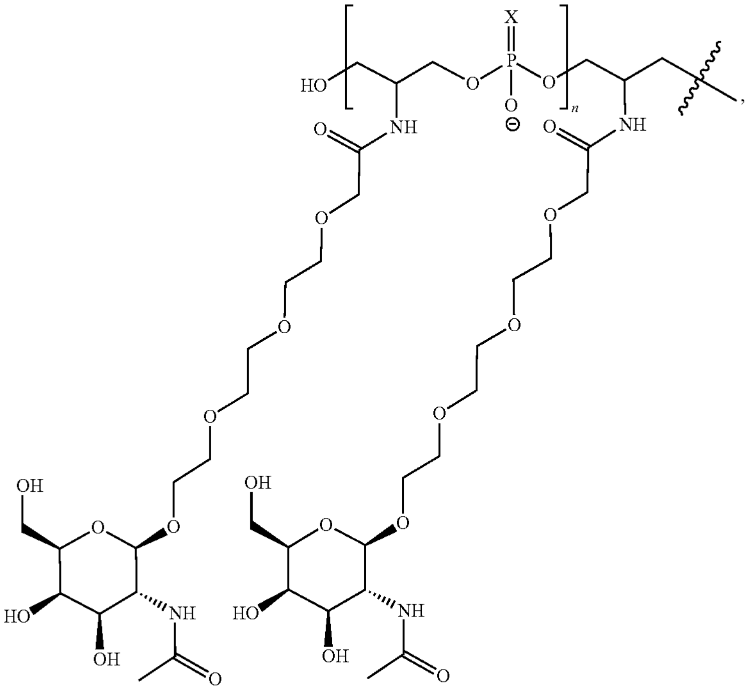
, or
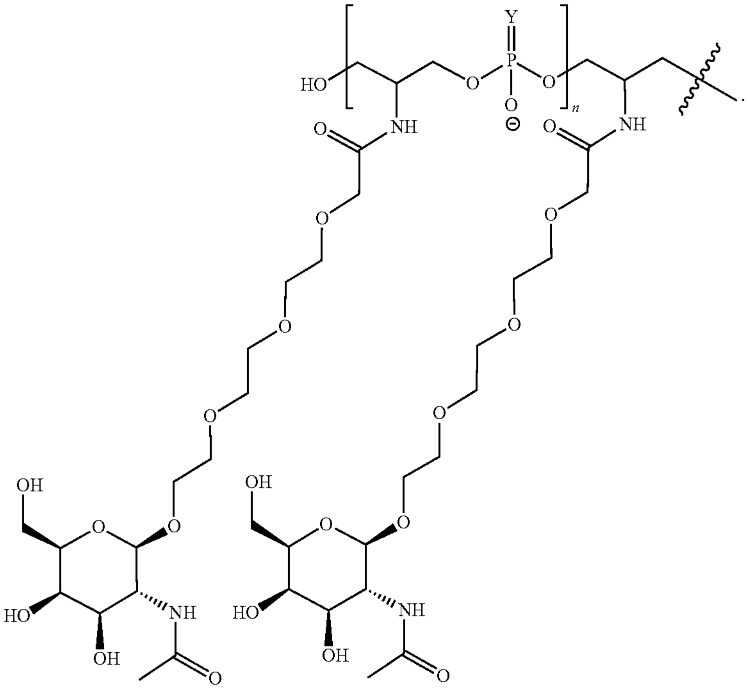
.

5. The antisense oligonucleotide of claim 4, wherein the conjugate moiety is the trivalent GalNAc moiety:

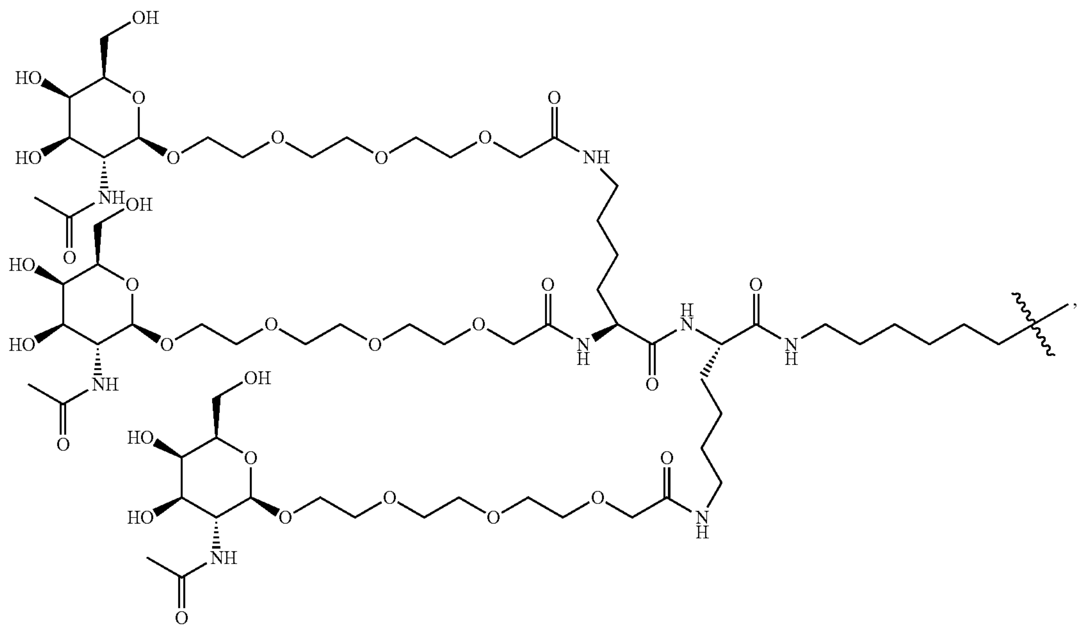

, or

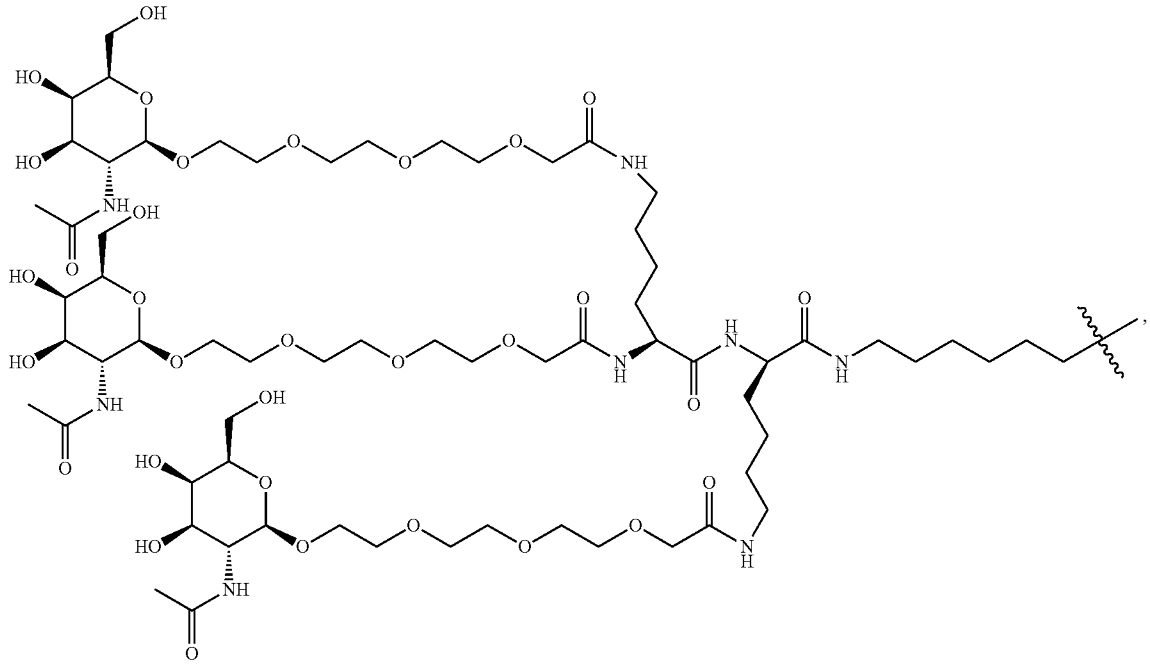

, or a mixture of both trivalent GalNAc moieties.

6. The antisense oligonucleotide of claim 2, comprising a linker positioned between the antisense oligonucleotide and the conjugate moiety.

7. The antisense oligonucleotide of claim 6, wherein the linker comprises 2 to 5 consecutive phosphodiester-linked nucleosides.

8. The conjugate that is:
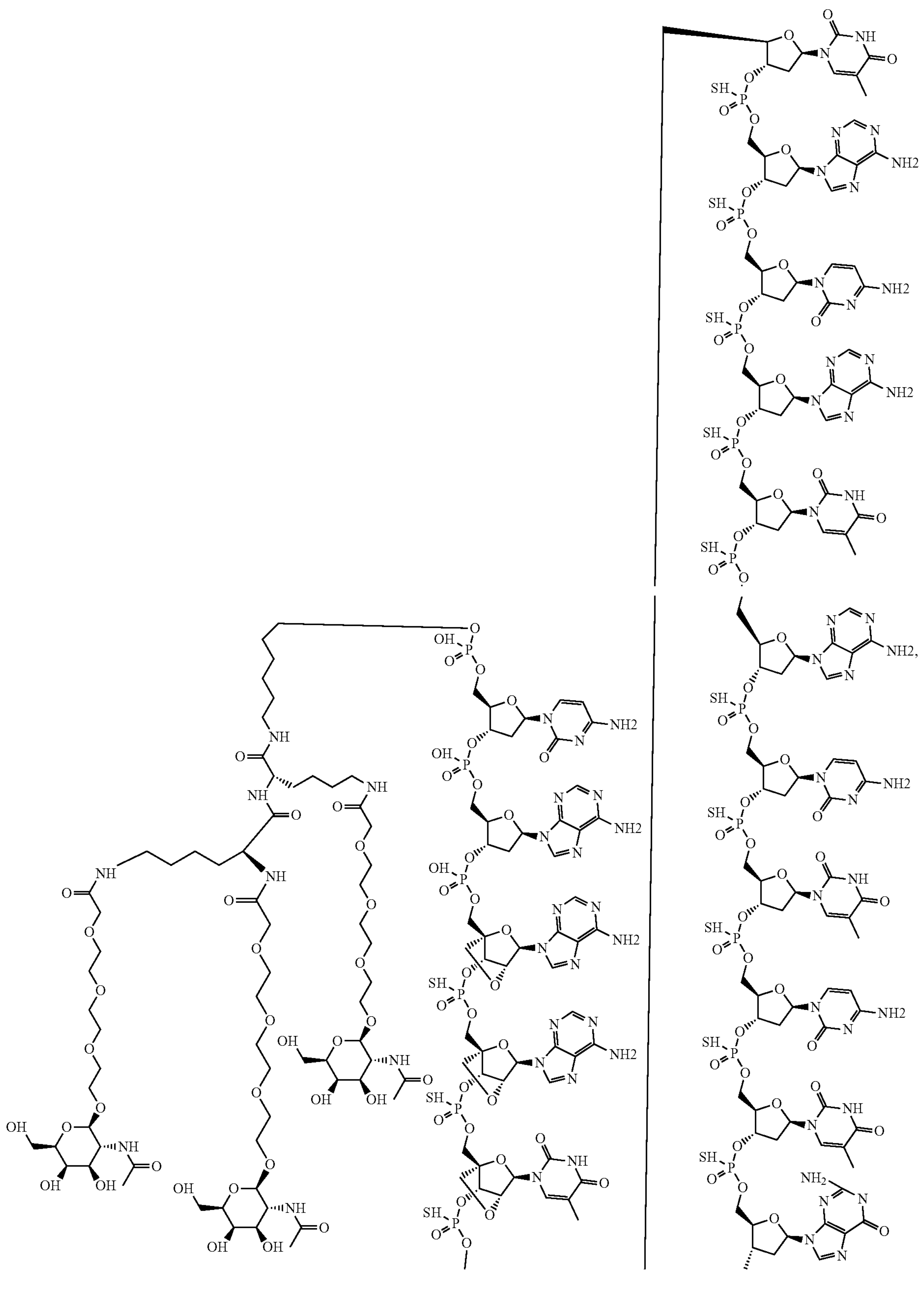

-continued
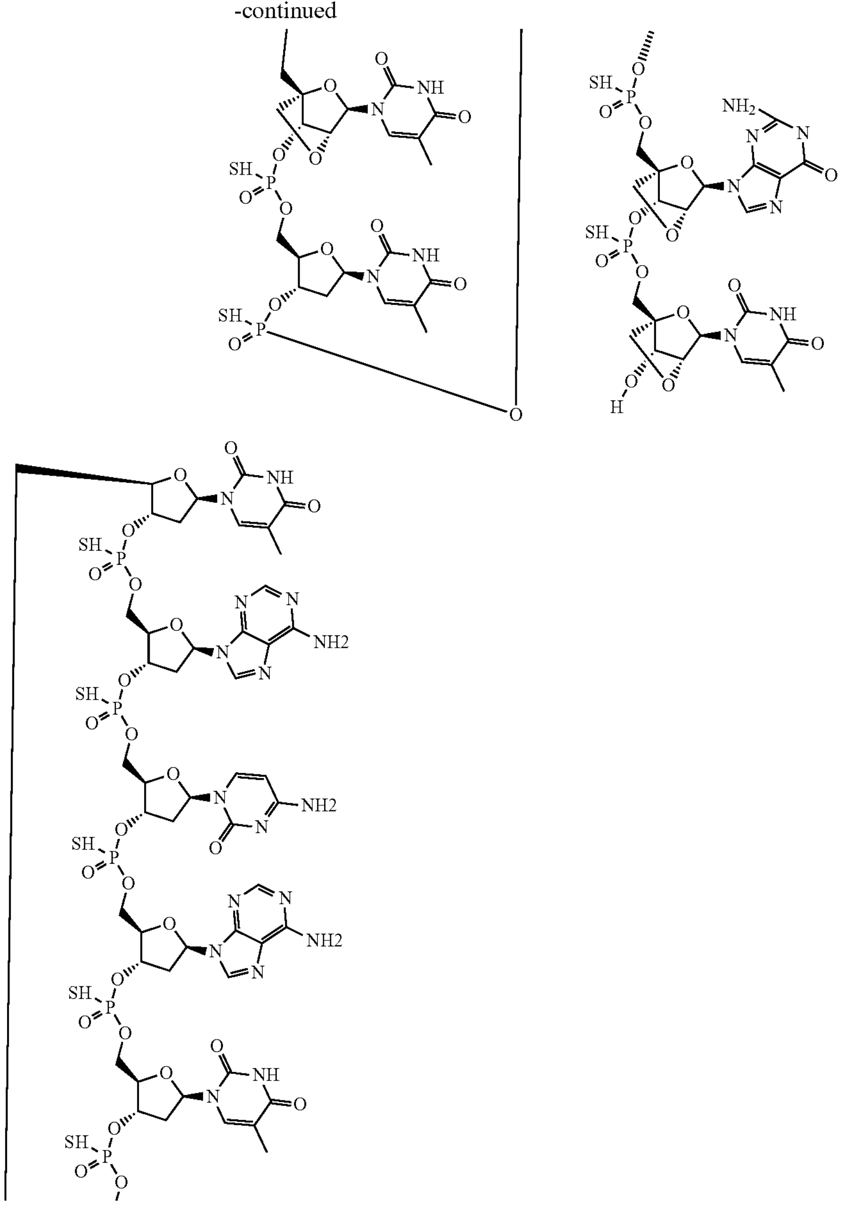

-continued
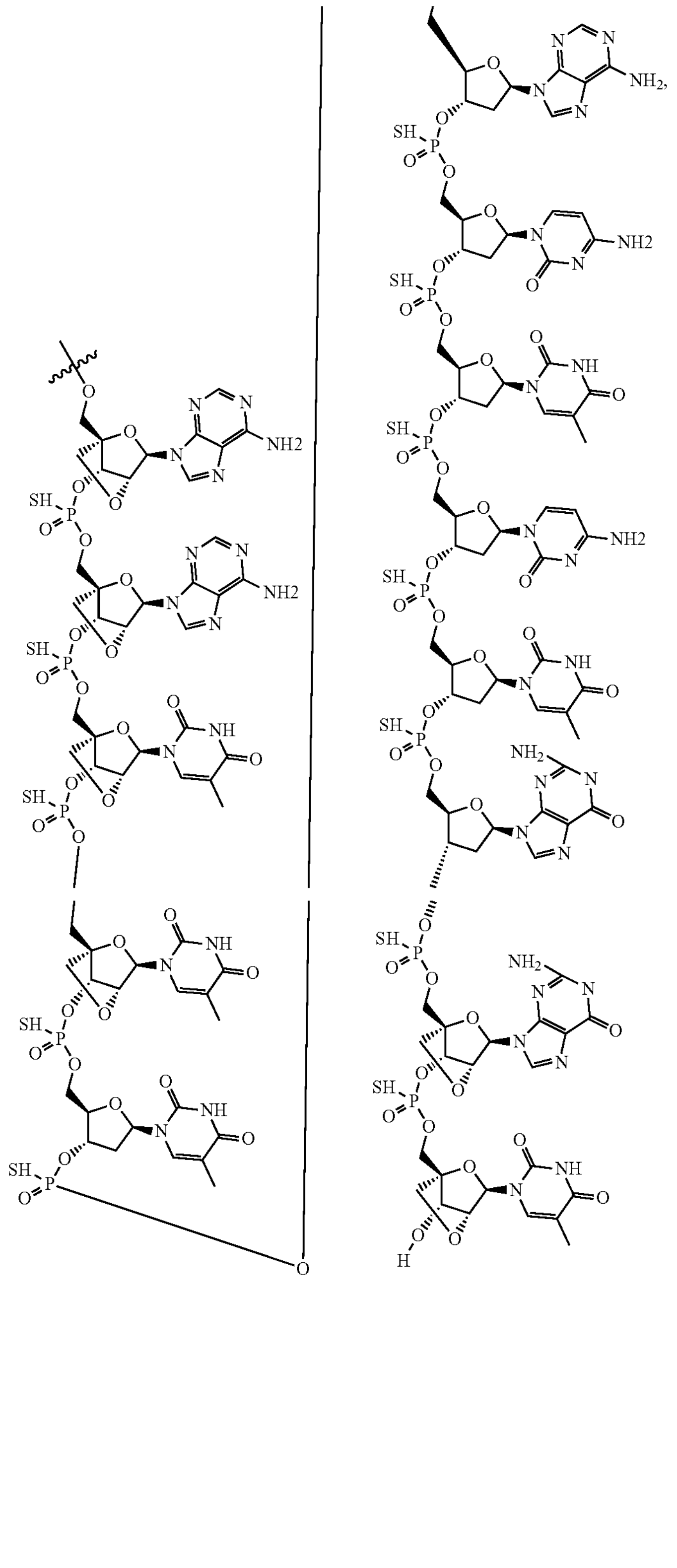

-continued
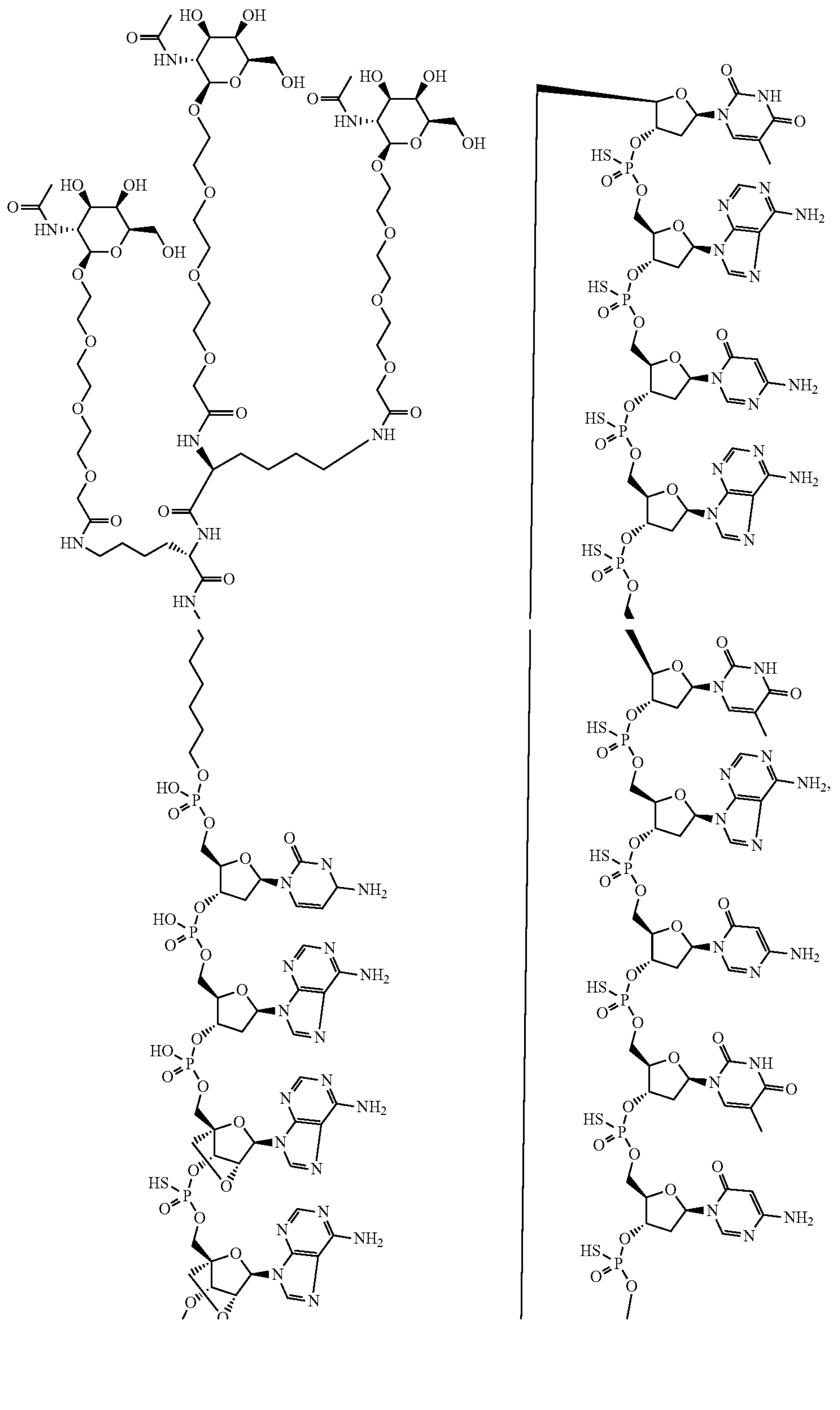

-continued
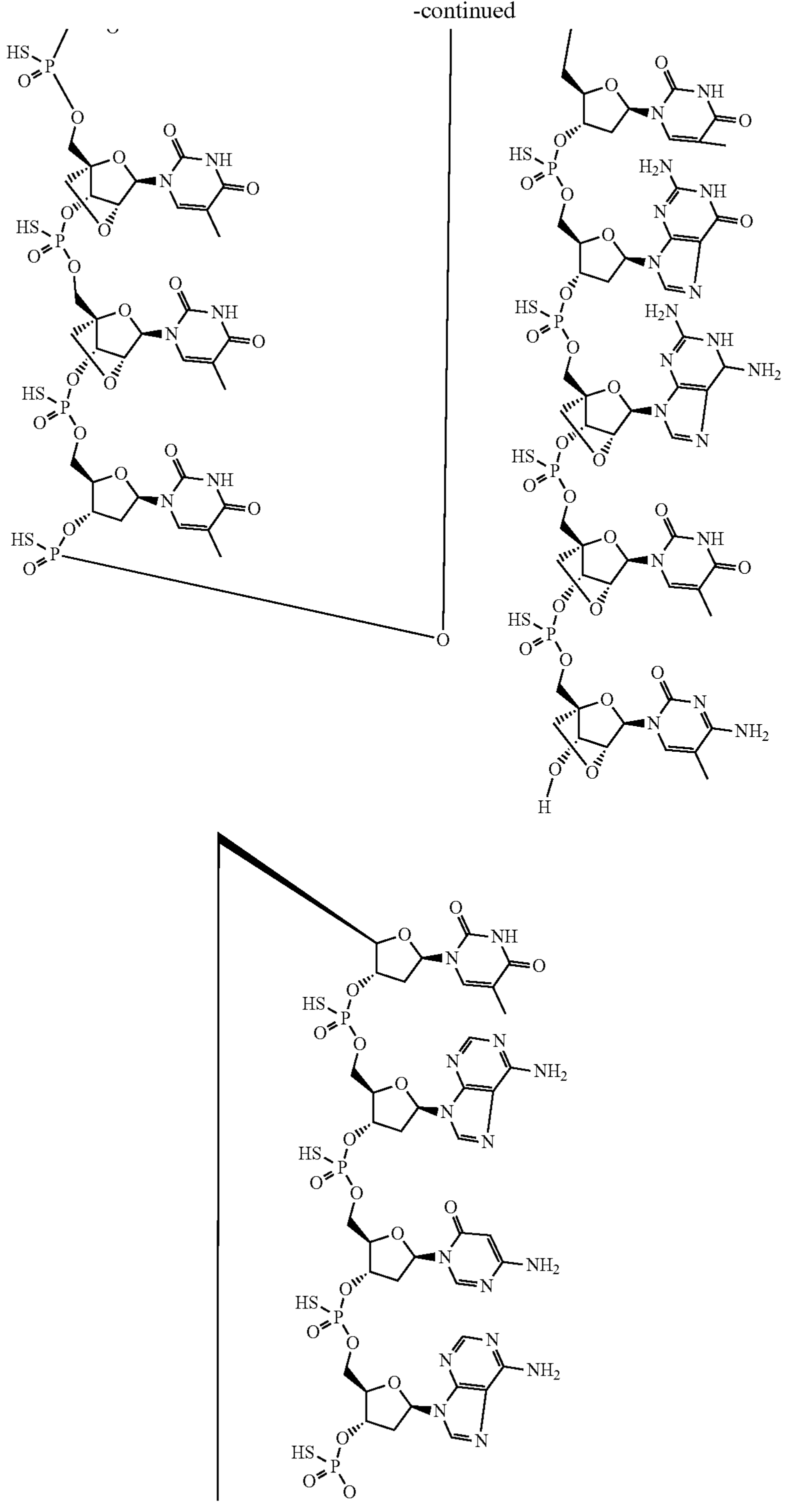

-continued
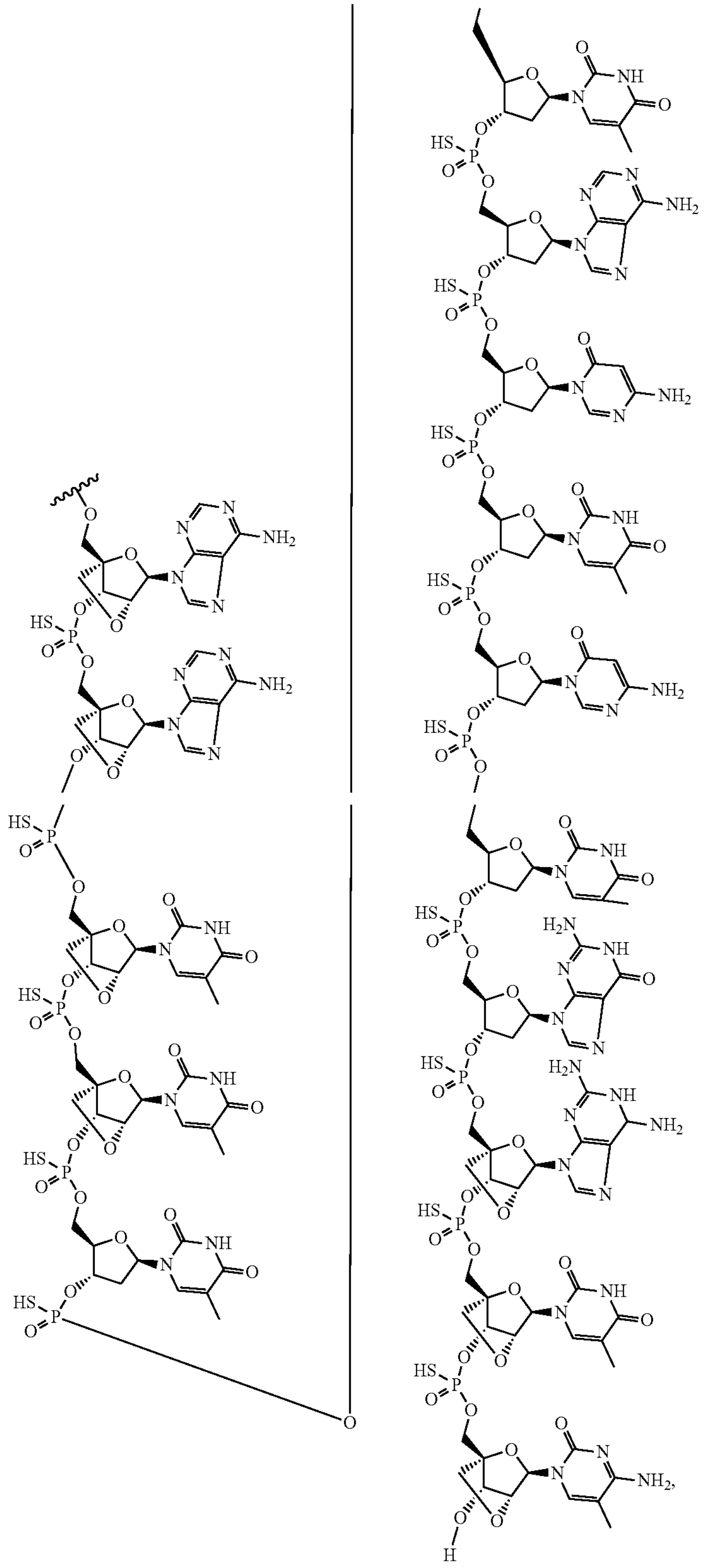

-continued
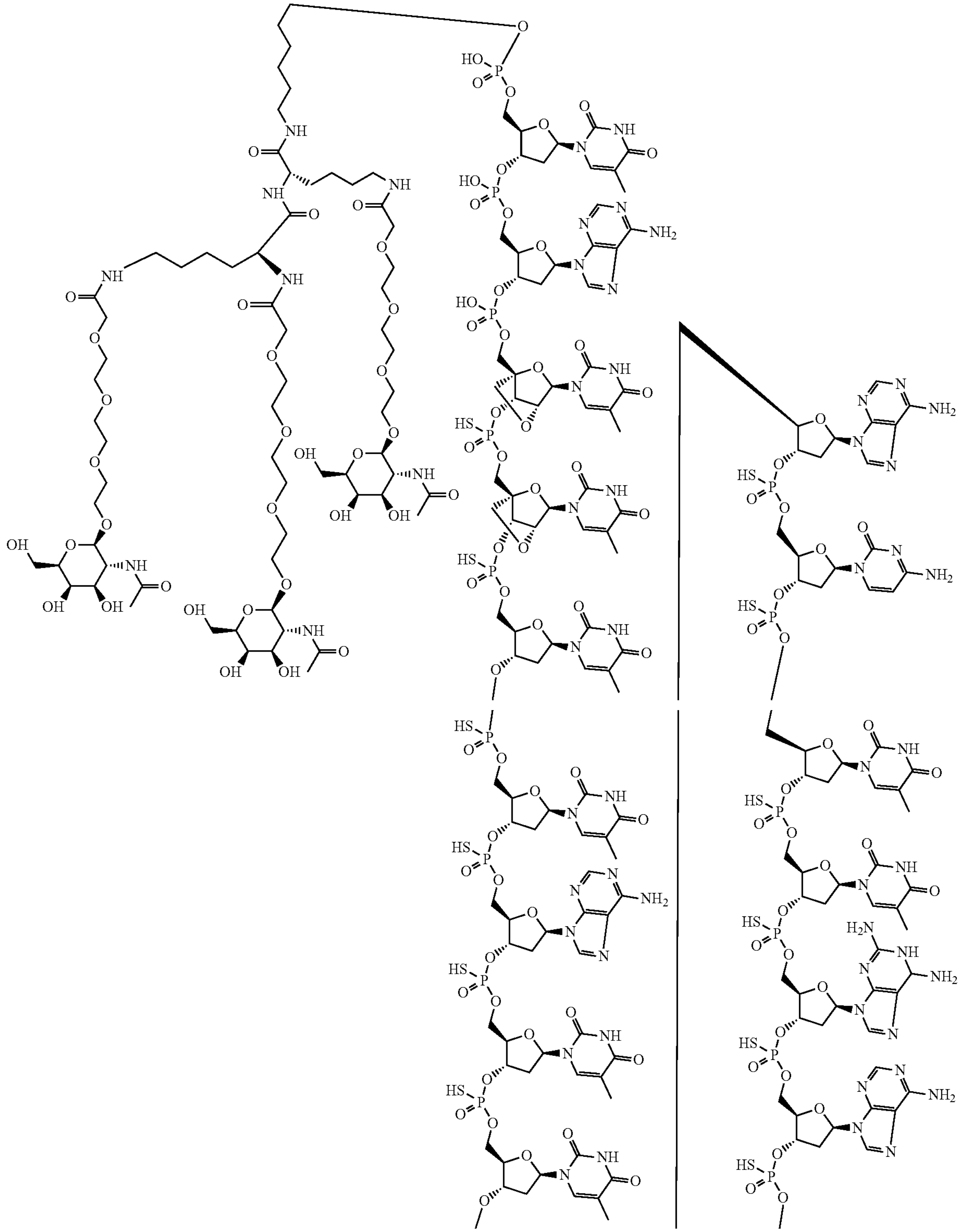

-continued
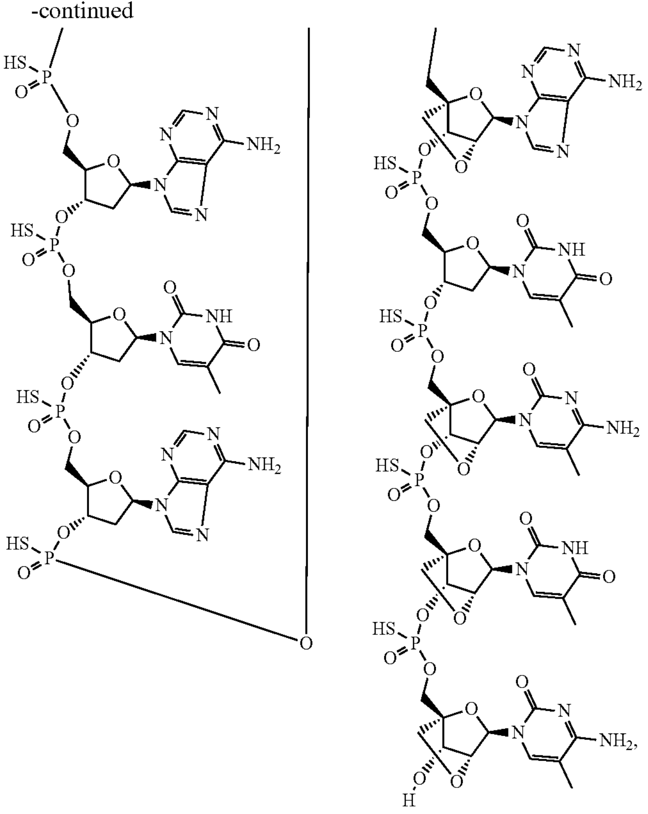
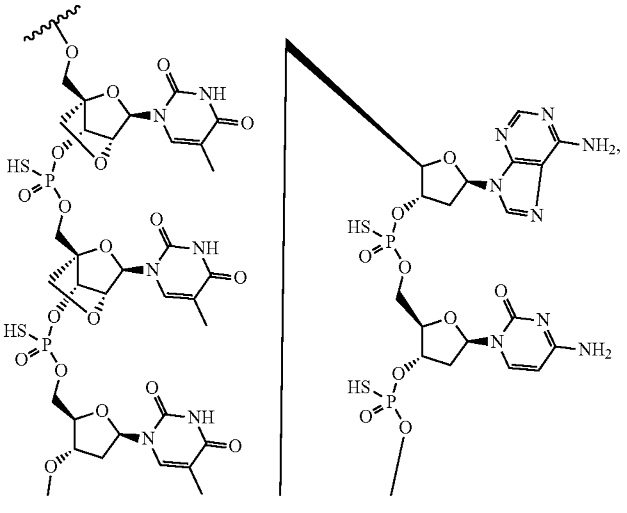

-continued
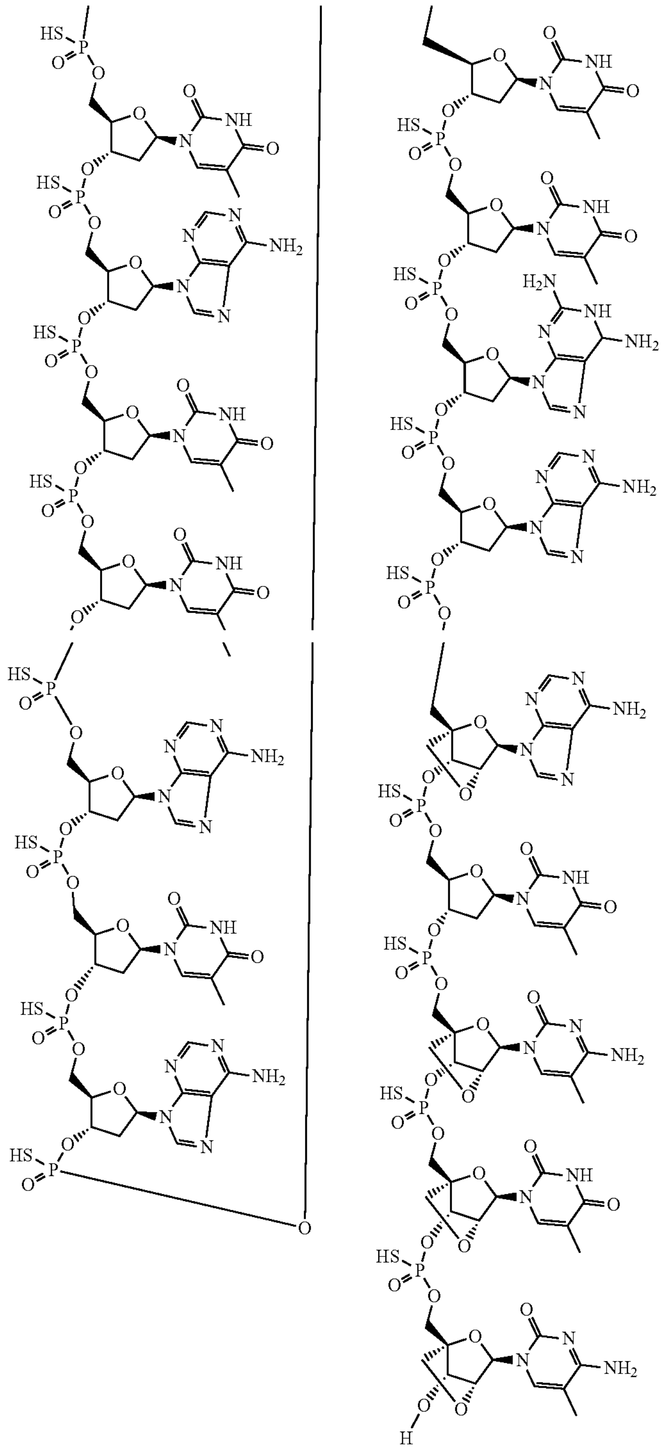

-continued
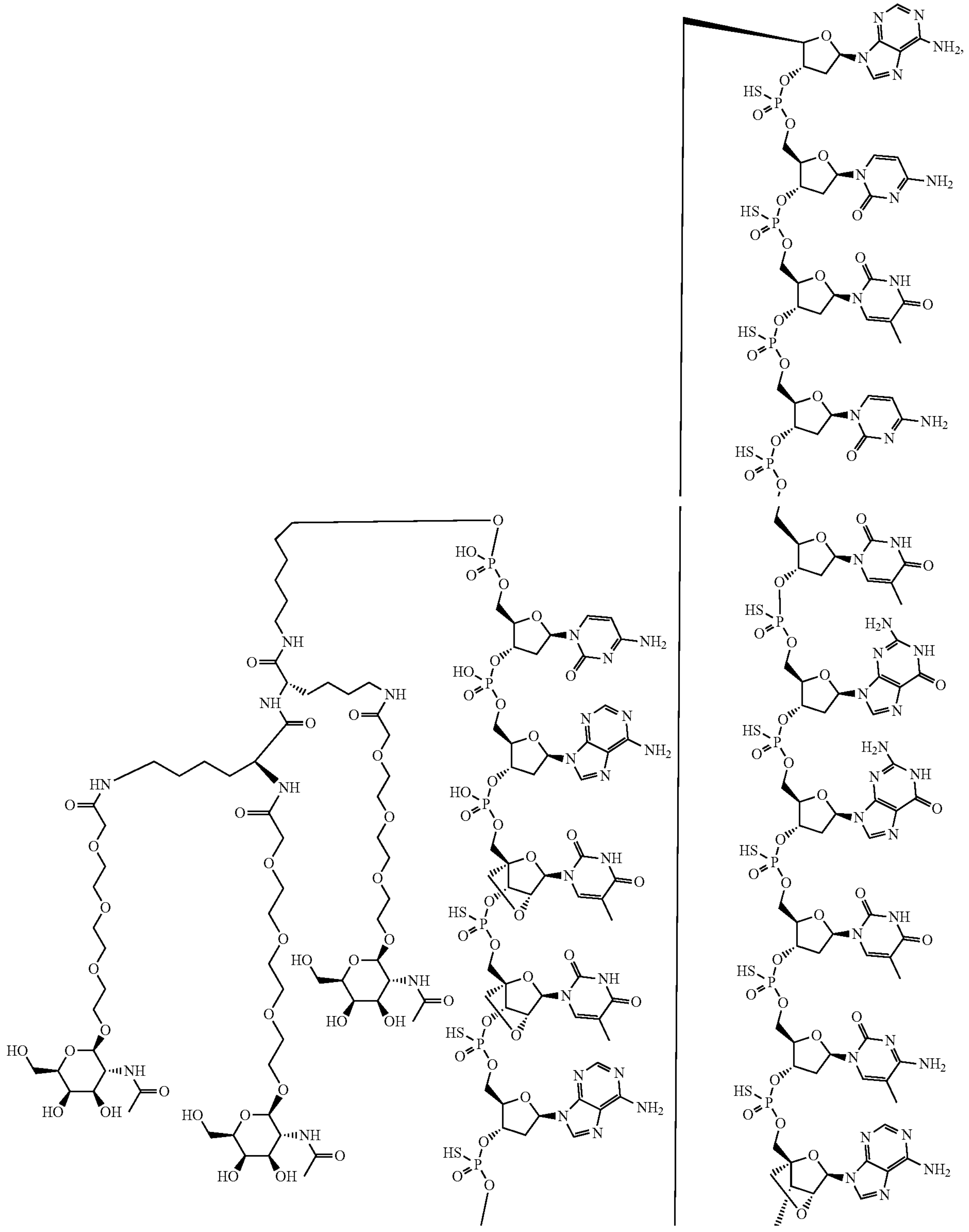

-continued
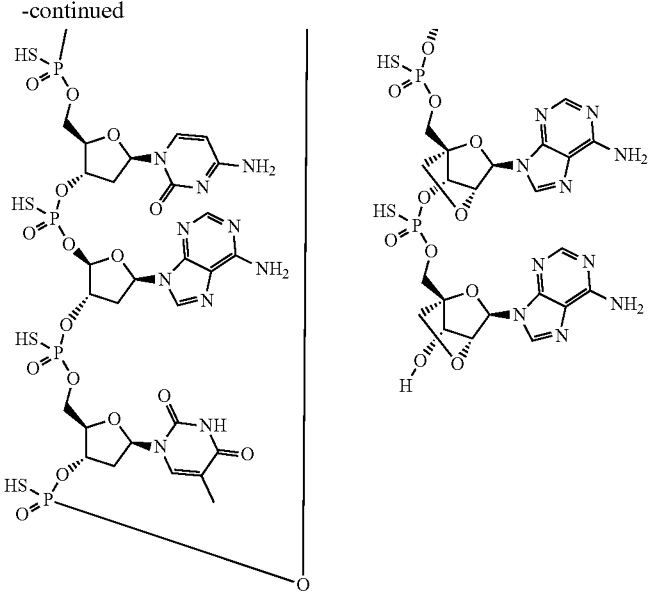
or,
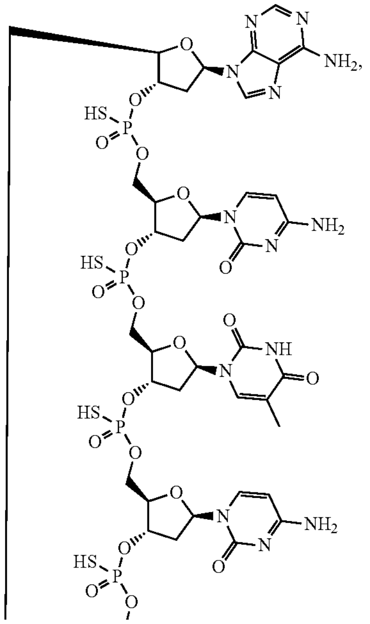

-continued
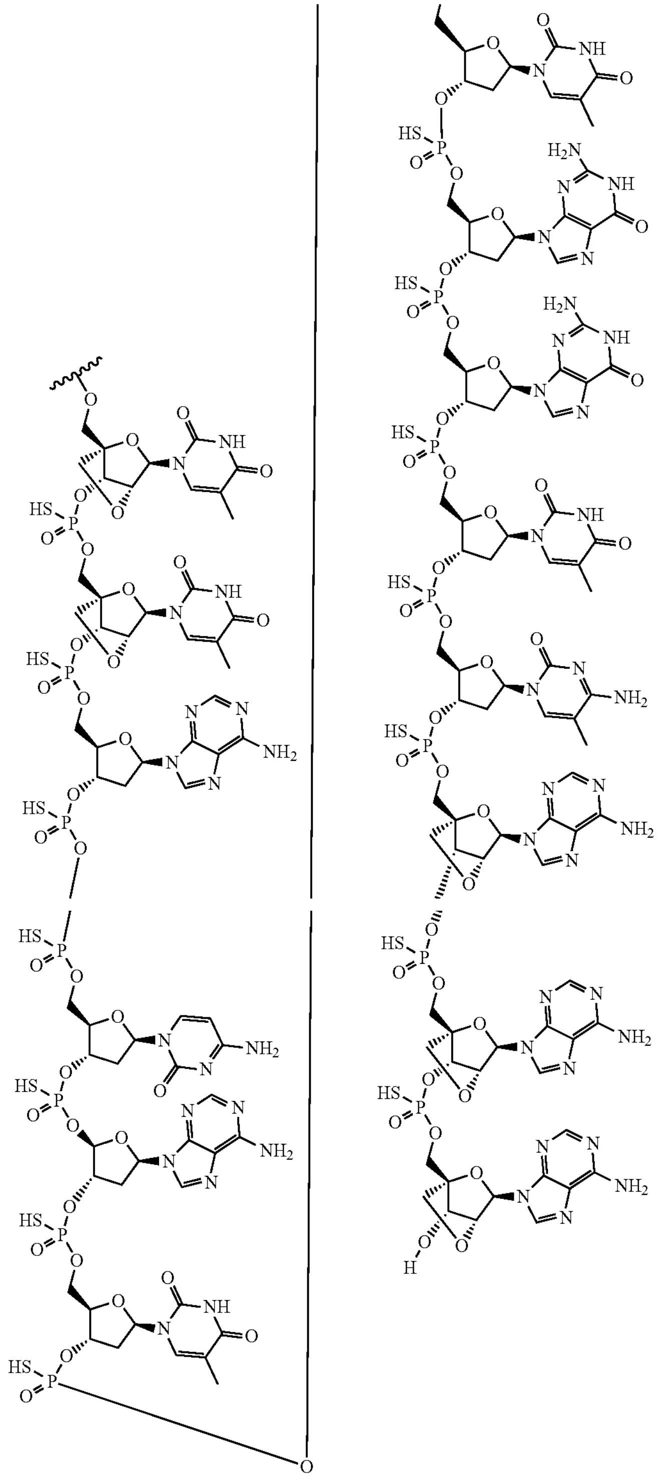

9. A pharmaceutically acceptable salt of the antisense oligonucleotide of claim 1.

10. A pharmaceutical composition comprising the antisense oligonucleotide of claim 1 and a pharmaceutically acceptable diluent, solvent, carrier, salt and/or adjuvant.

11. An in vitro method for modulating RTEL1 expression in a target cell which is expressing RTEL1, said method comprising administering the antisense oligonucleotide of claim 1, in an effective amount to said cell.

12. A method for treating a hepatitis B virus (HBV) infection in a subject in need thereof, comprising administering a therapeutically effective amount of the antisense oligonucleotide of claim 1 to the subject, wherein said administration results in inhibition of the HBV infection.

13. A pharmaceutically acceptable salt of the antisense oligonucleotide of claim 2.

14. A pharmaceutical composition comprising the antisense oligonucleotide of claim 2 and a pharmaceutically acceptable diluent, solvent, carrier, salt and/or adjuvant.

15. A pharmaceutical composition comprising the pharmaceutically acceptable salt of claim 9 and a pharmaceutically acceptable diluent, solvent, carrier, salt and/or adjuvant.

16. A pharmaceutical composition comprising the pharmaceutically acceptable salt of the conjugate of claim 13 and a pharmaceutically acceptable diluent, solvent, carrier, salt and/or adjuvant.

17. The method of claim 12, wherein the hepatitis B virus (HBV) infection is chronic HBV infection.

* * * * *

SEQUENCE LISTING

```
<160> NUMBER OF SEQ ID NOS: 71

<210> SEQ ID NO 1
<211> LENGTH: 38444
<212> TYPE: DNA
```

<213> ORGANISM: hsapiens

<400> SEQUENCE: 1
agtcagccct gctgccagcc agtgccgggt gctggggact cagggaggcc cgccgggacc 60
actgcgggac agtgagccga gcagaagctg gaacgcagga gaggaaggag agggggcggt 120
cagggctctc aggagccggg tcctgggcaa ggcgcagccg ttttcaaatt ttcaggaaag 180
cggtcggctc acactcgagc agtaaaaaga tgcctctggg gaggaggccc gtgcagctct 240
ccgggcaatg gtggtggctc ggcctagaga ggcggtagtg gaacgcagac cctggtgggg 300
gaatgacatc aagggaggag acgggcggga ccccagattt ctgcctgtgg gcgatggaag 360
tgaggttcac tggccagcgg agccggacac agaacgcgca aaacgccgtg taggcctgga 420
ggagccgaag agcaggcgga ccccctccgc gggggaacag tttccgccgg gagcacaaag 480
caacggaccg gaagtggggg gcggaagtgc agtgggctca gcgccgactg cgcgcctctg 540
cccgcgaaaa ctctgagctg gctgacagct ggggacgggt ggcggccctc gactggagtc 600
ggttgagttc ctgagggacc ccggttctgg aaggttcgcc gcggagacaa gtgagcagtg 660
agtcgcagtg accctacaag tggttctttt acccgagcgg ctcgtaggcg cgttgcggtt 720
tttcgaaact acagctcccg gcaggcccca agccgccctc ggggccgcgg gtcggcggat 780
tggccgcgct gcattttggg acctgtagtt tcctgcgctc gtggcgctgg cgccgcggcg 840
ttggctgagc ccttgaccgg ggctggaggg aagggccgac attcagtgtg tccgcgtctg 900
ttctgttagt cccagttccc gggcgggatt gaggcttaga gaagttgagt gatttgctga 960
gggctgcacg ggttggcatc ccggcatgct ctttcgctac tttggctgca tctggttgcc 1020
cacccgggcg gatggggaat ggactccagc cagccaggag ggcagagggc tggagaggca 1080
gggccggagg ttcagaccct ccgctctgac gttgcgcctg gtgaggccgg gaggggtgcc 1140
gcttgcctct tcagccctca cgctcttgtg gaagtcgcgg aattactgca ggcggaactt 1200
gcagcactgt gggcgtcttt tccagagaag gacggagttg tggggcggga ggataaggca 1260
aggcccagcc acttcgcatc ttcgccccgc cagctcctcg agatgggata taccagggtt 1320
gctctccaac cctctccgca ggagggactg atggaaacgc ctgggaaagt agcccggtac 1380
ccacaaaggc tgtctacaaa cagagtctta ctgtctttcc caggtctgtg ccatagggat 1440
tctcgaagag aacagcgttg tgtcccagtg cacatgctcg catcgcttac caggagtgcc 1500
cgagacccta agatgttcgg agtggttttt tcgcacagac ccgaatagcc tgcccctcag 1560
ccacgctctg tgcccttctg agaacaggct gatatgccca agatagtcct gaatggtgtg 1620
accgtagact tccctttcca gccctacaaa tgccaacagg agtacatgac caaggtcctg 1680
gaatgtctgc agcaggtaga gcacaggccc cgaggaaagg actgcgggtg ggtggagctt 1740
cagccaggac ggggtgtgct tccctctccc ggcccattcc agccaggccc ctccgggcca 1800
gaggcagcgt ctgtcataaa aagggctggt gttccaggtg gggtcagaga gaggattgac 1860
aagtaaaaac gatcgtcctt tgaagggggc cggcccctcc acacctgtgg gtatttctca 1920
tcaggcggga cgagagactg agaaaatgaa taagacacag agacaaagta tagagagaaa 1980
agtgggccca ggggaccggc gctcagcata cagaggacct gcaccggcac cagtctctga 2040
gtttcctcag tattcattaa ttactatttt cactatctca gcaagaggaa tgcggcagga 2100
cagcaaggtg atagtgggga gaaggtcagc aagaaaacgt gagcaaagga atctgggtca 2160
caaataagtt caagggaagg tactatgcct ggatgtgcac gtaggctagt tttatgcttt 2220
tctccaccca aacatctcgg tggagtaaag agtaacagag cagcattgct gccaatatgt 2280
ctcgcctcct gccacagggc ggcttttctc ctatctcaga attgaacaaa tgtacaatcg 2340
ggttttatac cgaaacattc agttcccagg ggcaggcagg agacagtggc cttcctctat 2400
ctcgactgca agaggctttc ctcttttact aatcctcagc acagaccctt cacgggtgtt 2460
gggctggggg actgtcaggt ctttcccatc ccacgaggcc atatttcaga ctatcacatg 2520
gagagaaacc ttgggcaata cccggctttc cagggcagag gtccctgcgg ctttccgcag 2580
tgcatcgtgc ccctggttta tcgagactgg agaatggcga tgacttttac caagcatact 2640
gcctgtaaac atattgttaa caaggcacgt tctgcacagc tctagatccc ttaaaccttg 2700
attccataca acacatgttt ctgtgagctc aaggctgggg caaagttaca gattaacagc 2760
atcttagggc aaagcaattg ttcagggtac aggtcaaaat ggagtgtgtt atgtcttccc 2820
tttctacata gacacagtaa cagtctgatc tctcttttcc ctacagtcct tgagggtgac 2880
agacttagga gtgccttggg ggcctctctg aggagcagct gatattcacg ggtcaggagg 2940
aagcatttcc attagagggg cagccggtgg ccagcctcac ttggaaggtc tttgaacctc 3000
gggggtgcag ggaggtggca gtggtgcagg ttgccttctc ctgggttcct tgaggtgccc 3060
tcttgtaccc ggctcacacc cttcccctcc ccgagtttcc tgctcaggtt cccgtctgag 3120
agcttgtatg taggacgtca gataggacag cataaatgtt tggatccaga aacgcagaac 3180
agtttcctat tttgagactt gacacctaat tagtcatctt actatttaag ctgaaaaata 3240
gtgtcgtgtt ttgggtaacg ttctgcaaat cgtttgctaa tggcggctga gttgcttcac 3300
gccctttagg gcaagagtgg gacttgcctg tggacttctc cgcggtccca cagggctctc 3360
gccacctggc agtggcctct gcatctgcaa agagctgccc gctggctgcc gaagcttgtc 3420
tcagggcagc ttgtgtggcc tcgcctcttc ctggcttccc cgtaaccctt gctccgaact 3480
ccgttcagaa ggtgaatggc atcctggaga gccctacggg tacagggaag acgctgtgcc 3540
tgctgtgcac cacgctggcc tggcgagaac acctccgaga cggcatctct gcccgcaaga 3600
ttgccgagag ggcgcaagga gagcttttcc cggatcgggc cttgtcatcc tggggcaacg 3660
ctgctgctgc tgctggagac cccataggtg accctagttc ccaggcctct cctggcctcc 3720
tgtggggatg gttggcaagg gatggcgctg agggtggggt gggcccatgg ggactcctgc 3780
cgtctctcaa gcagaactca aggagaattt tttagctgct gtataatttc tcgccatcgt 3840
gggtgtaaac ctagggttgg gctttttttgc tgaattaggg cacggcagat gcccacttca 3900
cccatttttg ataaaccagt atctggggtg tcagattctt ggctgtctgc agggccgagt 3960
tagccgaatg ccacctgcct ttgatacgtg agaacgttgt ctgagaaccg tgacttctgt 4020
gcttgcttgt gtctggtcag cttgctacac ggacatccca aagattattt acgcctccag 4080
gacccactcg caactcacac aggtcatcaa cgagcttcgg aacacctcct accggtgggt 4140
cagacgagtt tacacctgtc tcggggtcct caagagaacc agcttggcat ggtgctgagt 4200
ccacagcccc atgctgtgct gtggtggagg gtggtggtct ttctagacgc tcccccgaag 4260
tgtgcagagc gctggtgccc aggggtgggg tgcggcctgg gctgcctcca atgcccatta 4320
cttgtgagga agcagctttg catctgtgtg ctgaccttgg gcgggcgtcc tgagctcctc 4380
gcaggtgctg ttgtagcagc tgtgcagtag gtcagggctg gcccccagtg cagctttgca 4440
catgaagtag gaggaggccc tgctgcttgt cagagcccag cagagtcttg gtgttctgtc 4500
gggttcctgt ggccggacca gtggcagggt gctgtggaag ctgtcgaatc tcctccctct 4560
gtccagtacc cccgctcgtc ttctagctcc ctcctacgcc cgggccacgt ttcagttatg 4620

-continued

```
ctcacttcct ctgaccgccg aggctcctgc gtgtctccat acagctcacg ctgcagggcc   4680
acgctgtggg tgttggagac agctcctcct cgacccacgg tgctctctcc caccaggcct   4740
aaggtgtgtg tgctgggctc ccgggagcag ctgtgcatcc atcctgaggt gaagaaacaa   4800
gagagtaacc atctacaggt aggctcctgg gctcccgctc cggctcagtg tccgacaggc   4860
gagtgctgct gggtgtccag agccccaggc tgcgctcccg ctgggctagg gtttgaagtt   4920
cactggggga ctgcaggga ggacctggtg ggggtgggga ctggcttcgg tcctttcttg   4980
gccgtgcttc agctgcgcac tctgcccttc ctcccacaga tccacttgtg ccgtaagaag   5040
gtggcaagtc gctcctgtca tttctacaac aacgtagaag gtacaagcag ctgggtggga   5100
ccagggtcgg gttggagtgt gtgcagcctc tcagggtgga gctcagtggt gtcacagcct   5160
ggttgtgctt gcccggtggg gcggccagtg cggccatgta cctgggccct gtcttctgac   5220
tcggggccac ccatgttaga cttctgtgtg gaagagctca cacagtggtc tgagacagcc   5280
agccggcaag actgcctctg gctggtgcct ggggccttgg attttgggaa ggctccctcc   5340
atttcctgat gagagggtct ccctgcacct aacctgctgg tgcaaacagt aggggttttg   5400
ctgaacaccg gctttctctt cggggacttt gttgcttgcc cagcagcagg tgctccagtg   5460
accggccctc ataccatctt gggagggtgt cctggaagcc gtgtctggcc tcccgcgacc   5520
ctgccccgtg tgtctttttc ctgtgctgac cttgctgcgg aaaattatgg ccctgagtgt   5580
gactccaggc tgagtcctgt gggtccaaca cgggatgcct tggggcctct tctggagacg   5640
ggatgtgagt gacaggagcc ggccggggca gcttgccctg tgactgcacg tggccacagc   5700
ctgtgagggc cgggggtgct tctccaccca cgtggctgcc cctcgggtat gtcaagggct   5760
tctggggctc atcacggggt cctagagaca gtggcagggt gcaccccgt tggctgccct   5820
tacagtttct gtgacctgag ggtggcatct gtgcagtcgg cgcggtctgt gcttctgtgg   5880
gatcagggtt ccctctgttt cctgcctcag ttggggctca agcctcaggt gaggtggccc   5940
cggagcactc agaaggcatc ggcggtcctg tgggctgctt tctgcactca cgtttgctga   6000
gtgctcagtg tgccaggact gaggaccctg aagctgctct tgtatttagg gcggcgctcc   6060
cctggcagag actgagccag gtggtcccgc atgacccact accaggcgtt tctgggccct   6120
ggcccttgga gggacagggt gggcggaaca tgggcctgca gggaggctcc cgcttactgg   6180
aggcatgtgc tgtgttgctg gagacatcct ctgtgttgct tcttgttcgc tgtggttttt   6240
ggtctggtgg caccaaggac cctcagtcat cttgatgtgt ggttgtccag gccttttttgt   6300
tggtcctaag aaggggctct gcctttgtgc cccaggttc cctgacagga gctgccggct   6360
cgtcccggtg atgcctgcag gacgtgactc tgggacgggg ggttgggcag atgtgctgat   6420
ggaaattctc aagcaggcgt catttccgag gtcctcacct ggatttccag gacaggagtg   6480
cctgctgggt gtccccagtc ccatgcagcg gggtccttg ggatagcatg gaacgctgag   6540
catgggcctg gccggccgtg gtcctggaca agggcagtgc cccggtggct gctgggcctg   6600
ggacctggtg gggacgctgg gcctggtacc tggtggggat gctgggcctg ggacctggtg   6660
gggaggcctc tgactgcctc ctggtgctgc ttccgtctgt gttaggcctc tgggtattgg   6720
ggcccccatc tgtctcctcc tccaggcctg tggactcaga ccaggaagac acaggccagc   6780
ccctgcctgt cccccttggc ttgggctctc actgcccgac ctggcgggag gttgcctagc   6840
cgtgaacctt cgcaccctgt ctgccaccgg acaggctgtg agggggtgtc tgcagcacct   6900
gcaccggcct gagcatcttc agagtgggct gcagctcctg gaggggtctg agaggaaggg   6960
aggcaggtat tttgggcgaa tgaggagaca gctggagagc tggcaccctt cctggcctgc   7020
```

-continued

```
gtcctgtgag gactctggtt ggggacagca agcttggggt cagcctgggg cagagcctct   7080
gggacggccc cgcccctcgt gccccttccc ctcgcagctc ctgtcctcgc cccgccctca   7140
gctctccgcc aggcaaggtt tggcaagtgc cgctgtgcgg cagtgcctgc tgattggctg   7200
gtctgttgct atggtgctgc ccaggggtgt gcttttcctc ccctgccttc cctgctatcc   7260
ctgggagtat ctggggttgg gtcatcgctg gtgtgtgtga gtgtgtgtgt gtgtgtatgt   7320
gcacgtgtgc atatgtgtgc gcttctggcc tctgcagctg agtcctggcc ctcggggggc   7380
ctggcacctc ctggggacag gcacaaagca gccatgatgg agtcgggagc tgggggaggc   7440
cccattgccc cacgtggctg ccctgtgact ctggggtgct tgttagaaga ggtatctggt   7500
tctgtctgtg tttaagcaac tccctaagga attcttgtgg ttccagtttg gggggcctgt   7560
actgtagagg caagggaggg gcaggacatc ccccagactc tgacttctga agccttttct   7620
gcccggggcc tctccgccag tacaggcagt gtcctttgcc agggctgcca tgctgcagag   7680
gggagtgggc cactgtttag cccaggaaaa cctggctctc ccttagctgg aagttctggg   7740
cctgttgtgg ttggcaggga agctgagtga cggtgctaat cacaggggca cctgcagggg   7800
tttgtgggag atgcctctgt gggttggggc gataggctga ggggctgttc ttccctgccc   7860
tgaggagggc tgagtgtagc cgccactcct gtcctgtctt gggctgtctc ggagaggatg   7920
cgtagaaccc tcgggatcct gctggcctcc gtctggtcca ccctgaacct caggccttct   7980
gggggcagag gaggattccc tcaggatcac tcgggtgggg gcctctcttg ggcacctgag   8040
accctcagtg ggtgctttgt ggcgcgttca cggttggtgg gggacgccca gccctgcccg   8100
ccgtgtagga gccgttctgt cctgggcatc cccctgtggt ctgggactta gtggaccctg   8160
agggtgtgtg tttacccctg cctcacacct gcagaaaaaa gcctggagca ggagctggcc   8220
agccccatcc tggacattga ggacttggtc aagagcggaa gcaagcacag gtgagacccc   8280
tcagtgaggc cacgaccact gtccttccat ggcccagctc tcctgtgacc tgtggaggcc   8340
cggatatatt tcttcacttt tctttgttcc tttttaaatt atgaaactaa ccaccattca   8400
gtacgaaaaa gtttaagcag ctctgaggaa gatagagtaa aaaattgtct ccctcttccc   8460
tggccctcag ccatccccgg tggccaccgt ggagtgtgga cggagccctg caggcctgtg   8520
tctgtgcgga agcacgcgca gttttgtctg cacagactgt cctgcagttg gctgttttca   8580
ctcagcgttg tgggtatagc ttcccatgct ggtgctggca gctcggcctt gttcttttga   8640
ggacagcaga tgtctcctat gtctacctct tacagcttca gagattcaag ttataataaa   8700
gctcttctta tattgagggg gaaacctccc tccccctttt ttttgaaaca gggtctcgct   8760
ctgctaccca ggctgcagtg cagtgtcaca gtcttggctc actgcagcct cagcctccca   8820
ggctcaagcg attttcccac ctcagcctcc caagtagccg ggactgcagg cacacaccac   8880
catgcctggt taatttttgt attttttgta cagacagggt ctcactctgt tgctcaggcc   8940
agtctcctga gctcgagagt tccacctgcc ttggcctccc aaagtgctgg gattacaggc   9000
gtgagacccc atgcctggcc agctcttttt tttttttttt tttttttgga gacggagtct   9060
cgctctgtcg cccaggctgg agtgcagtgg tgcgatctcg gctcactgca agctccgcct   9120
cccgagttca cgccattctc ctgcctcagc ctcccgagta gctgggacta caggtgcccg   9180
ccaccacgtc tggctaattt tctgtatttt tagtagagac ggggtttcac cgtgttagcc   9240
aggatggtct cgatcttctg accttgtgat ccgcccacct cggcctccca aagtgctggg   9300
attacaggag tgagccaccg cgcccggccc agctctgctt tttcttagtg gttctgcgtt   9360
```

-continued

```
gtgtttgttt ctatccagga atagggttgg ttttactttt ccatcgagtt tttaaagaga   9420
cgacgattta catggtcgga aactcacgag gactccccat cccttggtcg gaaactcaca   9480
tggactcccc atcccttggt cagaaactca cgtggactcc catccatccc aggcagcagc   9540
ttcccacctg ggccctacgt gcaggatgag ggctccttcc gggtcagaag acatggcggc   9600
ctcggggcac cgtcccctgc atggggtgct cacaggatct tctcctctct ccttcccagg   9660
gtgtgccctt actacctgtc ccggaacctg aagcagcaag ccgacatcat attcatgccg   9720
tacaattact tgttggatgc caaggtgggg gctcagtcct gtagctgacg actcctgatg   9780
tccaggggtg tccctgggct tgggaacagc tgtccgagcc tttgctgctt cagggcctta   9840
gatcagcagg cctgggtggg aggactcacc tctgtcactg ggcaggggct caacctggcc   9900
agacacactt gtgagcagcc ccaggccaca ggtcagtttt ctgagcagtc tgggagcggg   9960
caggctggtg ggagtgagga gagacctcca ggctgtggtc cataggccag tgcccgctct  10020
tgatcctgac agctcaggtt ctctccttca cgtcaggcca tgggaggcac cgagaacaca  10080
ggaagcccac tgactcccct cttcccagcg cgtgcccggc cccacactca ctccccctcc  10140
cagcatgtgc ccggcttcac actcactccc ctcttcccag tgcatgcccg gccccacact  10200
cactcccccc acagcatgtg cccggcctga cactcactcc cctcctccca gtgtgtgccc  10260
agccccactc ccttccgccc cgtgtgccca gccccacgct cactcccccc gccagcatgt  10320
gcccggcccc acactcaact cccctcctcc cagtgtgtgc ccggccctgc tgccctcctc  10380
cccatgtgcc ctgcttttgt gccccacact ttttacttag tgcaggtggg atcacacgcc  10440
acgggtcaat ggtttgtgtg ttcacgtgac gatggcgtgg tgacgtttcc agatcccgtc  10500
gttggttcgc tcattctcgg ggtgtatatt tattgagagc tcatcatgct gggtgctatt  10560
ccaggcatag caagactggc ttcactcaca tggagctttg attctagtgg tggggacagg  10620
tggacagcaa aagagtaagc acgtgagctg atgatactga agggaaatag agcagaggga  10680
ggaggcggag accgagccaa gcgggcccaa gtgcgatgtc ggcgggaggt ggggaatgct  10740
ggtgggtctg aggggagcct cagcaggtgc agcagagcaa gggaagaggt gagtgggggc  10800
ggctgggggg ccgactcctg ggaagctgta gcagaacccc acagagagct ggtgaggttt  10860
gccgtggttg tgggtgactc ggtgctttga gccctggctg cccctgggaa ccatctggag  10920
agcttctaac ccaaccaggc ccctccctgg gacagttata tcacagctgg taagccgagt  10980
ctaacacttt cacggaaacg cagaagatct aaaacagcaa gatgaccgtg aagaagaaca  11040
gagctggagg actcacctcg ctggtttcaa gactcctcta aagctgcagg agtggaggtg  11100
gagatggccc agctcaggca caggcctgca ggccatggag aaggcagcaa gctcaagctg  11160
acccacacgc atgtggtcat tgtttttttt ttcagttgga atctcactct gtcacccagg  11220
ttggagtgca gtggcaccat ctcggctcac tgcagccccc gcccctaggt tctagcgatt  11280
ctcccacatc agcctcccga gtagctggga ttacaggcgt gcgccaccat gcctggccct  11340
tggtgattgt tttttgacaa acatgccaat ttaattgaga gaggaaatga aggttgattt  11400
ctggttttct gaaaaaatgg tgctaagaac agctggatat ctgttcggaa aacagtgaat  11460
cttaactctt gttttaccct gtataaacct aaatgtaaaa gctaaactaa aagttataga  11520
aaggaacatg ggggaggtct ttgcaacttt ggggtaggca gagatttctt agtatggata  11580
cacaaggcac tagccatgaa gaaaaacatt aaaatttaga cttcaccaaa atttaaagct  11640
tcaactctgt ggaagagttg agaaaatgaa aaagcagtta aagaaaggga gaaaatactt  11700
ctttcaaagg acttaaaaaa ttttttcagc cctcctctga tttgaaagga cctttgacca  11760
```

-continued

```
gagtatgtaa aattctccca taactaagca aacaacccac ttaaccactg ggaagggatc  11820
tggacagacg tttcaccaag atgggtggaa tggccagtta accactggga gagcatccgg  11880
acagacgttt cgccaagatg ggtggaatgg ccagttaacc actgggagag catccggaca  11940
gacgtttcgc caagatgggt ggaatggcca gttaaccact gggagagcat ccggacagac  12000
gtttcgccaa gatgggtgga atggccagtt aaccactggg agagcatccg gacagacgtt  12060
tcgccaagat gggtggaatg gccagttaac cactgggaga gcatccggac agacgtttcg  12120
ccaagatggg tggaatggcc agttaaccac tgggagagca tccggacaga cgtttcgcca  12180
agatgggtgg aatggccagt taaccactgg gagagcatcc ggacagacgt ttcgccaaga  12240
tgggtggaat ggccagttaa ccactgggag agcatccgga cagacgtttc gccaagatgg  12300
gtggaatggc cagttaacca ctgggagagc atccggacag acgtttcgcc aagatgggtg  12360
gaatggccag ttaaccactg ggagagcatc cggacagacg tttcgccaag atgggtggaa  12420
tggccagtta accactggga gagcatccgg acagacgttt cgccaagatg ggtggaatgg  12480
ccagttaacc actgggagag catccggaca gacgtttcgc caagatgggt ggaatggcca  12540
gttaaccact gggagagcat ccggacagac gtttcgccaa gatgggtgga atggccagtt  12600
aaccactggg agagcatccg gacagacgtt tcaccaaggt ggatggaatg accagttgag  12660
cacatggaaa gtcgcccagc atctccagtc ataggagaag gcagattaaa gccacgggga  12720
gccgacactg tggtcccact ggcatggctg aaattcagaa gccctgagtg tggcatgagg  12780
atgtggaaca gctggatctc atccatcgct gtgaagttgt gtagccactc cacaaacgtg  12840
tggcaaacag ccgagccggg agaagggaag acgtgttcaa agattcatat gtggccaggc  12900
tcagtggctc acgcctgtaa tcccagaact ttaggggcca aggctggggg atcgcttaag  12960
cccaggagtt tgagaccagc ctaggcaaca tagggagacc ccatctcaaa aaaaaaaaaa  13020
aagaaaaaag aaaagacttc agtgtgcagg tttaccagag ttttgtttgc agttgccaaa  13080
actgggaagc agcccgcgtg agcccatcca caggtgaatg gacagaccgt ggtacccgaa  13140
cactaacagc agccacgggc gtggactgtg gtcacacagc agcagggagc cgatgagtct  13200
cggacatgct aacccagaga ggcccattga ggaggaccta ctgtttttttg tgtttttgtt  13260
ttttgttttg aaatggagtc tcgctctgtg gtgcaggctg gagtgcagtg gtgtggtctt  13320
ggctcactgc agcttccgcc tcttgggttc aaacagttct cctgcctcag ccttccgagt  13380
agctgggact acaggcaccc gccaccacac ccggctaatt tttgtatttt cagtagagac  13440
ggcagttcgc catgttggcc aggctggtcc caaactcctg accttgtcat ccactcactt  13500
tggcctccca aagtgctgag gttgcaggca tgaaccaccg cacccggctg gacctactgt  13560
tttattccat ttatgtgaca ctctattaat agaaaaggca ggggtggggc tggtggttat  13620
atggtgcaca taactgccag aactcagtac acttaaaatg aacatcttaa tgtgtgaaat  13680
tttttttttt gagacggggt cttgctctgt cacccaggct agagtgcagt ggtgcgatct  13740
ccactcactg caagctctgc ctcctgggtt cacgccattc tcctgcctca gcctcccgag  13800
tagctgggac tacaggcgcc cgccaccacg cctggctaat tttttttttt tttttgtatt  13860
tttagtagag acggggtttc acagtgttcg ccaggctggt ctcgatctcc tgacctcgtg  13920
atccgcctgc ctcggcctcc gaaagtgctg ggcttgcagg cgtgagccac catgcccggc  13980
caatgtgtga aaatttaaaa gtaccaaagc tggaccccac cccagattgc tcccatgaca  14040
ctctgtgggt gggacctggg agttgggttt tgttttgttt tgttttgttt ttgagatgaa  14100
```

-continued gtctcactct gtcgcctagg ctggagtgca gtgacacaat ctcggctcac attaacctct 14160
gcctcccaga tgaaagcgat tctcctgcct cagccttctg agtagctggg attacaggca 14220
cacaccacca cccccctgcta atttttgtat ttttagtaga gacggggttt taccatgttg 14280
gccaggctgg tcttgaactc ctgacctcgt gatccgcccg cctcggcctc ccaaagtgct 14340
gggattacag gcgtgagcca ccgcgcctgg ctgggagttg ggtttgtaaa tctccctgag 14400
tggggctggg gcagggaact gctgggtctg ggtcttcctg gctcctctgg tctgtggctt 14460
cctgactgcg gtggccgggg gctcccaggg catcgtggcc gtctgtcttg ctgagcgtgg 14520
cacgtgcctt tccatgctgt ggaggagcgt ctcccggtat ggcgaactgc tggttagggt 14580
ggggcggtgt tgccaggtca tccaggtctg gcctctgctc tcgacatcgc cggcgctgtt 14640
gctcatctgc gcttgtgatg ttcgatgcct gctgcacatg tcttggcttc cctctttccc 14700
ggcctctgtg agctccagcg ctgcgtccct tctcttcctc ctgtagagcc gcagagcaca 14760
caacattgac ctgaagggga cagtcgtgat ctttgacgaa gctcacaacg tggtgagtct 14820
ccgctggcct cctaaacacc tcctattgct tctggccttt ttgtcaagag ccacgcaaac 14880
ctttctggag gggctctggc caaactcctg aagccctagg tgcccaggac tggggactga 14940
gcacaccagg agcttctgcc accccctccc gccctgatcc gatgcctctg ctggggctgg 15000
agactggcca gctgggccag ggacctgccc gtcaggcgca gggcccccac aggccgctca 15060
ccagaccctt tccctccagc cagctcgggg tcagcctggg ccagggctgt ctcctctgcc 15120
ctcggcagca gcaggcttgt ggtcttgcct gcagtgtctc tgcccttccg gccacatggc 15180
ttgagactga ggcaggagaa tcgcttgaac cttggaggca gaggctgcag tgagccagga 15240
tcacaccact gcattccagc ctgggtgaca aagcgggatt ctgtgtcaaa aaaaaaaatg 15300
ttgactgggc gcgctagctc atgcctataa tcccagcact ttgggaggct gaggtgggcg 15360
gatcacgagg tcaagagatc aagaccatcc tggccaacat agtgaaacac cgtctctact 15420
aaaaatacaa aaaaattagc tgggcgtggt ggcgtgtgcc tatagtccca gctactcagg 15480
aggctgaggc aggagaatca ctcgaaccca ggaggtagag gttgcaatga gccaagatca 15540
caccactgta ctccagcctg gtgacagagc aagactccgt ctcaaaaaaa ataaaatcaa 15600
aaagaataat tggcaattcc agtgaaataa ttgtttgttt gtttgttgag acagggtctc 15660
cttctgtcgt ccaggctgga gttcagtggt atgatcttgg cccactgcaa cctccacctc 15720
ctgggctcaa gccatcctcc cacctcagcc tcccgagtag ccgggactac aggtgcacac 15780
caccacgccc ggctaatttt tgtatttttt gtagaggcgg ggtttcccag cgttgcccag 15840
gctggtcttg aacccctgag ctcaagtgat ctgcccacct tggcctccca aagtgctggg 15900
attacaggtg tgagccaccg cgcccggcct gaaacaatcg tttctaaata ttggtgtggg 15960
ccacacagtc atgtttggac ctacttgtgg ccttttacag accccaggcc aaggctttgg 16020
gaacttggct gtcagcctcc tgtgccttct gcaccccccac cccatttctg ctttctggaa 16080
cccccgatcc tgtcctgttc tgtggtgatt cgggtgtgct tgggctctag gagaagatgt 16140
gtgaagaatc ggcatccttt gacctgactc cccatgacct ggcttcagga ctggacgtca 16200
tagaccaggt gctggaggag cagaccaagg cagcgcagca gggtgagccc cacccggagt 16260
tcagcgcgga ctcccccagc ccaggtgcgt tcatagccag actgcttggt cctgaggcct 16320
gcgctgctgc agggtgagcc ccacccggag ttcagcacgg actcccccag cccaggtgcg 16380
ttcatagcca ggctgcttgg tcctgaggcc cgtgctactg cagtgggcag cctgccctgt 16440
ggctgtgtgt ggtcggcctg ggcaccatct attcaggctg gcactgcagg gcatccgctt 16500
ctctcagagg cttcttgggt gtgaattctt cagggtcctg tagcctgtgg aagggctggt 16560
attgttcagt agttctggta ttttccaaag acctatgtct tctcccagcc agtatcaact 16620
tggcctctac tgtgtaaaac tggaaaactc tactttgtga agctgagttg ggagcatcgc 16680
ttgaggccag gagtttgaga ccagcctggg caacatggcg gaacctcgcc cctgccaaaa 16740
aattagccag gtgtggtggt gtgctcctgt ggtccaagct tttccggagg ccgaagtggg 16800
aggcgtgctt gagcctggga ggcagagctt ccggtgcccc agatgactcc actgcactcc 16860
agcctgggcg gcagagtgag gccatctcaa aaaaaaaaaa aaggaaaact aaatatattc 16920
actgtaaggg cattttgcat ctttaaatga cccacaaatc tggcatgcat cagctgctct 16980
gcctgtaggt tccttcccag tgtttgtcca gaggtgtatt tccacacagc gctagtcacg 17040
gcatacgtgg aaaacgtgga aacccttcat ggatgttgtc agttggtcta tattttcttt 17100
cttttttttt tttttgagat ggagtttcac ttttgttgcc caggctggag tgcaatggcg 17160
cgatcttggc tcactgcaac ctccgcctcc tgggttcaag caattctcct gcctcagcct 17220
cccaagtagc tgggatcaca ggcgtgcacc accacgccca gctaattttg tatttttagt 17280
agagatggtt tctccgtgtt ggccaggctg gtctcgaact cctgacctca cgtgatccac 17340
ccgcttcggc ctcccaaagt gctgggatta caggcgtgag ccgccacgcc cggcctttgt 17400
ccatattttc tacatggctt ctgtaaacag ctgactagga gtctgtgtga atatcttcat 17460
aggttctgct gtgacactac ttgctcgtga gcatctccag gtgtaaacag catcagcttc 17520
ccccattttc ctttaaaatc gcacatgtgg acggacacca cggggaccct ggaccctggg 17580
gagccccgtc ctcacccttc tcaccaggat ggctgcttgg tagagagtga gtttgcaaag 17640
ttggcatttg tttagtacag aagttatcag gtgttctggc tttagaatcc ctttatatat 17700
atatatatat acatatattt aagtgacagg gtctcactct gttgcccagg ctggaatgtg 17760
gtggtacaat caaagttccc tgtagcctcg gcctcctggg ctcatgggat cttcccgtct 17820
cagcgtctta aagcgccggg accacaggtg tgcaccactg ccaccggctc tcaagattgc 17880
cacgcaggga gttgcagtgg gggaaggggt tcctgggact ttgaacgctc cacctccctc 17940
ctctccacag tcccccaacc ccacctctct aacggggtgg acggccgcct ctttccatcc 18000
ttcgcttggc gcagggtggg gagagtgaca ggtctccttc cctcatctcg gcagctgcca 18060
tttcatcgct tacataacgt gggagaaaca tccacccacc cccaggcctg tgtgaacatc 18120
accacggggc cttctccact cttcagtttt gttagttact tgatgtgcag ggctttttgt 18180
tgtaactagt gggggacgtg tggtggggtg ggcttctgcc atctcattca ggaccagaac 18240
ttcagttttc atccctatct gttcccccac ccctttggag atggggtctc actctgtcac 18300
ccaggctgga gagcggtggt gccatcacgg ctcactgcag cctccacctc ctgcagcctc 18360
cacctcttgg gctcaagtga tcctcctgcc tcggcctccc aagctcctgg gactacaggc 18420
gtgtgccact gtgcttggca gggtccattc ttttcctcac actttattta ttgaagagcc 18480
caggccgttt accctgcaga gtcggaatct gtacaggagg ggcagccaca cgagttcccc 18540
ggtttactct gaacttaggt ggcttgaggg ccccagttag actgcggcca ccgtttgccg 18600
ggctccagat gggacgtcct ttctatcaga aggctcacag tatctccttt cccgtttctt 18660
cccatgtgaa cattgttgct gctgaacacc tgaatatgtt aatcactggg ggcttgcaag 18720
atggcagtgt gctaattcca tcatctagtc agttagcagg aataacttag gaccacgccc 18780
tgcaccatat cagctatgtg gtgatcccat tcacacagga aaggtgggac aaatgctggg 18840

```
ggtgggccgg gtgtgctgtc tcacacctgt catcccagca ctttgggagg cccaggcagg  18900
cggatcacga ggtcagagat tgagaccatc ctggccaaca cggtgaaacc ccgtctctac  18960
taaaaataca aaaaaattag ccaggtgtgg tggtgcatgc ttgtaatccc agctacttgg  19020
gaggctgagg caggagaatc acttgaaccc aggaggcgga ggttgcagtg agccgagatc  19080
gcaccattgc actccagcct ggcgacagag cgagactccg tctcaaaaat caatcagtca  19140
atcaagtgtc atcactgaat gtttgtgtgt gaacgtgggg attggtcctg ccccatgctc  19200
cctcctgaat ctcactcctg acctcagttg ctgcaccttg aggtgttttc atgtgggctc  19260
ttgtgtcctg accccggcgg ttgtggcctc tttgctgtct gggagtcagg atttttcaca  19320
ctcatgtcct gctccagacc tggaatcagc caagtctcca agaagccctg ctttcttttc  19380
ctgcaagacg gtatttcaag acccgccatg cggcagcggg ttggtcatgg ttactgggtt  19440
ggtcgttgtt actgggtgtt ttcgtggaga tacagccata cgcacaggtg tgttcacaaa  19500
tgttaattct aaaggtcaaa cacccggcca ggcataaggg ctcagcggta atcccagcac  19560
tttgggagac caagactggt ggatcacctg aggtcaggag tttaagacca gcctgagcaa  19620
cagggtgaaa ccccatctct actaaaaatg cgaaaattag ccgggcatgg tggcgcacac  19680
ctatagtccc agctagtcgg gagacagaca cgagaattgc ttgaacctgg gacatggagg  19740
ttgcagtgag cagagatggc gctgctgcac ccctgcctgg gtgacagagt gacaccctgt  19800
ctcaaaaatg aatagataaa taaagataaa acacctgctc ctcttggtgt ctccagtttg  19860
gatttggcct gtgtagcctc ttccttcgcc tgttggtgga tttggcctgc acggattctg  19920
tgtggcctct tccttcccct gttggtggat ttggcctgca cggattctgt gtggcctctt  19980
ccttcccctg ttggtggatt tggcctgcac ggattctgtg tggcctcttc cttcccctgt  20040
tggtggattt ggcctgcacg gattctgtgt ggcctcttcc ttcccctgtt ggtggatttg  20100
gcctgcacgg attctgtgtg gcctcttcct tcccctgttg gtggatttgg cctgcacgga  20160
ttctgtgtgg cctcttcctt cccatgttgg tggatttggc ctgcatggat tctgtgtggc  20220
ctcttccttt ccatgttggt gtcctttttt ccatgccagg aatcctggtt ctcaagggcg  20280
gggttgttgg cacgagcgtg atgcagactg cctttgctgc ctttctcttg cccagggctg  20340
aacatggagc tggaagacat tgcaaagctg aagagtaagt gttgccctcc ccgcctcctt  20400
gcagctgggt ggggcctcct ccttgcgagg aggtgggtga cacctcctcg acccacagtg  20460
atcctgctgc gcctggaggg ggccatcgat gctgttgagc tgcctggaga cgacagcggt  20520
gtcaccaagc cagggaggtg agaggcgggg agccagcccc ttcactgcag gcccagccta  20580
gagctagaaa cgggccatgg tgcagtcctg ggctgtcaca tcacgagtga ggcctgtttt  20640
caggcctgtt ttcccttttt gagacctggg aggagcacct gctttgcatg atctggttgc  20700
tgagatgttg agaggagcag cacacactcc cacgggacag cacacagccc cccacggaac  20760
ggcacacaca cccatggaac agcacacaca ctcccacgaa cagcacacac actcccacga  20820
acagcacaca cactcccacg gaacagcaca cacacccacg gaacggcaca cacacccacg  20880
gaacagcaca cacactccca cggaacagca cacacaccca cggaacggca cacactccca  20940
cggaacggca cactctccca cggaacagca cactctccca cggaacagca cacacactcc  21000
cacggaacag cacacacacc cacggaacgg cacacactcc cacggaacag cagactctcc  21060
cacggaacag cacacacact cccacagaca gcacacacac acccacggaa cagcacactc  21120
tcccacgcgg ggccgctggg tttcctgcag tttctcctcc tccaggcctt tccctggacc  21180
ctggtccagt ccgtcatttg agcacaggtg cctgttagaa cgagaccttc ttgttaggac  21240
```

gatgagtgtc ccagccacca cctcttttgg actccgggag gcctggaacg ttctgaacgc 21300
tccgtggggc tccagtcttc tccgcagcca gggcagcagg gtttgctgtc tgtcctgcag 21360
gcagatgagg agtcagggct ggggcctgtg tgggggctct cctgagcgca cagccgccga 21420
ggtggagcgt gttctgcctg agcgccgacc tggtcggggg aatcccagtt gcttccaggt 21480
ggagccactg tcctcagcgt aatgctcaag gctctggcct ggctcctcgg ccaccctgca 21540
ccctcagggt cccctcctgt agcttctgct gccccatcac tgtcactctc caaagctttg 21600
gggactctgc ccagagccac cgcctcccag aagcccctga caacctcttg acgacccccct 21660
agtgacccca tccctcccct ctgacggcgg cccctgctct gaggcggctt cttttcctcg 21720
gtgctgttct cgtgctggcc aggcctcctc tccccacctg gaggctcctg agggcggagg 21780
cctctcacct ccaatgctgg cgtcccctgg agggctgaat ttgtttccga gggaaggaaa 21840
cttccacagt tgttgccttc agttccaaag ctgcagcctg atttccccct ccaggctcga 21900
gcctgttttc ttctcggcag ctacatcttt gaccagtgtc gtccccccctc aggcccgagc 21960
ctgccttctt ctcctcagtt cccaaagctg cagtctggtc cccccgccag gctcgagcct 22020
gccttcttct cctcggcagc tacatctttg agctgtttgc tgaagcccag atcacgtttc 22080
agaccaaggg ctgcatcctg gactcgctgg accagatcat ccagcacctg gcaggacgtg 22140
agtgctggca cggggtcttt ggtgcgggca aatgtggcgt agggggtgca gcaggcctcc 22200
atcttggcag tcagggctcc cctggccgtc acctggccgt cagcaggaac aggcccacag 22260
aacctcatct tctgatcggg gcgtggaggc gttagtgcca cttgccagct gccgtagagc 22320
ctgtcccagt tctgcagctg gcggcttcgt cctacagcct catcccatta ttctgctttt 22380
gagaaagagc agcccaaggc cctagctggc ttgtggggcc tctggcttct ccacaccacc 22440
ccgagttctg cttctcagag ttgtggggtc cagaggcttt gcccagaggc ggtgtcccca 22500
tgggctgctc tggtttgaga cgccgggccc agcggggtct ctcctctgct gcgctcccgg 22560
gtgctgggga gggtggcttt tgctgcttca acccttaggc gaccatagag cctcttttca 22620
agtcccactg accccttgg agactctgtc cctgcctggc ttctctcctg gctgctggga 22680
agagcaggcg aactgcccgc cctgaatgga tgctgcgctc caccctgggc cccccattgg 22740
gcaggagatg gagcttggca gtcgggctga gcgggctcat gctggaaggg ccggggctgg 22800
ggtcggggcc tcccctgcct gcagtgtggg tgtcagcgcc ctgctgccct ccaggtgctg 22860
gagtgttcac caacacggcc ggactgcaga agctggcgga cattatccag gtggggcctg 22920
ctcctctgtg gcatctcctt ccctgatgga agccgggcgg gtgccttctc ctgctgtatt 22980
agttaactga ttctagactt ggggatggga gaaaggcccc tacaccacct gtttctgatt 23040
ggcaaactct cggctccttt ccagtgccct aaacccacac tgggcctcct gcagggatgg 23100
gggaggacga ggtctggtgg cacatgccca gggtgatgct ggtgagggag gacgcaaagg 23160
acagtggggg ccggggagcc gctcctgccc tgtccgggcc ctcaggccag gggggaccca 23220
ctgctggcag ccccagcagc cccagctgca cgcagatgaa gagctctgga cacacgcggc 23280
ttcctgaaca gcttctccag ggacagacaa atggggaccc tgcaggttcc cggcaggggt 23340
gtccctggga gcccatgatt gggggtgcga ccctggcccc cttctcattg gccccgtcct 23400
gtcctgcaat gcccgtccca tgtgaggtct gcttctggct ccatgcctat ggcagcacct 23460
gctttccctg gcgtagaggt gcttgtccgg tttgtggagg gcacgcccca ttttgggtgc 23520
tctgggcacg ttgcctctcc ggggcctcgg tggctttttt agaagcagac tcagaagtcc 23580
ctgactgggg aagccaaggc acaggtggct gtgtggagcc ctgtgaggcc tcctctgtgc 23640
tgcccacgct gtacctgctg gccacacgag atcatggcag ggttaggcag ggctgcccag 23700
cgctatgaca gcttcatgag tgtccatctg gcctgtgggg tgcttgagct gggggaggcc 23760
gcagaagaac cctgggatgc atggctggcc tgtgcatgct gctgggcatg gagctgcaga 23820
tcccggaaca agcaggcact gccttctcct tcacagacgc agctctgagc gggggcgaga 23880
cctgggcagg gaccaggtgg ggtgggcaca gggtggtggg gcccaggctc agccctccct 23940
ccactgtggc cgtctctgtg gccagtgacg ccacagcctg tgtcttctct gtgcggtagc 24000
tggggctgga aggacagcac tgccttgtcc tcccaactcc tccccaaagg cacggtgggc 24060
atcccaggcc cagacccctc tgtctgtggc tcctgcctgc caagggctgc tgtgctgtcc 24120
cgcatggagt gtggttggct cttcaagcag gaggccgtgc acctatcagg cggacctgct 24180
tccatgtccc tgatgggtca ctgcaaagca cctccagcac atggccaggc gaggtagccc 24240
tgcagcccag ggcctggagg gcaggtgtga gctggcccgg gcctgtccct ccctggaata 24300
cagcttccca ggctcccact tatggagaag tctcctccac actatggaac tgaatcctag 24360
aatgtggctt ctgaggttcc tacactcgaa ctgaatcctg gaatgcggct tccaaggctt 24420
ccagctatgg agaagactcc acactctgga accgaatcct ggaacgcggc ctcccaggcc 24480
cccagctatg gagaagactc cacactctgg aaccgaatcc tggaacgcgg cctcccaggc 24540
ccccagctat ggagaagact ccacactctg gaaccggatc ctggaacgcg gcctcccagc 24600
ctcccactta aggagaagtc tccacactct ggaaccggat cctggaacgt ggcctcccag 24660
gcccccactt aaggagaaga ctccacactc tggaaccgaa tcctgcacac tccatcggtt 24720
tggaatttcc tttggctgct gctctaagta gccgctggtg gatgactcag cttctgccag 24780
ccctcgggtg cctggaggat gagggactgc acacagtgct cacccgcgtt ggctcctgag 24840
cccctgcagg tgtgggcggt gcccataggg ctggtgctgg gttgggcctg cagccctgag 24900
tcacaggtga ccctgggggc agagtggggc cagtggcccc aggaagagga tgtgggatgc 24960
acagctcagc tggaggcgaa ctccaggcag ggtcaggccg tgtgctcgga agtcagggct 25020
tagctggagg caaactctgg gcagtgctgg cccgtgttgg ggaaccagtt gcccctgggc 25080
ccccgtgaga ctgctgggtc ctcatccctc tctgcctgag gccggagctg ccctgggctg 25140
aggcacaggg ggatttgtgg tggtgttttt ttgagaaagg gtctcgcttt gtcacccccgg 25200
ctggagtgca ggggcttgat cacagctcac tgcagcctca acctcctggg cccaagtgat 25260
cctcttgcct cagccacccg aggagctgtg aacacaggtg tgcaccaccg cactcagcta 25320
atttttaaaa ttttttttgta gagatgaggt cttgccatgt ttcccaggct ggtctcaaac 25380
tcctgggctc aggcagtctg cccgccttgg cctcccaaag tgctgggatt acaggcaaga 25440
gcttccatgc ctgcccagca gaaggctttt cgaaggaagc tgtttcctga ggcagactca 25500
gccctgctca tggcagccac cagcgtgggg gtgaacttgt tctgttactt ccatccccgt 25560
gggccaaatg ctttggtaaa acacaaggcc ctgtgtttag ctgtcttgac agtgaaaatg 25620
gctgggaagg aaggaaggaa cggaaggaaa tttctctctc cttctgtgcg tacccaggca 25680
cgtgcacatg catgcagagt acgcacacac gcacgcacgc ctgcacaaat ccacgcatgt 25740
tgccaagtct ctgtgttcca gccgtggtgt ctgcccccccg gtgttctcta gttcggcttc 25800
tccgcatttc tgtgaatgat tccggcttct tggtgttccc agcagaactc cctcaagtct 25860
gcggcggggc tctgacggcg gtggcttggc tgacatggcc acattgctga gcctgttggg 25920
ggctttgcgt tcctgttctg gccgtttttg gctcgttttc caggaacggt cgtcacgcgc 25980

```
tcctctccta gtgcaggcat cattcctttc ccattgattt gcagggttct ctgtaagttc  26040
tgaggatccc atatacatat actctctgta agttctgagg atcccatata catattctct  26100
ctctaagttc tgaggatccc atatacatat tctctctcta agttctgagg atcccatgcc  26160
gacatacata ttctttcctt gtctcatgct ggtcattttt tccattttca tgacaggttt  26220
ggtgaacaca tgtttccttg tcagattttt gttctgagct tgtgcctccc gaccaagatg  26280
ctaaaccggg tcttgtgtat tctccaaact gcactgtaga gtgacggagc tttgtgtctg  26340
ggcctccatg ccttctgacg tcacctgtgg gggtgtgaaa ggcagactct accttgattt  26400
ttcccagcac gccacaccgg tggttctgtg cgctgaccga gcggctcggc ttcccccaac  26460
tccactgggc acctgccaca cttttcctca tgtttttgtt cactgtggtt ttgtcgtaag  26520
tcctggtgtt ggcctgaacc aatttctttt tgtttgtttt tgagacagag ttttgctctt  26580
gttgcccagg ctggagtgca gtggcgcgat ctcggctcac tgcaagctcc gcctcccggg  26640
ttcacgccat tctcctgcct cagcctccca aatacctggg attataggca cctgccacca  26700
cgcctggcta attttttgta tttttagtag agacgaggtt tcaccgtgtt agccaggatg  26760
gtctcgatct cctgacctcg tgatccgcct cccaaagtgc tgggattaca ggcatgagcc  26820
accgtgccca gcctgatatt tttagtagaa atggggtttt gccatgttgg ccaggctggt  26880
ctcgaactcc tgacctcagg tgatcctctc accttggcct cccagagtgc tgggattacg  26940
ggtgtgagcc accacgcccg gcctcttgtt cttttgaaac ctgccctgac gtttttttcca  27000
tagtgcatct tggagtcagc gtgtctactt cctgtaaaaa tcttactgtg attttgacta  27060
gaatgtgttg aattcctgtt ttttttttga gtcagggtct ctctgttgcc caggctggag  27120
tgcagtggga ccatcacagc tcactgcagc ctcaacctcc tgggctcagg ggatcctctc  27180
agctcaacct cccaagtagc tgggaccaca ggcacatgcc accatgcccg gctaggtttt  27240
tttttttttt tttttggtga acaccctggg gttgcaccat gttgcccagg ctggtctcga  27300
actcctgggt tcgggcagtt tgctcctctc agcctcccgg agtgctggga ttacaggcct  27360
gagccactgc actaggccat gttgaatttc tagattaatt tggggccctc aggggcacag  27420
agaggagggc tgggccagtt ggcgggagga gaggcccctc gggctgccgc attttcagtg  27480
catggagatg gcctatgttg ggggaacaca gagctcaccg ggggtccctg cagggaggag  27540
aaagggtcag gcaggtgcca gctcctgtcc attggcctgg ggctgcatga tggcaggggc  27600
cggtgaaccg atgacccctg ggtgtcctgt gaccttctgt gtatgcggct gatgctgcag  27660
aaagtcgggt ggcctcaggc tcctgacggg gctgcacttc ctctgccttt cagattgtgt  27720
tcagtgtgga cccctccgag ggcagccctg gttccccagc agggctgggg gccttacagt  27780
cctataaggt aggggccacc tccaggaggc aggtggaggg cagcccttgt tccccggcag  27840
ggctgggggc cttacagtcc tataaggtgg gggccacctc caggaggcag gtggggctgg  27900
gggtcttctg gtcctaaaag gtaaggggct gcccccagga catgggcggg gcctccacac  27960
tcctggtcct gtcccctcca ggtgcacatc catcctgatg ctggtcaccg gaggacggct  28020
cagcggtctg atgcctggag caccactgca gccagaaagc gaggtacaga cctgggccca  28080
cacgctcccc gcccgcccgg gtgcagtgcc cggcaccacc atgccacagg ctaggcacat  28140
gcccagccgt ggatctcctg cccccatggg cctggccacc ttctccatat ccaggccaat  28200
ccagagcatt ctcctcactg tccctctgaa gattggagtt actgagagac gtaggagatg  28260
gcctgatggc accgtgacct gcccagagtc acctggttgg tggtggcaga gccacagccc  28320
```

agccaggcct ccctgctggg acacgctcgt ttatgccgag gccgtcagca cagagcctcc 28380
acagtgaggc acggctctgc ctgctgcctc cacgcagcgc ctggccgggc caagcctcag 28440
ggtcacatct gaagggggcc cggctggccc tgttgtccga agcccctggt gcgctcagcc 28500
ccgaggcccc acgtgccttc ttggcttcct gtgctccgtg gcgtcttcga gtcggtgctg 28560
ccggggacgc tgtgtggatg gggtctgtga gtgtgccctc ggctccgtgt ccggagccct 28620
gtggttcttg ggtgtatct ggccccaccc ccactgcgtg gtgtccaggg tggggcttca 28680
cggctgcagc tgcgggagct gctgcccctg ccttgtgctc cagtggggcc ttgcctctgg 28740
gcttggttcg tccctctctg gaacattctt tctcagctgc tgtccgaccc atggtggcat 28800
gacgtggccc tggctgaagc agcccttgtg cggttgctgt ggttgggtct gcctggccga 28860
gccggaaggg aagggctggg agggcgtcag ggtggcgtgg cttgaccccc gctcggtgat 28920
ggtcctgcag caaggcctct cccagcagga agcgtccatc ccggggggag gccggcgccc 28980
ctcacgcagt tggggttgcg ggaggcagtg cgtgcctgag gcagccggtg cacagattcc 29040
aagggcctgg aatctgtttg ttccattgac ctctgatgtc acttgacttc tcagaagcag 29100
ccactccctg cactgggcgt ttgtaggaaa tgagctcctg gaggaggggg tggggaagtt 29160
cccccattgc agggcacact cagccccagg aaggaaacgt gcctcgtccc tgctgactcc 29220
gaatcgcagt cagagtcgtt ctgcttgtgc cgtgttgaat tcccggcatc cggcatccag 29280
actcagcctc ctccccaggc cacggccgcc gtggccagtc ggtcaagccc ttctaggaac 29340
ttcctttgag ctggcgccct tgttcactgc tgacgccact cagaggcttg tgcacgtgtc 29400
ctgcttccag gcagagctgg gaactcgcac cccgtcttct gcacgcggcc gtggaatgtc 29460
gggatgccgg cgcttccttc ccgtgtgctc ttggcggggt gggcttcttg ccctgagccg 29520
catgtcacag tttctgcaga agtttagggt tggagtgggc tgacctctct gcaggtgtcc 29580
ccagcctctg cctggggtct gcctcctact cccaggaccc cctgtccccc agaggggccc 29640
caagctggca ggctcacact cagggcagcc tcctttgttc tgacttctgc acagtgggcc 29700
tgggtggctg cccgcggctc gcttgcttga tgccagtggg tggagagggt gatgggcaga 29760
gaggcaggtg gtcaggcccc cagtcccgtc ctcacactct gtgccctctg ccgcccccg 29820
ccccacaggg aaggtgctga gctactggtg cttcagtccc ggccacagca tgcacgagct 29880
ggtccgccag ggcgtccgct ccctcatcct taccagcggc acgctggccc cggtgtcctc 29940
ctttgctctg gagatgcaga tgtacgggcc acccctgcca gggcctgagc accggtgaca 30000
cctctgacat cagcggggtg gaagtggtgg gggtccccat gagccgggtg ctgggggtct 30060
cgggcctcga gggctaaagg ggtgctggtg cacttcccca ctgtctgctc cctctggcca 30120
cgctcagccc tttcccagtc tgcctggaga acccacacat catcgacaag caccagatct 30180
gggtgggggt cgtccccaga ggccccgatg gagcccagtt gagctccgcg tttgacagac 30240
ggtgagggcc tgtccctggg ccctgctggg gtgggaggtg ggggagcact gaggcctgag 30300
gtcctgagca gtggcctctc cggctctagg ttttccgagg agtgcttatc ctccctgggg 30360
aaggctctgg gtgagtgccc tgaatgcccc agctgtgccc atcctggatc ctggacccct 30420
gctcccaaga gctggtaggg aaccctgcag acatcctgcc cctgccttga ccccggcccc 30480
tgcacttcca ggcaacatcg cccgcgtggt gccctatggg ctcctgatct tcttcccttc 30540
ctatcctgtc atggagaaga gcctggagtt ctggcgggtg cgtctcccct gtgttctggg 30600
cggggtgggt gagggcaggg ctggagcatg aagcaggcag tggtcacagc tcctgcttgc 30660
cctcatcgga tcggcggcgt gaccagggct gccgtgtccc tgcctcttcc tcccacaggc 30720

```
ccgcgacttg gccaggaaga tggaggcgct gaagccgctg tttgtggagc ccaggagcaa  30780
aggcagcttc tccgaggtcg gcacttggcc ggggctctgg gcctgctgcc ccctcgtgcc  30840
tcccctgcct ctcacagctt ccccaaggct gaccactggc cctgaccatg ggctccggcg  30900
gctcccgctg cctcttcagg gctcctgcgt ttccttcctg gccctgagtg ttgcctctta  30960
tcttacaaag cccccagcac cgggtgggtg tggtaacagt ggccctcctg tctgagtagc  31020
cctagtcggc caccctggcc ctggggttcc ccgtgttttc tgggaagcac tgagcaggcg  31080
tggggtcagc ctgggatccg tgccaggaag aagcttccag aacccgattg gccttcctgg  31140
ctaggacgat ccttcatctt ggagcatgag acctgggtct ccctcatggg ggaggaaggg  31200
gctggggggg ggctccaggc tcagcctcac caactttcct tccagaccat cagtgcttac  31260
tatgcaaggg ttgccgcccc tgggtccacc ggcgccacct tcctggcggt ctgccggggc  31320
aaggtgagct ctccagggcc ctctgccctg acctggttgc ctgttccctg gtgggtgctt  31380
atggctcccc agcagactct gggccctggg ggctgcccgg tcccctcctt gggtcccacg  31440
agagcgactg ctggccctgc tgggagcgtg tcctgctctg ggcctgggca ggcaggatgg  31500
gagtttcctg gccacaagag ttggaggtgg cgtctgggag ctgtggaccc caagtggggt  31560
cctgacccac agatggagct tcctcccacc cctggttggg gacggagcct cggggaaggt  31620
ggctgggctg ggtgtgggca ccagggagag gagcccccac ggccccaggc agctccctgg  31680
tgtgtcccct aggccagcga ggggctggac ttctcagaca cgaatggccg tggtgtgatt  31740
gtcacgggcc tcccgtaccc ccacgcatg gacccccggg ttgtcctcaa gatgcagttc  31800
ctggatgaga tgaagggcca gggtggggct gggggccagg tgagttacag cagggtgggg  31860
ctggggtaag gcggtctggt gactgagccc ccgccccgtg gccaagggag cccccgtgac  31920
cgagccgcct cgccccacag ttcctctctg ggcaggagtg gtaccggcag caggcgtcca  31980
gggctgtgaa ccaggccatc gggcgagtga tccggcaccg ccaggactac ggagctgtct  32040
tcctctgtga ccacaggtgc gtgcagtccg gtggcaggcg cggcgccagg ggacacgccc  32100
acaccccact gggcccctgg actctccttc cccacatgag gccccgtctc ctccagagcc  32160
tctccggcta ctcggggtca gcgtggggcc cctgcagcag atgagggtct tcacttcggt  32220
gaactgaacc cttgaagcgg ctgtgggcag ggcagcaggg ctatggccac cccccaggtt  32280
cgcctttgcc gacgcaagag cccaactgcc ctcctgggtg cgtccccacg tcagggtgta  32340
tgacaacttt ggccatgtca tccgagacgt ggcccagttc ttccgtgttg ccgagcgaac  32400
tgtgagttcc tgcccaggga ggggatgagg gtgttgtccc cagaggagcc agaaatgggt  32460
ccacccaccc ccatggttct gcagatgcca gcgccggccc cccgggctac agcacccagt  32520
gtgcgtggag aagatgctgt cagcgaggcc aagtcgcctg gccccttctt ctccaccagg  32580
aaagctaaga gtctggacct gcatgtcccc agcctgaagc agaggtcctc aggtgcggac  32640
gggcagcgct gggtgggcgg tgtgggggtg gcggagcggg cggcgtgggg cgggcagcac  32700
caggcgccca gggcggaggc gactcacctg gctttgtgcg cttcccctcc cacctccaaa  32760
ggctgcctct ccctcctagg gcagggcccc cacgggctgc aaccctcccc tacaggcaga  32820
gaacgcccca ggcaaggatg ccccccgagg ctgagactcc ccccaatagc agggaggaca  32880
cccacaggca ggaccccaag tgctgggact ctcccccaag aggggctttg ccacaggcag  32940
ggaccccagc tggggccccc cgtgggcttc actgcgcact cgggtgcccc tgcagggtca  33000
ccagctgccg gggaccccga gagtagcctg tgtgtggagt atgagcagga gccagttcct  33060
```

-continued

```
gcccggcaga ggcccagggg gctgctggcc gccctggagc acagcgaaca gcgggcgggg  33120
agccctggcg aggagcaggt acagttccag ggccttggga tggacacaga ccctctgtct  33180
cctgaggcca acccgacccc gcccatctgg cctcaggcac ctccccacac acccctgtaa  33240
atcccctgcc tggcaggcag gcgggcaagc gggcggggga tcccagctgc ctggctgtct  33300
gtgggtcctc caccccacct cacccacagg ctgctggctc ccaggtggtg catgccctgg  33360
ccctccgcgg gtgcccccca catcactttg gttctctggc gggtcagctt ggctcagtgc  33420
actcaaggtc gggtgcccct gccactggct gcgcttgagg ctggcctttc tccaggaatg  33480
tgctgcgggt ggaacccagg ttccttcttc cttggggcct tttgccccag aagcccataa  33540
ttcctcaggc caacccgaaa ttttctccct gcttcctgct gggagccatt cccctcttcc  33600
tgcccatccc tgcccttcag gcccctggag tgagctccag gtgcaggcac caggcacctg  33660
tgtccccttc ctgccagccc ctcgctgtgg tcggactgtc ttccctggac ctgctcttac  33720
aagtcaccac ctgcgagcct catgagccgc tggtgtgact tggacaggac caagttgtgg  33780
cactgtcacc ggggtgtgct gtgccccccct cccccgacct ccatcttggc tcagggctcc  33840
ttgggaccat cttccctgtg cgtccaggtg ctttgggacc ccagagtgtg tggttggggt  33900
ctgtgtgtgg ttgtgagctg tgtcctcctc aggcccacag ctgctccacc ctgtccctcc  33960
tgtctgagaa gaggccggca gaagaaccgc gaggagggag gaagaagatc cggctggtca  34020
gccacccggt gcgtgagctg tccctgcacc tgtgccgacc accatagaca cgcatgggaa  34080
cgcagccgtg ggtgccccca gccacggctg gtcccgatgg gaccagggaa tccaccccca  34140
ggagctgatg tccagggcag ctgtgatgct gacggccagg ggctcaagtg tgtggtttct  34200
tctgcagggg gctcatgagt cccagctgga atcaggcccc acccttgggc aggtttggca  34260
tggggcctgc agcactgggc ttggccctgg catttccctc aagtgtggat gcacacctgc  34320
ctcatgtgag ggacacagcc cattcctagc cttggatcaa agaacggagt tatagccgga  34380
gccaggaagc cccctgcctg ctggaaaacc ccaagtgtgg cggcctttgt ccatgtccct  34440
tggcttctgg gaagaactgg gtggtgccca ggcagggctg gtgccatcag gaagtgggtg  34500
gctgctgagg ggcctgggct ggcgagggcc tgggtgggga gtgcctgggc cgcccctgcc  34560
ttggtttcca cgtttccgtg ttggtctggg gtgtgtagag agatgggcac tgctcatccg  34620
gaagcccctc cttgtgcgct gccatcctgg gagcctcagc cgcatccgct gtggggcagg  34680
gggcttgagg gaggaggaga gagacgggcc atgcaggacc cctggcttga ggcagagcca  34740
atctaccctt tgcccattca ctgctctcag ttccctgcca gcctctcact gtgtgacctc  34800
agacgggccc agccccacag ctttcttccc gcagcccctc cctatgtcca tccagccagc  34860
cagtttctca ggcagcagcc ccacctcggc agtcactgtc ccagggaacg ctcaatgttc  34920
caaggaaggc tctgcagccc cagggaccag atgatgaggc tggccctgat ggagcctcgg  34980
gcctgtgtcc tgcaggagga gcccgtggct ggtgcacaga cggacagggc caagctcttc  35040
atggtggccg tgaagcagga gttgagccaa gccaactttg ccaccttcac ccaggccctg  35100
caggactaca agggttccga tgacttcgcc gccctggccg cctgtctcgg cccccctcttt  35160
gctgaggacc ccaagaagca caacctgctc caaggtgccc tggcttgcag aggccaccca  35220
ccctgagggc agtgctgccg ccgcgtgtgg ggtgggggcc atctgggtcc aaggtggtct  35280
ctgttctcta gagaaaaagg ggcagatggg gacagacgcc ccttcctcta caggcttcta  35340
ccagtttgtg cggccccacc ataagcagca gtttgaggag gtctgtatcc agctgacagg  35400
acgaggctgt ggctatcggc ctgagcacag cattccccga aggcagcggg cacagccggt  35460
```

cctggacccc actggtaaat ggggccccag gtgggaccct cagactcctg cgtggaaggc 35520
agtgtgggcc agagtcctgg gctgcttggg gtgggcatcc tcgggccctg cttggccccg 35580
cctctctgtt cccctatggg agtgatgggg gcctccacct ccaccaccag caccagcagc 35640
accacctcca cctccacctc cacctccacc tccaccacca cctccacctc caccaccacc 35700
tcctccacca ccaccacctc caccaccacc accaccacca ccacctccac ctccaccacc 35760
tccacctcca ccaccaccac ctccacctcc accaccacca cctccacctc caccaccacc 35820
tccaccacca ccacctccac ctccaccacc acctccacca ccaccaccac caccaccacc 35880
accaccacca ccacctccac caccaccacc tgcaccacca cctccacctc caccaccacc 35940
accacctcca cctccaccag cagcagcatc acttgttggg gagaccctgt gcaactccat 36000
gcacagccct gtccctgcca tagccccgac ccctaagcac agccctgtcc aactgccaca 36060
cgtcccctgc ctcccatgca tggtcctggg gggtcaactg cacacgccag ggtcctaggg 36120
tcctagaccc ctgtcctccc tgtttctgcc tctgtttggg gtggagtcca agtctccaga 36180
ggcggaagca tctgtgttcg tgtgttaatg aacagcccct acagagttcc cctagttcac 36240
ccagggggga acctagcctg ttgggacgac cccagatccc ttctgggctt ggtactcact 36300
gggatatcct catgcctgca cccagcctac ggctctgagc tcctgagtgg ggctttggcc 36360
tgcccgccac tgttccagcc cccatccagc aggctggtgt ctcctctgat gcccccagca 36420
cccaggcgtg tacctgcctg ggttttcccg ccctggtctg aggtgggtga ggcctggcct 36480
ccctagccag ccctgccccc ccaccccagg gaactttcca gatgctctcg accagctttg 36540
tggctctaca tctcttcatc aggaagaacg gcgccggatc ccaagctgac cgtgtccacg 36600
gctgcagccc agcagctgga cccccaagag cacctgaacc agggcaggcc ccacctgtcg 36660
cccaggccac ccccaacagg tagctgactc ctgaaccgtg tgcagcctac gacttggtgg 36720
gtccctcagt ggcttcacga ggctaactct tgagtgtggc cggggctgcc cctgtgggga 36780
gccatctcat ggtggggact gctcccggtt ctgcaccccg cagttgtcct gagcagctct 36840
ccaggagttc ctggaggaag ggcgggcagg gcggtgggac tctcagtcct ccaccccagc 36900
gccactctga gccatgctac tcccacacca ggagaccctg gcagccaacc acagtggggg 36960
tctggagtgc ccagagcagg gaagcagggc cagcacgccg tgagcgccta cctggctgat 37020
gcccgcaggg ccctggggtc cgcgggctgt agccaactct tggcagcgct gacagcctat 37080
aagcaagacg acgacctcga caaggtgctg gctgtgttgg ccgccctgac cactgcaaag 37140
ccagaggact tccccctgct gcacagcaag tggccctggc gtggggaaca gccggtgggg 37200
tggggggcag gggacaaaat gggggctgtg ccgggtctga ttgaagctcc ccgcagggtt 37260
cagcatgttt gtgcgtccac accacaagca gcgcttctca cagacgtgca cagacctgac 37320
cggccggccc tacccgggca tggagccacc gggaccccag gaggagaggc ttgccgtgcc 37380
tcctgtgctt acccacaggg ctccccaacc aggtagggca cctgcctggc tgctcctggc 37440
agcgccccaa ccgcacgcag ccctgggagt gagcagcaaa gccccaggcc cccctcagac 37500
tcaagtctct gtctccaggc ccctcacggt ccgagaagac cgggaagacc cagagcaaga 37560
tctcgtcctt ccttagacag aggccagcag ggactgtggg ggcgggcggt gaggatgcag 37620
gtcccagcca gtcctcagga cctccccacg ggcctgcagc atctgagtgg ggtgagcctc 37680
atgggagaga catcgctggg cagcaggcca cgggagctcc gggcgggccc ctctcagcag 37740
gctgtgtgtg ccagggctgt ggggcagagg acgtggtgcc cttccagtgc cctgcctgtg 37800

```
acttccagcg ctgccaagcc tgctggcaac ggcaccttca ggttggtgcc tggccactac  37860

agttcctgct gggtgtagcc ccaggtgatg ggctgagggg gaaagggcag gcccttgtcc  37920

tggtggcaac gcctggcaga cgtgtgcagt gggccggttg tctcacaggc ctctaggatg  37980

tgcccagcct gccacaccgc ctccaggaag cagagcgtca tgcaggtctt ctggccagag  38040

ccccagtgag tgcccacgga ggcccccagc acacccaacg tggcttgatc acctgcctgt  38100

ccagctctgg tgggccaaga acccacccaa cagaataggc cagcccatgc cagccggctt  38160

ggcccgctgc aggcctcagg caggcggggc ccatggttgg tccctgcggt gggaccggat  38220

ctgggcctgc ctctgagaag ccctgagcta ccttggggtc tggggtgggt ttctgggaaa  38280

gtgcttcccc agaacttccc tggctcctgg cctgtgagtg gtgccacagg ggcaccccag  38340

ctgagcccct caccgggaag gaggagaccc ccgtgggcac gtgtccactt ttaatcaggg  38400

gacagggctc tctaataaag ctgctggcag tgcccaggac ggtg                   38444


<210> SEQ ID NO 2
<211> LENGTH: 37214
<212> TYPE: DNA
<213> ORGANISM: mfascicularis
<220> FEATURE:
<221> NAME/KEY: misc_feature
<222> LOCATION: (4525)..(4624)
<223> OTHER INFORMATION: n is a, c, g, or t
<220> FEATURE:
<221> NAME/KEY: misc_feature
<222> LOCATION: (4914)..(5013)
<223> OTHER INFORMATION: n is a, c, g, or t
<220> FEATURE:
<221> NAME/KEY: misc_feature
<222> LOCATION: (9472)..(9571)
<223> OTHER INFORMATION: n is a, c, g, or t
<220> FEATURE:
<221> NAME/KEY: misc_feature
<222> LOCATION: (16613)..(17049)
<223> OTHER INFORMATION: n is a, c, g, or t
<220> FEATURE:
<221> NAME/KEY: misc_feature
<222> LOCATION: (19812)..(19911)
<223> OTHER INFORMATION: n is a, c, g, or t
<220> FEATURE:
<221> NAME/KEY: misc_feature
<222> LOCATION: (35806)..(36357)
<223> OTHER INFORMATION: n is a, c, g, or t

<400> SEQUENCE: 2

atgcccaaga tagtcctgaa tggtgtgacc atagacttcc cattccagcc ctacaaatgc     60

caacaggagt acatgaccaa ggtcctggaa tgcctgcagc aggtagagca caggctggga    120

ggaaaggact gcaggcaggt ggagctgggg ctgggtgtgc gtccctctcc cgacccattc    180

cagccaggcc cctccagagg cagcctctgt cataaaaagg ctggtgttcc aggtggggtc    240

agagagagga ttgacaagta aaaacatcgt ccttgagagt gacagactta gtgccttggg    300

ggcctctgag gagcggctgg tattcacagg tcaggaggaa gcatttccat cagaggggca    360

gccgggggcc agcctcactt tgaaggtctt tgaacctttg gggtgcaggg aggtggcagc    420

ggcgcaggtt gccttctcct gggttccttg aggtgccctc ttgtacccgg ctcacacccc    480

tcccctcccc gagtttcccg ctcaggttcc catctgagag ctcgtatgta ggacatcaga    540

taggacagcg taagtgtttg gatctggaaa cacagaacag tttcctattt tgagacttga    600

tgcctaatta gtcatcttac tatttaggct gaaaaatact gttgcatttc gggtaacgtt    660

ctgcaaatgg tctgctgatg gcagctggag ttgcttcacg ccctttaggg caagagtgga    720

aagtgtcctg cggacttatc catggtcccg tggggctctc gccacctgac agcggcctct    780
```

-continued

```
gcatctgcga agagctgccc actggctgct gaggcttgtc tcagggtggt ttgtgtggcc    840
ttgcctcttc ctggcttccc cgtaaccctt gcccccaact ctgttcagaa ggtgaacggc    900
attctggaga gccccacggg cacggggaag acgctgtgcc tgctgtgtac cacgctggcc    960
tggcgagaac acctccgaga caccatctct gcccgcaaga ttgccgagag ggttcaaggg   1020
gagcttttcc cgaatcaggc cttgtcgtcc tggggcaacg ctgctgctgc tgctgaagat   1080
cccataggtg accctagttc ccaggccttc cctgacctcc tgtggggatg gctggcaagg   1140
gatggcgctg agggtagggt gggcccatgg ggacttctgc cagcagagct caaggagaat   1200
tttgtagctg ccacataatt tctcgccatc gtgggtataa acctagggtt gggctttttt   1260
gctgaattag ggcgtggcag gtgtacactt cgcccgtttg tgataaacga gtctctgggg   1320
tgtcagattc ttggctgtct gcagggctga gttagccgaa tgccacccgc ctttaacacg   1380
tgagaaccat gacctctgtg cttgcttgtg tctgggcagc ttgctacacg gatatcccaa   1440
agatcattta cgcctccagg acccactcgc aactcacgca ggtcatcaac gagcttcgga   1500
acacctccta ccggtgggtc agacgagttc acgcctgtct tggggtcctc gagagaacca   1560
gcttgacgtg gtgctgggtc cacagaccac gctgtgctgt agtggagggg gcggtctttc   1620
cagacgctcc ccagaagtat gcagtgtgct ggtgcccagg ggtggggcgg ggcccgggct   1680
gtccctagtg cccattactt gtgaggaggc agctttgcat ttgtgtgctg accttgggct   1740
ggcgtcctga gctcctttca ggtgctgttg tggcagctgt gtggcaggtc agggccggcc   1800
cccagtgcag ctttgcacat gaagtgggag gaggccctgc cgcttgtcag agccctgcag   1860
agtcttggtg ttctgtcggg ttcctgtgga ggggccgatg gcggggtgct gtggaagctg   1920
tcgaatctcg tccctctgtc cagttccccc gcttgtctcc ttgctccctc ctactcccgg   1980
gccacgatcc tatgccgggg ccactctcct gcacccggac cacgctccta cgcccaggcc   2040
actctcctac gcctggacca cattgcagtt atgctgactt cctctggctg ccagtgctcc   2100
tgtgtgtctc catacagctc acgctgcggg accacgctgt ggctgttgga ggcagctcct   2160
cctccaccca tagtgctctc tccctccagg cctaaggtgt gtgtgctggg ctcccgggag   2220
cagctgtgca tccatccaga ggtgaagaaa caagagagta accacatgca ggtgggctcc   2280
tggctcccgc tccggctcag ggttccgtga ggcgagtgct gctgggtatc cagagtccca   2340
ggctgtgctc ctgctgggct ggggttcgaa gttcactggg ggactgcagg cgagggcctg   2400
gtgggggtgg ggactggctc gggtcctttc ttggccatac tccagccgcg cactctgccc   2460
ttcctcccgc agatccactt gtgccgcaag aaggtggcaa gtcgctcctg tcatttctac   2520
aacaacgtgg aaggtacagg cagctcggtg ggaccaggct tgggttggag tgtgtgcagc   2580
ctctcagggc gtcagcctgg ttgtgcttgc cgggtggggc ggccagtgca gccgtgtacc   2640
tgggcactgt cttctgactc gggaccaccc gtgttagtct tctgtgtgga agagctcacc   2700
cagtggtctg agacagccag ccggccggac tgcctgtggc tggtgcctgg ggccttggat   2760
tttgggaagg ctccctccat ttccggacga gaagggctcc ctgcacctga ctactggtgc   2820
atacagcagc ggttttgctg aacacctgct ttgtcttcgg ggagcctgag gttttgttgc   2880
ttgcccagca gcgggtgctc ctgtgaccgg cccttgtacc atcttgggag ggtgtcctgg   2940
aagccgtgtc tggcctcccc cgaccttgcc gcatgtgtct ttgtcctgtg ctgacgttgc   3000
agagaaaaat tacagccccg agcgtgactc caggctgagt cctgtgggtc cgacacggga   3060
ggccttgggg cctcttcagg agacgggatg agtgagtgat gggagcagag ccagggcacc   3120
```

-continued

```
tcgccctgtg actgcaggtg gccacagcct gtgagggcca ggggtgcttc tccacccacg   3180
tggctgcccc tcgggtatgt caggggcttc tggggctctt cacgaggtct cagagacagt   3240
agcagggtgt gcccccgtcg gctgccctta cagtttctgt gacctgaggg tggcatctgt   3300
gcggttggca tggcctgagc ttctgtggga tcagagttcc ctttgtttcc tgcctcagtt   3360
ggggctcaag cctcaggtga cgtggccctg gagcacctgg aaggcgtcgg cggtcctgcg   3420
ggctgctgtc tgcactcgtg tttgctgagt gctcagtatg ccaggactga ggaccctgaa   3480
gctgctgtta tatttaggac ggttctcccc tggcagagac ggagccgggt ggtcccgcct   3540
gacccaccac caggcgtttc tgggccctgg agggacaggg tgggcggaac atgggcctgc   3600
agggagacct ccacttactg gaggctcgtg ctgtgttgct ggaggcatct tctgtgttgc   3660
ttcttgtttg ctgtgtcttt tgttctggtg gcaccaagga cctccagtca ccttgatgtg   3720
tggttgtcca ggcctttttg gtggtcctga gaaggggtct gaggggctct gcctctgccg   3780
ccaggttccc tgatggaagc tgcccactcg tcctggtggt gcccacagga cgtgactctg   3840
gcacaggagg gcagatgtgc tgttggagat tctcagcccg tcgtcgtcat ttccaaagtc   3900
ctcacccgca tttctgggac aggacaggag tgcctgctgg gtgtccccgg tcccatgcag   3960
cgggggtcct tgggatagtg tggaacgctg agtgtgggcc tgtccggcgg tggtcctgga   4020
caagggtagc acccctgtgg ccgccgggcc tggtgcctgg tgcctagcgg ggaggccgct   4080
gaccgcctcc tgtgctgctt ccatccgtgt caggcctctg ggtgttgggc cccatctgt    4140
ctccccccag gcctgtggga tcagtccaag aagactcaat ccagccccag cctgtccccc   4200
ttggcttggg ctctcactgc ccgacctggc aggaggttgc ctagcggtga acctttgcat   4260
cctgtctgcc ccctggacag gctctgaggg ggtgtctgca acacctgtgc cagcctgggc   4320
atcttttttt tttttttttt cttttgagac gaaatctcgc tctgccgccc aggctggagt   4380
gcagtggcgt gatctcagct cactgcaagc tccacctccc gggttcacgc cattctcctg   4440
cctcagcctc ccgagtagtt gggactacag gtgcccgcca ccatgcccgg ctaatttttt   4500
gtattttttt tctttttttt tttgnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnntttgag acggagtctc gctatgtcgc ccagggtgga gtgcagtggc cggatctcag   4680
ctcactgcaa gctccgcctc ccgggttttt acgccattct cctgcctcag cctcccgagt   4740
agccgggact acaggcgccc gccacctcgc ccggctagtt ttttgtattt tttagtagag   4800
acggggtttc actgtgttag ccaggatggt ctcgaactcc tgacctcgtg atccgcccgt   4860
ctcggcctcc caaagtgctg ggattacagg cttgagccac cgcgcccggc cttnnnnnnn   4920
nnnnnnnnnn nnnnnnnnnn nnnnnnnnnn nnnnnnnnnn nnnnnnnnnn nnnnnnnnnn   4980
nnnnnnnnnn nnnnnnnnnn nnnnnnnnnn nnnttttgta tattttttta gtagagatgg   5040
ggtttcaccg tgttagccag gatggtctcg atgatctgac cgcgtgatcc gcccacctcg   5100
gcctcccaaa gtgctgggat tgcaggcttg agccaccgtg cccggccagc ctgggcatct   5160
ttagagtggg ctgcagctcc tggaggggtc tgagaggaag gaaggcaggt attttgtgaa   5220
tgaagagaca gctagagagc tggcaccctt cctggcctgc gtcctgtgag gactctggtt   5280
ggggacagca agcttggggt tagcctgggg cagagcctct gggaggcccc tgccccttgt   5340
ccccccttccc cttgcagctc ctgtcctcgc cccgccctca gctctctgcc agggaaggtt   5400
tggcaagtgc cgctgtgcgg cagtgcgtgc tgattggctg gtcgttgcta tggtgccgct   5460
cagggatatg cttttcctcc cctgccttcc ctgctatccc tgggagcatc tggagttgag   5520
```

tcatcgctgg tgtgtgtgtg tgtgtgtgag tgtgtgtgtg agtgtgtgag tgtgtgtgtg 5580
cgtgtgtgtg tgtgtgtgtg agtgtgtgag tgtgtgtgtg tgagtgtgtg tgtgagtgtg 5640
tgtgtgtgtg agtgtgtgtg tgtgtgtgtg tgtgtgtgtg tgtgagtgtg tgtgtgagtg 5700
tgtgtgtgtg tgtgtgtgtg tgagtgtgtg tgtgtgtgtg tgtgtcagtg tgtgtgtgtg 5760
tgtgtgtgtg tgtgtgagtg tgtgtgtgtg tgtgtgtgtg tgagtgtgtg tgtgagtgtg 5820
tgtgtgagtg tgtgtgtgag tgtgtgtgag tgtgtgtgag tgtgtgtgtg agtgtgtgtg 5880
agagtgtgtg tgagagtgtg tgtgagtgtg tgtgtgtgag tgtgtgtgtg agtgtgtgtg 5940
tgagagtgtg tgtgtgagtg tgtgtgtgtg tgtgagagtg tgtgtgtgtg agtgtgtgtg 6000
tgtgagtgtg tgtgtgtgtg tttgtgcccg tgtgcgcctc tggcctctgc agctgagtcc 6060
tggctctcag gggcctggc acctcccggg gatgggcaca aagcagccac gatgcagccg 6120
ggagctgggg aaggccccat tgccccacac ggctgcccta agactctggg gtgcttcttg 6180
gaagaggtcc ttgcttctgt ctgtgtttaa gcagctccct aaggagttct tgtggttcca 6240
ggttgggggc ctgtgctgtg gaggcgaggg aggggcagga cccccaactc cctgaagcct 6300
tttctggcct ggtcctctca gccagcatag gcagggccct ttcccagggc tgccatgctg 6360
cagaggggag cgggccacta tgtagcctag gaaaacctga cgttccttcc gctggcagtt 6420
ctgggcctgt tgtggttggc agggaagctg agccacggtg ctcatcacag gggcacctcc 6480
aggatttttg ggagatgcct ccgtgggctg gggcgatacg ctgaggagct gttcttccct 6540
gccctgagga gggctgagtg tagccgtcac ccctgtcctg tcttgggctg tctcagggag 6600
gatgcataga accctcggaa ccctgctggc ccttgtctga tccaccctca acctcaggcc 6660
ttctaggggc acaggagggc tccgtcggga tcactgcggg tgggggcctc ccttggacac 6720
ctgagaccct caatgggtgc tttgtggcac gttcatgatt ggggcggggg gcacccagcc 6780
ctgcctgccg tgtaggagct gttctgtcct gggcgtccct ctgtggttgg gacccggagg 6840
gtgtgtgttt accccgcctc acacctgcag agaaaggcct ggagcaggag ttggccagcc 6900
ccatcctgga catcgaggac ttggtcaaga gcggaagcaa gcacaggtga gacccctcag 6960
tgaggccacg accactgtcc ttccatggcc cagctctcct gtgacctgtg gaggcccaga 7020
tatgtttctt ccctttttctt tgttcctttc taagtcgtga aactaaccac cgtttagtgt 7080
gagaaagttg aagcagctct gaggaacgta gagtaaaaag cgaaaccgcc tccctcttcc 7140
ctggccgtca gccaccccag gagccaccgt ggagcgggga cagagccctg caggctcgtg 7200
tctgtgtgga agcacgcacg gttttgtctg cacagactgt tctgcagttt gccgttttca 7260
ctcagcgttg tgggtagctt cgcatgctgg tgctggtcgt ccggcttcgt tcttctgagg 7320
acagcaaata tgtcctttgt ccacctcttt tatagtttca gagattcaag ttataataaa 7380
gcttttctta tattgagggg gagagctcct gcccctcttt tttttttag acagagtctc 7440
gctctgctgt ccaggctgga gtgcagcgtc gtgatcttgg ctcactgcag tctcaacctc 7500
ccaggctcaa gtgattctct cagctcagcc tcccaagtag ctgggactgc aggcatgcac 7560
caccacgcct ggttaatttt tgtatttttt gtacggacaa ggtctcactc tgttgctcag 7620
tccagtcttg aactcctgag ctcaagagtt ccacccgcct cggcctccca aagttctggg 7680
attccaggcg tgagcaccac gcccgaccca gctctgcttt gttttagtgg ttctgtttgt 7740
gtttgtttct gatgacctct atccaggaat agggttggtt tttcttttcc atggagtttt 7800
taaagagatg atgatttaca tggtttaaaa ctcatgtgga ctccccgtcc atcccagaca 7860

-continued

```
gcggcttccc acctggaccc catgctcagg attagggctc cttccgggtc agaagatgtg   7920
gcggccccgg cctcgggtca ccgtcccctg cacggggtgc tcacagcatc ttcccctctc   7980
ctcgttccca gggtgtgccc ttactacctg tcccggaacc tgaagcagca agccgacatc   8040
gtcttcatgc cgtacaatta cttgttggat gccaaggtgg gggctcagtc tgcgtcgctg   8100
acaactcctg atgtccaggg gggttcctgg gcttgggaaa ggccgtccga gcctttgctg   8160
ctgcagggac ttagagcagc aggcctgggt gggagagctc acctgtcact gggcaggggc   8220
tcaacctggc cagacacact tgtgagcacc cccaggccct gggtcagttg ttctgagcaa   8280
tctgggagtg ggcaggctgg tgggagtgag gagaggcctc caggctgtgg tccacaggcc   8340
agcgcccact cttgatcctg acagctcagg ttctctcctt cacgtccgat cacaggaagc   8400
aaagcactga gaacacggga agcccactca ctcccctcct cccagcccca cactcactcc   8460
cccccatgcc cggccccaca ctcacttccc tcctcgtagc ctgtactcac ccacatgctg   8520
ttgtgcccca cactttttat ttagtgcagg tggcatctcg ccgcgggtca gtgacttgtg   8580
ttcacgtggc gatgacgtgg tgacgcttcc agatccctcc attggtttgc tcattctcag   8640
ggtgtatatt tatcaagagc ccatcgtgct gggggctgtt ctaggcatag caagactggc   8700
ttcattcatg tggagctttg attctagcgg tggggacagg tagacagcag aagagtaagc   8760
ccgtgagccg atgagactga agagaagtag agcagagcga ggaggtggag acagagccga   8820
gtgggcaggg cccaagtgcg atgtcggcag gagatgggga atgctgatgt gtctgagggg   8880
agcccgagct ggtgcagcag agcaagggag gaggcggggg gccgactcct gggcagcgat   8940
tgtagaaccc cacggagagc tggtgaggtt tgccgtggtt gcaggtgact cggtgctttg   9000
agccgtggct gcccctggga accacctgga gagcttctaa cccaaccagg cccttccctg   9060
ggacaattct gtcacagctg gtaagctaag tccaacactt tcacggaaac acagaagatc   9120
taaaacggca cgatgaccgt gaagaacaga gctggaggac tcacctcact ggtttcaaga   9180
ctcctctaaa actgcaggag tggaggtgga gacggctcag ctcaggcaca agcctgcagg   9240
ccatggagaa ggcagcaagc tccagctgac ccacacgctt gcggtcattg ttttttttt   9300
ttagttggaa tctccctctg tcaccccagt tggactgcag tggcaccatc tcggctcact   9360
gcagccccca cctcctgggt tcaagcgatt ctcccacatc agcctcccga gtcactggga   9420
ttacaggcgt gcgccaccac gccctgcccg tgatgattgt ttttttttt tnnnnnnnnn   9480
nnnnnnnnnn nnnnnnnnnn nnnnnnnnnn nnnnnnnnnn nnnnnnnnnn nnnnnnnnnn   9540
nnnnnnnnnn nnnnnnnnnn nnnnnnnnnn nttttgagac agagtctcgc tgtgtcgccc   9600
agggtggagt gcagtggccg gatctcagct cactgcaagc tctgcctccc gggtttttac   9660
gccattctcc tgcctcagcc tcccgagtgg ccgggactac aggcacccac cacctcgccc   9720
ggctagtttt ttgtattttt tagtagagac ggggtttcac cgtgttagcc aggatggtct   9780
cgaactcctg acctcgtgat ccgcccgtct cggcctccca aagtgctggg attacaggct   9840
tgagccaccg cgcccggccg atgattgttt tttgacaaat gcgccaatgt aattgagaga   9900
ggaaatgaag gttgattttt ggttttctga aaaagtggtg ctaagaacag ctggatatct   9960
gtttggaaaa cagcgaatct taactcttgc tttactctat ataaacctaa atgtaaaagc  10020
taaactaaag gttatagaaa gaaacatggg ggggtctttg caactctggg gtaggcagag  10080
attccttagt gtggatacat aaggcactag ccgtgaagaa aaacataaaa tttggatttc  10140
accaaaattt aaagcttcaa cacttgagaa gacttgagaa aattaaagag cagttatgga  10200
aagggagaaa atgcttctgt ctttcagagg acttaaaaaa catttttcag ccctcctcat  10260
```

attttaaagg acctttgacc agagtatgta aaattctctc ataactaagc aaaaaaccca 10320
tttaaccagt gggaaaggat ctgcacagac gtttcaccaa gatggacgga gtggccagtt 10380
gggcacatgg aaggacgccc agcatctcca gtcacaggag aaggcagatt aaagccacgg 10440
ggagccggca ctacggtccc gctagcatgc tgaaattcag aagcctgagt gtggcacgag 10500
gaggtggaac agctggatct catccattgc tcctaagctg tgaagctgtg tagccactcc 10560
acaaacacgt gtggcgaaca gccgaaccgg gagaagggaa gacgtgttca aagatttgtg 10620
tgtggccagg ctcagtggct cacacctgta atcccagaac tttaggggcc aaggctcagg 10680
gatcgcttac gcccaggagt ctgagaccag cctgggcaac atagggagac cccatctcaa 10740
aaaaaaagaa aaaagaaaaa aaaagactta aatgtgcaag tttaccagag ctttgtttaa 10800
gttgccagaa ctgggaagcc gcccacgtga gtccatccac tggtgaacgg acaaaccgtg 10860
gttcgcaaac cccaacagca gccgcgggca tgggctgtgg tcacacagca gcagggagcc 10920
agtgagtctc agatgtgcta acccagaggc caactgagga ggacctactg tttttttgttt 10980 tttgattttt gttttgagac agagtcttgc tctgtggtgc aggctggagt gcagtggtgt 11040
ggtctcggct cactgcagcc tctgcctctc gggttcaagc agttctcctg cctcagcctt 11100
ccgagtatct gggactacag gcacccgcca ccacacccgg ctaatttttg tatttttagt 11160
agagacggca tttcgccatg ttggccaggc tggtttcaaa ctcctgacct tgtgatccac 11220
tcaccttggc ctcccaaagt gctgggatta caggcgtgag ccaccgcacc cagctggacc 11280
tactgtttta ttccgtttat atgacgctgt attaatagaa gaggcagggg tagagctggt 11340
ggttatgtgg tgcacttaac tgccagaact cagtaccctt aaaatgggca tcttaatgtg 11400
tgaaaactta aaagtaccaa agctggaccc caccccagct tgctcccatg acactctgtg 11460
gtgggacctg ggagttgggg tttttttttt ttttttttcag atggagtctc actctgttgc 11520
ccaggctgga gtgcagtggt gcaatcttgg ctcactgcaa cctctgcctc ccagattaaa 11580
gcgattctcc tgcctcagcc ttctgagtag ctggggttac aggcgcacac caccacgccc 11640
ggctaatttt tgtgttttta gtagagatgg ggtttcacca tgttggtcag gctggtctcg 11700
aactcctgac ctcatgatcc acccgcctcg gcctcccaca gtgctgggat tacaggtggg 11760
agccaccgcg cccggcctgg agttgggttt gtaaatctcc ctgagtgggg ccggggcaga 11820
gaactgctgg gtctgggtct tcctggctcc tgtggtctgt ggctggctga ctgcggtggc 11880
cgggggctcc caggacgtcg tggccgtccg tcttgctgag cgtggcgcgt gcctttccat 11940
gctgtgcgtg agcgtctccc ggcgtggcga gctgctgctt cgggtggggc ggtgttgcca 12000
ggttgccatc cagatctggc ctctcctctc cacgtcgccg gcggtgtttg tcatcggcac 12060
ttgcgatgtt cgatgccggc cacatgtgcc ttggtttccc tccttcctgc ccctgtgagc 12120
tccagcaccg tgtcccttct cttcctcctg tagagccgca gagcacacag cattgacctg 12180
aaggggacgg tcgtgatctt tgacgaagct cacaatgtgg tgagtctcca ctgcctccta 12240
aacgcctcct gtttcttcaa gagcagcgca aacctttctg gaggggctct ggccaaaccc 12300
ttgcagcctt cggtgcccag gactgaggac tgagcacccc aggagcttct gcaccccttc 12360
ccactctgat ccgatgcctc tgctggggct ggagactggc cagctgggcc agggacctgc 12420
ccctcaggcg cagggccccc acaggccgct ccccaggcct tccctctagc cagctagggg 12480
tcagcctggg ccaggggtgt ctcctctgcc ctcggcttct gtcaccaggg cagcagcagg 12540
cgtgtggtct cgcctgcagt gtctctgccc ttccggccac atggcctgag gctgaggcag 12600

-continued aattgcttga accctggagg tggaggctgc ggtgagccag gatcacaccg ctgcactcca 12660
gcctgggtga cagagcggga ttctgtgtca aaaaaaaaaa aaatgttgac tgggcgcagt 12720
aggtcatgcc tataatccca gcactttggg aggccgaggc gggcggatca tgaagtcaag 12780
agatcaagac tatcctggcc aacatagtga aaccccattt ctactaaaaa tacaaaaata 12840
ttagctgggc gtggtggtgg gtgcctatag tcccagctac tcaggaggct gaggcaggag 12900
aattgctcga acccgggagg tggaggttgt agtgagccaa gatcacacta ttgcactcta 12960
gcctggtgac agcgagactc cgtctcaaaa aaaaaaaaaa aaaaaaaatt ggcaactcca 13020
ttgaaataat tgtttgtttg tgttttgaga cagggtctca ttctgtcgtc caggctggag 13080
ttcagtggtg tgatcttggt ccactgcaac ctccacctcc tgggctcaag ccatcctcct 13140
acttcatcct cccaagtaac caggactaca ggtgcacacc accacgcctg gctaattttt 13200
gtatttttttg tagagatggg gttttgcatc attgcccagg ctggttttga actcctgagc 13260
tcaagtgatc tgtccacctc agcctcccaa agtgctggga tcacaggtgt gagccgctgc 13320
gcctggcctg aaataatcgt ttctcaatat tggtgtgggc cagacagtcg tgtttggacc 13380
tgcttgtggc ctggccttag agaccccagg gcgtggcttt ggggacttgg ctgtcagcct 13440
cctgtgcctt ctgcacccaa ccccattcct gctttctgga acccccgatc ctatcctgct 13500
ctgtggtgat ccgggtgatt tgggctcccg atcctatcct gctctgtggt gatccgtgtg 13560
attcgggctc ctgatcctat cctgctcggt ggtgatcccg gtgattcggg cccccgatcc 13620
tatcctgctc tgtggtgatc cgggtgattc gggctcctga tcctatcccg ctctgtggtg 13680
atctgggtga ttcaggctcc cgatcctgtc ctgctctgtg gtgatccggg tgattcaggc 13740
tcctgatcct atcctgctct gtggtgatcc cggtgattcg ggcccccaat cctatcctgc 13800
tctgtggtga tcccggtgat tccggctccc gatcctgtcc tgctgtgtgg tgatcccggt 13860
gattcgggcc cccaatccta tcccgctctg tggtggtccg ggtgatttgg gctcctgatc 13920
ctgtcctgct ctgtggtgat ccgtgtgatt caggctcctg atcctgtcct gctcggtggt 13980
gatcccagtg attcgggccc ccgatcctat cctgctctgt ggtgatccgt gtgattcggg 14040
ctcctgatcc tatcctgctc tgtggcgatc ccggtgattt gggctcccga tcctatcctg 14100
ctctgtggtg atctgggtgt gctcggactc caggagaaga tgtgtgaaga atcagcgtcc 14160
tttgacctga ccccccatga cctggcttca ggactggacg tcatagacca ggtgctggag 14220
gagcagacca agactgtgca gctgggcgag ccccacccgg agttcagcac agactccccc 14280
agcccaggtg cgttcatagc caggctgctc ggtcctgagg cctgcgctgc tgcagggggc 14340
agcctgccct gtggctgtgt gtggtcggcc tgggcactgt ctgttcaggc tggcactgca 14400
gggcacccac ttctctcaga ggcttctcgg gtgtgaattg tttggggtcc tgtaggctgt 14460
ggaagggctg gtatcgttca gtagttctgg tattttccga agacctatgt cttctcccag 14520
ccagtgtcaa cttggcctct actgtgtaaa attagagaac tatactttgt gaagctgaga 14580
tgggagcatc gcttgaggcc aggagttcga gaccagcctg ggcaacatag cgaaacctcg 14640
cctctgccaa aaaattagcc aggtgtggtg gtatggtcct gtggtcctgt ggtcagagct 14700
tttctggagg ctgaagtggg aggagctctt gagcccggga ggcagagctt gccccagatg 14760
gctccactgt actccagcct gggtgacaga gtgaggctgt ctccaaaaaa aaaaaaaaaa 14820
aaagtaaaac taactatatt cactgtaagg gcattttgcg tgtttaaatg acccacacat 14880
cgggcctgca tcacttgctg tgcccgtaga ttccttccca gtgttcgtcc agaggcgtat 14940
ttccacacag cgctagtcac ggcgtacgtg gaaaacgcgg aaaccccccat ggatgtggtc 15000

```
ggttggtctg tactgtctgt gttttcttcc tttctttttt tttttgagat ggagttccac  15060
tcttgttgcc caggctggag tgcaatggtg cgatcttggc tcaccgcaac ttcctcctcc  15120
caggttcaag tgattctcct gcttcagcct cccaagtacc tgggactaca ggcgcgcgcc  15180
accacgccca gctaattttg tatttttagc agagtcaggg tttctccatg ttggccaggc  15240
tggtctcaaa ctccaggtga tccgcccacc tcggcctcct gaagtgctgg gatccaggcg  15300
tgagccgccg cgcccggcct gtgtcgtgtt ttctgcgtgg cctctgtaaa cagctgacta  15360
ggagtctgtg agcatcttca ttggttccgc tgtgacttgc gtgtgagcat ctccagcatc  15420
agctttcctc attttccttt aaaatcgcac atgtggatgg acaccatggg gaccctggac  15480
cctgggcagc ctcgtcctca cctttctcac cagggtggct gcttgggaga gagtgagttt  15540
gcgaacttgg catttgttct ggctgtagga tccgtttata tatatacata tatttaagtg  15600
acagggtctg actctgttgc ccaggctgga atgcggtggc gtgatcttag ctccctgtag  15660
cctcagcctc ctgggctcgt ggggtcttcc cgtctcagcc tcttaaagca ccgggaccgc  15720
aggcggtcgc cactgccatc ggatctcaag gctgccacgc agggcgctgc agtaggggaa  15780
ggggttcctg ggactttgaa cgctccacct ccctcttctc cacagtcccc caaccccacc  15840
tctaactggg agtggatggc cacctctttc catcctttgc ctggcgcagg gtggggagaa  15900
tgacaggtct ccttcccgca tctcggcagc tgccctttcg tcggttatat gacgtgggag  15960
agaccccggc cacccccagg gctgtgtgac gtgggagaga ccccggccac ccccagggct  16020
gtgaacaccg ccacaggggc cttctccact cttcagtttt gttagttacg tgacgtgcag  16080
ggcttttcgt tgtaactagt gggggacgtg tggtgagggg ggcttctgcc gtctcattca  16140
ggaccggaac ttcagttttc atcgctattt gtcctcctac gcctttggag atggggtctc  16200
gctctgttac ccaggctgga gagcagtggt gccatcaggg ctcacggcag cctcctcctc  16260
ctgcagcctc cgcctcttgg gctcacacaa tcctcctgcc tcggcctccc aaactcctgg  16320
gacgactaca gacgtgcgcc accgtgcttg gcagggttca ttcttttcct cacactttat  16380
ttattggaga gcccggtaga gcgcccggtt tgcacgatct ggttgttgag acgttgagag  16440
gaaccctgcg gagtctgaat ctgggtatgg gaggggcagt cacacgagtt ccccggtgtc  16500
ctcgtctcct ccgcacttag gtgcccttag gtggcttgag gaccccagtt agactggggc  16560
cacccctttgc ctggctccag gcgggatgtc ctttcttttt tttttttttt ttnnnnnnnn  16620
nnnnnnnnnn nnnnnnnnnn nnnnnnnnnn nnnnnnnnnn nnnnnnnnnn nnnnnnnnnn  16680
nnnnnnnnnn nnnnnnnnnn nnnnnnnnnn nnnnnnnnnn nnnnnnnnnn nnnnnnnnnn  16740
nnnnnnnnnn nnnnnnnnnn nnnnnnnnnn nnnnnnnnnn nnnnnnnnnn nnnnnnnnnn  16800
nnnnnnnnnn nnnnnnnnnn nnnnnnnnnn nnnnnnnnnn nnnnnnnnnn nnnnnnnnnn  16860
nnnnnnnnnn nnnnnnnnnn nnnnnnnnnn nnnnnnnnnn nnnnnnnnnn nnnnnnnnnn  16920
nnnnnnnnnn nnnnnnnnnn nnnnnnnnnn nnnnnnnnnn nnnnnnnnnn nnnnnnnnnn  16980
nnnnnnnnnn nnnnnnnnnn nnnnnnnnnn nnnnnnnnnn nnnnnnnnnn nnnnnnnnnn  17040
nnnnnnnnnc tgggactaca ggcgcccgcc acctcgcccg gctagttttt tgtatttttt  17100
agtagagacg gggtttcacc gtgtcagcca ggatggtctc gatctcctga cctcgtgatc  17160
cgcccgcctc ggcctcccaa agtgctggga ttacaggctt gagccaccgc gcccggccgg  17220
gatgtccttt ctatcaggag gctcacagta tctgctttcc agtttcttct gatgttaatg  17280
ttgttgctgc tgaacacctg actctgttga ttattggggg attgcaagat ggtagtgtcc  17340
```

caattctgtc gcttagtcag ttagcaggaa taatctagca ccatgctctg catcgcatca 17400
gccgtgtggt gatcccattc acacaggaaa ggcgggataa atgctggctg tgggccgggt 17460
gtgctgtccc gcatctgtaa tcccagcact ttgggaggcc agggcggtcg gatcacgagg 17520
tcagagattg agaccatcct ggccaacatg gtgaaacccc gtctctacta aaaatacaaa 17580
aaaaaaccca aaacatgagt gggctgtggt ggcgcgtgct tgtaatccca gctaccgggg 17640
agactgaggc aggagaatca cttgaacccg gggggcggag gttgcagaga gctgagatcg 17700
cgccactgca ctccagcctc acaacaaagc gagactctgt ctcagtaatc aatcagtcaa 17760
tcaatcagac gtcatcagtg aatgtacgtg agcgtgtagg gattggtcct gctccgcgcg 17820
ccaccctcaa tctcacttct gacctccgtt ctccacctcg aggtgttttc atgtgggccc 17880
gtgtgtcctg accccagcag ttgtggcctc tttgctgtct gggagtcagg atttttcaca 17940
ctcatgtcct gctccagacc tggaatcagc caagtctcca agaagctctg gtttcttttc 18000
ctgcaaggtg gtatttcagg acccacgatg cggcaacagg ctggtcatgg ttactgggtt 18060
ggtcattgtt actgggtgtt tttgtggaga tacatccata cgcacagatg tgttcacaaa 18120
tgttaactct gaaggtaaac cacccggctg ggcacaaggg ctcaccggta atcccagcac 18180
tttgggagac cgagacagtt ggatgacctg aggtcgggag tttaagacca gcctgggcaa 18240
catggtgaaa ccccatctct actaaaaacg caaaaattag ccaggtgtgg tggcacacgc 18300
cggtagtccc agctagttgg gagacagaca tgctggaacc tgggacacgg aggttgcaga 18360
gagcagagat agtgccgctg caccccagcc tgggtgatag ggtgacaccc tgtctccaaa 18420
ataaatagat aaataaaggg aaaacgcctc ctcttggtgt ctccagtttg gactggctgg 18480
catgggttcc ggtagcctct tcccccatgg tggcgtcctt ttttccatgc cgggaatcct 18540
ggttctcaag ggcggggttg ttggtctgag tgtgacacag actgtgcctt tgctgccttt 18600
ctcttgccca gggctgaaca tggagctgga agacattgca aagctgaaga gtaagtgctg 18660
ccctccccac cttcttgcgg ctgggtgggg cctccccctg atgcctcctc aacccgacct 18720
gcagtgatcc tgctccgcct ggagggggcc atcgatgcca ttgagctgcc tggagacgac 18780
agcggtgtca ccaagccagg gaggtgagag gcggggagcc agctgcttca ctggaggccc 18840
agcctggagc tagagatagg ccatggtgca gtcctaggct gtcccaccag tgaggcctgt 18900
tttcaggccc gttttccctt tttgagacct ggtaggagca cctggtttgc atgatctggt 18960
tgttgagacg ttgagaggaa gagcacacgc atccacggaa cagcacacgc atccacggaa 19020
cagcacacgc atccacggaa cagcacacac tcccacggaa cagcacacgc atccacggaa 19080
cagcacccac tcccacggaa cagcacacac acccacggaa cagcacatgc ttccacggaa 19140
cagcacatgc ttccacggaa cagcacaccc ccacggaacg gcacccacgg aacagcacgc 19200
acgcccccac agaacagcac acacccccac agaacagcac ccacgccccc acggaacagc 19260
acacacaccc acggaacagc acacacgccc ccacagaaca gcacacaccc ccacggaaca 19320
gcacacgcac ccatggaaca gcacccacgg aacagcacac actcccacgg aacagcacac 19380
gcccccacgg aacagcacac acacccacgg aacagcacac actcccacgg aacagtacac 19440
gcatccacgg aacagcacac acgcccacgg aacagcacac gcatccacgg aacagcacac 19500
actcccatgg aacagcacac gcatccacag aacagcacac acactcccac ggaacagcac 19560
acaacagcac acactcccac ggaacagcac acgcccccac ggaacagcac acacacccac 19620
ggaacagcac acactcccac ggaacagcac acgcccccac ggaacagcac acacacccac 19680
ggaacagcac acacgccccc acagaacagc acacaccccc acggaacagc acacgcaccc 19740

-continued atggaacagc acccacggaa cagcacacac tcccacggaa cagcacacgc acccacggaa 19800
cagcacacac annnnnnnnn nnnnnnnnnn nnnnnnnnnn nnnnnnnnnn nnnnnnnnnn 19860
nnnnnnnnnn nnnnnnnnnn nnnnnnnnnn nnnnnnnnnn nnnnnnnnnn ngcacccacg 19920
gaacagcacg cacgccccca cagaacagca cacaccccca cagaacagca cccacgcccc 19980
cacggaacag cacacacacc cacggaacag cacacacgcc cccacagaac agcacacacc 20040
cccacggaac agcacacgca cccatggaac agcacccacg gaacagcaca cactcccacg 20100
gaacagcaca cgcccccacg gaacagcaca cactcccacg gaacagcaca cgcccccacg 20160
gaacagcaca cacacccacg gaacagcaca cactcccacg gaacagtaca cgcatccacg 20220
gaacagcaca cacgcccacg gaacagcaca cgcatccacg gaacagcaca cactcccatg 20280
gaacagcaca cgcatccaca gaacagcaca cacactccca cggaacagca cacactccca 20340
tggaacagca cacacacacc cacggaacag cacacacgcc cacggaacag cacacactcc 20400
cacggaacag cacacacatc cacggaacag cacccacgga acagcaccca cgcccgcatg 20460
gaacagcacc cacggaacaa cacacacccc cacggaacag cacacacccc cacggaacaa 20520
cacacactcc cacggaacaa cacacacccc cacggaacaa cacacacccc cacggaacag 20580
cacacacacc cacggaacaa cacacactcc cacggaacaa cacacacccc cacggaacaa 20640
cacacacccc cacggaacag cacacacacc ccccacggaac aacacacacc cccacggaac 20700
agcacacact cccatggaac agcacacaca cccacggaac agcacacaca cacccacgga 20760
acagcacaca cacgcccacg gaacagcaca cacccccacg gaacagcaca cacccccacg 20820
gaacagcaca cacccccacg gaacagcaca cacacgccca cggaacagca cacacgccca 20880
tgcggggccg ctgggtttcc tgcagtttgt cctcctccag gcctttccct ggacctcctc 20940
aggtgcctgt tagaatgaga ccttcttgtt aggacgatga gtgtcccagc caccacctct 21000
tttggactcc gggaggcccg gaacattctg aaggctccgt gggtctcctg tcttctccgc 21060
ggccagggca gcagcatttg ttgtctgtcc tgcaggcaga tgagggtcag gcctggggcc 21120
cgtgtggggc tccactgagt gcacagccgc caaggcgagc gcgttctgcc tgagcgctga 21180
ccttgtggcg actcccagtt gcttccaggt ggagccagtg tcctcagcgt aatgctcaag 21240
gctctggcgt ggctcctcgg ccacctgcac ccccaggggc ccctcctgta gcttctgctg 21300
ccgccatcac tgtcactctc ccaaggcttt ggggactctg cccagagccg ctgcctccca 21360
gaagcccctg acgacccccc ggcgacccca tccctccctc tgatgacggc ctctgccccg 21420
aggcggcttt tccttggtgc tgttcttgtg ccggccaggc ctccacttcc catctggagg 21480
ctcctgaggg cggaggcctc tcacccccaa tgccggcgtc ccctggaggg ctcagtttgt 21540
ttccgaggga aggaaacttc cacagttgct gccttcagtt cccaaagctg cagcctgatc 21600
ccccgtccag gctcgagcct gccttcttct cctcgcagct acatctttga gctgtttgct 21660
gaagcccgga tcacgtttca gaccaagggc tgcatcctgg actcgctgga ccagatcatc 21720
cagcacctgg ccggacgtga gtgccggggc ggggtccttg gtgtgggcag acgtggcgta 21780
gggggtgcag caggcctcca tcctggcagt cagggctcgc ctggccatca cctggccgtc 21840
agcaggaaca ggctcacaga acctcacctg gtcggggcgt ggaggcgtta gtgccggttg 21900
cccactgccg tagagcctgt cccagttctg cagctggcgg cttcgtcctg cagactcatc 21960
ccattattcc ccttttaagg aagagcagcc caaggccctg gctgggttgt ggggcctcag 22020
gcttctccac acaccctgag ttctgcttct cagagctgtg ggtccagag gctttgccca 22080

-continued gaggcagtgt cgtcatgggc tgctctggtt tgagatgccg gcccgccggg gcctctgctg 22140
tgctcccagg tgctggggag ggcggctctt gctgcttcaa accttaggtg accatagagc 22200
ctcttttcaa gttccaccgg ccccccttgga gacgctgtcc ctgcctggct gctctcctgg 22260
ctgctgggaa gggcaggcga gctgcccgcc ctgagtggac actgcgctcc accctgggcc 22320
ccccgttggg caggagatgg agcttggcag tcgggctgag ctggcttatg gctggaaggg 22380
cgggggctgg ggtcggggcc tcccctgcct gcagtgcggg tgtcagcgcc cggcatgcta 22440
cctccccagg tgctggagtg ttcaccaaca cggccggact gcagaagctg gcggacatca 22500
tccaggtggg gcctgctcct ctggcgtctc cttccctgat ggaagccggg cgggtgcctt 22560
ctcctgctgt attagttact gactctagac gtgggggtgg gagaacggcc cccacaccac 22620
ctgtttccga ctggcaaacg cttggctcct ttcctgtgac ccaaacccac actgggcctc 22680
ccgcggggat gggggaggac gaggtctggt ggcccgtgcc cagggtgacg ctggtggggg 22740
aggacgtgaa ggggagtggg ggccagggag ccgctcctgc cctgtccggg ccctcaggcc 22800
ggggggaccc actcctggca gccccagcta cacgcagatg aagagctctg gacacacgta 22860
gcttcctgaa cagcttctcc agggacagac aaacggggac cctgcaggtt gccggcgggg 22920
gtgtccctgc gagcccatga tgggggatgc ggccccggcc cccttcttgg ccccgtcctg 22980
ccctgtgatg cccgtcccct cccatgtgag gttgctcctg gctctgtgcc tgtggcagca 23040
cctgctttcc ctgaggcaga cggcttgtg cggtttgtgg agggcaagcc ccatttttgg 23100
gtgctctggg cacacacttg cctctcctgg acctcggtgc attttttaga agcagaccca 23160
caagtccctg actgggaggc catcagtcct tggggaaacc gaggcacagg tggctgtgtg 23220
gagccatgtg aggctgcctc tgtgctgccc acactgaacc tcctggccac acgaggtcat 23280
ggcagggtta ggtggggctg cccagctctg tgacaacttc gtgagtgtcc gcctggggtg 23340
gggggtgctt gagctggggg aggccgcaga agaaccctgg aatgtaccgc cggcctgtgc 23400
atgcagtgcg gtgctctgtg catgctactg ggcgtggagc tgcaggcccc aggacgacca 23460
ggcactgcct tcttcataga cgtggctctg agcaggggcg agacctgggc agggaccagg 23520
tggggtgggc acagcaggtg gtagggccca ggctcagccc tacctccacc gtggccttct 23580
ctgcggccag tgatgccaca gccagtgtct tctctgtgtg gcagctgggg ctggaaagac 23640
ggcactgcta tgtctcccag ctcctcccca aaagcacggt gggcatccca gggccagacc 23700
cctctctctg tggctcctgc ctgccaaggg ctgctttgcc gtcccgcctg gagcgtggtt 23760
ggctcttcaa gcaggaggcc gtgcacctgc caggcggacc tgcttccatg tcctgacggg 23820
tcactcaaag cacctccagc acatggccat cgaggcagcc ctgcagccca gggcctggag 23880
ggcaggtgtg agctggcccg ggcctgcccc tccctggaat gtggcttccc aggctccagt 23940
atggagcagt gtccacactc tggaaccaaa tcttgttcac cccattggtt tggaatttcc 24000
tttggctgct gctctaagta gccactggga gatgactcag ctcctcccaa ccctggggac 24060
tgcacaccgt gttcaccctc ggctgctcct gagtccctgc aggtgtgggc actgctcata 24120
gggctgctgc tgggctggac ttgcagccct gaggcacagg tgaccctggg gacagagtgg 24180
ggctagagtg gggctagtgg ccccaggaag aggatgtggg atgcacggtt cagttggagg 24240
caagtccggg cagggccagg ctgtgtgctg gggaggtaga gcttagctgg aggcaaactc 24300
tgggcagtgc tggcccgtgc tgggcagcca gtcaccgctg ggcccctgtg agactagtgg 24360
gtcccctttc ttctctgcct gagctgccct ggggctgaag cacggggcgg tttgtagtgg 24420
tgttttttg agacagggtc tcgctctgtc accccagcgg gagtgcaggg ccttgtcacc 24480

```
agctcactgc agcctcagcc tcctgggccc aggccatcct cttgcctcag ccacctgagt  24540
agctgggaac acaggcgtgc accaccacgc ccggctaatt ttaaaagctt ttttgtggag  24600
atggggtctt ggcgtgcacc accacgctcg gctaattttt taaattttta tgtggagatg  24660
ggtcttgcca tgttgcccag gctggtctca aagtcctggg ctccggcagt ctgcccacct  24720
tggcctccca cagtgctggg attacaggta agagcttcca ggcctgccca tcagagggct  24780
ggctttttga gggaagctgt ttcctgaggc agcctcagcc cctgctcatg gcagcccctg  24840
gtgtcatggt gaatttgttc tgttgtttcc atccctgtgg gccaaatgct ttggtaaaac  24900
gcaaggcctt gtatttagct gtcttgacag tgaaaatggc tgggaaggaa ggaaggaagg  24960
aatggaagga agtttctctc tcccgtgcat acccaggcac gtgcacacgt gcgcagtcca  25020
cgcacgctgc cggtctctgt cccagccgcg gtgccggccc ccgtgttctc cagttcagct  25080
tctccgcatt tctgtgaacg attccggctt cttgatgttc ccagcagaac tccctcaagc  25140
cttcggcttc tccagggctc tgacggcggc tgggctgacg tggccgctct gcggagcctg  25200
ttggggcttc acgttcctgt tctggccatt tccggctctt tttccgggaa gggtcatcac  25260
gcgctctttt cctagtgcag gcatcgtccc tttcccgttg atttgcaggg ttctctgtaa  25320
gatctgagga acacgtgcca acatattctt tcctggtctc gtgctggtca tttttttccat  25380
tttcacgaca ggtttggtga acagatgttt ccttgtcatc agacttttgt cttgagcttg  25440
tatcccccga ccaagatgct aaactgggtc ttgtgtgttc tccaaactgc actgtagggt  25500
ggcggagctt tgtgtcgggg cctccgcacc ttccggcgtc acctgtgggg gtgtgaaagg  25560
cagactctac ctggattttt cccagcacgc cacaccggtg gttccgtctg ctgaccgagt  25620
ggctcggctt ctcccaactc cgctgggcac ctgccacact gttttcctca cggttttgtt  25680
cgtggtggtt ttgtcgtaag tcctggtgtc ggccagaacc aatttctgtt tttgtttgtt  25740
tttgagatgg agtttcgctc ttgtcgccca gggtggagtg cagtggtacg atcttggctc  25800
actgtaacct ccgcctcctg ggttcaaatg attctcctgc ctcagcctcc tgagtagctg  25860
ggattacagg tgcttgccac cacgcccagc taattttcat atttttagta gagacggggt  25920
tttgccgtgt gggccaggct ggtctcgaac ccctgacctc aggtgatcct ctcgcctcag  25980
cctcccagag tgctgggatt acaggtgtga gccgccgcgc ccggcctctt gttcttctta  26040
aacctgccct gatgttttct ccatgatgca tgttggagtc aacctgtctg cttcctttaa  26100
aaatcttgct gtgattttga ctggaatgtg tggaattcct gtgtttttga gtcagtgtct  26160
ctctgttgcc cagtctggag tgcagtggga ccatcacagc tcactgcagc ctcaacctcc  26220
tgggctcagg ggatcctctc agcccagcct cccaagtagc tgggaccacg gcacgtgcca  26280
ccacgcccgg ctagttttca tattttttg gtggagaccc cagggttgca ccatgttgcc  26340
caggctggtc tcgaactcct gggttcgggc agttcgcccc tctcggcctc tcagagtgct  26400
gggattacag gcgtgagcca ctgcactagg ccatgttgaa tttctagatt aatttgggac  26460
ccttaggggc acagagagga gggctgggcc agctggtggg aggagaggcc tctcgggctg  26520
ccgcatttcc agtgcacgga gatggcctgc gtagggggaa cagagctcac tgggggtccc  26580
tccagggagg agaaagggtc aggcaggtgc cagctcctgt ccatcagcct ggggctgcat  26640
gatggcaggg gctggtgaac cgatgacctc tgggtgtcct gtgaccttcc gtgtgtgggg  26700
ctgatgccgc agaagatcag gtggcctcca gggctccggg ctctggcctc aggctcctca  26760
cgggactgca cctcctctct ttcagattgt gtttagtgtg gacccctccg agggcagccg  26820
```

```
tggttccccg gcagggctgg gacccttaca gtcctataag gtaggggcca cctccaggag  26880
gcaggtgggg ctgggggtcc tgcagtcctg aaaggtaagc ggctgccccc aggacacggg  26940
cggggtctcc acacttctgg tcctgtcccc tccaggtgca cgtccatcct gatgctggtc  27000
accggaggac ggctcagcgg tctgatgcct ggagcaccac tgcagccaga aagcgaggta  27060
cagacctggg cccacactct ccccgcccgc ccgggtgtgg tgctcagcac cagcatgcca  27120
caggctaggc acgtggccag ccgtgggtct cctgcccccc tgggcctggc caccttctcc  27180
atgtccaggc caatccagag cgttctcctc actgtccctc tgaaggctgg agttactgag  27240
agacatggga gagggcctga tggcaccgtg acctgcccag agtcacctgg ttggtggcgg  27300
cagagccaca gctcagccag gccttcctgc tgggacacac tggtttatgc caaggccgtc  27360
agcacggagc cccacagtga ggcacagctt tccctgctgc ctccacccag cgcctggctg  27420
ggccaagcct cagggtctca tctgaagggg gcccgactgg ccctgttgtc cgaagcctct  27480
ggtgcgctcg gccctgaggc cccacgtgcc ttgttggctt cctgtgctct gtggcgtctt  27540
cgagtcggtg ctgccgggta cctgtgtgga tggggcccgt gagtgggccc tcggctccgt  27600
gtccagagtc ctgtggttct tggagtgtgt ccggccccac ccggccatgt ggtgtccaag  27660
gggggctttg tggcggcagc ggtgggagct gctgcccctt ctcgtgctcc agtggggcct  27720
tgcctctggg cttggttcgt tcctctctgg aacgttcttt ctcagagctc tctggcccgc  27780
ggtggcacga cgtggccctg gctgaagcag cccccgcgtg gttgctgtgg ttggtctgcc  27840
tggccgagcc ggaaggggag gcccgggagg gcgtcagggt tgcgtggctt gacccccggt  27900
cggtggctcg gtgatggcct cgtggcaagg cgtctcccag caggaagcgt ccatcctggg  27960
gggtcgtggg aggcggcgcg tgcctgaggc agctggcgca cagatcctga gggcctggaa  28020
tctatttgtt ccattgacct gtgacgtcac ttgacttctg agaagcagcc gctccctgcg  28080
ttgggtgttt gtaggaaatg agttcctgga ggcggaggtc gggaagttcc cccgctgcag  28140
ggcacgctca gccccaggaa gcggggtgac ctttgctggg agaggtgcct tgtccctgct  28200
gaccccgagt cacagtcagc gtcgttctgc ttgtgccgtg tttaattcct ggtgtccggt  28260
gcccaggctc agtctcctcc ccaggccgcg gccgctgcgg tcagtcagtc aagcacttct  28320
aggaacttcc tttgaaccgg tgcccttgtt cgctgctgac gccactcgga ggcttcctgg  28380
cggagcgggg aactcgcact tcctcttgtg cgcgtccctg gaatgtcggg acgctggcgc  28440
ttgcttcccg tgcgctcttg gcgggatgag cttgccctga gctgcatgtc actgtttctg  28500
cagaagttta gggttggagt tggctgacct ctctggaggt gtccccagca tctgcctggg  28560
gtctgcctcg tactcccggg acccccagtc ccccagaggg gaccccagct ggcagactgc  28620
gctcacactc agggcagcct cctttgttct gacttctgca cgctgggcct gggtggctgt  28680
gggcggctca cttgcttgat gccagtgggt gagagggtga tgggcagaga ggcaggcggt  28740
caggccccca gtcccgtcct cacaccctgt gtcccctgct cccctccgcc ccacagggaa  28800
ggtgttgagc tactggtgct tcagtcccgg ccacagcatg cgcgagctgg tccgccaggg  28860
cgtccgctcc ctcatcctta ccagcggcac gctggccccg gtgtcctcct ttgccctgga  28920
gatgcagatg tacgggccac ccctgccagg ggcctaagca ctggtgacgc ctgtgacgtt  28980
agtggggtgg gagtgctggg ggtccccatg agccggggtg ctgggggtct tgggcctcac  29040
tgggggtctc gggccttgag ggctaaaggg gtgctggtgt ccttccccac tgtctgtccc  29100
tccggccacg ctcagccctt tcccggtctg cctggagaac ccacacatca tcgacaagca  29160
ccagatctgg gtgggggtcg tccccagagg tcccgacgga gcccagctga gctccgcgtt  29220
```

tgacagacgg tgagggcctg tccctgggcc gtgctggggt gcgaggtcgg ggagtactga 29280
gccctgaggc cctgagcagt ggcctctcgg ctctgtgcag gttttctgag gagtgcttgt 29340
cctccctggg gaaggctctg ggtaagtgcc cggcacaccc cagctgtgcc catcctggat 29400
cctggaccct gctcccaaga gctggtaggg accccggaag acgccccgcc cctgccctga 29460
ccccagcccc tgcacttcca ggcaacatcg cccgcgtggt gccctacggg ctgctgatct 29520
tcttcccttc ctatcctgtc atggagaaga gcctggagtt ctggcgagta tgtctcccct 29580
gtgtgtcctg ggtggggtgg gtgagggcag ggctggagca cgaagcaggc agtggccaca 29640
gctcctgcct gccctcatcg gatcggcggc gtaaccaggg ctgccgtgtc cctgcctctt 29700
cctcccacag gcccgcgact tggccaggaa gatggaggca ctgaagccgc tgtttgtgga 29760
gcccaggagc aaaggcagct tctccgaggt cagcacttgg ccggggctct gggtctgctg 29820
ccccctcgtg cctcccgtgc ccctcacagc ttccccgagg ctgaccacca gccctgacca 29880
cgggctctgg cggctcccgc ctgcctcttc agggcccctg cgtttccttc ctggccctga 29940
gtgttgcctc ttatcttaca aagcccccag cactgggtgg gtgtggcgac agtggtcctc 30000
ctgcctgagg agctatagcc ggcggccacc ctggccctgg gattccccgt gttttctggg 30060
aagcactgag caggcgcagg atcagcctgg gatccgtgcc aggaagaagt ttccagaacc 30120
cagttggcct tcctggctag gatagtcctt catcttggag gatgagacct gggtctccct 30180
catgggggaa gaaggggccg aggtgggctc caggctgagc ctgaccaact ttccttccag 30240
accatcagtg cttactatgc aagggtcgct gcccctgggt ccaccggcgc caccttcctg 30300
gcggtgtgcc ggggcaaggt gagctctctg ggccctctg tcctgacccg gttgcctgtt 30360
ccccagtggg tgctcatggc tcctcagctg actttgggcc ctgggggctg cctggtcccc 30420
tccttgggcc ccacaagagc aaagcactgg tggcctgctg ggagcgtgcc ccgctctggg 30480
tcgggcaggc aggatgcagg aggttcctgg ccacgagagt tggaggtggc gtctgggagc 30540
tgtggacccc aagtggggtc ctgacccata gatggggctt cctcccaccc ctggttggag 30600
cccccatggc cccaggcagc tccctggtgt gtcccccagg ccagcgaggg gttggacttc 30660
tcagacacga atggccgtgg tgtgatcgtc acgggcctcc cgtacccccc ccgcatggac 30720
ccccgggttg tcctcaagat gcagttcctg gacgagatga agggccaggg tggggctggg 30780
ggccaggtga gttacagcag ggcggggctg gggtaaggca atctggcgac tgagcccccc 30840
tgtgaccacg ggagcccctg tgaccgagcc tcctcgccct ccagttcctc tctgggcagg 30900
agtggtaccg gcagcaggcg tccagggcgg tgaaccaggc catcgggcga gtgatccggc 30960
accgccagga ctacggggct gtcttcctct gtgaccacag gtgcgtgcag tccgggggca 31020
ggcgtggcgc caggggacac ggccacatcc cactgggccc tggactcctt ccccacatga 31080
ggccccgtct cccccagagc ctctctggcg actcggggtc agcctgaggc ccctgcggca 31140
gatgagggtc ttcacttggg tgaactgacc ccctgaagcg gctgtgggca gggcagcagg 31200
gctgtggcca ccccccaggt tcgcctttgc tgatgccaga gcccagctgc cctcctgggt 31260
gcgtcctcac gtcagggtgt acgacaactt cggccacgtc atccgagacg tggcccagtt 31320
cttccgtgtt gccgagcgaa ctgtgagttt ctgcccaggg aggggatgag ggtgttgtcc 31380
ccagaggagc cagaaatggg cccacccacc cccagtggtt ctgcagatgc cagcaccggc 31440
cccccgggct gcagcaccca gtttgcgtga aggagaagat gctgtcaggg aggccaagtc 31500
gcctgacccc ctcctctcca ccaggaaagc taagagtctg gacctgcatg tccccagcct 31560

-continued gaagcagagg tcctcaggtg cagatggcca gtgcgggacg ggcagtgtgg ggcgggcggg 31620
gcaggcggat tggggcgggc cgtgtggggc aagcagcggg gcaggtggtg tggggcgggc 31680
ggcaccaggc gcccagggtg gaggcggctc acctggcttt atgcactgcc cctcccacct 31740
ccaaaggctg tgtctgcctc ctagggtggg gttcccacgg gctggaaccc tcccctacag 31800
gcagagaagg cctcaggcaa agacgcgccc caaggctggg actcccccta atagcaggga 31860
ggacacccac aggcaggggc ccccaaatgc tgggaccctc cctcaggagg ggctccgtca 31920
taggcaggga cccccagctg gggccccgcg gtgggcttca ctgcgcactc gggtactctg 31980
caggatcacc agctgccggg gaccccgaga gtagcctgtg tgtggagtat gagcaggagc 32040
cagttcctgc ccggcagagg cccagggggc tgctggccgc cctggagcac agtgaacagc 32100
gggccgggga ccttggcgag gagcaggtgc agttccaggg ccttgggatg gacacagacc 32160
ctctgtctcc tgaggccaac cccaccccgc ccatctgact tcaggcacct ccccacacac 32220
ccctgtaaat cccctgcctg tggggcgggc aggcaggtga gggatcccag ctgcctggct 32280
gtgtgtgtgc cctccacctc gcctcaccca caggctgctg gctcccaggt ggtgcatgcc 32340
ctggccctca gcgggtgccc ccacatcact ttgattctct ggcaggtcag cttggctcag 32400
ggcactcaag gtcgggtgcc cctgcccctg gctgtgcctg aggctggcct ttctccagga 32460
atgtgctgcg gttgggaccc aggttccttc ctccttgggg ccttttgccc cagaagccca 32520
taatttctca gctttctccc tgcttcctgc tgggggccgt tctcttgctg cctgtccctg 32580
cccttcaggc tcctggagtg agccccgggt gcaggcacca gacacctgtg tccccttcct 32640
gccagcccct cgctgtggtc ggactgtcct tcctggacct gctcttacgt gtcaccacct 32700
gtgagcctca tgagccgctg gcgtgacttg gacaggacca agttgtggga ctgtcaccag 32760
ggtgtgccgc gcccctcccc cgaccttcgt cttggctact gctcagggct ccttggggcc 32820
atcttccctg tgggcccagg tgctttgggg ccctggagtg tgtggttgga accacagctg 32880
tgtcctcctc aggcccacag ctgctccacc ctgtccctcc tggctgagaa gaggccggca 32940
gaggagctgc gaggagggag gaagaagatc cggctggtca gccacctggt gcgtgagctg 33000
tccctgcacc tgtgccgacc accatagaca cgtgtgggaa cccggccctg ggtgccccca 33060
gccaagttgg gatgtgggcc cgatgggacc agggaagtta cccccgggag ctgatgtcca 33120
gggcggctgt gaagctgtcg gcccaagggc tcaagggcag ctgggatcag gccccgccct 33180
tgggcaggct tggtttgggg gctgcagcac tgggtttggc cctggcattt ccctcaagtg 33240
tggacgtgca cctgcctcat tcgaggggcg cagcccattc ccagccttgg atgaaagaac 33300
cgagttatag tcggagccag gaagccccct gcctgctgga aagccccaag tgtggcagcc 33360
tttgtccatg tcccttggct tctgggaaga actgggtggt gcccaggcag ggctggtgcc 33420
atcaggaagt gggcggctgc cgagggggcct gggctgttga gggcctgggt ggggagtgcc 33480
ggggctgccc ctgccttggt ttccacgttt ccgtgttggt ctggggtgtg tggagagatg 33540
agcaccgctt cttgggaagc ccctccctat gatctgccat cctggagcct cagctgtgtc 33600
cgctgtgggg tgggggcttt agggaggagg agagaggacc cccagcttga gggagagcca 33660
gtctaccctt tgcccattcg ctgccctcgg ttccctgcca gcctctcact gtgtgaccca 33720
gacaggccca gccccgcagc tttcctcccg cagcacctcc gtgtccatcc agccaaccag 33780
tttctcaggc agcagccccc gctcagcaat cactgtcccg gggaacaccc aatgctccaa 33840
ggaaggctct gcagctccag ggacgggatg atgaggctgg ccctgatgga gcctcgggcc 33900
tgtgtgctgc aggaggagcc cgtggctggc gcacagatgg acagggccaa gctcttcatg 33960
gtggctgtga agcaggaact gagccaagcc aactttgcca ccttcaccca ggccctgcag 34020
gactacaagg gttccgatga cttcgccgcc ctggccgcct gtctcggccc cctctttgct 34080
gaggacccca agaagcacag cctgctccaa ggtgccctgg cttgcagggg ccgcccatcc 34140
tgagggcagt gctgccgctg tgtggggtgg gggccatctg ggtccaaggt tgtctctgtt 34200
ctctagagaa aagggggcgg atggggacag acaccccttc ctctacaggc ttctaccagt 34260
ttgtgcggcc tcaccacaag gagcagtttg aggaggtctg tatccagctg acgggacggg 34320
gctgcggcta ccggccagag cacagcgttc cccgaaggca gcgggcacag ccagccctgg 34380
accccactgg taaatggggc ctcgggtggg accctcagac tcctccgtgg aaggcaccgg 34440
agtcctgggc tggttggggt gggcatccct ggggccctgc gtggccccgc ctctctgttc 34500
ccgtgtggga gtgatggggg ccaccccca ccaccagcag cagtatcact tgttggggag 34560
accctgtgca actccacgca gggccctgcc cttcccatag cccctgaccc ctacgcacag 34620
ccctgtccag ctgccgcacg tgtcccctgc cccccatgca cagccctggg gagtccactg 34680
cacacgccag ggtcctagac ccctagaccc ctagatccct gtcctcccgt cctccctact 34740
tctgcctttg cctagggtgg agtccaagcc tccagaggtg ggagtgtctg tgttcgtgct 34800
tgttaacgaa cagcccccat agagctcctc cagtgtaggg ttcacccagc ggggaaccta 34860
acctgttggg aagaccccag acccccttctg ggcttggtac ccaccctggg gctctaagct 34920
cctgagcagg gctttggcct gcctgccact gttccagccc ccatccagca gttggtgtct 34980
cctctgctgc cccggcacct gggcacgtgt gcctgcctgg gttttcccgc cctggtccga 35040
ggtgggtgag gcctggcctc cccagccagc ccttcccccct ccccggggga actttccagg 35100
tgcttgggac cagctttgtg gctctccatc tcttcatcag gaaggacagc gctagatccc 35160
aagctgactg tgtccaaggc tgcagcccag cagctggacc cccgagagca cctgaaccag 35220
ggcaggcccc acctgtcgcc cagaccaccc cccacaggta gctgagtcct gaactgtgtg 35280
cagcctgtga cttggtgggt tcctcagtgg cttgatgagg ctaacacttg agtgtggctt 35340
gagcctttga accggaggtg ccagtggagc tgcccctgtg gggagcatct cctggtgggg 35400
gctcccggtt ctgtaccccg cagttgtcct gagcagctct ccaggagttc gtgggaggaa 35460
gggcaggcag ggtggtggga ctctcagtcc tctgccccag cgccactctg agccatgcta 35520
ctcccacacc aggaggccct ggcagccacc cacagcaggg gtccagagcg cccagagcag 35580
ggaagcaggg ccagcgcgcc gtgagcgcct acctggcaga tgtccgcagg gccctggggt 35640
ctgcaggctg tagccagctc ttggcagcac tgacagccta caagcaagac gatgacctcg 35700
acaaggtgct ggccgtgctg gccgccctga ccactgcaaa gccggaggac ttccccctgc 35760
tgcagagcaa gtggcctggg cgtgggggac agccagtggg gtgggnnnnn nnnnnnnnnn 35820
nnnnnnnnnn nnnnnnnnnn nnnnnnnnnn nnnnnnnnnn nnnnnnnnnn nnnnnnnnnn 35880
nnnnnnnnnn nnnnnnnnnn nnnnnnnnnn nnnnnnnnnn nnnnnnnnnn nnnnnnnnnn 35940
nnnnnnnnnn nnnnnnnnnn nnnnnnnnnn nnnnnnnnnn nnnnnnnnnn nnnnnnnnnn 36000
nnnnnnnnnn nnnnnnnnnn nnnnnnnnnn nnnnnnnnnn nnnnnnnnnn nnnnnnnnnn 36060
nnnnnnnnnn nnnnnnnnnn nnnnnnnnnn nnnnnnnnnn nnnnnnnnnn nnnnnnnnnn 36120
nnnnnnnnnn nnnnnnnnnn nnnnnnnnnn nnnnnnnnnn nnnnnnnnnn nnnnnnnnnn 36180
nnnnnnnnnn nnnnnnnnnn nnnnnnnnnn nnnnnnnnnn nnnnnnnnnn nnnnnnnnnn 36240
nnnnnnnnnn nnnnnnnnnn nnnnnnnnnn nnnnnnnnnn nnnnnnnnnn nnnnnnnnnn 36300

-continued

```
nnnnnnnnnn nnnnnnnnnn nnnnnnnnnn nnnnnnnnnn nnnnnnnnnn nnnnnnnggg  36360

ggcaggggca gggtggggac cgtgccgggt ctgagtgaag ctccccgcag ggttcagcat  36420

gtttgtgcgt ccacaccaca agcagcgctt ctcacagacg tgcacagacc tgaccggcag  36480

accctccctg ggcacggagc caccaggacc ccaggaggag agtcttgccg tgcctcctgt  36540

gctcacccac agggctcccc aaccaggtag ggcgcctgcc tggctgctcc tgacagtgcc  36600

ccaaccgcac gcagccctgg gagtgagcag caaagcccca ggccctgctc agactcagtc  36660

tccgtctcca ggcccctcac ggtccgagaa gcccggaaag acccagagcg agatctcgac  36720

cttccttaga cagaggccag cagggactgt gggggcgggc ggtgaggctg cagggcccag  36780

ccagtcccca ggacctcccc acgggcctgc agcatctgag tggggtgagc ctcctgggag  36840

agaccttgct gggcagcagg ctgcgggagc tccgagcggg cccctctcag caggctgtgt  36900

gtgccagggc tgtggggcgg aggatgtggt gcccttccag tgccctgcct gtgatttcca  36960

gcgctgccaa gcctgttggc aacggcacct tcaggttggt gcctggtcac tacagttcct  37020

gctgggtgta gccccaggtg gtgggctgag gggaaagggg ccgggtatag ccccaggtgg  37080

tgggctggtg gcaacgcctg gcaggtgcgt ccagcgggcc ggttgtctta caggcctcta  37140

ggacgtgccc atcctgccac accgcctcca ggaagcagag cgtcacgcag gtcttctggc  37200

cagagcccca gtga                                                    37214


<210> SEQ ID NO 3
<211> LENGTH: 18
<212> TYPE: DNA
<213> ORGANISM: artificial
<220> FEATURE:
<223> OTHER INFORMATION: oligonucleotide compound 3_1

<400> SEQUENCE: 3

aattttacat actctggt                                                   18


<210> SEQ ID NO 4
<211> LENGTH: 19
<212> TYPE: DNA
<213> ORGANISM: artificial
<220> FEATURE:
<223> OTHER INFORMATION: oligonucleotide compound 4_1

<400> SEQUENCE: 4

aattttacat actctggtc                                                  19


<210> SEQ ID NO 5
<211> LENGTH: 18
<212> TYPE: DNA
<213> ORGANISM: artificial
<220> FEATURE:
<223> OTHER INFORMATION: oligonucleotide compound 5_1

<400> SEQUENCE: 5

ttacatactc tggtcaaa                                                   18


<210> SEQ ID NO 6
<211> LENGTH: 21
<212> TYPE: DNA
<213> ORGANISM: artificial
<220> FEATURE:
<223> OTHER INFORMATION: oligonucleotide compound 6_1

<400> SEQUENCE: 6

ctttattata acttgaatct c                                               21
```

<210> SEQ ID NO 7
<211> LENGTH: 22
<212> TYPE: DNA
<213> ORGANISM: Homo sapiens

<400> SEQUENCE: 7
tttgaccaga gtatgtaaaa tt 22

<210> SEQ ID NO 8
<211> LENGTH: 18
<212> TYPE: DNA
<213> ORGANISM: Homo sapiens

<400> SEQUENCE: 8
accagagtat gtaaaatt 18

<210> SEQ ID NO 9
<211> LENGTH: 19
<212> TYPE: DNA
<213> ORGANISM: Homo sapiens

<400> SEQUENCE: 9
gaccagagta tgtaaaatt 19

<210> SEQ ID NO 10
<211> LENGTH: 18
<212> TYPE: DNA
<213> ORGANISM: Homo sapiens

<400> SEQUENCE: 10
tttgaccaga gtatgtaa 18

<210> SEQ ID NO 11
<211> LENGTH: 21
<212> TYPE: DNA
<213> ORGANISM: Homo sapiens

<400> SEQUENCE: 11
gagattcaag ttataataaa g 21

<210> SEQ ID NO 12
<211> LENGTH: 21
<212> TYPE: DNA
<213> ORGANISM: artificial
<220> FEATURE:
<223> OTHER INFORMATION: Primer

<400> SEQUENCE: 12
ggagtgtgga ttcgcactcc t 21

<210> SEQ ID NO 13
<211> LENGTH: 20
<212> TYPE: DNA
<213> ORGANISM: artificial
<220> FEATURE:
<223> OTHER INFORMATION: Primer

<400> SEQUENCE: 13
agattgagat cttctgcgac 20

<210> SEQ ID NO 14
<211> LENGTH: 27
<212> TYPE: DNA

<213> ORGANISM: artificial
<220> FEATURE:
<223> OTHER INFORMATION: probe

<400> SEQUENCE: 14
aggcaggtcc cctagaagaa gaactcc 27

<210> SEQ ID NO 15
<211> LENGTH: 21
<212> TYPE: DNA
<213> ORGANISM: artificial
<220> FEATURE:
<223> OTHER INFORMATION: primer

<400> SEQUENCE: 15
ccatcctgga cattgaggac t 21

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
caggttccgg gacaggtagt a 21

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
cgtctgtgcc ttctcatctg c 21

<210> SEQ ID NO 18
<211> LENGTH: 20
<212> TYPE: DNA
<213> ORGANISM: artificial
<220> FEATURE:
<223> OTHER INFORMATION: primer

<400> SEQUENCE: 18
gcacagcttg gaggcttgaa 20

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
ccgtctgaac tatcctgccc 20

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
gccgtagtcg gtgtactcgt 20

<210> SEQ ID NO 21
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 21
gaattttaca tactctggt 19

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
gaattttaca tactctggtc 20

<210> SEQ ID NO 23
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 23
caaaaaacag taggtcc 17

<210> SEQ ID NO 24
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 24
gagggaggtg gagcgtt 17

<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
agctttatta taacttgaat 20

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
ttttacatac tctggtcaaa 20

<210> SEQ ID NO 27
<211> LENGTH: 18
<212> TYPE: DNA
<213> ORGANISM: Artificial Sequence
<220> FEATURE:

<223> OTHER INFORMATION: Antisense oligonucleotide

<400> SEQUENCE: 27
ttttacatac tctggtca 18

<210> SEQ ID NO 28
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 28
gagaatttta catactctgg 20

<210> SEQ ID NO 29
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 29
gcatccaaca agtaattgt 19

<210> SEQ ID NO 30
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 30
ggtgggtgga tgtttc 16

<210> SEQ ID NO 31
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 31
ggtggtgtgg agaagc 16

<210> SEQ ID NO 32
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 32
ggcatccaac aagtaatt 18

<210> SEQ ID NO 33
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 33
ggaataaaac agtaggtc 18

<210> SEQ ID NO 34
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 34
gccattttca ctgtcaa 17

<210> SEQ ID NO 35
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 35
gtgcagaagt cagaacaaa 19

<210> SEQ ID NO 36
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 36
caaaatgccc ttacagtga 19

<210> SEQ ID NO 37
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 37
ggaataaaac agtaggt 17

<210> SEQ ID NO 38
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 38
aattttacat actctgg 17

<210> SEQ ID NO 39
<211> LENGTH: 16
<212> TYPE: DNA
<213> ORGANISM: Artificial Sequence
<220> FEATURE:
<223> OTHER INFORMATION: oligo

<400> SEQUENCE: 39
aattttacat actctg 16

<210> SEQ ID NO 40
<211> LENGTH: 17
<212> TYPE: DNA
<213> ORGANISM: Artificial Sequence
<220> FEATURE:
<223> OTHER INFORMATION: oligo

<400> SEQUENCE: 40
ttacatactc tggtcaa 17

<210> SEQ ID NO 41
<211> LENGTH: 16
<212> TYPE: DNA
<213> ORGANISM: Artificial Sequence
<220> FEATURE:
<223> OTHER INFORMATION: oligo

<400> SEQUENCE: 41
ttacatactc tggtca 16

<210> SEQ ID NO 42
<211> LENGTH: 15
<212> TYPE: DNA
<213> ORGANISM: Artificial Sequence
<220> FEATURE:
<223> OTHER INFORMATION: oligo

<400> SEQUENCE: 42
ttacatactc tggtc 15

<210> SEQ ID NO 43
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 43
ttacatactc tggt 14

<210> SEQ ID NO 44
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 44
ttacatactc tgg 13

<210> SEQ ID NO 45
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 45
ttacatactc tg 12

<210> SEQ ID NO 46
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 46
gaattttaca tactctgg 18

<210> SEQ ID NO 47
<211> LENGTH: 17

<212> TYPE: DNA
<213> ORGANISM: Artificial Sequence
<220> FEATURE:
<223> OTHER INFORMATION: Antisense oligonucleotide

<400> SEQUENCE: 47
gaattttaca tactctg 17

<210> SEQ ID NO 48
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 48
gaattttaca tactct 16

<210> SEQ ID NO 49
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 49
gaattttaca tactc 15

<210> SEQ ID NO 50
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 50
gaattttaca tact 14

<210> SEQ ID NO 51
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 51
gaattttaca tac 13

<210> SEQ ID NO 52
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 52
gaattttaca tactctggt 19

<210> SEQ ID NO 53
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 53
gaattttaca tactctgg 18

<210> SEQ ID NO 54
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 54
gaattttaca tactctg 17

<210> SEQ ID NO 55
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 55
gaattttaca tactct 16

<210> SEQ ID NO 56
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 56
gaattttaca tactc 15

<210> SEQ ID NO 57
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 57
gaattttaca tact 14

<210> SEQ ID NO 58
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 58
caaaaaacag taggtc 16

<210> SEQ ID NO 59
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 59
caaaaaacag taggt 15

<210> SEQ ID NO 60
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 60
caaaaaacag tagg 14

<210> SEQ ID NO 61
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 61
caaaaaacag tag 13

<210> SEQ ID NO 62
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 62
caaaaaacag ta 12

<210> SEQ ID NO 63
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 63
caaaaaacag t 11

<210> SEQ ID NO 64
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 64
gagggaggtg gagcgt 16

<210> SEQ ID NO 65
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 65
gagggaggtg gagcg 15

<210> SEQ ID NO 66
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 66
gagggaggtg gagc 14

<210> SEQ ID NO 67
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 67
gagggaggtg gag 13

<210> SEQ ID NO 68
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 68
gagggaggtg gag 13

<210> SEQ ID NO 69
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 69
gagggaggtg g 11

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
gtttttcacc tctgcctaat catc 24

<210> SEQ ID NO 71
<211> LENGTH: 23
<212> TYPE: DNA
<213> ORGANISM: Artificial Sequence
<220> FEATURE:
<223> OTHER INFORMATION: Primer

<400> SEQUENCE: 71
gcaaaaagtt gcatggtgct ggt 23